US008420352B2

United States Patent
Oyler et al.

(10) Patent No.: US 8,420,352 B2
(45) Date of Patent: Apr. 16, 2013

(54) PROTEIN DELIVERY SYSTEM TO GENERATE PLURIPOTENT STEM (IPS) CELLS OR TISSUE SPECIFIC CELLS

(75) Inventors: George A. Oyler, Baltimore, MD (US); Yung-Nien Chang, Elkridge, MD (US)

(73) Assignee: Synaptic Research, LLC, Baltimore, MD (US)

( * ) Notice: Subject to any disclaimer, the term of this patent is extended or adjusted under 35 U.S.C. 154(b) by 72 days.

(21) Appl. No.: 12/870,782

(22) Filed: Aug. 27, 2010

(65) Prior Publication Data

US 2011/0053244 A1 Mar. 3, 2011

Related U.S. Application Data

(60) Provisional application No. 61/275,297, filed on Aug. 27, 2009.

(51) Int. Cl.
C07K 14/33 (2006.01)
C12N 1/20 (2006.01)
C12N 15/62 (2006.01)
C12P 21/02 (2006.01)

(52) U.S. Cl.
USPC ...... 435/69.7; 435/69.1; 435/252.7; 530/350; 530/825

(58) Field of Classification Search ............ None
See application file for complete search history.

(56) References Cited

U.S. PATENT DOCUMENTS

| | | | |
|---|---|---|---|
| 6,086,900 A | 7/2000 | Draper | |
| 7,601,332 B2 | 10/2009 | Vlahov | |
| 2003/0082143 A1 | 5/2003 | Larocca | |
| 2003/0103957 A1 | 6/2003 | McKerracher | |
| 2003/0161809 A1 | 8/2003 | Houston | |
| 2003/0166160 A1 | 9/2003 | Hawley | |
| 2004/0013687 A1 | 1/2004 | Simpson | |
| 2005/0147593 A1 | 7/2005 | Kinch | |
| 2005/0153923 A1 | 7/2005 | Kinch | |
| 2006/0099150 A1 | 5/2006 | Houston | |
| 2006/0110409 A1* | 5/2006 | Shone et al. ............... | 424/239.1 |
| 2006/0134103 A1 | 6/2006 | Hawley | |
| 2006/0210527 A1 | 9/2006 | Davis | |
| 2007/0184048 A1 | 8/2007 | Foster | |
| 2007/0203332 A1 | 8/2007 | Graupner | |
| 2009/0047263 A1 | 2/2009 | Yamanaka et al. | |
| 2009/0053248 A1 | 2/2009 | Simpson | |
| 2009/0191159 A1 | 7/2009 | Sakurada et al. | |
| 2009/0203141 A1 | 8/2009 | Lin et al. | |
| 2010/0093090 A1 | 4/2010 | Deng | |
| 2010/0093092 A1 | 4/2010 | Bamdad | |

FOREIGN PATENT DOCUMENTS

| | | |
|---|---|---|
| WO | 9842876 | 10/1998 |
| WO | 0053236 | 9/2000 |
| WO | 0111960 | 2/2001 |
| WO | 2004009126 | 1/2004 |
| WO | 2008124133 | 10/2008 |
| WO | 2008151058 | 12/2008 |
| WO | 2009009441 | 1/2009 |
| WO | 2009032456 | 3/2009 |
| WO | 2009067756 | 6/2009 |
| WO | 2009067757 | 6/2009 |
| WO | 2009073523 | 6/2009 |
| WO | 2009102983 | 8/2009 |
| WO | 2009157593 | 12/2009 |
| WO | 2010013845 | 2/2010 |
| WO | 2010050626 | 5/2010 |

OTHER PUBLICATIONS

Goodnough et al. Development of a delivery vehicle for intracellular transport of botulinum neurotoxin antagonists. FEBS Lett 513: 163-168, 2002.*
Ho et al. Recombinant botulinum neurotoxin A heavy chain-based delivery vehicles for neuronal cell targeting. Protein Engin Design Selection 24(3): 247-253, 2011.*
Kern et al. Adaptation of *Clostridium difficile* toxin A for use a protein translocation system. Biochem Biophys Res Comm 405: 570-574, 2011.*
Krautz-Peterson et al. Retargeting *Clostridium difficile* toxin B to neuronal cells as a potential vehicle for cystolic delivery of therapeutic biomolecules to treat botulism. J Toxicol 2012: 1-12, 2012, ID # 760142.*
Ohishi et al. Visualizations of binding and internalization of two non-linked protein components of botulinum C2 toxin in tissue culture cells. Infect Immun 60(11): 4648-4655, 1992.*
Schmitt et al. Bacterial toxins: friends or foes? Emerging Infect Diseases 5(2): 224-234, 1999.*
Yang et al. Expression of recombinant *Clostridium difficile* toxin A and B in *Bacillus megaterium*. BMC Microbiol 8: 192, 2008 (13 pages).*
Barth, H., et al.; The Binary *Clostridium bitulinum* C2 Toxin as a Protein Delivery System: Identification of the Minimal Protein Region Necessary for Interaction of Toxin Components, J. Biol. Chem. 277(7):5074-81 (2002).
Barth, et al.; Binary actin-ADP-Ribosylating toxins and their use as molecular Trojan horses for drug delivery into eukaryotic cells, Curr. Med. Chem. 15(5):459-69 (2008).
Dobson, et al.; Carrier Mediated Cellular Uptake of Pharmaceutical Drugs: An Exception or the Rule? Nat. Rev. Drug. Discov. 7(3):2005-20 (Mar. 2008).
Johnson, Eric A.; Clostridial Toxins as Theraputic Agents: Benefits of Nature's Most Toxic Proteins, Annu. Rev. Microbiol. 53:551-75 (1999).
Pust, et al.; A Cell-Premeable Fusion Toxin as a Tool to Study the Consequences of Actin-ADP-Ribosylation Caused by the *Salmonella enterica* Virulence Factor SpvB in Intact Cells, J. Biol. Chem. 282(14):10272-82 (Apr. 2007).

(Continued)

*Primary Examiner* — Bridget E Bunner
(74) *Attorney, Agent, or Firm* — Whiteford, Taylor & Preston, LLP; Joseph L. Morales

(57) ABSTRACT

A novel protein delivery system to generate induced pluripotent stem (iPS) cells is described. The delivery system comprises a construct with a receptor binding domain that recognizes a receptor in a somatic cell, a translocation domain that allows the transfer of an inducer into the cytosolic space, and a cargo bearing domain to which the inducer is attached and facilitates transfer of the inducer into the cell.

42 Claims, 17 Drawing Sheets

OTHER PUBLICATIONS

Figure 6:
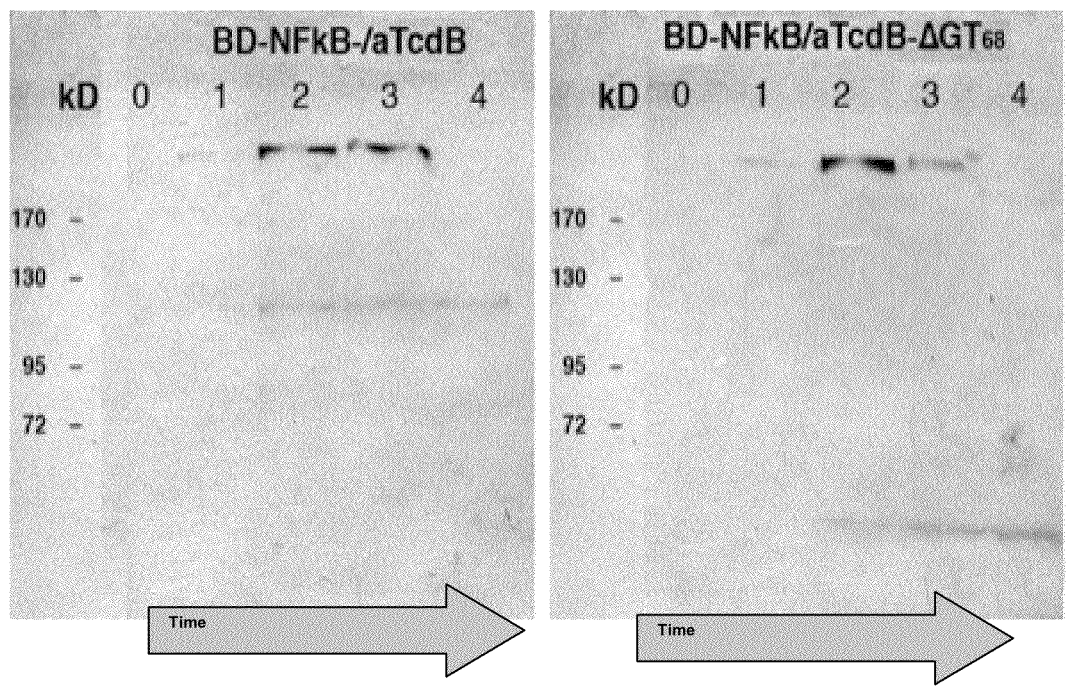

Spyres, et al.; Cytosolic Delivery and Characterization of the TcdB Glucosylating Domain by Using a Heterologous Protein Fusion, Infect. Immunol. 69(1):599-601 (Jan. 2001).

Tenzer, et al.; Smart Bacterial Toxins: Autocatalytic Cleavage of Clostridial Toxins—a Target for Novel Therapeutic Strategies? B.I.F. Futura 23 (2008).

Yamanaka, Shinya, Pluripotency and Nuclear Reprograming, Phil. Trans. R. Soc. B. 363:2079-87 (2008).

Yamanaka, Shinya, A Fresh Look at iPS Cells, Cell 137: 13-17 (Apr. 2009).

Takahashi, et al.; Induction of Pluripotent Stem Cells from Mouse Embryonic and Adult Fibroblast Cultures by Defined Factors, Cell 126:663-76 (Aug. 2006).

Yu, et al.; Induced Pluripotent Stem Cell Lines Derived from Human Somatic Cells, Sciencexpress (Nov. 20, 2007).

Takahashi, et al.; Induction of Pluripotent Stem Cells from Adult Human Fibroblasts by Defined Factors, Cell 131:1-12 (Nov. 30, 2007).

Zhou, et al.; In Vivo Reprogramming of Adult Pancreatic Exocrene Cells to β Cells, Nature 455: 627-633 (Oct. 2, 2008).

Miura, et al.; Variation in the Inducement of Pluripotent Stem Cell Lines. Nat. Biotechnol. 27(8):743-745 (Aug. 2009).

Carpenter, et al.; Developing Safe Therapies from Human Pluripotent Cells, Nat. Biotechnol. 27(7): 606-613; (Jul. 2009).

Statfeldt, et al.; Induced Pluripotent Stemcells Generated without Viral Integration, Sciencexpress (Sep. 25, 2008).

Yu, et al.; Human Induced Pluripotent Stem Cells Free of Vector and Transgene Sequences, Science 324(5928): 797-801 (May 8, 2009).

Harui, et al.; Frequency and Stability of Chromosonal Integration of Adrenovirus Vectors, J. Virology 73(7): 6141-6146 (Jul. 2009).

Niwa, et al.; Quantitative Expression of Oct 3/4 Defines Differentation, Dedifferentation or Self-Renewal of ES Cells, Nat. Genetics 24:372-376 (Apr. 2000).

Frankel and Pabo; Cellular Uptake of the Tat Protein from Human Immunodeficiency Virus, Cell 55: 1189-1193 (Dec. 23, 1988).

Green and Lowenstein; Autonomous Domains of Chemically Synthesized Human Immunodeficiency Virus Tat Trans-Activator Protein, Cell 55: 1179-1188 (Dec. 23, 1988).

Kwon, et al.; Cellular Manipulation of Human Embryotic Stem Cells by TAT-PDX1 Protein Transduction, Mol. Therapy 12(1): 28-32 (Jul. 2005).

Kim, et al.; Generation of Human Induced Pluripotent Stem Cells by Direct Delivery of Reprogramming Proteins, Cell Stem Cell 4: 472-476 (Jun. 5, 2009).

Wadia, et al.; Transducible TAT-H Fusogenic Peptide Enhances Escape of TAT-fusion Proteins after Lipid Raft Macropinocytosis, Nature Med. 10(3): 310-315 (Mar. 2004).

Zhou, et al.; Generation of Induced Pluripotent Stem Cells Using Recombinant Proteins, Cell Stem Cell 4:1-4 (May 8, 2009).

Bade, et al.; *Botulinum neurotoxin* Type D Enables Cystolic Delivery of Enzymatically Deficient Cargo Proteins to Neurones via Unfolded Translocation Intermediates J. Neurochem. 91: 1461-1472 (2004).

Pfeifer, et al.; Cellular Uptake of the *Clostridium dificile* Toxin B, J. Biochem. 278(45): 44535-44541 (Nov. 7, 2003).

Voth and Ballard; *Clostridium dificile* Toxins Mechanism of Action and Role in Disease, Clin. Microbiol. Rev. 18 (2):247-263 (Apr. 2005).

Ho, et. al.; Crystal Structure of Receptor-Binding C-terminal Repeats from *Clostridium dificile* Toxin A, PNAS 102 (51): 18373-18378 (Dec. 20, 2005).

Greco, et al.; Carbohydrate Recognition by *Clostridium dificile* Toxin A, Nature Struct. & Mol. Biol. 13(5); 460-461 (May 2006).

Egerer, et al.; Auto-catalytic Cleavage of *Clostridium dificile* Toxins A and B Depends on Cysteine Protease Activity, J. Biol. Chem. 282(35): 25314-25321 (Aug. 31, 2007).

Egerer, et al.; Autocatalytic Processing of *Clostridium dificile* Toxin B, J. Biol. Chem. 284(6): 3389-3395 (Feb. 6, 2009).

Chavez-Olarte, et al.; Toxins A and B from *Clostridium dificile* Differ with Respect to Enzymatic Potencies, Cellular Substrate Specificities, and Surface Binding to Cultured Cells, J. Clin. Invest. 100(7): 1734-1741 (Oct. 1997).

Yang, et al.; Expression of Recombinant *Clostridium dificile* Toxin A and B in *Bacillus magneterium*, BMC Microbiolology 2008, 8:192 (Nov. 6, 2008).

Hofmann, et al.; Localization of the Glucosyltransferase Activity of *Clostridium dificile* Toxin B to the N-terminal Part of the Holotoxin, J. Biol. Chem. 272(17): 11074-11078 (Apr. 25, 1997).

Narazaki, et al.; Directed and Systematic and Differentiation of Cardiovasular Cells from Mouse Induced Pluripotent Stem Cells, Circulation. 118: 498-506 (Jul. 14, 2008).

Yamanaka, Shinya; Strategies and New Developments in the Generation of Patient-Specific Pluripotent Stem Cells Cell Stem Cell 1: 39-45 (Jul. 2007).

Geisemann, et al.; Processing of *Clostridium difficile* toxins, J. Med. Microbiol. 57:690-96 (2008).

Ebihara, Chiaki et al. "Preparation of a Claudin-Targeting Molecule Using a C-Terminal Fragment of Clostridium perfringens Enterotoxin." Jan. 2006. Journal of Pharmacology and Experimental Therapeutics, vol. 316, No. 1. pp. 255-260.

* cited by examiner

Biological activity — GT
Cutting — CPD
Delivery — HR, TD
Binding — RBD

N — GT | CPD | HR | TD | RBD — C

Figure 1A

| GT | CPD | HR | TD | RBD |   WT TcdB
| mGT | CPD | HR | TD | RBD |   aTcdB
| Cargo | mGT | CPD | HR | TD | RBD |   aTcdB-M1
| Cargo | mGT | CPD | HR | TD | RBD |   aTcdB-M2
| Cargo | CPD | HR | TD | RBD |   aTcdB-M3

Figure 1B

MDEQQSQAVAPVYVGGMDEKTTGWRGGHVVEGLAGELEQLRARLEHHPQGQREPS-GA-AGH
LASDFAFSPPPGGGGDGPGGPEPGWVDPRTWLSFQGPPGGPGIGPGVGPGSEVWGIPPCPPPYEF
CGGMAYCGPQVGVGLVPQGGLETSQPEGEAGVGVESNSDGASPEPCTVTPGAVKLEKEKLEQN
PEESQDIKALQKELEQFAKLLKQKRITLGYTQADVGLTLGVLFGKVFSQTTICRFEALQLSFKNM
CKLRPLLQKWVEEADNNENLQEICKAETLVQARKRKRTSIENRVRGNLENLFLQCPKPTLQQISH
IAQQLGLEKDVVRVWFCNRRQKGKRSSSDYAQREDFEAAGSPFSGGPVSFPLAPGPHFGTPGYG
SPHFTALYSSVPFPEGEAFPPVSVTTLGSPMHSN-AAA-SLVNRKQLEKMANVRFRTQEDEYVAIL
DALEEYHNMSENTVVEKYLKLKDINSLTDIYIDTYKKSGRNKALKKFKEYLVTEVLELKNNNLT
PVEKNLHFVWIGGQINDTAINYINQWKDVNSDYNVNVFYDSNAFLINTLKKTVVESAINDTLESF
RENLNDPRFDYNKFFRKRMEIIYDKQKNFINYYKAQREENPELIIDDIVKTYLSNEYSKEIDELNT
YIEESLNKITQNSGNDVRNFEEFKNGESFNLYEQELVERWNLAAASDILRISALKEIGGMYLAVA
MLPGIQPDLFESIEKPSSVTVDFWEMTKLEAIMKYKEYIPEYTSEHFDMLDEEVQSSFESVLASKS
DKSEIFSSLGDMEASPLEVKIAFNSKGIINQGLISVKDSYCSNLIVKQIENRYKILNNSLNPAISEDN
DFNTTTNTFIDSIMAEANADNGRFMMELGKYLRVGFFPDVKTTINLSGPEAYAAAYQDLLMFKE
GSMNIHLIEADLRNFEISKTNISQSTEQEMASLWSFDDARAKAQFEEYKRNYFEGSL-GEDDNLD
FSQNIVVDKEYLLEKISSLARSSERGYIHYIVQLQGDKISYEAACNLFAKTPYDSVLFQKNIEDSEI
AYYYNPGDGEIQEIDKYKIPSIISDRPKIKLTFIGHGKDEFNTDIFAGFDVDSLSTEIEAAIDLAKEDI
SPKSIEINLLGCNMFSYSINVEETYPGKLLLKVKDKISELMPSISQDSIIVSANQYEVRINSEGRREL
LDHSGEWINKEES-IIKDISSKEYISFNPKENKITVKSKNLPELSTLLQEIRNNSNSSDIELEEKVMLT
ECEINVISNIDTQIVEERIEEAKNLTSDSINYIKDEFKLIESISDALCDLKQQNELEDSHFISFEDISET
DEGFSIRFINKETGESIFVETEKTIFSEYANHITEEISKIKGTIFDTVNGKLVKKVNLDTTHE-VNTLN
AAFFIQSLIEYNSSKESLSNLSVAMKVQVYAQLFSTGLNTITDAAKVVELVSTALDETIDLLPTLSE
GLPIIATIIDGVSLGAAIKELSETSDPLLRQEIEAKIGIMAVNLTTATTAIITSSLGIASGFSILLVPLA
GISAGIPSLVNNELVLRDKATKVVDYFKHVS-LVETEGVFTLLDDKIMMPQDDLVISEIDFNNNSI
VLGKCEIWRMEGGSGHTVTDDIDHFFSAPSITYREPHLSIYDVLEVQKEELDLSKDLMVLPNAPN
RVFAWETGWTPGLRSLENDGTKLLDRIRDNYEGEFYWRYFAFIADALITTLKPRYEDTNIRINLD
SNTRSFIVPIITTEYIREKLSYSFYGSGGTYALSLSQYNMGINIELSESDVWIIDVDNVVRDVTIESD
KIKKGDLIEGILSTLSIEENKIILNSHEINFSGEVNGSNGFVSLTFSILEGINAIIEVDLLSKSYKLLISG
ELKILMLNSNHIQQKIDYIGFNSELQKNIPYSFVDSEGKENGFINGSTKEGLFVSELPDVVLISKVY
MDDSKPSFGYYSNNLKDVKVITKDNVNILTGYYLKDDIKISLSLTLQDEKTIKLNSVHLDESGVA
EILKFMNRKGNTNTSDSLMSFLESMNIKSIFVNFLQSNIKFILDANFIISGTTSIGQFEFICDENDNIQ
PYFIKFNTLETNYTLYVGNRQNMIVEPNYDLDDSGDISSTVINFSQKYLYGIDSCVNKVVISPNIYT
DEINITPVYETNNTYPEVIVLDANYINEKINVNINDLSIRYVWSNDGNDFILMSTSEENKVSQVKIR
FVNVFKDKTLANKLSFNFSDKQDVPVSEIILSFTPSYYEDGLIGYDLGLVSLYNEKFYINNFGMM
VSGLIYINDSLYYFKPPVNN-LITGFVTVGDDKYYFNPINGGAASIGETIIDDKNYYFNQSGVLQTG
VFSTEDGFKYFAPANTLDENLEGEAIDFTGKLIIDENIYYFDDNYRGAVEWKELDGEMHYFSPET
GKAFKGLNQIGDYKYYFNSDGVMQKGFVSINDNKHYFDDSGVMKVGYTEIDGKHFYFAENGE
MQIGVFNTEDGFKYFAHHNEDLGNEEGEEISYSGILNFNNKIYYFDDSFTAVVGWKDLEDGSKY
YFDEDTAEAYIGLSLINDGQYYFNDDGIMQVGFVTINDKVFYFSDSGIIESGVQNIDDNYFYIDDN
GIVQIGVFDTSDGYKYFAPANTVNDNIYGQAVEYSGLVRVGEDVYYFGETYTIETGWIYDMENE
SDKYYFNPETKKACKGINLIDDIKYYFDEKGIMRTGLISFENNNYYFNENGEMQFGYINIEDKMF
YFGEDGVMQIGVFNTPDGFKYFAHQNTLDENFEGESINYTGWLDLDEKRYYFTDEYIAATGSVII
DGEEYYFDPDTAQLVISE-HHHHHH

Figure 2A

MDEQQSQAVAPVYVGGMDEKTTGWRGGHVVEGLAGELEQLRARLEHHPQGQREPS-GA-AGH
LASDFAFSPPPGGGGDGPGGPEPGWVDPRTWLSFQGPPGGPGIGPGVGPGSEVWGIPPCPPPYEF
CGGMAYCGPQVGVGLVPQGGLETSQPEGEAGVGVESNSDGASPEPCTVTPGAVKLEKEKLEQN
PEESQDIKALQKELEQFAKLLKQKRITLGYTQADVGLTLGVLFGKVFSQTTICRFEALQLSFKNM
CKLRPLLQKWVEEADNNENLQEICKAETLVQARKRKRTSIENRVRGNLENLFLQCPKPTLQQISH
IAQQLGLEKDVVRVWFCNRRQKGKRSSSDYAQREDFEAAGSPFSGGPVSFPLAPGPHFGTPGYG
SPHFTALYSSVPFPEGEAFPPVSVTTLGSPMHSN-AA-YAAAYQDLLMFKEGSMNIHLIEADLRNF
EISKTNISQSTEQEMASLWSFDDARAKAQFEEYKRNYFEGSL-GEDDNLDFSQNIVVDKEYLLEKI
SSLARSSERGYIHYIVQLQGDKISYEAACNLFAKTPYDSVLFQKNIEDSEIAYYYNPGDGEIQEIDK
YKIPSIISDRPKIKLTFIGHGKDEFNTDIFAGFDVDSLSTEIEAAIDLAKEDISPKSIEINLLGCNMFSY
SINVEETYPGKLLLKVKDKISELMPSISQDSIIVSANQYEVRINSEGRRELLDHSGEWINKEES-IIK
DISSKEYISFNPKENKITVKSKNLPELSTLLQEIRNNSNSSDIELEEKVMLTECEINVISNIDTQIVEE
RIEEAKNLTSDSINYIKDEFKLIESISDALCDLKQQNELEDSHFISFEDISETDEGFSIRFINKETGESI
FVETEKTIFSEYANHITEEISKIKGTIFDTVNGKLVKKVNLDTTHE-VNTLNAAFFIQSLIEYNSSKE
SLSNLSVAMKVQVYAQLFSTGLNTITDAAKVVELVSTALDETIDLLPTLSEGLPIIATIIDGVSLGA
AIKELSETSDPLLRQEIEAKIGIMAVNLTTATTAIITSSLGIASGFSILLVPLAGISAGIPSLVNNELVL
RDKATKVVDYFKHVS-LVETEGVFTLLDDKIMMPQDDLVISEIDFNNNSIVLGKCEIWRMEGGSG
HTVTDDIDHFFSAPSITYREPHLSIYDVLEVQKEELDLSKDLMVLPNAPNRVFAWETGWTPGLRS
LENDGTKLLDRIRDNYEGEFYWRYFAFIADALITTLKPRYEDTNIRINLDSNTRSFIVPIITTEYIRE
KLSYSFYGSGGTYALSLSQYNMGINIELSESDVWIIDVDNVVRDVTIESDKIKKGDLIEGILSTLSIE
ENKIILNSHEINFSGEVNGSNGFVSLTFSILEGINAIIEVDLLSKSYKLLISGELKILMLNSNHIQQKI
DYIGFNSELQKNIPYSFVDSEGKENGFINGSTKEGLFVSELPDVVLISKVYMDDSKPSFGYYSNNL
KDVKVITKDNVNILTGYYLKDDIKISLSLTLQDEKTIKLNSVHLDESGVAEILKFMNRKGNTNTS
DSLMSFLESMNIKSIFVNFLQSNIKFILDANFIISGTTSIGQFEFICDENDNIQPYFIKFNTLETNYTLY
VGNRQNMIVEPNYDLDDSGDISSTVINFSQKYLYGIDSCVNKVVISPNIYTDEINITPVYETNNTYP
EVIVLDANYINEKINVNINDLSIRYVWSNDGNDFILMSTSEENKVSQVKIRFVNVFKDKTLANKLS
FNFSDKQDVPVSEIILSFTPSYYEDGLIGYDLGLVSLYNEKFYINNFGMMVSGLIYINDSLYYFKPP
VNN-LITGFVTVGDDKYYFNPINGGAASIGETIIDDKNYYFNQSGVLQTGVFSTEDGFKYFAPANT
LDENLEGEAIDFTGKLIIDENIYYFDDNYRGAVEWKELDGEMHYFSPETGKAFKGLNQIGDYKY
YFNSDGVMQKGFVSINDNKHYFDDSGVMKVGYTEIDGKHFYFAENGEMQIGVFNTEDGFKYFA
HHNEDLGNEEGEEISYSGILNFNNKIYYFDDSFTAVVGWKDLEDGSKYYFDEDTAEAYIGLSLIN
DGQYYFNDDGIMQVGFVTINDKVFYFSDSGIIESGVQNIDDNYFYIDDNGIVQIGVFDTSDGYKY
FAPANTVNDNIYGQAVEYSGLVRVGEDVYYFGETYTIETGWIYDMENESDKYYFNPETKKACK
GINLIDDIKYYFDEKGIMRTGLISFENNNYYFNENGEMQFGYINIEDKMFYGEDGVMQIGVFNT
PDGFKYFAHQNTLDENFEGESINYTGWLDLDEKRYYFTDEYIAATGSVIIDGEEYYFDPDTAQLV
ISE-HHHHHH

Figure 2B

MDEQQSQAVAPVYVGGMDEKTTGWRGGHVVEGLAGELEQLRARLEHHPQGQREPS-GA-AGH
LASDFAFSPPPGGGGDGPGGPEPGWVDPRTWLSFQGPPGGPGIGPGVGPGSEVWGIPPCPPPYEF
CGGMAYCGPQVGVGLVPQGGLETSQPEGEAGVGVESNSDGASPEPCTVTPGAVKLEKEKLEQN
PEESQDIKALQKELEQFAKLLKQKRITLGYTQADVGLTLGVLFGKVFSQTTICRFEALQLSFKNM
CKLRPLLQKWVEEADNNENLQEICKAETLVQARKRKRTSIENRVRGNLENLFLQCPKPTLQQISH
IAQQLGLEKDVVRVWFCNRRQKGKRSSSDYAQREDFEAAGSPFSGGPVSFPLAPGPHFGTPGYG
SPHFTALYSSVPFPEGEAFPPVSVTTLGSPMHSN-AAA-SLISKEELIKLAYSIRPRENEYKTILTNLD
EYNKLTTNNNENKYLQLKKLNESIDVFMNKYKTSSRNRALSNLKKDILKEVILIKNSNTSPVEKN
LHFVWIGGEVSDIALEYIKQWADINAEYNIKLWYDSEAFLVNTLKKAIVESSTTEALQLLEEEIQN
PQFDNMKFYKKRMEFIYDRQKRFINYYKSQINKPTVPTIDDIIKSHLVSEYNRDETVLESYRTNSL
RKINSNHGIDIRANSLFTEQELLNIYSQELLNRGNLAAASDIVRLLALKNFGGVYLAVAMLPGIHS
DLFKTISRPSSIGLDRWEMIKLEAIMKYKKYINNYTSENFDKLDQQLKDNFKLIIESKSEKSEIFSK
LENLNVSDLEIKIAFALGSVINQALISKQGSYLTNLVIEQVKNRYQFLNQHLNPAIESDNNFTDTT
KIFHDSLFNSATAENSMFLTKIAPYLQVGFMPEARSTISLSGPGAYASAYYDFINLQENTIEKTLK
ASDLIEFKFPENNLSQLTEQEINSLWSFDQASAKYQFEKYVRDYTGGS-LSEDNGVDFNKNTALD
KNYLLNNKIPSNNVEEAGSKNYVHYIIQLQGDDISYEATCNLFSKNPKNSIIIQRNMNESAKSYFL
SDDGESILELNKYRIPERLKNKEKVKVTFIGHGKDEFNTSEFARLSVDSLSNEISSFLDTIKLDISPK
NVEVNLLGCNMFSYDFNVEETYPGKLLLSIMDKITSTLPDVNKNSITIGANQYEVRINSEGRKELL
AHSGKWINKEEA-IMSDLSSKEYIFFDSIDNKLKAKSKNIPGLASISEDIKTLLLDASVSPDTKFILN
NLKLNIESSIGDYIYYEKLEPVKNIIHNSIDDLIDEFNLLENVSDELYELKKLNNLDEKYLISFEDIS
KNNSTYSVRFINKSNGESVYVETEKEIFSKYSEHITKEISTIKNSIITDVNGNLLDNIQLDHTSQ-VN
TLNAAFFIQSLIDYSSNKDVLNDLSTSVKVQLYAQLFSTGLNTIYDSIQLVNLISNAVNDTINVLPT
ITEGIPIVSTILDGINLGAAIKELLDEHDPLLKKELEAKVGVLAINMSLSIAATVASIVGIGAEVTIFL
LPIAGISAGIPSLVNNELILHDKATSVVNYFNHLS-ESKKYGPLKTEDDKILVPIDDLVISEIDFNNN
SIKLGTCNILAMEGGSGHTVTGNIDHFFSSPSISSHIPSLSIYSAIGIETENLDFSKKIMMLPNAPSRV
FWWETGAVPGLRSLENDGTRLLDSIRDLYPGKFYWRFYAFFDYAITTLKPVYEDTNIKIKLDKDT
RNFIMPTITTNEIRNKLSYSFDGAGGTYSLLLSSYPISTNINLSKDDLWIFNIDNEVREISIENGTIKK
GKLIKDVLSKIDINKNKLIIGNQTIDFSGDIDNKDRYIFLTCELDDKISLIIEINLVAKSYSLLLSGDK
NYLISNLSNTIEKINTLGLDSKNIAYNYTDESNNKYFGAISKTSQKSIIHYKKDSKNILEFYNDSTLE
FNSKDFIAEDINVFMKDDINTITGKYYVDNNTDKSIDFSISLVSKNQVKVNGLYLNESVYSSYLDF
VKNSDGHHNTSNFMNLFLDNISFWKLFGFENINFVIDKYFTLVGKTNLGYVEFICDNNKNIDIYF
GEWKTSSSKSTIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNKKILQKIRIKGIL
SNTQSFNKMSIDFKDIKKLSLGYIMSNFKSFNSENELDRDHLGFKIIDNKTYYYDEDSKLVKGLIN
INNSLFYFDPIEFN-LVTGWQTINGKKYYFDINTGAALTSYKIINGKHFYFNNDGVMQLGVFKGPD
GFEYFAPANTQNNNIEGQAIVYQSKFLTLNGKKYYFDNNSKAVTGWRIINNEKYYFNPNNAIAA
VGLQVIDNNKYYFNPDTAIISKGWQTVNGSRYYFDTDTAIAFNGYKTIDGKHFYFDSDCVVKIG
VFSTSNGFEYFAPANTYNNNIEGQAIVYQSKFLTLNGKKYYFDNNSKAVTGLQTIDSKKYYFNT
NTAEAATGWQTIDGKKYYFNTNTAEAATGWQTIDGKKYYFNTNTAIASTGYTIINGKHFYFNTD
GIMQIGVFKGPNGFEYFAPANTDANNIEGQAILYQNEFLTLNGKKYYFGSDSKAVTGWRIINNKK
YYFNPNNAIAAIHLCTINNDKYYFSYDGILQNGYITIERNNFYFDANNESKMVTGVFKGPNGFEY
FAPANTHNNNIEGQAIVYQNKFLTLNGKKYYFDNDSKAVTGWQTIDGKKYYFNLNTAEAATG
WQTIDGKKYYFNLNTAEAATGWQTIDGKKYYFNTNTFIASTGYTSINGKHFYFNTDGIMQIGVF
KGPNGFEYFAPANTDANNIEGQAILYQNKFLTLNGKKYYFGSDSKAVTGLRTIDGKKYYFNTNT
AVAVTGWQTINGKKYYFNTNTSIASTGYTIISGKHFYFNTDGIMQIGVFKGPDGFEYFAPANTDA
NNIEGQAIRYQNRFLYLHDNIYYFGNNSKAATGWVTIDGNRYYFEPNTAMGANGYKTIDNKNF
YFRNGLPQIGVFKGSNGFEYFAPANTDANNIEGQAIRYQNRFLHLLGKIYYFGNNSKAVTGWQTI
NGKVYYFMPDTAMAAAGGLFEIDGVIYFFGVDGVKAPGIYG-HHHHHH

Figure 2C

MDEQQSQAVAPVYVGGMDEKTTGWRGGHVVEGLAGELEQLRARLEHHPQGQREPS-GA-AGH
LASDFAFSPPPGGGGDGPGGPEPGWVDPRTWLSFQGPPGGPGIGPGVGPGSEVWGIPPCPPPYEF
CGGMAYCGPQVGVGLVPQGGLETSQPEGEAGVGVESNSDGASPEPCTVTPGAVKLEKEKLEQN
PEESQDIKALQKELEQFAKLLKQKRITLGYTQADVGLTLGVLFGKVFSQTTICRFEALQLSFKNM
CKLRPLLQKWVEEADNNENLQEICKAETLVQARKRKRTSIENRVRGNLENLFLQCPKPTLQQISH
IAQQLGLEKDVVRVWFCNRRQKGKRSSSDYAQREDFEAAGSPFSGGPVSFPLAPGPHFGTPGYG
SPHFTALYSSVPFPEGEAFPPVSVTTLGSPMHSN-AA-ASAYYDFINLQENTIEKTLKASDLIEFKFP
ENNLSQLTEQEINSLWSFDQASAKYQFEKYVRDYTGGS-LSEDNGVDFNKNTALDKNYLLNNKI
PSNNVEEAGSKNYVHYIIQLQGDDISYEATCNLFSKNPKNSIIIQRNMNESAKSYFLSDDGESILEL
NKYRIPERLKNKEKVKVTFIGHGKDEFNTSEFARLSVDSLSNEISSFLDTIKLDISPKNVEVNLLGC
NMFSYDFNVEETYPGKLLLSIMDKITSTLPDVNKNSITIGANQYEVRINSEGRKELLAHSGKWINK
EEA-IMSDLSSKEYIFFDSIDNKLKAKSKNIPGLASISEDIKTLLLDASVSPDTKFILNNLKLNIESSIG
DYIYYEKLEPVKNIIHNSIDDLIDEFNLLENVSDELYELKKLNNLDEKYLISFEDISKNNSTYSVRFI
NKSNGESVYVETEKEIFSKYSEHITKEISTIKNSIITDVNGNLLDNIQLDHTSQ-VNTLNAAFFIQSLI
DYSSNKDVLNDLSTSVKVQLYAQLFSTGLNTIYDSIQLVNLISNAVNDTINVLPTITEGIPIVSTILD
GINLGAAIKELLDEHDPLLKKELEAKVGVLAINMSLSIAATVASIVGIGAEVTIFLLPIAGISAGIPS
LVNNELILHDKATSVVNYFNHLS-ESKKYGPLKTEDDKILVPIDDLVISEIDFNNNSIKLGTCNILA
MEGGSGHTVTGNIDHFFSSPSISSHIPSLSIYSAIGIETENLDFSKKIMMLPNAPSRVFWWETGAVP
GLRSLENDGTRLLDSIRDLYPGKFYWRFYAFFDYAITTLKPVYEDTNIKIKLDKDTRNFIMPTITT
NEIRNKLSYSFDGAGGTYSLLLSSYPISTNINLSKDDLWIFNIDNEVREISIENGTIKKGKLIKDVLS
KIDINKNKLIIGNQTIDFSGDIDNKDRYIFLTCELDDKISLIIEINLVAKSYSLLLSGDKNYLISNLSN
TIEKINTLGLDSKNIAYNYTDESNNKYFGAISKTSQKSIIHYKKDSKNILEFYNDSTLEFNSKDFIAE
DINVFMKDDINTITGKYYVDNNTDKSIDFSISLVSKNQVKVNGLYLNESVYSSYLDFVKNSDGHH
NTSNFMNLFLDNISFWKLFGFENINFVIDKYFTLVGKTNLGYVEFICDNNKNIDIYFGEWKTSSSK
STIFSGNGRNVVVEPIYNPDTGEDISTSLDFSYEPLYGIDRYINKVLIAPDLYTSLININTNYYSNEY
YPEIIVLNPNTFHKKVNINLDSSSFEYKWSTEGSDFILVRYLEESNKKILQKIRIKGILSNTQSFNKM
SIDFKDIKKLSLGYIMSNFKSFNSENELDRDHLGFKIIDNKTYYYDEDSKLVKGLININNSLFYFDP
IEFN-LVTGWQTINGKKYYFDINTGAALTSYKIINGKHFYFNNDGVMQLGVFKGPDGFEYFAPAN
TQNNNIEGQAIVYQSKFLTLNGKKYYFDNNSKAVTGWRIINNEKYYFNPNNAIAAVGLQVIDNN
KYYFNPDTAIISKGWQTVNGSRYYFDTDTAIAFNGYKTIDGKHFYFDSDCVVKIGVFSTSNGFEY
FAPANTYNNNIEGQAIVYQSKFLTLNGKKYYFDNNSKAVTGLQTIDSKKYYFNTNTAEAATGW
QTIDGKKYYFNTNTAEAATGWQTIDGKKYYFNTNTAIASTGYTIINGKHFYFNTDGIMQIGVFKG
PNGFEYFAPANTDANNIEGQAILYQNEFLTLNGKKYYFGSDSKAVTGWRIINNKKYYFNPNNAIA
AIHLCTINNDKYYFSYDGILQNGYITIERNNFYFDANNESKMVTGVFKGPNGFEYFAPANTHNNN
IEGQAIVYQNKFLTLNGKKYYFDNDSKAVTGWQTIDGKKYYFNLNTAEAATGWQTIDGKKYYF
NLNTAEAATGWQTIDGKKYYFNTNTFIASTGYTSINGKHFYFNTDGIMQIGVFKGPNGFEYFAPA
NTDANNIEGQAILYQNKFLTLNGKKYYFGSDSKAVTGLRTIDGKKYYFNTNTAVAVTGWQTIN
GKKYYFNTNTSIASTGYTIISGKHFYFNTDGIMQIGVFKGPDGFEYFAPANTDANNIEGQAIRYQN
RFLYLHDNIYYFGNNSKAATGWVTIDGNRYYFEPNTAMGANGYKTIDNKNFYFRNGLPQIGVFK
GSNGFEYFAPANTDANNIEGQAIRYQNRFLHLLGKIYYFGNNSKAVTGWQTINGKVYYFMPDTA
MAAAGGLFEIDGVIYFFGVDGVKAPGIYG-HHHHHH

Figure 2D

MDEQQSQAVAPVYVGGMDEKTTGWRGGHVVEGLAGELEQLRARLEHHPQGQREPS-GA-YNM
METELKPPGPQQTSGGGGGNSTAAAAGGNQKNSPDRVKRPMNAFMVWSRGQRRKMAQENPK
MHNSEISKRLGAEWKLLSETEKRPFIDEAKRLRALHMKEHPDYKYRPRRKTKTLMKKDKYTLP
GGLLAPGGNSMASGVGVGAGLGAGVNQRMDSYAHMNGWSNGSYSMMQDQLGYPQHPGLNA
HGAAQMQPMHRYDVSALQYNSMTSSQTYMNGSPTYSMSYSQQGTPGMALGSMGSVVKSEASS
SPPVVTSSSHSRAPCQAGDLRDMISMYLPGAEVPEPAAPSRLHMSQHYQSGPVPGTAINGTLPLS
HM-AAA-SLVNRKQLEKMANVRFRTQEDEYVAILDALEEYHNMSENTVVEKYLKLKDINSLTDI
YIDTYKKSGRNKALKKFKEYLVTEVLELKNNNLTPVEKNLHFVWIGGQINDTAINYINQWKDVN
SDYNVNVFYDSNAFLINTLKKTVVESAINDTLESFRENLNDPRFDYNKFFRKRMEIIYDKQKNFIN
YYKAQREENPELIIDDIVKTYLSNEYSKEIDELNTYIEESLNKITQNSGNDVRNFEEFKNGESFNLY
EQELVERWNLAAASDILRISALKEIGGMYLAVAMLPGIQPDLFESIEKPSSVTVDFWEMTKLEAI
MKYKEYIPEYTSEHFDMLDEEVQSSFESVLASKSDKSEIFSSLGDMEASPLEVKIAFNSKGIINQGL
ISVKDSYCSNLIVKQIENRYKILNNSLNPAISEDNDFNTTTNTFIDSIMAEANADNGRFMMELGKY
LRVGFFPDVKTTINLSGPEAYAAAYQDLLMFKEGSMNIHLIEADLRNFEISKTNISQSTEQEMASL
WSFDDARAKAQFEEYKRNYFEGSL-GEDDNLDFSQNIVVDKEYLLEKISSLARSSERGYIHYIVQL
QGDKISYEAACNLFAKTPYDSVLFQKNIEDSEIAYYYNPGDGEIQEIDKYKIPSIISDRPKIKLTFIG
HGKDEFNTDIFAGFDVDSLSTEIEAAIDLAKEDISPKSIEINLLGCNMFSYSINVEETYPGKLLLKV
KDKISELMPSISQDSIIVSANQYEVRINSEGRRELLDHSGEWINKEES-IIKDISSKEYISFNPKENKIT
VKSKNLPELSTLLQEIRNNSNSSDIELEEKVMLTECEINVISNIDTQIVEERIEEAKNLTSDSINYIKD
EFKLIESISDALCDLKQQNELEDSHFISFEDISETDEGFSIRFINKETGESIFVETEKTIFSEYANHITE
EISKIKGTIFDTVNGKLVKKVNLDTTHE-VNTLNAAFFIQSLIEYNSSKESLSNLSVAMKVQVYAQ
LFSTGLNTITDAAKVVELVSTALDETIDLLPTLSEGLPIIATIIDGVSLGAAIKELSETSDPLLRQEIE
AKIGIMAVNLTTATTAIITSSLGIASGFSILLVPLAGISAGIPSLVNNELVLRDKATKVVDYFKHVS-
LVETEGVFTLLDDKIMMPQDDLVISEIDFNNNSIVLGKCEIWRMEGGSGHTVTDDIDHFFSAPSIT
YREPHLSIYDVLEVQKEELDLSKDLMVLPNAPNRVFAWETGWTPGLRSLENDGTKLLDRIRDNY
EGEFYWRYFAFIADALITTLKPRYEDTNIRINLDSNTRSFIVPIITTEYIREKLSYSFYGSGGTYALSL
SQYNMGINIELSESDVWIIDVDNVVRDVTIESDKIKKGDLIEGILSTLSIEEENKIILNSHEINFSGEVN
GSNGFVSLTFSILEGINAIIEVDLLSKSYKLLISGELKILMLNSNHIQQKIDYIGFNSELQKNIPYSFV
DSEGKENGFINGSTKEGLFVSELPDVVLISKVYMDDSKPSFGYYSNNLKDVKVITKDNVNILTGY
YLKDDIKISLSLTLQDEKTIKLNSVHLDESGVAEILKFMNRKGNTNTSDSLMSFLESMNIKSIFVNF
LQSNIKFILDANFIISGTTSIGQFEFICDENDNIQPYFIKFNTLETNYTLYVGNRQNMIVEPNYDLDD
SGDISSTVINFSQKYLYGIDSCVNKVVISPNIYTDEINITPVYETNNTYPEVIVLDANYINEKINVNI
NDLSIRYVWSNDGNDFILMSTSEENKVSQVKIRFVNVFKDKTLANKLSFNFSDKQDVPVSEIILSF
TPSYYEDGLIGYDLGLVSLYNEKFYINNFGMMVSGLIYINDSLYYFKPPVNN-LITGFVTGDDKY
YFNPINGGAASIGETIIDDKNYYFNQSGVLQTGVFSTEDGFKYFAPANTLDENLEGEAIDFTGKLII
DENIYYFDDNYRGAVEWKELDGEMHYFSPETGKAFKGLNQIGDYKYYFNSDGVMQKGFVSIND
NKHYFDDSGVMKVGYTEIDGKHFYFAENGEMQIGVFNTEDGFKYFAHHNEDLGNEEGEEISYS
GILNFNNKIYYFDDSFTAVVGWKDLEDGSKYYFDEDTAEAYIGLSLINDGQYYFNDDGIMQVGF
VTINDKVFYFSDSGIIESGVQNIDDNYFYIDDNGIVQIGVFDTSDGYKYFAPANTVNDNIYGQAVE
YSGLVRVGEDVYYFGETYTIETGWIYDMENESDKYYFNPETKKACKGINLIDDIKYYFDEKGIM
RTGLISFENNNYYFNENGEMQFGYINIEDKMFYGEDGVMQIGVFNTPDGFKYFAHQNTLDENF
EGESINYTGWLDLDEKRYYFTDEYIAATGSVIIDGEEYYFDPDTAQLVISE-HHHHHH

Figure 3A

MDEQQSQAVAPVYVGGMDEKTTGWRGGHVVEGLAGELEQLRARLEHHPQGQREPS-GA-YNM
METELKPPGPQQTSGGGGGNSTAAAAGGNQKNSPDRVKRPMNAFMVWSRGQRRKMAQENPK
MHNSEISKRLGAEWKLLSETEKRPFIDEAKRLRALHMKEHPDYKYRPRRKTKTLMKKDKYTLP
GGLLAPGGNSMASGVGVGAGLGAGVNQRMDSYAHMNGWSNGSYSMMQDQLGYPQHPGLNA
HGAAQMQPMHRYDVSALQYNSMTSSQTYMNGSPTYSMSYSQQGTPGMALGSMGSVVKSEASS
SPPVVTSSSHSRAPCQAGDLRDMISMYLPGAEVPEPAAPSRLHMSQHYQSGPVPGTAINGTLPLS
HM-AA-YAAAYQDLLMFKEGSMNIIHLIEADLRNFEISKTNISQSTEQEMASLWSFDDARAKAQFE
EYKRNYFEGSL-GEDDNLDFSQNIVVDKEYLLEKISSLARSSERGYIHYIVQLQGDKISYEAACNL
FAKTPYDSVLFQKNIEDSEIAYYYNPGDGEIQEIDKYKIPSIISDRPKIKLTFIGHGKDEFNTDIFAGF
DVDSLSTEIEAAIDLAKEDISPKSIEINLLGCNMFSYSINVEETYPGKLLLKVKDKISELMPSISQDSI
IVSANQYEVRINSEGRRELLDHSGEWINKEES-IIKDISSKEYISFNPKENKITVKSKNLPELSTLLQE
IRNNSNSSDIELEEKVMLTECEINVISNIDTQIVEERIEEAKNLTSDSINYIKDEFKLIESISDALCDLK
QQNELEDSHFISFEDISETDEGFSIRFINKETGESIFVETEKTIFSEYANHITEEISKIKGTIFDTVNGK
LVKKVNLDTTHE-VNTLNAAFFIQSLIEYNSSKESLSNLSVAMKVQVYAQLFSTGLNTITDAAKV
VELVSTALDETIDLLPTLSEGLPIIATIIDGVSLGAAIKELSETSDPLLRQEIEAKIGIMAVNLTTATT
AIITSSLGIASGFSILLVPLAGISAGIPSLVNNELVLRDKATKVVDYFKHVS-LVETEGVFTLLDDKI
MMPQDDLVISEIDFNNNSIVLGKCEIWRMEGGSGHTVTDDIDHFFSAPSITYREPHLSIYDVLEVQ
KEELDLSKDLMVLPNAPNRVFAWETGWTPGLRSLENDGTKLLDRIRDNYEGEFYWRYFAFIAD
ALITTLKPRYEDTNIRINLDSNTRSFIVPIITTEYIREKLSYSFYGSGGTYALSLSQYNMGINIELSES
DVWIIDVDNVVRDVTIESDKIKKGDLIEGILSTLSIEEENKIILNSHEINFSGEVNGSNGFVSLTFSILE
GINAIIEVDLLSKSYKLLISGELKILMLNSNHIQQKIDYIGFNSELQKNIPYSFVDSEGKENGFINGS
TKEGLFVSELPDVVLISKVYMDDSKPSFGYYSNNLKDVKVITKDNVNILTGYYLKDDIKISLSLTL
QDEKTIKLNSVHLDESGVAEILKFMNRKGNTNTSDSLMSFLESMNIKSIFVNFLQSNIKFILDANFI
ISGTTSIGQFEFICDENDNIQPYFIKFNTLETNYTLYVGNRQNMIVEPNYDLDDSGDISSTVINFSQK
YLYGIDSCVNKVVISPNIYTDEINITPVYETNNTYPEVIVLDANYINEKINVNINDLSIRYVWSNDG
NDFILMSTSEENKVSQVKIRFVNVFKDKTLANKLSFNFSDKQDVPVSEIILSFTPSYYEDGLIGYDL
GLVSLYNEKFYINNFGMMVSGLIYINDSLYYFKPPVNN-LITGFVTVGDDKYYFNPINGGAASIGE
TIIDDKNYYFNQSGVLQTGVFSTEDGFKYFAPANTLDENLEGEAIDFTGKLIIDENIYYFDDNYRG
AVEWKELDGEMHYFSPETGKAFKGLNQIGDYKYYFNSDGVMQKGFVSINDNKHYFDDSGVMK
VGYTEIDGKHFYFAENGEMQIGVFNTEDGFKYFAHHNEDLGNEEGEEISYSGILNFNNKIYYFDD
SFTAVVGWKDLEDGSKYYFDEDTAEAYIGLSLINDGQYYFNDDGIMQVGFVTINDKVFYFSDSG
IIESGVQNIDDNYFYIDDNGIVQIGVFDTSDGYKYFAPANTVNDNIYGQAVEYSGLVRVGEDVYY
FGETYTIETGWIYDMENESDKYYFNPETKKACKGINLIDDIKYYFDEKGIMRTGLISFENNNYYFN
ENGEMQFGYINIEDKMFYFGEDGVMQIGVFNTPDGFKYFAHQNTLDENFEGESINYTGWLDLDE
KRYYFTDEYIAATGSVIIDGEEYYFDPDTAQLVISE-HHHHHH

Figure 3B

MDEQQSQAVAPVYVGGMDEKTTGWRGGHVVEGLAGELEQLRARLEHHPQGQREPS-GA-YNM
METELKPPGPQQTSGGGGGNSTAAAAGGNQKNSPDRVKRPMNAFMVWSRGQRRKMAQENPK
MHNSEISKRLGAEWKLLSETEKRPFIDEAKRLRALHMKEHPDYKYRPRRKTKTLMKKDKYTLP
GGLLAPGGNSMASGVGVGAGLGAGVNQRMDSYAHMNGWSNGSYSMMQDQLGYPQHPGLNA
HGAAQMQPMHRYDVSALQYNSMTSSQTYMNGSPTYSMSYSQQGTPGMALGSMGSVVKSEASS
SPPVVTSSSHSRAPCQAGDLRDMISMYLPGAEVPEPAAPSRLHMSQHYQSGPVPGTAINGTLPLS
HM-AAA-SLISKEELIKLAYSIRPRENEYKTILTNLDEYNKLTTNNNENKYLQLKKLNESIDVFMN
KYKTSSRNRALSNLKKDILKEVILIKNSNTSPVEKNLHFVWIGGEVSDIALEYIKQWADINAEYNI
KLWYDSEAFLVNTLKKAIVESSTTEALQLLEEEIQNPQFDNMKFYKKRMEFIYDRQKRFINYYKS
QINKPTVPTIDDIIKSHLVSEYNRDETVLESYRTNSLRKINSNHGIDIRANSLFTEQELLNIYSQELL
NRGNLAAASDIVRLLALKNFGGVYLAVAMLPGIHSDLFKTISRPSSIGLDRWEMIKLEAIMKYKK
YINNYTSENFDKLDQQLKDNFKLIIESKSEKSEIFSKLENLNVSDLEIKIAFALGSVINQALISKQGS
YLTNLVIEQVKNRYQFLNQHLNPAIESDNNFTDTTKIFHDSLFNSATAENSMFLTKIAPYLQVGF
MPEARSTISLSGPGAYASAYYDFINLQENTIEKTLKASDLIEFKFPENNLSQLTEQEINSLWSFDQA
SAKYQFEKYVRDYTGGS-LSEDNGVDFNKNTALDKNYLLNNKIPSNNVEEAGSKNYVHYIIQLQ
GDDISYEATCNLFSKNPKNSIIIQRNMNESAKSYFLSDDGESILELNKYRIPERLKNKEKVKVTFIG
HGKDEFNTSEFARLSVDSLSNEISSFLDTIKLDISPKNVEVNLLGCNMFSYDFNVEETYPGKLLLSI
MDKITSTLPDVNKNSITIGANQYEVRINSEGRKELLAHSGKWINKEEA-IMSDLSSKEYIFFDSIDN
KLKAKSKNIPGLASISEDIKTLLLDASVSPDTKFILNNLKLNIESSIGDYIYYEKLEPVKNIIHNSIDD
LIDEFNLLENVSDELYELKKLNNLDEKYLISFEDISKNNSTYSVRFINKSNGESVYVETEKEIFSKY
SEHITKEISTIKNSIITDVNGNLLDNIQLDHTSQ-VNTLNAAFFIQSLIDYSSNKDVLNDLSTSVKVQ
LYAQLFSTGLNTIYDSIQLVNLISNAVNDTINVLPTITEGIPIVSTILDGINLGAAIKELLDEHDPLLK
KELEAKVGVLAINMSLSIAATVASIVGIGAEVTIFLLPIAGISAGIPSLVNNELILHDKATSVVNYFN
HLS-ESKKYGPLKTEDDKILVPIDDLVISEIDFNNNSIKLGTCNILAMEGGSGHTVTGNIDHFFSSPS
ISSHIPSLSIYSAIGIETENLDFSKKIMMLPNAPSRVFWWETGAVPGLRSLENDGTRLLDSIRDLYP
GKFYWRFYAFFDYAITTLKPVYEDTNIKIKLDKDTRNFIMPTITTNEIRNKLSYSFDGAGGTYSLL
LSSYPISTNINLSKDDLWIFNIDNEVREISIENGTIKKGKLIKDVLSKIDINKNKLIIGNQTIDFSGDID
NKDRYIFLTCELDDKISLIIEINLVAKSYSLLLSGDKNYLISNLSNTIEKINTLGLDSKNIAYNYTDE
SNNKYFGAISKTSQKSIIHYKKDSKNILEFYNDSTLEFNSKDFIAEDINVFMKDDINTITGKYYVDN
NTDKSIDFSISLVSKNQVKVNGLYLNESVYSSYLDFVKNSDGHHNTSNFMNLFLDNISFWKLFGF
ENINFVIDKYFTLVGKTNLGYVEFICDNNKNIDIYFGEWKTSSSKSTIFSGNGRNVVVEPIYNPDT
GEDISTSLDFSYEPLYGIDRYINKVLIAPDLYTSLININTNYYSNEYYPEIIVLNPNTFHKKVNINLD
SSSFEYKWSTEGSDFILVRYLEESNKKILQKIRIKGILSNTQSFNKMSIDFKDIKKLSLGYIMSNFKS
FNSENELDRDHLGFKIIDNKTYYYDEDSKLVKGLININNSLFYFDPIEFN-LVTGWQTINGKKYYF
DINTGAALTSYKIINGKHFYFNNDGVMQLGVFKGPDGFEYFAPANTQNNNIEGQAIVYQSKFLTL
NGKKYYFDNNSKAVTGWRIINNEKYYFNPNNAIAAVGLQVIDNNKYYFNPDTAIISKGWQTVN
GSRYYFDTDTAIAFNGYKTIDGKHFYFDSDCVVKIGVFSTSNGFEYFAPANTYNNNIEGQAIVYQ
SKFLTLNGKKYYFDNNSKAVTGLQTIDSKKYYFNTNTAEAATGWQTIDGKKYYFNTNTAEAAT
GWQTIDGKKYYFNTNTAIASTGYTIINGKHFYFNTDGIMQIGVFKGPNGFEYFAPANTDANNIEG
QAILYQNEFLTLNGKKYYFGSDSKAVTGWRIINNKKYYFNPNNAIAAIHLCTINNDKYYFSYDGI
LQNGYITIERNNFYFDANNESKMVTGVFKGPNGFEYFAPANTHNNNIEGQAIVYQNKFLTLNGK
KYYFDNDSKAVTGWQTIDGKKYYFNLNTAEAATGWQTIDGKKYYFNLNTAEAATGWQTIDGK
KYYFNTNTFIASTGYTSINGKHFYFNTDGIMQIGVFKGPNGFEYFAPANTDANNIEGQAILYQNKF
LTLNGKKYYFGSDSKAVTGLRTIDGKKYYFNTNTAVAVTGWQTINGKKYYFNTNTSIASTGYTII
SGKHFYFNTDGIMQIGVFKGPDGFEYFAPANTDANNIEGQAIRYQNRFLYLHDNIYYFGNNSKA
ATGWVTIDGNRYYFEPNTAMGANGYKTIDNKNFYFRNGLPQIGVFKGSNGFEYFAPANTDANNI
EGQAIRYQNRFLHLLGKIYYFGNNSKAVTGWQTINGKVYYFMPDTAMAAAGGLFEIDGVIYFFG
VDGVKAPGIYG-HHHHHH

Figure 3C

MDEQQSQAVAPVYVGGMDEKTTGWRGGHVVEGLAGELEQLRARLEHHPQGQREPS-GA-YNM
METELKPPGPQQTSGGGGGNSTAAAAGGNQKNSPDRVKRPMNAFMVWSRGQRRKMAQENPK
MHNSEISKRLGAEWKLLSETEKRPFIDEAKRLRALHMKEHPDYKYRPRRKTKTLMKKDKYTLP
GGLLAPGGNSMASGVGVGAGLGAGVNQRMDSYAHMNGWSNGSYSMMQDQLGYPQHPGLNA
HGAAQMQPMHRYDVSALQYNSMTSSQTYMNGSPTYSMSYSQQGTPGMALGSMGSVVKSEASS
SPPVVTSSSHSRAPCQAGDLRDMISMYLPGAEVPEPAAPSRLHMSQHYQSGPVPGTAINGTLPLS
HM-AA-ASAYYDFINLQENTIEKTLKASDLIEFKFPENNLSQLTEQEINSLWSFDQASAKYQFEKY
VRDYTGGS-LSEDNGVDFNKNTALDKNYLLNNKIPSNNVEEAGSKNYVHYIIQLQGDDISYEATC
NLFSKNPKNSIIIQRNMNESAKSYFLSDDGESILELNKYRIPERLKNKEKVKVTFIGHGKDEFNTSE
FARLSVDSLSNEISSFLDTIKLDISPKNVEVNLLGCNMFSYDFNVEETYPGKLLLSIMDKITSTLPD
VNKNSITIGANQYEVRINSEGRKELLAHSGKWINKEEA-IMSDLSSKEYIFFDSIDNKLKAKSKNIP
GLASISEDIKTLLLDASVSPDTKFILNNLKLNIESSIGDYIYYEKLEPVKNIIHNSIDDLIDEFNLLEN
VSDELYELKKLNNLDEKYLISFEDISKNNSTYSVRFINKSNGESVYVETEKEIFSKYSEHITKEISTI
KNSIITDVNGNLLDNIQLDHTSQ-VNTLNAAFFIQSLIDYSSNKDVLNDLSTSVKVQLYAQLFSTG
LNTIYDSIQLVNLISNAVNDTINVLPTITEGIPIVSTILDGINLGAAIKELLDEHDPLLKKELEAKVG
VLAINMSLSIAATVASIVGIGAEVTIFLLPIAGISAGIPSLVNNELILHDKATSVVNYFNHLS-ESKK
YGPLKTEDDKILVPIDDLVISEIDFNNNSIKLGTCNILAMEGGSGHTVTGNIDHFFSSPSISSHIPSLSI
YSAIGIETENLDFSKKIMMLPNAPSRVFWWETGAVPGLRSLENDGTRLLDSIRDLYPGKFYWRFY
AFFDYAITTLKPVYEDTNIKIKLDKDTRNFIMPTITTNEIRNKLSYSFDGAGGTYSLLLSSYPISTNI
NLSKDDLWIFNIDNEVREISIENGTIKKGKLIKDVLSKIDINKNKLIIGNQTIDFSGDIDNKDRYIFLT
CELDDKISLIIEINLVAKSYSLLLSGDKNYLISNLSNTIEKINTLGLDSKNIAYNYTDESNNKYFGAI
SKTSQKSIIHYKKDSKNILEFYNDSTLEFNSKDFIAEDINVFMKDDINTITGKYYVDNNTDKSIDFSI
SLVSKNQVKVNGLYLNESVYSSYLDFVKNSDGHHNTSNFMNLFLDNISFWKLFGFENINFVIDK
YFTLVGKTNLGYVEFICDNNKNIDIYFGEWKTSSSKSTIFSGNGRNVVVEPIYNPDTGEDISTSLDF
SYEPLYGIDRYINKVLIAPDLYTSLININTNYYSNEYYPEIIVLNPNTFHKKVNINLDSSSFEYKWST
EGSDFILVRYLEESNKKILQKIRIKGILSNTQSFNKMSIDFKDIKKLSLGYIMSNFKSFNSENELDRD
HLGFKIIDNKTYYYDEDSKLVKGLININNSLFYFDPIEFN-LVTGWQTINGKKYYFDINTGAALTS
YKIINGKHFYFNNDGVMQLGVFKGPDGFEYFAPANTQNNNIEGQAIVYQSKFLTLNGKKYYFDN
NSKAVTGWRIINNEKYYFNPNNAIAAVGLQVIDNNKYYFNPDTAIISKGWQTVNGSRYYFDTDT
AIAFNGYKTIDGKHFYFDSDCVVKIGVFSTSNGFEYFAPANTYNNNIEGQAIVYQSKFLTLNGKK
YYFDNNSKAVTGLQTIDSKKYYFNTNTAEAATGWQTIDGKKYYFNTNTAEAATGWQTIDGKKY
YFNTNTAIASTGYTIINGKHFYFNTDGIMQIGVFKGPNGFEYFAPANTDANNIEGQAILYQNEFLT
LNGKKYYFGSDSKAVTGWRIINNKKYYFNPNNAIAAIHLCTINNDKYYFSYDGILQNGYITIERN
NFYFDANNESKMVTGVFKGPNGFEYFAPANTHNNNIEGQAIVYQNKFLTLNGKKYYFDNDSKA
VTGWQTIDGKKYYFNLNTAEAATGWQTIDGKKYYFNLNTAEAATGWQTIDGKKYYFNTNTFIA
STGYTSINGKHFYFNTDGIMQIGVFKGPNGFEYFAPANTDANNIEGQAILYQNKFLTLNGKKYYF
GSDSKAVTGLRTIDGKKYYFNTNTAVAVTGWQTINGKKYYFNTNTSIASTGYTIISGKHFYFNTD
GIMQIGVFKGPDGFEYFAPANTDANNIEGQAIRYQNRFLYLHDNIYYFGNNSKAATGWVTIDGN
RYYFEPNTAMGANGYKTIDNKNFYFRNGLPQIGVFKGSNGFEYFAPANTDANNIEGQAIRYQNR
FLHLLGKIYYFGNNSKAVTGWQTINGKVYYFMPDTAMAAAGGLFEIDGVIYFFGVDGVKAPGIY
G-HHHHHH

Figure 3D

MDEQQSQAVAPVYVGGMDEKTTGWRGGHVVEGLAGELEQLRARLEHHPQGQREPS-MLVSKF
ENSVKNSNKNYFTINGLMGYYFENDFFNLNIISPTLDGNLTFSKEDINSILGNKIIKSARWIGLIKPSI
TGEYILSTNSPNCRVELNGEIFNLSLNTSNTVNLIQGNVYDIRIEQLMSENQLLKNYEGIKLYWET
SDIIKEIIPSEVLLKPNYSNTNEKSKFIPNNTLFSNAKLKANANRDTDRDGIPDEWEINGYTVMNQ
KAVAWDDKFAANGYKKYVSNPFKPCTANDPYTDFEKVSGQIDPSVSMVARDPMISAYPIVGVQ
MERLVVSKSETITGDSTKSMSKSTSHSSTNINTVGAEVSGSLQLAGGIFPVFSMSASANYSHTWQ
NTSTVDDTTGESFSQGLSINTAESAYINPNIRYYNTGTAPVYNVTPTTTIVIDKQSVATIKGQESLI
GDYLNPGGTYPIIGEPPMALNTMDQFSSRLIPINYNQLKSIDNGGTVMLSTSQFTGNFAKYNSNG
NLVTDGNNWGPYLGTIKSTTASLTLSLPDQTTQVAVVAPNFSDPEDKTPRLTLEQALVKAFRLE
KKNGKFYFHGMEISANQKIQVFLDRNTNVDFENQLKNTANKDIMNCIIKRNMNILVKVITFKENI
SSINIINDTNFGVESMTGLSKRIKGNDGIYRASTKSFSFKSKEIKYPEGFYRMRFVIQSYEPFTCNFK
LFNNLIYSNSFDIGYYDEFFYFYCNGSKSFFDISCDIINSINRLSGVFLIELDKLII-HHHHHH

Figure 4A

MDEQQSQAVAPVYVGGMDEKTTGWRGGHVVEGLAGELEQLRARLEHHPQGQREPS-GA-AGH
LASDFAFSPPPGGGGDGPGGPEPGWVDPRTWLSFQGPPGGPGIGPGVGPGSEVWGIPPCPPPYEFC
GGMAYCGPQVGVGLVPQGGLETSQPEGEAGVGVESNSDGASPEPCTVTPGAVKLEKEKLEQNP
EESQDIKALQKELEQFAKLLKQKRITLGYTQADVGLTLGVLFGKVFSQTTICRFEALQLSFKNMC
KLRPLLQKWVEEADNNENLQEICKAETLVQARKRKRTSIENRVRGNLENLFLQCPKPTLQQISHI
AQQLGLEKDVVRVWFCNRRQKGKRSSSDYAQREDFEAAGSPFSGGPVSFPLAPGPHFGTPGYGS
PHFTALYSSVPFPEGEAFPPVSVTTLGSPMHSN-AA-MPIIKEPIDFINKPESEAKKWGKEEEKRWF
TKLNNLEEVAVNQLKNKEYKTKIDNFSTDILFSSLTAIEIMKEDENRNLFDVERIREALLKNTLDR
DAIGYVNFTPKELGINFSIRDVELDRDISDETLDKVRQQIINQEYTKFSFISLGLNDNSINESVPVIV
KTRVPTTFDYGVLNDKEAVALLLNQGFSIIPESAIITTIKGKDYILIEGSLSQELDFYNKGSEAWGA
ENYGDYISKLSHEQLGALEGYLHSDYKAINSYLRNNRVPNNDELNKKIELISSALSVKPIPQTLIAY
RRVDGIPFDLPSDFSFDKKENGEIIADKQKLNEFIDKWTGKEIENLSFSSTSLKSTPSSFSKSRFIFRL
RLSEGAIGAFIYGFSGFQAAQAILLNKNSTFKIFRITPITSIINRVTKMTQVVIDAEGIQNKEI-HHHH
HH

Figure 4B

MDEQQSQAVAPVYVGGMDEKTTGWRGGHVVEGLAGELEQLRARLEHHPQGQREPS-GA-MPII
KEPIDFINKPESEAKKWGKEEEKRWFTKLNNLEEVAVNQLKNKEYKTKIDNFSTDILFSSLTAIEI
MKEDENRNLFDVERIREALLKNTLDRDAIGYVNFTPKELGINFSIRDVELDRDISDETLDKVRQQII
NQEYTKFSFISLGLNDNSINESVPVIVKTRVPTTFDYGVLNDK-GA-AGHLASDFAFSPPPGGGGD
GPGGPEPGWVDPRTWLSFQGPPGGPGIGPGVGPGSEVWGIPPCPPPYEFCGGMAYCGPQVGVGL
VPQGGLETSQPEGEAGVGVESNSDGASPEPCTVTPGAVKLEKEKLEQNPEESQDIKALQKELEQF
AKLLKQKRITLGYTQADVGLTLGVLFGKVFSQTTICRFEALQLSFKNMCKLRPLLQKWVEEADN
NENLQEICKAETLVQARKRKRTSIENRVRGNLENLFLQCPKPTLQQISHIAQQLGLEKDVVRVWF
CNRRQKGKRSSSDYAQREDFEAAGSPFSGGPVSFPLAPGPHFGTPGYGSPHFTALYSSVPFPEGEA
FPPVSVTTLGSPMHSN-AA-LLNKNSTFKIFRITPITSIINRVTKMTQVVIDAEGIQNKEI-HHHHHH

Figure 4C

MDEQQSQAVAPVYVGGMDEKTTGWRGGHVVEGLAGELEQLRARLEHHPQGQREPS-GA-YNM
METELKPPGPQQTSGGGGGNSTAAAAGGNQKNSPDRVKRPMNAFMVWSRGQRRKMAQENPK
MHNSEISKRLGAEWKLLSETEKRPFIDEAKRLRALHMKEHPDYKYRPRRKTKTLMKKDKYTLP
GGLLAPGGNSMASGVGVGAGLGAGVNQRMDSYAHMNGWSNGSYSMMQDQLGYPQHPGLNA
HGAAQMQPMHRYDVSALQYNSMTSSQTYMNGSPTYSMSYSQQGTPGMALGSMGSVVKSEASS
SPPVVTSSSHSRAPCQAGDLRDMISMYLPGAEVPEPAAPSRLHMSQHYQSGPVPGTAINGTLPLS
HM-AA-MPIIKEPIDFINKPESEAKKWGKEEEKRWFTKLNNLEEVAVNQLKNKEYKTKIDNFSTDI
LFSSLTAIEIMKEDENRNLFDVERIREALLKNTLDRDAIGYVNFTPKELGINFSIRDVELDRDISDET
LDKVRQQIINQEYTKFSFISLGLNDNSINESVPVIVKTRVPTTFDYGVLNDKEAVALLLNQGFSIIP
ESAIITTIKGKDYILIEGSLSQELDFYNKGSEAWGAENYGDYISKLSHEQLGALEGYLHSDYKAINS
YLRNNRVPNNDELNKKIELISSALSVKPIPQTLIAYRRVDGIPFDLPSDFSFDKKENGEIIADKQKL
NEFIDKWTGKEIENLSFSSTSLKSTPSSFSKSRFIFRLRLSEGAIGAFIYGFSGFQAAQAILLNKNSTF
KIFRITPITSIINRVTKMTQVVIDAEGIQNKEI-HHHHHH

Figure 4D

MDEQQSQAVAPVYVGGMDEKTTGWRGGHVVEGLAGELEQLRARLEHHPQGQREPS-GA-MPII
KEPIDFINKPESEAKKWGKEEEKRWFTKLNNLEEVAVNQLKNKEYKTKIDNFSTDILFSSLTAIEI
MKEDENRNLFDVERIREALLKNTLDRDAIGYVNFTPKELGINFSIRDVELDRDISDETLDKVRQQII
NQEYTKFSFISLGLNDNSINESVPVIVKTRVPTTFDYGVLNDK-GA-YNMMETELKPPGPQQTSGG
GGGNSTAAAAGGNQKNSPDRVKRPMNAFMVWSRGQRRKMAQENPKMHNSEISKRLGAEWKL
LSETEKRPFIDEAKRLRALHMKEHPDYKYRPRRKTKTLMKKDKYTLPGGLLAPGGNSMASGVG
VGAGLGAGVNQRMDSYAHMNGWSNGSYSMMQDQLGYPQHPGLNAHGAAQMQPMHRYDVS
ALQYNSMTSSQTYMNGSPTYSMSYSQQGTPGMALGSMGSVVKSEASSSPPVVTSSSHSRAPCQA
GDLRDMISMYLPGAEVPEPAAPSRLHMSQHYQSGPVPGTAINGTLPLSHM-AA-LLNKNSTFKIFR
ITPITSIINRVTKMTQVVIDAEGIQNKEI-HHHHHH

Figure 4E

MDEQQSQAVAPVYVGGMDEKTTGWRGGHVVEGLAGELEQLRARLEHHPQGQREPS-GAAGHLASDFAFS
PPPGGGGDGPGGPEPGWVDPRTWLSFQGPPGGPGIGPGVGPGSEVWGIPPCPPPYEFCGGMAYCGPQVGV
GLVPQGGLETSQPEGEAGVGVESNSDGASPEPCTVTPGAVKLEKEKLEQNPEESQDIKALQKELEQFAKLL
KQKRITLGYTQADVGLTLGVLFGKVFSQTTICRFEALQLSFKNMCKLRPLLQKWVEEADNNENLQEICKAE
TLVQARKRKRTSIENRVRGNLENLFLQCPKPTLQQISHIAQQLGLEKDVVRVWFCNRRQKGKRSSSDYAQR
EDFEAAGSPFSGGPVSFPLAPGPHFGTPGYGSPHFTALYSSVPFPEGEAFPPVSVTTLGSPMHSNAAASLVNR
KQLEKMANVRFRTQEDEYVAILDALEEYHNMSENTVVEKYLKLK-MPITINNFNYSDPVDNKNILYLDTHL
NTLANEPEKAFRITGNIWVIPDRFSRNSNPNLNKPPRVTSPKSGYYDPNYLSTDSDKDPFLKEIIKLFKRINSR
EIGEELIYRLSTDIPFPGNNNTPINTFDFDVDFNSVDVKTRQGNNWVKTGSINPSVIITGPRENIIDPETSTFKL
TNNTFAAQEGFGALSIISISPRFMLTYSNATNDVGEGRFSKSEFCMDPILILMAALNAAMHNLYGIAIPNDQT
ISSVTSNIFYSQYNVKLEYAEIYAFGGPTIDLIPKSARKYFEEKALDYYRSIAKRLNSITTANPSSFNKYIGEYK
QKLIRKYRFVVESSGEVTVNRNKFVELYNELTQIFTEFNYAKIYNVQNRKIYLSNVYTPVTANILDDNVYDI
QNGFNIPKSNLNVLFMGQNLSRNPALRKVNPENMLYLFTKFCHKAIDGRSLYNKTLDCRELLVKNTDLPFI
GDISDVKTDIFLRKDINEETEVIYYPDNVSVDQVILSKNTSEHGQLDLLYPSIDSESEILPGENQVFYDNRTQN
VDYLNSYYYLESQKLSDNVEDFTFTRSIEEALDNSAKVYTYFPTLANKVNAGVQGGLFLMWANDVVEDFT
TNILRKDTLDKISDVSAIIPYIGPALNISNSVRRGNFTEAFAVTGVTILLEAFPEFTIPALGAFVIYSKVQERNEI
IKTIDNCLEQRIKRWKDSYEWMMGTWLSRIITQFNNISYQMYDSLNYQAGAIKAKIDLEYKKYSGSDKENI
KSQVENLKNSLDVKISEAMNNINKFIRECSVTYLFKNMLPKVIDELNEFDRNTKAKLINLIDSHNIILVGEVD
KLKAKVNNSFQNTIPFNIFSYTNNSLLKDIINEYFNNINDSKILSLQNRK-N-LITGFVTVGDDKYYFNPINGG
AASIGETIIDDKNYYFNQSGVLQTGVFSTEDGFKYFAPANTLDENLEGEAIDFTGKLIIDENIYYFDDNYRGA
VEWKELDGEMHYFSPETGKAFKGLNQIGDYKYYFNSDGVMQKGFVSINDNKHYFDDSGVMKVGYTEIDG
KHFYFAENGEMQIGVFNTEDGFKYFAHHNEDLGNEEGEEISYSGILNFNNKIYYFDDSFTAVVGWKDLEDG
SKYYFDEDTAEAYIGLSLINDGQYYFNDDGIMQVGFVTINDKVFYFSDSGIIESGVQNIDDNYFYIDDNGIVQ
IGVFDTSDGYKYFAPANTVNDNIYGQAVEYSGLVRVGEDVYYFGETYTIETGWIYDMENESDKYYFNPET
KKKACKGINLIDDIKYYFDEKGIMRTGLISFENNNYYFNENGEMQFGYINIEDKMFYFGEDGVMQIGVFNTP
DGFKYFAHQNTLDENFEGESINYTGWLDLDEKRYYFTDEYIAATGSVIIDGEEYYFDPDTAQLVISE-HHHH
HH

Figure 5A

MDEQQSQAVAPVYVGGMDEKTTGWRGGHVVEGLAGELEQLRARLEHHPQGQREPS-GA-YNMMETELK
PPGPQQTSGGGGGNSTAAAAGGNQKNSPDRVKRPMNAFMVWSRGQRRKMAQENPKMHNSEISKRLGAE
WKLLSETEKRPFIDEAKRLRALHMKEHPDYKYRPRRKTKTLMKKDKYTLPGGLLAPGGNSMASGVGVGA
GLGAGVNQRMDSYAHMNGWSNGSYSMMQDQLGYPQHPGLNAHGAAQMQPMHRYDVSALQYNSMTSS
QTYMNGSPTYSMSYSQQGTPGMALGSMGSVVKSEASSSPPVVTSSSHSRAPCQAGDLRDMISMYLPGAEV
PEPAAPSRLHMSQHYQSGPVPGTAINGTLPLSHM-AAA-MPITINNFNYSDPVDNKNILYLDTHLNTLANEPE
KAFRITGNIWVIPDRFSRNSNPNLNKPPRVTSPKSGYYDPNYLSTDSDKDPFLKEIIKLFKRINSREIGEELIYR
LSTDIPFPGNNNTPINTFDFDVDFNSVDVKTRQGNNWVKTGSINPSVIITGPRENIIDPETSTFKLTNNTFAAQ
EGFGALSIISISPRFMLTYSNATNDVGEGRFSKSEFCMDPILILMAALNAAMHNLYGIAIPNDQTISSVTSNIF
YSQYNVKLEYAEIYAFGGPTIDLIPKSARKYFEEKALDYYRSIAKRLNSITTANPSSFNKYIGEYKQKLIRKY
RFVVESSGEVTVNRNKFVELYNELTQIFTEFNYAKIYNVQNRKIYLSNVYTPVTANILDDNVYDIQNGFNIP
KSNLNVLFMGQNLSRNPALRKVNPENMLYLFTKFCHKAIDGRSLYNKTLDCRELLVKNTDLPFIGDISDVK
TDIFLRKDINEETEVIYYPDNVSVDQVILSKNTSEHGQLDLLYPSIDSESEILPGENQVFYDNRTQNVDYLNS
YYYLESQKLSDNVEDFTFTRSIEEALDNSAKVYTYFPTLANKVNAGVQGGLFLMWANDVVEDFTTNILRK
DTLDKISDVSAIIPYIGPALNISNSVRRGNFTEAFAVTGVTILLEAFPEFTIPALGAFVIYSKVQERNEIIKTIDN
CLEQRIKRWKDSYEWMMGTWLSRIITQFNNISYQMYDSLNYQAGAIKAKIDLEYKKYSGSDKENIKSQVE
NLKNSLDVKISEAMNNINKFIRECSVTYLFKNMLPKVIDELNEFDRNTKAKLINLIDSHNIILVGEVDKLKAK
VNNSFQNTIPFNIFSYTNNSLLKDIINEYFNNINDSKILSLQNRK-N-LITGFVTVGDDKYYFNPINGGAASIGE
TIIDDKNYYFNQSGVLQTGVFSTEDGFKYFAPANTLDENLEGEAIDFTGKLIIDENIYYFDDNYRGAVEWKE
LDGEMHYFSPETGKAFKGLNQIGDYKYYFNSDGVMQKGFVSINDNKHYFDDSGVMKVGYTEIDGKHFYF
AENGEMQIGVFNTEDGFKYFAHHNEDLGNEEGEEISYSGILNFNNKIYYFDDSFTAVVGWKDLEDGSKYYF
DEDTAEAYIGLSLINDGQYYFNDDGIMQVGFVTINDKVFYFSDSGIIESGVQNIDDNYFYIDDNGIVQIGVFD
TSDGYKYFAPANTVNDNIYGQAVEYSGLVRVGEDVYYFGETYTIETGWIYDMENESDKYYFNPETKKACK
GINLIDDIKYYFDEKGIMRTGLISFENNNYYFNENGEMQFGYINIEDKMFYFGEDGVMQIGVFNTPDGFKYF
AHQNTLDENFEGESINYTGWLDLDEKRYYFTDEYIAATGSVIIDGEEYYFDPDTAQLVISE-HHHHHH

Figure 5B

MDEQQSQAVAPVYVGGMDEKTTGWRGGHVVEGLAGELEQLRARLEHHPQGQREPS-GAAGHLASDFAFS
PPPGGGGDGPGGPEPGWVDPRTWLSFQGPPGGPGIGPGVGPGSEVWGIPPCPPPYEFCGGMAYCGPQVGV
GLVPQGGLETSQPEGEAGVGVESNSDGASPEPCTVTPGAVKLEKEKLEQNPEESQDIKALQKELEQFAKLL
KQKRITLGYTQADVGLTLGVLFGKVFSQTTICRFEALQLSFKNMCKLRPLLQKWVEEADNNENLQEICKAE
TLVQARKRKRTSIENRVRGNLENLFLQCPKPTLQQISHIAQQLGLEKDVVRVWFCNRRQKGKRSSSDYAQR
EDFEAAGSPFSGGPVSFPLAPGPHFGTPGYGSPHFTALYSSVPFPEGEAFPPVSVTTLGSPMHSNAAASLVNR
KQLEKMANVRFRTQEDEYVAILDALEEYHNMSENTVVEKYLKLK-MPITINNFNYSDPVDNKNILYLDTHL
NTLANEPEKAFRITGNIWVIPDRFSRNSNPNLNKPPRVTSPKSGYYDPNYLSTDSDKDPFLKEIIKLFKRINSR
EIGEELIYRLSTDIPFPGNNNTPINTFDFDVDFNSVDVKTRQGNNWVKTGSINPSVIITGPRENIIDPETSTFKL
TNNTFAAQEGFGALSIISISPRFMLTYSNATNDVGEGRFSKSEFCMDPILILMAALNAAMHNLYGIAIPNDQT
ISSVTSNIFYSQYNVKLEYAEIYAFGGPTIDLIPKSARKYFEEKALDYYRSIAKRLNSITTANPSSFNKYIGEYK
QKLIRKYRFVVESSGEVTVNRNKFVELYNELTQIFTEFNYAKIYNVQNRKIYLSNVYTPVTANILDDNVYDI
QNGFNIPKSNLNVLFMGQNLSRNPALRKVNPENMLYLFTKFCHKAIDGRSLYNKTLDCRELLVKNTDLPFI
GDISDVKTDIFLRKDINEETEVIYYPDNVSVDQVILSKNTSEHGQLDLLYPSIDSESEILPGENQVFYDNRTQN
VDYLNSYYYLESQKLSDNVEDFTFTRSIEEALDNSAKVYTYFPTLANKVNAGVQGGLFLMWANDVVEDFT
TNILRKDTLDKISDVSAIIPYIGPALNISNSVRRGNFTEAFAVTGVTILLEAFPEFTIPALGAFVIYSKVQERNEI
IKTIDNCLEQRIKRWKDSYEWMMGTWLSRIITQFNNISYQMYDSLNYQAGAIKAKIDLEYKKYSGSDKENI
KSQVENLKNSLDVKISEAMNNINKFIRECSVTYLFKNMLPKVIDELNEFDRNTKAKLINLIDSHNIILVGEVD
KLKAKVNNSFQNTIPFNIFSYTNNSLLKDIINEYFNNINDSKILSLQNRK-MRLAVGALLVCAVLGLCLAVPD
KTVRWCAVSEHEATKCQSFRDHMKSVIPSDGPSVACVKKASYLDCIRAIAANEADAVTLDAGLVYDAYLA
PNNLKPVVAEFYGSKEDPQTFYYAVAVVKKDSGFQMNQLRGKKSCHTGLGRSAGWNIPIGLLYCDLPEPR
KPLEKAVANFFSGSCAPCADGTDFPQLCQLCPGCGCSTLNQYFGYSGAFKCLKDGAGDVAFVKHSTIFENL
ANKADRDQYELLCLDNTRKPVDEYKDCHLAQVPSHTVVARSMGGKEDLIWELLNQAQEHFGKDKSKEFQ
LFSSPHGKDLLFKDSAHGFLKVPPRMDAKMYLGYEYVTAIRNLREGTCPEAPTDECKPVKWCALSHHERL
KCDEWSVNSVGKIECVSAETTEDCIAKIMNGEADAMSLDGGFVYIAGKCGLVPVLAENYNKSDNCEDTPE
AGYFAVAVVKKSASDLTWDNLKGKKSCHTAVGRTAGWNIPMGLLYNKINHCRFDEFFSEGCAPGSKKDS
SLCKLCMGSGLNLCEPNNKEGYYGYTGAFRCLVEKGDVAFVKHQTVPQNTGGKNPDPWAKNLNEKDYE
LLCLDGTRKPVEEYANCHLARAPNHAVVTRKDKEACVHKILRQQQHLFGSNVTDCSGNFCLFRSETKDLL
FRDDTVCLAKLHDRNTYEKYLGEEYVKAVGNLRKCSTSSLLEACTFRRP-HHHHHH

Figure 5C

MDEQQSQAVAPVYVGGMDEKTTGWRGGHVVEGLAGELEQLRARLEHHPQGQREPS-GA-YNMMETELK
PPGPQQTSGGGGGNSTAAAAGGNQKNSPDRVKRPMNAFMVWSRGQRRKMAQENPKMHNSEISKRLGAE
WKLLSETEKRPFIDEAKRLRALHMKEHPDYKYRPRRKTKTLMKKDKYTLPGGLLAPGGNSMASGVGVGA
GLGAGVNQRMDSYAHMNGWSNGSYSMMQDQLGYPQHPGLNAHGAAQMQPMHRYDVSALQYNSMTSS
QTYMNGSPTYSMSYSQQGTPGMALGSMGSVVKSEASSSPPVVTSSSHSRAPCQAGDLRDMISMYLPGAEV
PEPAAPSRLHMSQHYQSGPVPGTAINGTLPLSHM-AAA-MPITINNFNYSDPVDNKNILYLDTHLNTLANEP
EKAFRITGNIWVIPDRFSRNSNPNLNKPPRVTSPKSGYYDPNYLSTDSDKDPFLKEIIKLFKRINSREIGEELIY
RLSTDIPFPGNNNTPINTFDFDVDFNSVDVKTRQGNNWVKTGSINPSVIITGPRENIIDPETSTFKLTNNTFAA
QEGFGALSIISISPRFMLTYSNATNDVGEGRFSKSEFCMDPILILMAALNAAMHNLYGIAIPNDQTISSVTSNI
FYSQYNVKLEYAEIYAFGGPTIDLIPKSARKYFEEKALDYYRSIAKRLNSITTANPSSFNKYIGEYKQKLIRK
YRFVVESSGEVTVNRNKFVELYNELTQIFTEFNYAKIYNVQNRKIYLSNVYTPVTANILDDNVYDIQNGFNI
PKSNLNVLFMGQNLSRNPALRKVNPENMLYLFTKFCHKAIDGRSLYNKTLDCRELLVKNTDLPFIGDISDV
KTDIFLRKDINEETEVIYYPDNVSVDQVILSKNTSEHGQLDLLYPSIDSESEILPGENQVFYDNRTQNVDYLN
SYYYLESQKLSDNVEDFTFTRSIEEALDNSAKVYTYFPTLANKVNAGVQGGLFLMWANDVVEDFTTNILR
KDTLDKISDVSAIIPYIGPALNISNSVRRGNFTEAFAVTGVTILLEAFPEFTIPALGAFVIYSKVQERNEIIKTID
NCLEQRIKRWKDSYEWMMGTWLSRIITQFNNISYQMYDSLNYQAGAIKAKIDLEYKKYSGSDKENIKSQV
ENLKNSLDVKISEAMNNINKFIRECSVTYLFKNMLPKVIDELNEFDRNTKAKLINLIDSHNIILVGEVDKLKA
KVNNSFQNTIPFNIFSYTNNSLLKDIINEYFNNINDSKILSLQNRK-MRLAVGALLVCAVLGLCLAVPDKTVR
WCAVSEHEATKCQSFRDHMKSVIPSDGPSVACVKKASYLDCIRAIAANEADAVTLDAGLVYDAYLAPNNL
KPVVAEFYGSKEDPQTFYYAVAVVKKDSGFQMNQLRGKKSCHTGLGRSAGWNIPIGLLYCDLPEPRKPLE
KAVANFFSGSCAPCADGTDFPQLCQLCPGCGCSTLNQYFGYSGAFKCLKDGAGDVAFVKHSTIFENLANK
ADRDQYELLCLDNTRKPVDEYKDCHLAQVPSHTVVARSMGGKEDLIWELLNQAQEHFGKDKSKEFQLFS
SPHGKDLLFKDSAHGFLKVPPRMDAKMYLGYEYVTAIRNLREGTCPEAPTDECKPVKWCALSHHERLKCD
EWSVNSVGKIECVSAETTEDCIAKIMNGEADAMSLDGGFVYIAGKCGLVPVLAENYNKSDNCEDTPEAGY
FAVAVVKKSASDLTWDNLKGKKSCHTAVGRTAGWNIPMGLLYNKINHCRFDEFFSEGCAPGSKKDSSLCK
LCMGSGLNLCEPNNKEGYYGYTGAFRCLVEKGDVAFVKHQTVPQNTGGKNPDPWAKNLNEKDYELLCL
DGTRKPVEEYANCHLARAPNHAVVTRKDKEACVHKILRQQQHLFGSNVTDCSGNFCLFRSETKDLLFRDD
TVCLAKLHDRNTYEKYLGEEYVKAVGNLRKCSTSSLLEACTFRRP-HHHHHH

Figure 5D

MDEQQSQAVAPVYVGGMDEKTTGWRGGHVVEGLAGELEQLRARLEHHPQGQREPS-GAAGHLASDFAFS
PPPGGGGDGPGGPEPGWVDPRTWLSFQGPPGGPGIGPGVGPGSEVWGIPPCPPPYEFCGGMAYCGPQVGV
GLVPQGGLETSQPEGEAGVGVESNSDGASPEPCTVTPGAVKLEKEKLEQNPEESQDIKALQKELEQFAKLL
KQKRITLGYTQADVGLTLGVLFGKVFSQTTICRFEALQLSFKNMCKLRPLLQKWVEEADNNENLQEICKAE
TLVQARKRKRTSIENRVRGNLENLFLQCPKPTLQQISHIAQQLGLEKDVVRVWFCNRRQKGKRSSSDYAQR
EDFEAAGSPFSGGPVSFPLAPGPHFGTPGYGSPHFTALYSSVPFPEGEAFPPVSVTTLGSPMHSNAAASLVNR
KQLEKMANVRFRTQEDEYVAILDALEEYHNMSENTVVEKYLKLK-MPITINNFNYSDPVDNKNILYLDTHL
NTLANEPEKAFRITGNIWVIPDRFSRNSNPNLNKPPRVTSPKSGYYDPNYLSTDSDKDPFLKEIIKLFKRINSR
EIGEELIYRLSTDIPFPGNNNTPINTFDFDVDFNSVDVKTRQGNNWVKTGSINPSVIITGPRENIIDPETSTFKL
TNNTFAAQEGFGALSIISISPRFMLTYSNATNDVGEGRFSKSEFCMDPILILMAALNAAMHNLYGIAIPNDQT
ISSVTSNIFYSQYNVKLEYAEIYAFGGPTIDLIPKSARKYFEEKALDYYRSIAKRLNSITTANPSSFNKYIGEYK
QKLIRKYRFVVESSGEVTVNRNKFVELYNELTQIFTEFNYAKIYNVQNRKIYLSNVYTPVTANILDDNVYDI
QNGFNIPKSNLNVLFMGQNLSRNPALRKVNPENMLYLFTKFCHKAIDGRSLYNKTLDCRELLVKNTDLPFI
GDISDVKTDIFLRKDINEETEVIYYPDNVSVDQVILSKNTSEHGQLDLLYPSIDSESEILPGENQVFYDNRTQN
VDYLNSYYYLESQKLSDNVEDFTFTRSIEEALDNSAKVYTYFPTLANKVNAGVQGGLFLMWANDVVEDFT
TNILRKDTLDKISDVSAIIPYIGPALNISNSVRRGNFTEAFAVTGVTILLEAFPEFTIPALGAFVIYSKVQERNEI
IKTIDNCLEQRIKRWKDSYEWMMGTWLSRIITQFNNISYQMYDSLNYQAGAIKAKIDLEYKKYSGSDKENI
KSQVENLKNSLDVKISEAMNNINKFIRECSVTYLFKNMLPKVIDELNEFDRNTKAKLINLIDSHNIILVGEVD
KLKAKVNNSFQNTIPFNIFSYTNNSLLKDIINEYFNNINDSKILSLQNRK-STFTEYIKSRPGPETLCGAELVDA
LQFVCGDRGFYFNKPTGYGSSSRRAPQTGIVDECCFRSCDLRRLEMYCAPLKPAKSAEA-HHHHHH

Figure 5E

MDEQQSQAVAPVYVGGMDEKTTGWRGGHVVEGLAGELEQLRARLEHHPQGQREPS-GA-YNMMETELK
PPGPQQTSGGGGGNSTAAAAGGNQKNSPDRVKRPMNAFMVWSRGQRRKMAQENPKMHNSEISKRLGAE
WKLLSETEKRPFIDEAKRLRALHMKEHPDYKYRPRRKTKTLMKKDKYTLPGGLLAPGGNSMASGVGVGA
GLGAGVNQRMDSYAHMNGWSNGSYSMMQDQLGYPQHPGLNAHGAAQMQPMHRYDVSALQYNSMTSS
QTYMNGSPTYSMSYSQQGTPGMALGSMGSVVKSEASSSPPVVTSSSHSRAPCQAGDLRDMISMYLPGAEV
PEPAAPSRLHMSQHYQSGPVPGTAINGTLPLSHM-AAA-MPITINNFNYSDPVDNKNILYLDTHLNTLANEPE
KAFRITGNIWVIPDRFSRNSNPNLNKPPRVTSPKSGYYDPNYLSTDSDKDPFLKEIIKLFKRINSREIGEELIYR
LSTDIPFPGNNNTPINTFDFDVDFNSVDVKTRQGNNWVKTGSINPSVIITGPRENIIDPETSTFKLTNNTFAAQ
EGFGALSIISISPRFMLTYSNATNDVGEGRFSKSEFCMDPILILMAALNAAMHNLYGIAIPNDQTISSVTSNIF
YSQYNVKLEYAEIYAFGGPTIDLIPKSARKYFEEKALDYYRSIAKRLNSITTANPSSFNKYIGEYKQKLIRKY
RFVVESSGEVTVNRNKFVELYNELTQIFTEFNYAKIYNVQNRKIYLSNVYTPVTANILDDNVYDIQNGFNIP
KSNLNVLFMGQNLSRNPALRKVNPENMLYLFTKFCHKAIDGRSLYNKTLDCRELLVKNTDLPFIGDISDVK
TDIFLRKDINEETEVIYYPDNVSVDQVILSKNTSEHGQLDLLYPSIDSESEILPGENQVFYDNRTQNVDYLNS
YYYLESQKLSDNVEDFTFTRSIEEALDNSAKVYTYFPTLANKVNAGVQGGLFLMWANDVVEDFTTNILRK
DTLDKISDVSAIIPYIGPALNISNSVRRGNFTEAFAVTGVTILLEAFPEFTIPALGAFVIYSKVQERNEIIKTIDN
CLEQRIKRWKDSYEWMMGTWLSRIITQFNNISYQMYDSLNYQAGAIKAKIDLEYKKYSGSDKENIKSQVE
NLKNSLDVKISEAMNNINKFIRECSVTYLFKNMLPKVIDELNEFDRNTKAKLINLIDSHNIILVGEVDKLKAK
VNNSFQNTIPFNIFSYTNNSLLKDIINEYFNNINDSKILSLQNRK-STFTEYIKSRPGPETLCGAELVDALQFVC
GDRGFYFNKPTGYGSSSRRAPQTGIVDECCFRSCDLRRLEMYCAPLKPAKSAEA-HHHHHH

Figure 5F

PROTEIN DELIVERY SYSTEM TO GENERATE PLURIPOTENT STEM (IPS) CELLS OR TISSUE SPECIFIC CELLS

CROSS-REFERENCE TO RELATED APPLICATIONS

This application claims the benefit under 35 U.S.C. §119 (e) of U.S. Provisional Application No. 61/275,297, entitled "A NOVEL PROTEIN DELIVERY SYSTEM TO GENERATE INDUCED PLURIPOTENT STEM (iPS) CELLS OR TISSUE-SPECIFIC CELLS" and filed Aug. 27, 2009, which is incorporated herein by reference in its entirety.

FIELD OF THE INVENTION

This invention relates a protein delivery system for therapeutic purposes; more particularly, the protein delivery system can be utilized to deliver reprogramming factors for causing the differentiation of somatic cells into pluripotent stem (iPS) cells or tissue specific cells for regenerative medicine or disease treatment.

BACKGROUND OF THE INVENTION

In the past, pluripotent stem cells have been generated by means of nuclear transplant and cell fusion (Shinya Yamanaka, *Pluripotency and Nuclear Reprogramming*, Philos Trans R Soc Lond B Biol Sci. 363(1500): 2079-2087 (Jun. 27, 2008)). Both methods require embryonic stem cells, which pose ethical dilemmas for both research and therapeutic use. This issue is overcome by the recently discovered induced pluripotent stem (iPS) cells, which share the same attractive biological properties of embryonic stem (ES) cells (Yamanaka, *A Fresh Look at iPS Cells*. Cell 137:13-17 (S. 2009)).

Induced pluripotent stem cells were first produced from mouse fibroblasts in 2006 (Takahashi, Y. and S. Yamanaka, *Induction of Pluripotent Stem Cells from Mouse Embryonic and Adult Fibroblast Cultures by Defined Factors*, Cell 126: 663-676 (2006)) and human fibroblasts in 2007 (Yu Junying, et al., *Induced Pluripotent Stem Cell Lines Derived from Human Somatic Cells*, Science 318: 1917-1920 (2007), Takahashi, K., et al. *Induction of Pluripotent Stem Cells From Adult Human Fibroblasts by Defined Factors*, Cell 131: 861-872 (2007)) by forcing the expression of defined factors. Two sets of factors have been used to trigger the reprogramming of adult somatic cells to iPS cells in these studies: one includes Oct-3/4, Sox2, Klf4, and c-Myc (Takahashi, Cell 126: 663-676; Takahashi, Cell 131:861-872); and the other includes Oct4, Sox2, Nanog, and Lin28 (Junying, Cell 318:1917-1920). The reprogramming efficiency of these defined factors can be increased 10-fold by knocking down p53 activity.

In 2008, Melton's group demonstrated that by delivering a specific combination of three transcription factors, Ngn3 (also known as Neurog3), Pdx1, and Mafa, the differentiated pancreatic exocrine cells in adult mice were re-programmed into cells that closely resemble β-cells (Zhou, Q. et al., *In Vivo Reprogramming of Adult Pancreatic Exocrine Cells to β-cells*, Nature 455: 627-633 (2008)). The induced β-cells are morphologically indistinguishable from endogenous islet β-cells; they express genes essential for β-cell function and can ameliorate hyperglycemia by remodeling local vasculature and secreting insulin. This study suggests that adult somatic cells can be re-programmed to tissue specific cells directly by a specific combination of transcription factors without reversion to a pluripotent stem cell state.

The potential of iPS cells is enormous. However, the clinical application of iPS cells faces many obstacles (Yamanaka, Cell 137: 13-17; Miura, K. et al., *Variation in the Safety of Induced Pluripotent Stem Cell Lines*, Nature Biotechnology 27(8):743-745 (2009); Carpenter, M. et al., *Developing Safe Therapies From Human Pluripotent Stem Cells*, Nature Biotechnology 27: 606-613 (2009)). One major hurdle is directly related to the delivery vehicle for the re-programming factors. Initially, the re-programming factor genes were introduced into somatic fibroblast by retro or lentiviral vectors (Takahashi, Cell 126: 663-676; Junying, Cell 318:1917-1920; Takahashi, Cell 131:861-8723-5). The process of re-programming through retro or lentiviral vectors had an efficiency of only ~0.05% (Okita, K. et al., *Generation of Mouse Induced Pluripotent Stem Cells Without Viral Vectors*, Science 322: 949-953; Yamanaka, S. *Elite and Stochastic Models for Induced Pluripotent Stem Cell Generation*, Nature 460: 49-52 (2009)).

Insertional activation of an oncogene is always a great concern of using retro or lentiviral vectors since these vectors randomly integrate into the host's genome. Although transgenes are largely silenced in iPS cells, reactivation of c-myc transgene could lead to tumorigenesis (Okita, K., et al., *Generation of Germline-Competent Induced Pluripotent Stem Cells*, Nature 448: 313-318 (2007)). Leaky expression of these transgenes may also inhibit complete iPS cell differentiation and maturation, leading to a greater risk of teratoma formation (Yamanaka, Cell 137:13-17). In addition, the transgenes could be re-activated and expressed in cells that are re-differentiated from the iPS cells, leading to a risk of re-programming differentiation status of iPS cells or tumor formation.

A non-integrating viral vector such as an adenoviral vector was later used to deliver these re-programming factor genes (Zhou, Nature 455: 627-633; Stadtfeld, M. et al., *Induced Pluripotent Stem Cells Generated Without Viral Integration*, Science 322: 945-949 (2008)). However, large amounts of adenoviral vectors, which may cause cytopathic effect on cells, are required for effective transduction into cell types that lack the adenovirus receptor CAR. In addition, low level expression of some adenoviral genes may affect the transduced cells if a "non-gutless" adenoviral vector is chosen as a delivery vehicle.

Re-programming can also be accomplished via direct plasmid transfection (Okita, Science 322: 949-953; Yu, J. et al. *Human Induced Pluripotent Stem Cells Free of Vector and Transgene Sequences*, Science 324: 797-801 (2009)), but it is more than 100-fold less efficient than that of a retroviral vector (Okita, Science 322: 949-953). Both adenoviral vector transduction and plasmid transfection may not exclude stable integration. The integration frequencies of adenoviral vectors are ~$10^{-3}$ to $10^{-5}$ per cell (Harui, A. et al., *Frequency and Stability of Chromosomal Integration of Adenovirus Vectors*, J. Virology 73: 6141-6146 (1999)).

A comparison of methods to generate pluripotent stem cells is shown in table 1.

TABLE 1

Pros and Cons of three methods to create pluripotent stem cells

| | Use of human embryo | Application to human cells | Immuno-rejection | Chromosome abnormality |
|---|---|---|---|---|
| Nuclear transfer | Yes | unknown | Yes | normal |
| ES cell fusion | Yes | Yes | Yes | tetraploid |

TABLE 1-continued

Pros and Cons of three methods to create pluripotent stem cells

| | Use of human embryo | Application to human cells | Immuno-rejection | Chromosome abnormality |
|---|---|---|---|---|
| iPS Cells | No | Yes | No | vector insertion (oncogene deregulation) |

ES, embryonic stem cell;
iPS, induced pluripotent stem cells.

In 1998, Frankel and Green independently observed that HIV-1 Tat protein can penetrate cells in a receptor-independent fashion (Frankel, A. and C. Pabo, *Cellular Uptake of the Tat Protein from Human Immunodeficiency Virus*, Cell 55: 1189-1193 (1988); Green, M. and P. Loewenstein, *Autonomous Functional Domains of Chemically Synthesized Human Immunodeficiency Virus Tat Trans-Activator Protein*, Cell 55:1179-1188 (1988)). The Tat protein transduction domain (PTD) that contains the short basic arginine-rich region (aa 48-57) of HIV-1 Tat is widely used to deliver variety of molecules including peptides both in vitro and in vivo (Schwarze, S. R. et al., *In Vivo Protein Transduction: Delivery of a Biologically Active Protein Into Mouse*, Science 285: 1569-1572 (1999); Lindsay, M. A. *Peptide-Mediated Cell Delivery: Application in Protein Target Validation*, Current Opinion in Pharmacology 2:587-594 (2002); Kwon, Y. D., et al., *Cellular Manipulation of Human Embryonic Stem Cells by Tat-Pdx1 Protein Transduction*, Molecular Therapy 12: 28-32 (2005); Kim, D., *Generation of Human Pluripotent Stem Cells by Direct Delivery of Reprogramming Proteins*, Cell Stem Cell 4: 472-476 (2009); Wadia, J. S. et al., *Transducible Tat-HA Fusogenic Peptide Enhances Escape of Tat-Fusion Protein After Lipid Raft Macropinocytosis*, Nature Medicine 10:310-315 (2009); Zhou, H. et al., *Generation of Induced Pluripotent Stem Cells Using Recombinant Proteins*, Cell Stem Cell 4: 381-384.19-24 (2009)). This method to deliver molecules by a protein-based vehicle is called protein transduction. Binding of Tat-PTD to cell surface through ionic interaction leads to the internalization of Tat-fusion proteins by lipid raft-dependent macropinocytosis (Wadia, J. S., Nature Medicine 10:310-315). The majority of the Tat-fusion protein, however, remains trapped in macropinosomes, indicating that the escape of peptides or proteins from macropinosomes is an inefficient process (Wadia, J. S., Nature Medicine 10:310-315). Recently, poly-arginine (11R or 9R) PTD fused to C-terminus of the 4 re-programming factors (Oct4, Sox2, Klf4, and C-Myc) successfully re-programmed mouse embryonic fibroblast (Zhou, H. et al., *Generation of Induced Pluripotent Stem Cells using Recombinant Proteins*, Cell Stem Cell 4: 381-384 (2009)) and human newborn fibroblast (Kim, D., Cell Stem Cell 4: 472-476) cells to iPS cells but with very low efficiency.

SUMMARY OF THE INVENTION

The present invention is a novel protein-based system for delivering reprogramming factors to adult somatic cells to generate iPS cells or tissue specific cells without using gene expression vectors. The system comprises a construct with a receptor binding domain, a translocation domain, a cargo bearing domain and an inducer. The receptor binding domain directs the construct to a somatic cell. The translocation domain facilitates the transport of the cargo bearing domain and inducer into the cell. The cargo bearing domain delivers the inducer into the cell. In one embodiment of the invention, the construct utilizes exotoxin domains for the binding, translocation, and cargo functions of the construct. Some of such exotoxins include *C. difficile* TcdA and TcdB toxins, *C. botulinum* BoNTs A through G and C2 toxins. The various domains of the construct can be swapped in order to accommodate various sizes of inducers and to direct the inducers to somatic cells having specific binding receptors.

The constructs can be used to deliver pluripotency inducers into somatic cells and cause the cells to become iPS cells. Another embodiment of the present invention further provides a method for generating iPS cells in which somatic cells are exposed to the construct bearing one or more inducers. The construct may also be utilized with other constructs, such as lentiviruses, small protein delivery systems, or small molecules to generate iPS cells

BRIEF DESCRIPTION OF THE DRAWINGS

The above and other features, aspects, and advantages of the present invention are considered in more detail, in relation to the following description of embodiments thereof shown in the accompanying drawings, in which:

FIG. 1A is a graphical representation of the *C. difficile* structure.

FIG. 1B is a graphical representation of various possible constructs using the *C. difficile* configuration.

FIGS. 2A through 2D are graphical representations of the various domains of constructs containing Oct4 and TcdB/TcdA, which are referenced as SEQ ID Nos. 1 through 4. Dashes represent transitions between domains, tags, and spacers.

FIGS. 3A through 3D are graphical representations of the various domains of constructs containing Sox2 and TcdB/TcdA, which are referenced as SEQ ID Nos. 5 through 8. Dashes represent transitions between domains, tags, and spacers.

FIG. 4A through 4E are graphical representations of the various domains of constructs containing Oct4/Sox2 and C2I and C2II, which are referenced as SEQ ID Nos. 9 through 13. Underlined sequences are mutations that inactivate the active site of the toxin. Dashes represent transitions between domains, tags, and spacers.

FIG. 5A through 5F are graphical representations of the various domains of constructs containing Oct4/Sox2 and BoNTs and other RBDs, which are referenced as SEQ ID Nos. 14 through 18. Underlined sequences are mutations that inactivate the active site of the toxin. Dashes represent transitions between domains, tags, and spacers.

FIG. 6 is a time-course Western blot analysis showing recombinant TcdB protein expression by *B. megaterium* 2-3 hours after induction.

FIG. 7 is a picture showing mouse colorectal tumor CT26 cells exposed to TcdB and atoxic TcdB.

FIG. 8A is a graphical representation of a test construct of TcdB and TcdB with SNAP as a cargo.

FIG. 8B is and SDS-Page gel showing the purified SNAP-TcdB construct.

FIG. 8C shows a Western blot analysis of the purified samples using an anti-SNAP-tag antibody.

FIG. 8D is a chart showing that the SNAP-TcdB construct is as toxic as wild-type TcdB.

DETAILED DESCRIPTION

The invention summarized above may be better understood by referring to the following description, which should be read in conjunction with the accompanying claims and drawings in which like reference numbers are used for like parts. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent constructs and cell lines do not depart from the spirit and scope of the invention in its broadest form.

As used herein, the term "construct" refers to a recombinant polypeptide having an amino acid sequence that includes an inducer sequence and a cargo delivery sequence. The construct may have other elements. For example, the construct may include a receptor binding domain (RBD), a translocation domain (TD), a cargo bearing domain (CBD), and a cleavage sequence (CS). As described in more detail below, the RBD allows the construct to identify and bind to a cell bearing the receptor. The TD allows the CBD, which may include an inducer, to be transported into the cytosol. The CBD may be an inactivated organic activity domain of a toxin. More specifically, it is understood that the CBD is rendered atoxic to the target cells by methods known in the art. In some embodiments, the CBD may be an inducer directly linked to the TD. The CS may be an intrinsic cysteine protease domain (CPD) or another protease sequence that allows the CBD carrying, for example, a pluripotency inducer to be released from the construct inside the cell.

An "inducer" is a transcription factor that among other properties may, when introduced in a somatic cell, aid in the transformation of the somatic cell into an iPS cell. The following inducers have been identified: Oct3/4, Sox2, Klf4, c-Myc, Nanog, lin28, hTERT (human telomerase), and SV40 large T-antigen. Other inducers may include MafA, Pdx-1, Ngn3, SV-40 T-ag, DPPA4, DPPA5, ZIC3, BCL-2, h-RAS, TPT1, SALL2, NAC1, DAX1, TERT, ZNF206, FOXD3, REX1, UTF1, p53 siRNA. In addition to the factors described above, inducers may also include p53 inhibitors, such as antibodies and antibody fragments that target p53, siRNAs, antisense RNA/DNA, and ribozymes.

A person of ordinary skill in the art understands that "substantially identical" homologs of the sequences described herein constitute exemplary embodiments of the present invention. Two amino acid sequences are "substantially identical" if (i) have only conservative amino acid substitutions that do not significantly affect the folding activity of the resulting polypeptide; (ii) the number of gaps between or insertions in, deletions of and substitutions of, is no more than 10%, preferably 5%, of the number of amino acid residues that occur over the length of the shortest of two aligned sequences; or (ii) no more than 30%, preferably 20%, more preferably 15%, or 10%, of the amino acid residues vary between the two sequences. Other methods as described by Houston et al. in United States Application Publication Number US2003/0161809A1 may also be used to determine whether two sequences are substantially identical.

*Clostridium* exotoxins are equipped with all the mechanisms for efficient cellular uptake and cytosolic delivery of their N-terminal enzymatic domain and can be used to deliver re-programming proteins to adult somatic cells. In particular, *Clostridium* exotoxins exhibit modular multi-domains that allow the toxin to efficiently translocate its N-terminus enzymatic domain, and anything attached to that N-terminus, into the cytosol. For example, Both *Clostridium botulinum* neurotoxin type D (BoNT-D) and *Clostridium difficile* toxin type B (TcdB) have demonstrated the ability to deliver a cargo appended to the N-terminus of the toxins into the cytosol (Bade, S. et al., *Botulinum Neurotoxin Type D Enables Cytosolic Delivery of Enzymatically Active Cargo Proteins to Neurons Via Unfolded Translocation Intermediates*, J. Neurochemistry 91: 1461-147225-26 (2004); Pfeifer, G. et al., *Cellular Uptake of Clostridium difficile Toxin B, Translocation of the N-terminal Catalytic Domain Into the Cytosol of Eukaryotic Cells*, J. of Boil. Chem. 278:44535-44541 (2003)).

I. *C. difficile* TcdA and TcdB Pluripotency Inducer iPS Cell Constructs.

One embodiment of the present invention consists of a *C. difficile* toxin A (TcdA) and B (TcdB) construct having three functional domains as shown in FIG. 1: (a) the RBD binds target cells for endocytosis; (b) the TD promotes cytosolic delivery of the enzymatic domain of the toxin; and (c) the CBD, which is and inactive portion of the GT enzymatic domain, carrying an inducer. FIG. 1A shows the primary structure of *Clostridium difficile* toxin with the N-terminal glucosyltransferase domain (GT), the intrinsic cysteine protease domain (CPD), the central translocation domain (TD), including a hydrophobic region (HR), and the C-terminal receptor binding domain (RBD). The CBD is located within the GT domain for engineering recombinant proteins.

As shown in FIG. 1B, various different constructs of TcdB mutants are made atoxic by truncation of the GT. Protein structure of the wild type TcdB, atoxic TcdB (aTcdB), and recombinant fusion proteins aTcdB-M1 aTcdB-M2, and aTcdB-M3. The aTcdB-M1 allows the inducer to be appended to the N-terminus of aTcdB. The aTcdB-M2 has the cargo attached to the truncated glucosyltransferase (GT) domain, and the aTcdB-M3 has the cargo replacing the entire GT domains.

The RBD of TcdA and TcdB RBDs bind to cell-surface carbohydrates, including Gal-α1, 3-Gal-β1, 4-GalNAc, as an initial step. These cell-surface carbohydrates are found in most somatic cells. Thus, the TcdA RBD will bind most somatic cells. After the RBD binds its receptor, the CBD is internalized by receptor-mediated endocytosis. The hydrophobic region (HR) in the TD enables the corresponding part of toxin to insert itself into the endosomal membrane to create a pore through which the CBD can translocate into the cytosol. The translocated can then be separated from the rest of the construct and released into cytosol by autoproteolysis, catalyzed by an intrinsic cysteine protease domain (CPD) located adjacent to the autocleavage site in the N-terminal part of TD as shown in FIG. 1B. As a result, as described herein, a construct that includes the RBD and TD of TcdA and TcdB can be used to introduce pluripotency inducers into somatic cells.

The CBD is an inactivated GT domain carrying an inducer. The GT domain can be inactivated using various methods known to a person of ordinary skill in the art. The GT domain can be truncated. The activity can also be demolished by amino acid substitutions in its sequence. In one embodiment of the present invention, the GT of TcdA is rendered inactive by the following deletions D285A and D287A, and the GT of TcdB is rendered inactive by the following deletions D286A and D288A. In some embodiments of the present invention various lengths of the GT domain may be utilized in which the portion of the domain responsible for the activity is deleted. The inactivation of the GT domain makes TcdA or TcdB atoxic and viable for use in a construct for generating iPS cells. The inactivated GT domain becomes a CBD to which an inducer can be attached. FIG. 1B shows various possible configurations of a construct in accordance with one embodiment of the present invention.

FIG. 2A through 2D illustrate various constructs, in accordance with several embodiments of the present invention, that utilize the various domains of TcdB and Oct 4 and Sox 2. In FIG. 2A, the sequence of an Oct4-aTcdB construct (SEQ ID No 1) is provided with the following domains: Streptavidin Binding Peptide (SBP) (aa1-55); the Oct4 sequence (aa57-416); CBD (aa420-961); CPD (aa962-1185); TD (aa1186-2269), which includes a Hydrophobic Region (aa1374-1546); RBD (aa2270-2784); and a His tag (aa2785-2790). In FIG. 2B, the sequence of an Oct4-aTcdB(dGT) construct (SEQ ID No 2) is provided with the following domains: a Streptavidin Binding Peptide (SBP) (aa1-55); the Oct4 sequence (aa57-416); CBD(aa419-488); CPD (aa489-712); TD(aa713-1796), which includes a Hydrophobic Region (aa901-1073); RBD (aa1797-2311); and a His tag (aa2312-2317). It is understood that the SBP and His tag are simply tags for the construct, which may be interchanged with other tags or completely removed without affecting the constructs ability to cause an Oct 4 (the inducer) to be translocated into the cytosolic space.

In FIG. 2C, the sequence of an Oct4-aTcdA construct (SEQ ID No 3) is provided with the following domains: a Streptavidin Binding Peptide (SBP) (aa1-55); the Oct4 sequence (aa58-416); CBD (aa420-959); CPD (aa960-1187); TD (aa1188-2267), which includes a Hydrophobic Region (aa900-1376); RBD (aa2268-3128); and a His tag (aa3128-3134). In FIG. 2D, the sequence of an Oct4-aTcdA(dGT) construct (SEQ ID No 4) is provided with the following domains: a Streptavidin Binding Peptide (SBP) (aa1-55); the Oct4 sequence (aa58-416); CBD(aa419-486); CPD (aa487-714); TD(aa715-1794), which includes a Hydrophobic Region (aa903-1075); RBD (aa1795-2655); and a His tag (aa2656-2661).

Similarly, FIGS. 3A through 3D illustrate constructs utilizing TcdA, TcdB and Sox2. In FIG. 3A, the sequence of a Sox2-aTcdB construct (SEQ ID No 5) is provided with the following domains: a Streptavidin Binding Peptide (SBP) (aa1-55); the Sox2 sequence (aa58-373); CBD (aa377-918); CPD (aa919-1142); TD (aa1143-2226), which includes a Hydrophobic Region (aa1331-1503); RBD (aa2268-2741); and a His tag (aa2742-2747). In FIG. 3B, the sequence of an Sox2-aTcdB(dGT) construct (SEQ ID No 6) is provided with the following domains: a Streptavidin Binding Peptide (SBP) (aa1-55); the Sox2 sequence (aa58-373); CBD(aa376-445); CPD (aa446-669); TD(aa670-1753), which includes a Hydrophobic Region (aa858-1030); RBD (aa1754-2268); and a His tag (aa2269-2274).

In FIG. 3C, the sequence of a Sox2-aTcdA construct (SEQ ID No 7) is provided with the following domains: a Streptavidin Binding Peptide (SBP) (aa1-55); the Sox2 sequence (aa58-373); CBD (aa377-916); CPD (aa917-1144); TD (aa1145-2224), which includes a Hydrophobic Region (aa1333-1505); RBD (aa2225-3085); and a His tag (aa3086-3091). In FIG. 3D, the sequence of an Sox2-aTcdA(dGT) construct (SEQ ID No 8) is provided with the following domains: a Streptavidin Binding Peptide (SBP) (aa1-55); the Sox2 sequence (aa58-373); CBD(aa376-443); CPD (aa444-671); TD(aa672-1751), which includes a Hydrophobic Region (aa860-1032); RBD (aa1752-2612); and a His tag (aa2613-2618).

II. *C. botolinum* Neurotoxin Pluripotency Inducer iPS Cell Constructs.

*C. botolinum* neurotoxin (BoNT) is another candidate of *Clostridium* exotoxins that can be used for pluripotent inducer delivery. The BoNT construct consist of a RBD that recognizes specific neuronal receptors. The heavy chain (Hc) of the BoNT toxins functions as the TD for the construct. The CBD of a construct in one embodiment of the present invention can be a *C. botulinum* neurotoxin light chain or a truncated light chain that has its non-palmitoylated preventing anchoring of the light chain to the membrane. The light chain is selected from of the BoNT type A through G to provide different longevity of the pharmacological effect of the inducer being delivered by the construct.

III. Clostridial C2 Toxin Constructs.

The Clostridial C2 toxin has a binary toxin structure in which the C2II chain is responsible for cellular receptor binding, endocytosis, pore formation, and translocation of the C2I enzymatically active ADP-ribosylating chain. A construct in accordance with one embodiment of the present invention can be created by fusion of the pluripotency inducer to the C2II chain. Omission of part of the C2I chain renders the construct atoxic and safe for use as a promoter of generation of iPS cells. Alternatively, the C2I domain can be inactivated by modifications or deletions of the active site. Also, some of the residues may be altered as shown in the figures below.

FIGS. 4A through 4E show some representative examples of constructs that can be made in accordance with one embodiment of the present invention. In FIG. 4A, a basic C2II construct is presented with a SBP and a His tag (SEQ ID No. 9). FIG. 4B shows a construct having Oct4 and an inactivated C2I domain (SEQ ID No. 10). The C2I domain can be inactivated by point mutations at aa600, 602, 804, 805, and 807 of the construct. The SBP and Histidine tags are optional. FIG. 4C shows a construct having Oct4 and a truncated C2I (SEQ ID No. 11), which truncation renders it inactive. FIG. 4D shows a construct having Sox2 and an inactivated C2I sequence (SEQ ID No. 12). FIG. 4E shows a truncated C2I with Sox 2 (SEQ ID No 13).

IV. *Clostridium* Toxin Domain Swapping.

The various *Clostridium* toxins bind to different cell types. The RBDs of the *Clostridium* toxins can be interchanged/swapped proving a variety of different constructs capable of delivering inducers to somatic cells. By domain swapping of the C-terminal RBD, one can create different constructs for cell-type or tissue-specific delivery. In one embodiment the RBD of TcdA or TcdB can be replaced with the RBD selected from BoNT for targeting neuronal cells. In another embodiment the RBD of TcdA or TcdB can be replaced with a ligand that binds to a cell-type or tissue-specific cell surface receptor and triggers the receptor-mediated internalization. In all, permutated protein-based delivery vehicles for different utility can be created by combination of the N-terminal domain swapping and C-terminal domain swapping.

Beyond a delivery vehicle itself, the C-terminus RBD of the BoNT can be used to replace the RBD of TcdA or TcdB and to create a protein delivery vehicle specifically targeting neuronal cells. Similarly, the RBD of TcdA or TcdB can be used to replace the BoNT's RBD resulting in non-cell-specific targeting of the inducer by the BoNT construct. Furthermore, the BoNT light chain can be used to replace the N-terminus of TcdB or TcdA to enhance desired biological function of cargo proteins that are fused to the N-terminus of BoNT light chain. The light chain is selected from BoNT type A to G, preferably the light chain of *C. botulinum* neurotoxin type A. Therefore, by using domain swap between *Clostridium* exotoxins, as shown herein, various pluripotency inducer delivery vehicles can be synthesized.

FIGS. 5A through 5D show some representative examples of constructs that can be made in accordance with one embodiment of the present invention. In FIG. 5A, Oct4 is attached to a BoNT/C1 as the TD and a TcdB RBD (SEQ ID No. 14). In the construct of FIG. 5A the activity of the light chain of BoNT/C1 can be destroyed by the modifications shown. FIG. 5B shows a Sox 2 with a BoNT/C1 TD and a TcdB RBD (SEQ ID No. 15). FIG. 5C shows a construct having Oct4 as the inducer, C2I as the TD and Transferrin as the RBD (SEQ ID No. 16). FIG. 5D is similar to FIG. 5C but utilizes Sox 2 instead of Oct4 (SEQ ID No. 17). FIG. 5E provides a further example of a construct in accordance with one embodiment of the present invention in which the inducer is Oct4, the CBD and TD are provided by BoNT/C1 and the RBD corresponds to ILGF (SEQ ID No. 18). FIG. 5F provides a further example of a construct in accordance with one embodiment of the present invention in which the inducer is Sox2, the CBD and TD are provided by BoNT/C1 and the RBD corresponds to ILGF (SEQ ID No. 19).

A person of ordinary skill in the art would recognize that the constructs can be made by standard methods. For example, the construct can be expressed in *E. coli* or algae systems by standard methods. Humphreys, David P. et al. *High-Level Periplasmic Expression in Escherichia coli Using a Eukaryotic Signal Peptide: Importance of Codon Usage at the 59 End of the Coding Sequence*, Protein Expression and Purification 20, 252-264 (2000); Griswold, Karl E. et al., *Effects of Codon Usage Versus Putative 50-mRNA Structure on the Expression of Fusarium solani cutinase in the Escherichia coli Cytoplasm*, Protein Expression and Purification 27: 134-142 (2003); Mayfield, Stephen P et al., *Chlamydomonas reinhardtii Chloroplasts as Protein Factories*, Current Opinion in Biotechnology, 18:126-133 (2007).

V. Examples

Preparation of Tcdb Construct

We have successfully demonstrated robust recombinant expression of *C. difficile* toxins using the *B. megaterium* expression system. Both the TcdA and TcdB genes were amplified from *C. difficile* (VPI 10463) genomic DNA by PCR. These PCR products were cloned into the *B. megaterium* expression vector pHis1522 (MoBiTec, Germany). We also created an atoxic TcdB gene by mutating amino acids critical for substrate binding in the glucosyltransferase domain. These constructs were used to transfect *B. megaterium* protoplasts (MoBiTec). Additionally, we also generated a complete synthetic genetic construct encoding TcdB to facilitate recombinant constructs in the future. A GT truncated mutant was also made from Gal4-TF/aTcdB with only 68 amino acids upstream of the self-cleavage site (−ΔGT68). Positive clones were selected for recombinant protein expression and purification of recombinant His-tagged recombinant TcdB (rTcdB) from bacterial lysate was performed by Ni-affinity chromatography following an ion-exchange fractionation. With these clones, we have performed small-scale time-course expression studies and found the peak expression for both recombinant proteins to be 2-3 hr after xylose induction as shown in FIG. 6.

We were able to obtain an average of 5-10 mg of highly purified recombinant proteins from the lysate of one liter of total bacterial culture. The purified rTcdB was functionally tested in mouse intestinal epithelial CT26 cells for their cytopathic and cytotoxic effects and glucosylation of Rac1. Exposure of cells to the highest dose possible of atoxic TcdB (aTcdB) for a prolonged period of time indicated that the mutant GT is virtually devoid of enzymatic activity (~5 logs) and exhibited dramatically reduced cytotoxicity (>5 logs). FIG. 4 shows that no cytopathic effect was observed on those cells treated with aTcdB.

Figure 7:
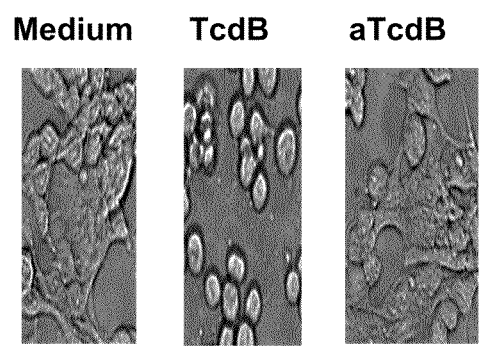

To verify that the recombinant TcdB is capable of delivering a fused cargo to cells, we appended a small enzyme (O6-alkylguanine-DNA alkyltransferase, called SNAP-tag by New England Biolabs) to the amino terminus of TcdB. We can efficiently express the chimeric fusion of SNAP-tag to active recombinant TcdB. The chimeric protein retains toxicity roughly equivalent to wild type TcdB, indicating that the cargo must have accessed the cell cytosol because it is appended to the glucosyltransferase domain of TcdB that causes the toxicity only after it reaches in the cytosol as shown in FIG. 7.

Demonstration of SNAP-TcdB Fusion Protein Construction, Purification, and Biological Functionality.

Figure 8:
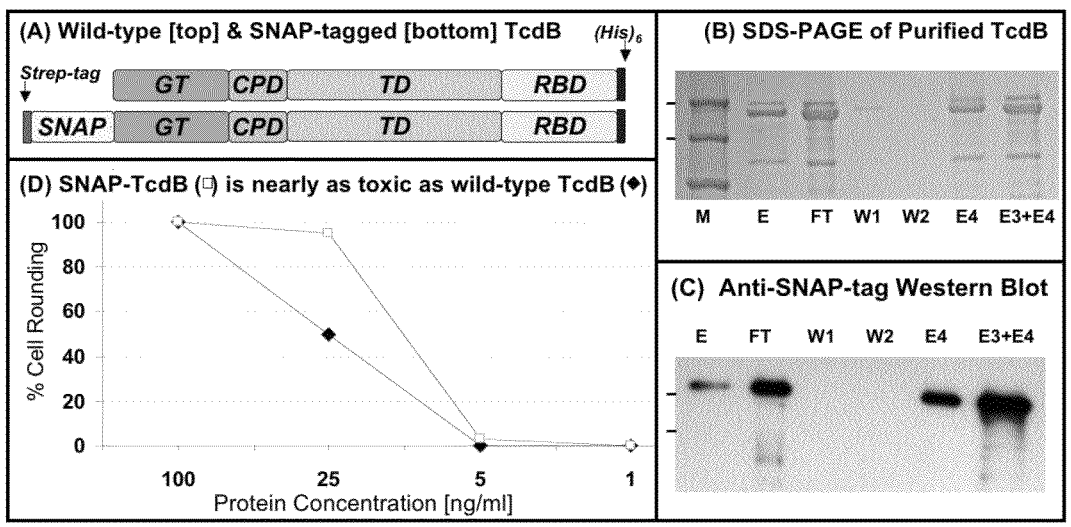

As shown in FIG. 8A, the domain structure of the N-modified SNAP-TcdB fusion is a 270 kD peptide in comparison to the wild-type which is 290 kD. The wild type TcdB construct had hexahistidine tag. The SNAP-TcdB construct was labeled with hexahistidine and streptavidin tags for affinity purification. FIG. 8B, shows the full-length SNAP-TcdB products recovered by streptavidin purification; the eluent (E) and flow through (FT) can be compared to the wild-type (W) samples, which yielded no products as expected. In FIG. 8C, a Western blot analysis of the purified samples show strong signals using an anti-SNAP-tag antibody. Finally, in FIG. 8D, Vero cells were exposed to different doses of purified SNAP-TcdB or wild-type TcdB for 1 hr and % of cell rounding was assessed. The results confirm that the addition of a fusion partner to TcdB does not adversely its biological function and remains able to delivery cargo to cells.

Construction & Functional Testing of the Reporter Constructs in Existing Cell-Based Systems.

The functional TcdB peptide described above can be used to develop the construct in accordance with one embodiment of the present invention. The construct can be constructed by adding the sequence of a pluripotency inducer to the N-terminal end of the aTcdB construct. The pluripotency inducer/TcdB construct can then be tested in one of two systems.

A mammalian reporter cell line used to detect the presence of a Gal4 DNA binding domain/NFkB activation domain-based chimeric transcription factor (Gal4-TF) can be modified to be used as a reporter for pluripotency inducer construct testing. The HEK293 cell line has a synthetic reporter construct integrated consisting of a Gal4-responsive promoter that expresses a bi-cistronic reporter gene containing the YFP Venus gene followed by a Gaussia luciferase gene (GLuc) gene. The Venus and Gluc are separated by a "self-cleavage" peptide 2A of the foot-and-mouth disease virus allowing independent expression of the two reporter proteins. Inclusion of both reporter genes permits instantaneous examination of cells microscopically for Venus fluorescence as well as detection of GLuc bioluminescence. With a Gal4 based transcription factor as a cargo appendage to aTcdB, this system can be used to test functional cellular delivery of a transcription factor/pluripotency inducer. The Gal4 DNA binding sequence promoter of the HEK293 Venus/Gluc reporter system can be replaced the with an Oct4/Sox2 element repeat 4 times. Other pluripotency inducers can also be tested by replacing the Gal4 DNA binding sequence promoter of the HEK293 Venus/Gluc reporter system with their respective sequences.

A second Oct4/Sox2-based cell line reporter may be utilized to test the construct. This second system consists of the DNA-binding regions required for Oct4 and Sox2 for site-specific promoter activation (Ambrosetti D-C et al., *Modulation of the Activity of Multiple Transcriptional Activation Domains by the DNA Binding Domains Mediates the Synergistic Action of Sox2 and Oct-3 on the Fibroblast Growth Factor-4 Enhancer*, J. Biological Chem. 275:23387-23397 (2000)). The promoter reporter gene construct referred to as pCATSO3 contains six copies of the HMG and POU motifs present in the FGF-4 enhancer located upstream of a basal SV40 promoter. The HMG motif binds Sox2 and the adjacent POU motif binds Oct4 (Chakravarthy, H. et al., *Identification of DPPA4 and Other Genes as Putative Sox2:Oct-3/4 Target Genes Using a Combination of in Silico Analysis and Transcription-Based Assays*, J. Cellular Physiology, 216:651-662 (2008); Rizzino, A. *Sox2 and Oct-3/4: A Versatile Pair of Master Regulators that Orchestrate the Self-Renewal and Pluripotency of Embryonic Stem Cells by Functioning as Molecular Rheostats*, System Biology and Medicine, WIREs Syst Biol Med 1(2), (2009)). HeLa cells, pCATSO3 expresses very low levels of the reporter gene (CAT). This promoter reporter gene construct is highly sensitive to the presence of Sox2 and Oct4, which are not expressed in HeLa cells at baseline. When HeLa cells are transfected with pCATSO3 along with expression vectors for Sox2 and Oct4, there is a robust stimulation (>40-fold) of the reporter gene. Sox2 and Oct4 each stimulate the reporter gene ~3-fold. Given the synergistic response to Sox2 and Oct4, this assay can provide a highly sensitive test to gauge the ability of the Sox2- and Oct4-aTcdB fusion proteins to work together cooperatively.

Demonstration of Bioactive Oct4 & Sox2 Delivery by aTcdB to Oct4/Sox2 Reporter Cell Lines.

For a cellular-based differentiation assay, we will take advantage of the finding made by the Smith and Rizzino laboratories, which have shown that small increases (~2-fold) in the levels of Oct4 or Sox2 trigger the differentiation of mouse ES cells (Niwa H, et al. *Quantitative Expression of Oct-3/4 Defines Differentiation, Dedifferentiation or Self-Renewal of ES Cells*, Nat Genet. 24:372-376 (2000); Kopp, J. et al., *Small Increases in the Levels of Sox2 Trigger the Differentiation of Embryonic Stem Cells*, Stem Cells 26:903-911 (2008)). In the case where Oct4 is elevated, ES cells differentiate within 48 hrs into cells that express markers of extraembryonic endoderm and trophectoderm (Niwa H, Nat Genet. 24:372-376). In the case where Sox2 is elevated, ES cells differentiate within 48 hrs into cells that express markers present in ectoderm, mesoderm and trophectoderm, but not endoderm (Kopp, J. Stem Cells 26:903-911). These differentiation markers are readily determined by RNA analysis using real-time RT-PCR (Kopp, J. Stem Cells 26:903-911). Using this assay, the individual functions of the Oct4-aTcdB fusion protein and the Sox2-aTcdB fusion protein can be assessed by determining their ability to drive the differentiation of ES cells into specific sets of differentiated cells.

For a cell-based transcription assay, we propose to test the ability of Oct4- and Sox2-aTcdB fusion proteins to stimulate the promoter/reporter gene construct that has been stably transfected into HeLa cells. This cell reporter system has been constructed and works well for this type of assay as described previously. The Sox2- and Oct4-aTcdB fusion proteins will be tested individually and in combination over a range of protein concentrations. For these studies, we will compare the ability of the Sox2- and Oct4-aTcdB fusion proteins to stimulate the promoter reporter gene construct with the ability of Sox2 and Oct4 delivered by lentiviral vectors to stimulate pCATSO3 (Nowling, T. et al., *Transactivation Domain of the Transcription Factor Sox-2 and its Associated Coactivator*, J. Biol. Chem. 275:3810-3818 (2000)).

Additionally, an Oct4/Sox2 reporter cell system closely related to the Gal4-TF cell line can be constructed and tested with direct plasmid transfection. A synthetic reporter construct containing Venus/GLuc expressed from the SO3 promoter, containing six copies of the HMG and POU motifs to bind Sox2/Oct4, can be cloned into a lentiviral vector. Both sox2 and oct4 genes can then be synthesized and cloned into a pcDNA mammalian expression plasmid. This system can be validated by co-transfecting HEK 293 cells with the reporter construct and both sox2 and oct4 expression plasmids. Activation of this reporter can be monitored by GLuc assay and Venus (YFP) bioluminescence. After confirming intracellular Oct4/Sox2 activity, Oct4 and Sox2 may be separately cloned into the aTcdB delivery plasmid for production of inducer constructs. The reporter can be further validated by plasmid transfection of one of the embryonic transactivators (i.e. Sox2) complemented by protein delivery of the other factor (i.e. Oct4) and vice versa to assay the reporter response to the individually delivered protein. Finally, the aTcdB inducer construct can be used to deliver both factors in order to test the combinatorial effect and efficiency of the iPS cell-generating system. For comparison, protein delivery peptides (e.g., Tat-Oct4) can be used to demonstrate increased efficiency of the pluripotency inducer constructs.

De-Differentiation of Mouse Embryonic Fibroblasts to iPS Cells by Delivery of Sox2 & Oct4 Via aTcdB The efficiency of the fusion protein-mediated reprogramming can be compared to the efficiency of reprogramming observed when MEFs are infected with a lentiviral vector that expresses the four well-characterized reprogramming transcription factors (Cox, J. L., and Rizzino, A. *Induced Pluripotent Stem Cells: What Lies Beyond the Paradigm Shift*, Experimental Biology and Medicine 235:148-158 (2010)). MEFs have been reprogrammed using a lentiviral vector that expresses a polycistronic transcript that codes for Oct4, Sox2, Klf4 and c-Myc, which are separated from one another by self-cleaving peptides (2A from the foot and mouth disease virus). Each pluripotency inducer construct can be tested by infecting MEFs with an inducible lentiviral vector (Tet-on) that expresses other pluripotency inducers. For example, the pluripotency inducer construct containing Oct4 an Sox2 can be tested by infecting MEFs with an inducible lentiviral vector that expresses only Klf4 and c-Myc in response to doxycycline. These cells can then be used to assess the ability of the Sox2- and Oct4-aTcdB fusion proteins added to the medium daily along with doxycycline, to promote the formation of MEFs.

In addition to determining the efficiency of reprogramming (percentage of cells reprogrammed), the quality of the iPS cells generated can be assessed by examining a wide-range of well established properties of pluripotent stem cells, including: expression of endogenous pluripotency transcription factors (e.g. endogenous Sox2, Oct4, Nanog, UTF1), the demethylation of the endogenous Oct4 and Nanog genes, expression of the cell surface marker SSEA-1, and the ability of the iPS cells to differentiate into cells that express markers from each of the embryonic germ layers using embryoid bodies. Rizzino, A. *Transcriptional Regulation in an In Vitro Model System for Mammalian Embryogenesis*, In "Hormones and Growth Factors in Development and Neoplasia", eds. R. B. Dickson and D. S. Salomon, John Wiley & Sons, New York, pp. 115-129 (1998)).

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A construct for generating induced Pluripotent Stem (iPS) cells, comprising:
a receptor binding domain, a translocation domain, a cargo bearing domain, and an inducer, wherein the receptor binding domain, translocation domain, and cargo domain are atoxic *Clostridium* toxin domains.

2. The construct of claim 1, wherein the *Clostridium* toxin is a *C. difficile* toxin.

3. The construct of claim 2, wherein the *C. difficile* toxin is TcdA.

4. The construct of claim 2, wherein the *C. difficile* toxin is TcdB.

5. The construct of claim 2, wherein the inducer is selected from the group consisting of Sox2, Oct 3/4, Klf4, c-Myc, Nanog, lin28, hTERT (human telomerase), and SV40 large T-antigen.

6. The construct of claim 1, wherein the *Clostridium* toxin is a *C. botulinum* toxin.

7. The construct of claim 6, wherein the *C. botulinum* toxin is selected from the group consisting of BoNTA, BoNTB, BoNTC, BoNTD, BoNTE, BoNTF and BoNTG.

8. The construct of claim 6, wherein a receptor binding domain of the *C. botulinum* toxin is replaced with a non-specific receptor binding domain.

9. The construct of claim 6, wherein the inducer is selected from the group consisting of Sox2, Oct 3/4, Klf4, c-Myc, Nanog, lin28, hTERT (human telomerase), and SV40 large T-antigen.

10. The construct of claim 1, wherein the *Clostridium* toxin is a clostridial C2 toxin.

11. The construct of claim 10, wherein the inducer is selected from the group consisting of Sox2, Oct 3/4, Klf4, c-Myc, Nanog, lin28, hTERT (human telomerase), and SV40 large T-antigen.

12. The construct of claim 1, wherein the inducer is Oct3/4.

13. The construct of claim 12, wherein the construct has a sequence comprising the amino acid sequence of SEQ ID NO: 1.

14. The construct of claim 12, wherein the construct has a sequence comprising the amino acid sequence of SEQ ID NO: 2.

15. The construct of claim 12, wherein the construct has a sequence substantially identical to a sequence selected from the group consisting of SEQ ID NO: 1 and SEQ ID NO: 2, wherein no more than 20% of the amino acid residues vary between the construct sequence and SEQ ID NO: 1 or SEQ ID NO: 2.

16. The construct of claim 1, wherein the inducer is Sox2.

17. The construct of claim 16, wherein the construct has a sequence comprising the amino acid sequence of SEQ ID NO: 5.

18. The construct of claim 16, wherein the construct has a sequence comprising the amino acid sequence of SEQ ID NO: 6.

19. The construct of claim 16, wherein the construct has a sequence substantially identical to a sequence selected from the group consisting of SEQ ID NO: 5, SEQ ID NO: 6, and SEQ ID NO: 7, wherein no more than 20% of the amino acid residues vary between the construct sequence and SEQ ID NO: 5, SEQ ID NO: 6, or SEQ ID NO: 7.

20. The construct of claim 1, wherein the inducer is selected from the group consisting of Klf4, c-Myc, Nanog, lin28, hTERT (human telomerase), and SV40 large T-antigen.

21. The construct of claim 1, wherein said cargo bearing domain is an inactive exotoxin domain.

22. A construct for generating induced Pluripotent Stem (iPS) cells, comprising:

(i) an atoxic *Clostridium* toxin comprising a receptor binding domain and a translocation domain; and (ii) an inducer.

23. The construct of claim 22, wherein the *Clostridium* toxin is a *C. difficile* toxin.

24. The construct of claim 23, wherein the *C. difficile* toxin is TcdA.

25. The construct of claim 23, wherein the *C. difficile* toxin is TcdB.

26. The construct of claim 23, wherein the inducer is selected from the group consisting of Sox2, Oct 3/4, Klf4, c-Myc, Nanog, lin28, hTERT (human telomerase), and SV40 large T-antigen.

27. The construct of claim 22, wherein the *Clostridium* toxin is a *C. botulinum* toxin.

28. The construct of claim 27, wherein the *C. botulinum* toxin is selected from the group consisting of BoNTA, BoNTB, BoNTC, BoNTD, BoNTE, BoNTF and BoNTG.

29. The construct of claim 27, wherein a receptor binding domain of the *C. botulinum* toxin is replaced with a non-specific receptor binding domain.

30. The construct of claim 27, wherein the inducer is selected from the group consisting of Sox2, Oct 3/4, Klf4, c-Myc, Nanog, lin28, hTERT (human telomerase), and SV40 large T-antigen.

31. The construct of claim 22, wherein the *Clostridium* toxin is a clostridial C2 toxin.

32. The construct of claim 31, wherein the inducer is selected from the group consisting of Sox2, Oct 3/4, Klf4, c-Myc, Nanog, lin28, hTERT (human telomerase), and SV40 large T-antigen.

33. The construct of claim 22, wherein the inducer is Oct3/4.

34. The construct of claim 33, wherein the construct has a sequence comprising the amino acid sequence of SEQ ID NO: 1.

35. The construct of claim 33, wherein the construct has a sequence comprising the amino acid sequence of SEQ ID NO: 2.

36. The construct of claim 33, wherein the construct has a sequence substantially identical to a sequence selected from the group consisting of SEQ ID NO: 1 and SEQ ID NO: 2, wherein no more than 20% of the amino acid residues vary between the construct sequence and SEQ ID NO:1 or SEQ ID NO: 2.

37. The construct of claim 22, wherein the inducer is Sox2.

38. The construct of claim 37, wherein the construct has a sequence comprising the amino acid sequence of SEQ ID NO: 5.

39. The construct of claim 37, wherein the construct has a sequence comprising the amino acid sequence of SEQ ID NO: 6.

40. The construct of claim 37, wherein the construct has a sequence substantially identical to a sequence selected from the group consisting of SEQ ID NO: 5, SEQ ID NO: 6, and SEQ ID NO: 7, wherein no more than 20% of the amino acid residues vary between the construct sequence and SEQ ID NO: 5, SEQ ID NO: 6, or SEQ ID NO: 7.

41. The construct of claim 22, wherein the inducer is selected from the group consisting of Klf4, c-Myc, Nanog, lin28, hTERT (human telomerase), and SV40 large T-antigen.

42. The construct of claim 22, further comprising a cargo domain.

* * * * *

```
                              SEQUENCE LISTING

<160> NUMBER OF SEQ ID NOS: 19

<210> SEQ ID NO 1
<211> LENGTH: 2790
<212> TYPE: PRT
<213> ORGANISM: Artificial Sequence
<220> FEATURE:
<223> OTHER INFORMATION: Fusion Peptide Human Oct4/C. difficile TcdB

<400> SEQUENCE: 1

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
            20                  25                  30

Leu Ala Gly Glu Leu Glu Gln Leu Arg Ala Arg Leu Glu His His Pro
        35                  40                  45

Gln Gly Gln Arg Glu Pro Ser Gly Ala Ala Gly His Leu Ala Ser Asp
    50                  55                  60

Phe Ala Phe Ser Pro Pro Pro Gly Gly Gly Gly Asp Gly Pro Gly Gly
65                  70                  75                  80

Pro Glu Pro Gly Trp Val Asp Pro Arg Thr Trp Leu Ser Phe Gln Gly
                85                  90                  95

Pro Pro Gly Gly Pro Gly Ile Gly Pro Gly Val Gly Pro Gly Ser Glu
            100                 105                 110

Val Trp Gly Ile Pro Pro Cys Pro Pro Pro Tyr Glu Phe Cys Gly Gly
        115                 120                 125

Met Ala Tyr Cys Gly Pro Gln Val Gly Val Gly Leu Val Pro Gln Gly
    130                 135                 140

Gly Leu Glu Thr Ser Gln Pro Glu Gly Glu Ala Gly Val Gly Val Glu
145                 150                 155                 160

Ser Asn Ser Asp Gly Ala Ser Pro Glu Pro Cys Thr Val Thr Pro Gly
                165                 170                 175

Ala Val Lys Leu Glu Lys Glu Lys Leu Glu Gln Asn Pro Glu Glu Ser
            180                 185                 190

Gln Asp Ile Lys Ala Leu Gln Lys Glu Leu Glu Gln Phe Ala Lys Leu
        195                 200                 205

Leu Lys Gln Lys Arg Ile Thr Leu Gly Tyr Thr Gln Ala Asp Val Gly
    210                 215                 220

Leu Thr Leu Gly Val Leu Phe Gly Lys Val Phe Ser Gln Thr Thr Ile
225                 230                 235                 240

Cys Arg Phe Glu Ala Leu Gln Leu Ser Phe Lys Asn Met Cys Lys Leu
                245                 250                 255

Arg Pro Leu Leu Gln Lys Trp Val Glu Glu Ala Asp Asn Asn Glu Asn
            260                 265                 270

Leu Gln Glu Ile Cys Lys Ala Glu Thr Leu Val Gln Ala Arg Lys Arg
        275                 280                 285

Lys Arg Thr Ser Ile Glu Asn Arg Val Arg Gly Asn Leu Glu Asn Leu
    290                 295                 300

Phe Leu Gln Cys Pro Lys Pro Thr Leu Gln Gln Ile Ser His Ile Ala
```

-continued

```
            305                 310                 315                 320
Gln Gln Leu Gly Leu Glu Lys Asp Val Val Arg Val Trp Phe Cys Asn
                    325                 330                 335

Arg Arg Gln Lys Gly Lys Arg Ser Ser Ser Asp Tyr Ala Gln Arg Glu
                    340                 345                 350

Asp Phe Glu Ala Ala Gly Ser Pro Phe Ser Gly Pro Val Ser Phe
                    355                 360                 365

Pro Leu Ala Pro Gly Pro His Phe Gly Thr Pro Gly Tyr Gly Ser Pro
                    370                 375                 380

His Phe Thr Ala Leu Tyr Ser Ser Val Pro Phe Pro Glu Gly Glu Ala
385                 390                 395                 400

Phe Pro Pro Val Ser Val Thr Thr Leu Gly Ser Pro Met His Ser Asn
                    405                 410                 415

Ala Ala Ala Ser Leu Val Asn Arg Lys Gln Leu Glu Lys Met Ala Asn
                    420                 425                 430

Val Arg Phe Arg Thr Gln Glu Asp Glu Tyr Val Ala Ile Leu Asp Ala
                    435                 440                 445

Leu Glu Glu Tyr His Asn Met Ser Glu Asn Thr Val Val Glu Lys Tyr
                450                 455                 460

Leu Lys Leu Lys Asp Ile Asn Ser Leu Thr Asp Ile Tyr Ile Asp Thr
465                 470                 475                 480

Tyr Lys Lys Ser Gly Arg Asn Lys Ala Leu Lys Lys Phe Lys Glu Tyr
                    485                 490                 495

Leu Val Thr Glu Val Leu Glu Leu Lys Asn Asn Asn Leu Thr Pro Val
                500                 505                 510

Glu Lys Asn Leu His Phe Val Trp Ile Gly Gly Gln Ile Asn Asp Thr
                515                 520                 525

Ala Ile Asn Tyr Ile Asn Gln Trp Lys Asp Val Asn Ser Asp Tyr Asn
                530                 535                 540

Val Asn Val Phe Tyr Asp Ser Asn Ala Phe Leu Ile Asn Thr Leu Lys
545                 550                 555                 560

Lys Thr Val Val Glu Ser Ala Ile Asn Asp Thr Leu Glu Ser Phe Arg
                    565                 570                 575

Glu Asn Leu Asn Asp Pro Arg Phe Asp Tyr Asn Lys Phe Phe Arg Lys
                    580                 585                 590

Arg Met Glu Ile Ile Tyr Asp Lys Gln Lys Asn Phe Ile Asn Tyr Tyr
                    595                 600                 605

Lys Ala Gln Arg Glu Glu Asn Pro Glu Leu Ile Ile Asp Asp Ile Val
                    610                 615                 620

Lys Thr Tyr Leu Ser Asn Glu Tyr Ser Lys Glu Ile Asp Glu Leu Asn
625                 630                 635                 640

Thr Tyr Ile Glu Glu Ser Leu Asn Lys Ile Thr Gln Asn Ser Gly Asn
                    645                 650                 655

Asp Val Arg Asn Phe Glu Glu Phe Lys Asn Gly Glu Ser Phe Asn Leu
                    660                 665                 670

Tyr Glu Gln Glu Leu Val Glu Arg Trp Asn Leu Ala Ala Ala Ser Asp
                    675                 680                 685

Ile Leu Arg Ile Ser Ala Leu Lys Glu Ile Gly Gly Met Tyr Leu Ala
                    690                 695                 700

Val Ala Met Leu Pro Gly Ile Gln Pro Asp Leu Phe Glu Ser Ile Glu
705                 710                 715                 720

Lys Pro Ser Ser Val Thr Val Asp Phe Trp Glu Met Thr Lys Leu Glu
                    725                 730                 735
```

-continued

Ala Ile Met Lys Tyr Lys Glu Tyr Ile Pro Glu Tyr Thr Ser Glu His
            740                 745                 750

Phe Asp Met Leu Asp Glu Glu Val Gln Ser Ser Phe Glu Ser Val Leu
            755                 760                 765

Ala Ser Lys Ser Asp Lys Ser Glu Ile Phe Ser Leu Gly Asp Met
770                 775                 780

Glu Ala Ser Pro Leu Glu Val Lys Ile Ala Phe Asn Ser Lys Gly Ile
785                 790                 795                 800

Ile Asn Gln Gly Leu Ile Ser Val Lys Asp Ser Tyr Cys Ser Asn Leu
                805                 810                 815

Ile Val Lys Gln Ile Glu Asn Arg Tyr Lys Ile Leu Asn Asn Ser Leu
            820                 825                 830

Asn Pro Ala Ile Ser Glu Asp Asn Asp Phe Asn Thr Thr Thr Asn Thr
            835                 840                 845

Phe Ile Asp Ser Ile Met Ala Glu Ala Asn Ala Asp Asn Gly Arg Phe
            850                 855                 860

Met Met Glu Leu Gly Lys Tyr Leu Arg Val Gly Phe Phe Pro Asp Val
865                 870                 875                 880

Lys Thr Thr Ile Asn Leu Ser Gly Pro Glu Ala Tyr Ala Ala Ala Tyr
                885                 890                 895

Gln Asp Leu Leu Met Phe Lys Glu Gly Ser Met Asn Ile His Leu Ile
                900                 905                 910

Glu Ala Asp Leu Arg Asn Phe Glu Ile Ser Lys Thr Asn Ile Ser Gln
            915                 920                 925

Ser Thr Glu Gln Glu Met Ala Ser Leu Trp Ser Phe Asp Asp Ala Arg
            930                 935                 940

Ala Lys Ala Gln Phe Glu Glu Tyr Lys Arg Asn Tyr Phe Glu Gly Ser
945                 950                 955                 960

Leu Gly Glu Asp Asp Asn Leu Asp Phe Ser Gln Asn Ile Val Val Asp
                965                 970                 975

Lys Glu Tyr Leu Leu Glu Lys Ile Ser Ser Leu Ala Arg Ser Ser Glu
            980                 985                 990

Arg Gly Tyr Ile His Tyr Ile Val Gln Leu Gln Gly Asp Lys Ile Ser
            995                 1000                1005

Tyr Glu Ala Ala Cys Asn Leu Phe Ala Lys Thr Pro Tyr Asp Ser
    1010                1015                1020

Val Leu Phe Gln Lys Asn Ile Glu Asp Ser Glu Ile Ala Tyr Tyr
    1025                1030                1035

Tyr Asn Pro Gly Asp Gly Glu Ile Gln Glu Ile Asp Lys Tyr Lys
    1040                1045                1050

Ile Pro Ser Ile Ile Ser Asp Arg Pro Lys Ile Lys Leu Thr Phe
    1055                1060                1065

Ile Gly His Gly Lys Asp Glu Phe Asn Thr Asp Ile Phe Ala Gly
    1070                1075                1080

Phe Asp Val Asp Ser Leu Ser Thr Glu Ile Glu Ala Ala Ile Asp
    1085                1090                1095

Leu Ala Lys Glu Asp Ile Ser Pro Lys Ser Ile Glu Ile Asn Leu
    1100                1105                1110

Leu Gly Cys Asn Met Phe Ser Tyr Ser Ile Asn Val Glu Glu Thr
    1115                1120                1125

Tyr Pro Gly Lys Leu Leu Leu Lys Val Lys Asp Lys Ile Ser Glu
    1130                1135                1140

Leu Met Pro Ser Ile Ser Gln Asp Ser Ile Ile Val Ser Ala Asn
    1145                1150                1155

```
Gln Tyr Glu Val Arg Ile Asn Ser Glu Gly Arg Arg Glu Leu Leu
    1160            1165            1170

Asp His Ser Gly Glu Trp Ile Asn Lys Glu Glu Ser Ile Ile Lys
    1175            1180            1185

Asp Ile Ser Ser Lys Glu Tyr Ile Ser Phe Asn Pro Lys Glu Asn
    1190            1195            1200

Lys Ile Thr Val Lys Ser Lys Asn Leu Pro Glu Leu Ser Thr Leu
    1205            1210            1215

Leu Gln Glu Ile Arg Asn Asn Ser Asn Ser Ser Asp Ile Glu Leu
    1220            1225            1230

Glu Glu Lys Val Met Leu Thr Glu Cys Glu Ile Asn Val Ile Ser
    1235            1240            1245

Asn Ile Asp Thr Gln Ile Val Glu Glu Arg Ile Glu Glu Ala Lys
    1250            1255            1260

Asn Leu Thr Ser Asp Ser Ile Asn Tyr Ile Lys Asp Glu Phe Lys
    1265            1270            1275

Leu Ile Glu Ser Ile Ser Asp Ala Leu Cys Asp Leu Lys Gln Gln
    1280            1285            1290

Asn Glu Leu Glu Asp Ser His Phe Ile Ser Phe Glu Asp Ile Ser
    1295            1300            1305

Glu Thr Asp Glu Gly Phe Ser Ile Arg Phe Ile Asn Lys Glu Thr
    1310            1315            1320

Gly Glu Ser Ile Phe Val Glu Thr Glu Lys Thr Ile Phe Ser Glu
    1325            1330            1335

Tyr Ala Asn His Ile Thr Glu Glu Ile Ser Lys Ile Lys Gly Thr
    1340            1345            1350

Ile Phe Asp Thr Val Asn Gly Lys Leu Val Lys Lys Val Asn Leu
    1355            1360            1365

Asp Thr Thr His Glu Val Asn Thr Leu Asn Ala Ala Phe Phe Ile
    1370            1375            1380

Gln Ser Leu Ile Glu Tyr Asn Ser Ser Lys Glu Ser Leu Ser Asn
    1385            1390            1395

Leu Ser Val Ala Met Lys Val Gln Val Tyr Ala Gln Leu Phe Ser
    1400            1405            1410

Thr Gly Leu Asn Thr Ile Thr Asp Ala Ala Lys Val Val Glu Leu
    1415            1420            1425

Val Ser Thr Ala Leu Asp Glu Thr Ile Asp Leu Leu Pro Thr Leu
    1430            1435            1440

Ser Glu Gly Leu Pro Ile Ile Ala Thr Ile Ile Asp Gly Val Ser
    1445            1450            1455

Leu Gly Ala Ala Ile Lys Glu Leu Ser Glu Thr Ser Asp Pro Leu
    1460            1465            1470

Leu Arg Gln Glu Ile Glu Ala Lys Ile Gly Ile Met Ala Val Asn
    1475            1480            1485

Leu Thr Thr Ala Thr Thr Ala Ile Ile Thr Ser Ser Leu Gly Ile
    1490            1495            1500

Ala Ser Gly Phe Ser Ile Leu Leu Val Pro Leu Ala Gly Ile Ser
    1505            1510            1515

Ala Gly Ile Pro Ser Leu Val Asn Asn Glu Leu Val Leu Arg Asp
    1520            1525            1530

Lys Ala Thr Lys Val Val Asp Tyr Phe Lys His Val Ser Leu Val
    1535            1540            1545

Glu Thr Glu Gly Val Phe Thr Leu Leu Asp Asp Lys Ile Met Met
```

-continued

```
                         1550                1555                1560

Pro Gln Asp Asp Leu Val Ile Ser Glu Ile Asp Phe Asn Asn Asn
    1565                1570                1575

Ser Ile Val Leu Gly Lys Cys Glu Ile Trp Arg Met Glu Gly Gly
    1580                1585                1590

Ser Gly His Thr Val Thr Asp Asp Ile Asp His Phe Phe Ser Ala
    1595                1600                1605

Pro Ser Ile Thr Tyr Arg Glu Pro His Leu Ser Ile Tyr Asp Val
    1610                1615                1620

Leu Glu Val Gln Lys Glu Glu Leu Asp Leu Ser Lys Asp Leu Met
    1625                1630                1635

Val Leu Pro Asn Ala Pro Asn Arg Val Phe Ala Trp Glu Thr Gly
    1640                1645                1650

Trp Thr Pro Gly Leu Arg Ser Leu Glu Asn Asp Gly Thr Lys Leu
    1655                1660                1665

Leu Asp Arg Ile Arg Asp Asn Tyr Glu Gly Glu Phe Tyr Trp Arg
    1670                1675                1680

Tyr Phe Ala Phe Ile Ala Asp Ala Leu Ile Thr Thr Leu Lys Pro
    1685                1690                1695

Arg Tyr Glu Asp Thr Asn Ile Arg Ile Asn Leu Asp Ser Asn Thr
    1700                1705                1710

Arg Ser Phe Ile Val Pro Ile Ile Thr Thr Glu Tyr Ile Arg Glu
    1715                1720                1725

Lys Leu Ser Tyr Ser Phe Tyr Gly Ser Gly Gly Thr Tyr Ala Leu
    1730                1735                1740

Ser Leu Ser Gln Tyr Asn Met Gly Ile Asn Ile Glu Leu Ser Glu
    1745                1750                1755

Ser Asp Val Trp Ile Ile Asp Val Asp Asn Val Val Arg Asp Val
    1760                1765                1770

Thr Ile Glu Ser Asp Lys Ile Lys Lys Gly Asp Leu Ile Glu Gly
    1775                1780                1785

Ile Leu Ser Thr Leu Ser Ile Glu Glu Asn Lys Ile Ile Leu Asn
    1790                1795                1800

Ser His Glu Ile Asn Phe Ser Gly Glu Val Asn Gly Ser Asn Gly
    1805                1810                1815

Phe Val Ser Leu Thr Phe Ser Ile Leu Glu Gly Ile Asn Ala Ile
    1820                1825                1830

Ile Glu Val Asp Leu Leu Ser Lys Ser Tyr Lys Leu Leu Ile Ser
    1835                1840                1845

Gly Glu Leu Lys Ile Leu Met Leu Asn Ser Asn His Ile Gln Gln
    1850                1855                1860

Lys Ile Asp Tyr Ile Gly Phe Asn Ser Glu Leu Gln Lys Asn Ile
    1865                1870                1875

Pro Tyr Ser Phe Val Asp Ser Glu Gly Lys Glu Asn Gly Phe Ile
    1880                1885                1890

Asn Gly Ser Thr Lys Glu Gly Leu Phe Val Ser Glu Leu Pro Asp
    1895                1900                1905

Val Val Leu Ile Ser Lys Val Tyr Met Asp Asp Ser Lys Pro Ser
    1910                1915                1920

Phe Gly Tyr Tyr Ser Asn Asn Leu Lys Asp Val Lys Val Ile Thr
    1925                1930                1935

Lys Asp Asn Val Asn Ile Leu Thr Gly Tyr Tyr Leu Lys Asp Asp
    1940                1945                1950
```

```
Ile Lys Ile Ser Leu Ser Leu Thr Leu Gln Asp Glu Lys Thr Ile
    1955                1960                1965

Lys Leu Asn Ser Val His Leu Asp Glu Ser Gly Val Ala Glu Ile
    1970                1975                1980

Leu Lys Phe Met Asn Arg Lys Gly Asn Thr Asn Thr Ser Asp Ser
    1985                1990                1995

Leu Met Ser Phe Leu Glu Ser Met Asn Ile Lys Ser Ile Phe Val
    2000                2005                2010

Asn Phe Leu Gln Ser Asn Ile Lys Phe Ile Leu Asp Ala Asn Phe
    2015                2020                2025

Ile Ile Ser Gly Thr Thr Ser Ile Gly Gln Phe Glu Phe Ile Cys
    2030                2035                2040

Asp Glu Asn Asp Asn Ile Gln Pro Tyr Phe Ile Lys Phe Asn Thr
    2045                2050                2055

Leu Glu Thr Asn Tyr Thr Leu Tyr Val Gly Asn Arg Gln Asn Met
    2060                2065                2070

Ile Val Glu Pro Asn Tyr Asp Leu Asp Asp Ser Gly Asp Ile Ser
    2075                2080                2085

Ser Thr Val Ile Asn Phe Ser Gln Lys Tyr Leu Tyr Gly Ile Asp
    2090                2095                2100

Ser Cys Val Asn Lys Val Val Ile Ser Pro Asn Ile Tyr Thr Asp
    2105                2110                2115

Glu Ile Asn Ile Thr Pro Val Tyr Glu Thr Asn Thr Thr Tyr Pro
    2120                2125                2130

Glu Val Ile Val Leu Asp Ala Asn Tyr Ile Asn Glu Lys Ile Asn
    2135                2140                2145

Val Asn Ile Asn Asp Leu Ser Ile Arg Tyr Val Trp Ser Asn Asp
    2150                2155                2160

Gly Asn Asp Phe Ile Leu Met Ser Thr Ser Glu Glu Asn Lys Val
    2165                2170                2175

Ser Gln Val Lys Ile Arg Phe Val Asn Val Phe Lys Asp Lys Thr
    2180                2185                2190

Leu Ala Asn Lys Leu Ser Phe Asn Phe Ser Asp Lys Gln Asp Val
    2195                2200                2205

Pro Val Ser Glu Ile Ile Leu Ser Phe Thr Pro Ser Tyr Tyr Glu
    2210                2215                2220

Asp Gly Leu Ile Gly Tyr Asp Leu Gly Leu Val Ser Leu Tyr Asn
    2225                2230                2235

Glu Lys Phe Tyr Ile Asn Asn Phe Gly Met Met Val Ser Gly Leu
    2240                2245                2250

Ile Tyr Ile Asn Asp Ser Leu Tyr Tyr Phe Lys Pro Pro Val Asn
    2255                2260                2265

Asn Leu Ile Thr Gly Phe Val Thr Val Gly Asp Asp Lys Tyr Tyr
    2270                2275                2280

Phe Asn Pro Ile Asn Gly Gly Ala Ala Ser Ile Gly Glu Thr Ile
    2285                2290                2295

Ile Asp Asp Lys Asn Tyr Tyr Phe Asn Gln Ser Gly Val Leu Gln
    2300                2305                2310

Thr Gly Val Phe Ser Thr Glu Asp Gly Phe Lys Tyr Phe Ala Pro
    2315                2320                2325

Ala Asn Thr Leu Asp Glu Asn Leu Glu Gly Glu Ala Ile Asp Phe
    2330                2335                2340

Thr Gly Lys Leu Ile Ile Asp Glu Asn Ile Tyr Tyr Phe Asp Asp
    2345                2350                2355
```

-continued

Asn Tyr Arg Gly Ala Val Glu Trp Lys Glu Leu Asp Gly Glu Met
2360             2365             2370

His Tyr Phe Ser Pro Glu Thr Gly Lys Ala Phe Lys Gly Leu Asn
2375             2380             2385

Gln Ile Gly Asp Tyr Lys Tyr Phe Asn Ser Asp Gly Val Met
2390             2395             2400

Gln Lys Gly Phe Val Ser Ile Asn Asp Asn Lys His Tyr Phe Asp
2405             2410             2415

Asp Ser Gly Val Met Lys Val Gly Tyr Thr Glu Ile Asp Gly Lys
2420             2425             2430

His Phe Tyr Phe Ala Glu Asn Gly Glu Met Gln Ile Gly Val Phe
2435             2440             2445

Asn Thr Glu Asp Gly Phe Lys Tyr Phe Ala His His Asn Glu Asp
2450             2455             2460

Leu Gly Asn Glu Glu Gly Glu Glu Ile Ser Tyr Ser Gly Ile Leu
2465             2470             2475

Asn Phe Asn Asn Lys Ile Tyr Tyr Phe Asp Asp Ser Phe Thr Ala
2480             2485             2490

Val Val Gly Trp Lys Asp Leu Glu Asp Gly Ser Lys Tyr Tyr Phe
2495             2500             2505

Asp Glu Asp Thr Ala Glu Ala Tyr Ile Gly Leu Ser Leu Ile Asn
2510             2515             2520

Asp Gly Gln Tyr Tyr Phe Asn Asp Asp Gly Ile Met Gln Val Gly
2525             2530             2535

Phe Val Thr Ile Asn Asp Lys Val Phe Tyr Phe Ser Asp Ser Gly
2540             2545             2550

Ile Ile Glu Ser Gly Val Gln Asn Ile Asp Asp Asn Tyr Phe Tyr
2555             2560             2565

Ile Asp Asp Asn Gly Ile Val Gln Ile Gly Val Phe Asp Thr Ser
2570             2575             2580

Asp Gly Tyr Lys Tyr Phe Ala Pro Ala Asn Thr Val Asn Asp Asn
2585             2590             2595

Ile Tyr Gly Gln Ala Val Glu Tyr Ser Gly Leu Val Arg Val Gly
2600             2605             2610

Glu Asp Val Tyr Tyr Phe Gly Glu Thr Tyr Thr Ile Glu Thr Gly
2615             2620             2625

Trp Ile Tyr Asp Met Glu Asn Glu Ser Asp Lys Tyr Tyr Phe Asn
2630             2635             2640

Pro Glu Thr Lys Lys Ala Cys Lys Gly Ile Asn Leu Ile Asp Asp
2645             2650             2655

Ile Lys Tyr Tyr Phe Asp Glu Lys Gly Ile Met Arg Thr Gly Leu
2660             2665             2670

Ile Ser Phe Glu Asn Asn Asn Tyr Tyr Phe Asn Glu Asn Gly Glu
2675             2680             2685

Met Gln Phe Gly Tyr Ile Asn Ile Glu Asp Lys Met Phe Tyr Phe
2690             2695             2700

Gly Glu Asp Gly Val Met Gln Ile Gly Val Phe Asn Thr Pro Asp
2705             2710             2715

Gly Phe Lys Tyr Phe Ala His Gln Asn Thr Leu Asp Glu Asn Phe
2720             2725             2730

Glu Gly Glu Ser Ile Asn Tyr Thr Gly Trp Leu Asp Leu Asp Glu
2735             2740             2745

Lys Arg Tyr Tyr Phe Thr Asp Glu Tyr Ile Ala Ala Thr Gly Ser

-continued

```
    2750                2755                2760

Val Ile  Ile Asp Gly Glu Glu  Tyr Tyr Phe Asp Pro  Asp Thr Ala
    2765                2770                2775

Gln Leu  Val Ile Ser Glu His  His His His His His
    2780                2785                2790

<210> SEQ ID NO 2
<211> LENGTH: 2317
<212> TYPE: PRT
<213> ORGANISM: Artificial Sequence
<220> FEATURE:
<223> OTHER INFORMATION: Fusion Protein Human Oct4/C. difficile aTcdB

<400> SEQUENCE: 2

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
            20                  25                  30

Leu Ala Gly Glu Leu Glu Gln Leu Arg Ala Arg Leu Glu His His Pro
        35                  40                  45

Gln Gly Gln Arg Glu Pro Ser Gly Ala Ala Gly His Leu Ala Ser Asp
    50                  55                  60

Phe Ala Phe Ser Pro Pro Pro Gly Gly Gly Gly Asp Gly Pro Gly Gly
65                  70                  75                  80

Pro Glu Pro Gly Trp Val Asp Pro Arg Thr Trp Leu Ser Phe Gln Gly
                85                  90                  95

Pro Pro Gly Gly Pro Gly Ile Gly Pro Gly Val Gly Pro Gly Ser Glu
            100                 105                 110

Val Trp Gly Ile Pro Pro Cys Pro Pro Pro Tyr Glu Phe Cys Gly Gly
        115                 120                 125

Met Ala Tyr Cys Gly Pro Gln Val Gly Val Gly Leu Val Pro Gln Gly
    130                 135                 140

Gly Leu Glu Thr Ser Gln Pro Glu Gly Glu Ala Gly Val Gly Val Glu
145                 150                 155                 160

Ser Asn Ser Asp Gly Ala Ser Pro Glu Pro Cys Thr Val Thr Pro Gly
                165                 170                 175

Ala Val Lys Leu Glu Lys Glu Lys Leu Glu Gln Asn Pro Glu Glu Ser
            180                 185                 190

Gln Asp Ile Lys Ala Leu Gln Lys Glu Leu Glu Gln Phe Ala Lys Leu
        195                 200                 205

Leu Lys Gln Lys Arg Ile Thr Leu Gly Tyr Thr Gln Ala Asp Val Gly
    210                 215                 220

Leu Thr Leu Gly Val Leu Phe Gly Lys Val Phe Ser Gln Thr Thr Ile
225                 230                 235                 240

Cys Arg Phe Glu Ala Leu Gln Leu Ser Phe Lys Asn Met Cys Lys Leu
                245                 250                 255

Arg Pro Leu Leu Gln Lys Trp Val Glu Glu Ala Asp Asn Asn Glu Asn
            260                 265                 270

Leu Gln Glu Ile Cys Lys Ala Glu Thr Leu Val Gln Ala Arg Lys Arg
        275                 280                 285

Lys Arg Thr Ser Ile Glu Asn Arg Val Arg Gly Asn Leu Glu Asn Leu
    290                 295                 300

Phe Leu Gln Cys Pro Lys Pro Thr Leu Gln Gln Ile Ser His Ile Ala
305                 310                 315                 320

Gln Gln Leu Gly Leu Glu Lys Asp Val Val Arg Val Trp Phe Cys Asn
                325                 330                 335
```

```
Arg Arg Gln Lys Gly Lys Arg Ser Ser Ser Asp Tyr Ala Gln Arg Glu
            340                 345                 350

Asp Phe Glu Ala Ala Gly Ser Pro Phe Ser Gly Gly Pro Val Ser Phe
            355                 360                 365

Pro Leu Ala Pro Gly Pro His Phe Gly Thr Pro Gly Tyr Gly Ser Pro
            370                 375                 380

His Phe Thr Ala Leu Tyr Ser Ser Val Pro Phe Pro Glu Gly Glu Ala
385                 390                 395                 400

Phe Pro Pro Val Ser Val Thr Thr Leu Gly Ser Pro Met His Ser Asn
                405                 410                 415

Ala Ala Tyr Ala Ala Ala Tyr Gln Asp Leu Leu Met Phe Lys Glu Gly
            420                 425                 430

Ser Met Asn Ile His Leu Ile Glu Ala Asp Leu Arg Asn Phe Glu Ile
            435                 440                 445

Ser Lys Thr Asn Ile Ser Gln Ser Thr Glu Gln Glu Met Ala Ser Leu
            450                 455                 460

Trp Ser Phe Asp Asp Ala Arg Ala Lys Ala Gln Phe Glu Glu Tyr Lys
465                 470                 475                 480

Arg Asn Tyr Phe Glu Gly Ser Leu Gly Glu Asp Asp Asn Leu Asp Phe
                485                 490                 495

Ser Gln Asn Ile Val Asp Lys Glu Tyr Leu Leu Glu Lys Ile Ser
            500                 505                 510

Ser Leu Ala Arg Ser Ser Glu Arg Gly Tyr Ile His Tyr Ile Val Gln
            515                 520                 525

Leu Gln Gly Asp Lys Ile Ser Tyr Glu Ala Ala Cys Asn Leu Phe Ala
            530                 535                 540

Lys Thr Pro Tyr Asp Ser Val Leu Phe Gln Lys Asn Ile Glu Asp Ser
545                 550                 555                 560

Glu Ile Ala Tyr Tyr Asn Pro Gly Asp Gly Glu Ile Gln Glu Ile
                565                 570                 575

Asp Lys Tyr Lys Ile Pro Ser Ile Ile Ser Asp Arg Pro Lys Ile Lys
            580                 585                 590

Leu Thr Phe Ile Gly His Gly Lys Asp Glu Phe Asn Thr Asp Ile Phe
            595                 600                 605

Ala Gly Phe Asp Val Asp Ser Leu Ser Thr Glu Ile Glu Ala Ala Ile
            610                 615                 620

Asp Leu Ala Lys Glu Asp Ile Ser Pro Lys Ser Ile Glu Ile Asn Leu
625                 630                 635                 640

Leu Gly Cys Asn Met Phe Ser Tyr Ser Ile Asn Val Glu Glu Thr Tyr
                645                 650                 655

Pro Gly Lys Leu Leu Leu Lys Val Lys Asp Lys Ile Ser Glu Leu Met
            660                 665                 670

Pro Ser Ile Ser Gln Asp Ser Ile Ile Val Ser Ala Asn Gln Tyr Glu
            675                 680                 685

Val Arg Ile Asn Ser Glu Gly Arg Arg Glu Leu Leu Asp His Ser Gly
            690                 695                 700

Glu Trp Ile Asn Lys Glu Ser Ile Ile Lys Asp Ile Ser Ser Lys
705                 710                 715                 720

Glu Tyr Ile Ser Phe Asn Pro Lys Glu Asn Lys Ile Thr Val Lys Ser
                725                 730                 735

Lys Asn Leu Pro Glu Leu Ser Thr Leu Leu Gln Glu Ile Arg Asn Asn
            740                 745                 750

Ser Asn Ser Ser Asp Ile Glu Leu Glu Glu Lys Val Met Leu Thr Glu
```

-continued

```
            755                 760             765
Cys Glu Ile Asn Val Ile Ser Asn Ile Asp Thr Gln Ile Val Glu Glu
            770             775             780

Arg Ile Glu Glu Ala Lys Asn Leu Thr Ser Asp Ser Ile Asn Tyr Ile
785             790             795             800

Lys Asp Glu Phe Lys Leu Ile Glu Ser Ile Ser Asp Ala Leu Cys Asp
                805             810             815

Leu Lys Gln Gln Asn Glu Leu Glu Asp Ser His Phe Ile Ser Phe Glu
            820             825             830

Asp Ile Ser Glu Thr Asp Glu Gly Phe Ser Ile Arg Phe Ile Asn Lys
            835             840             845

Glu Thr Gly Glu Ser Ile Phe Val Glu Thr Glu Lys Thr Ile Phe Ser
            850             855             860

Glu Tyr Ala Asn His Ile Thr Glu Glu Ile Ser Lys Ile Lys Gly Thr
865             870             875             880

Ile Phe Asp Thr Val Asn Gly Lys Leu Val Lys Lys Val Asn Leu Asp
                885             890             895

Thr Thr His Glu Val Asn Thr Leu Asn Ala Ala Phe Phe Ile Gln Ser
            900             905             910

Leu Ile Glu Tyr Asn Ser Ser Lys Glu Ser Leu Ser Asn Leu Ser Val
            915             920             925

Ala Met Lys Val Gln Val Tyr Ala Gln Leu Phe Ser Thr Gly Leu Asn
            930             935             940

Thr Ile Thr Asp Ala Ala Lys Val Val Glu Leu Val Ser Thr Ala Leu
945             950             955             960

Asp Glu Thr Ile Asp Leu Leu Pro Thr Leu Ser Glu Gly Leu Pro Ile
                965             970             975

Ile Ala Thr Ile Ile Asp Gly Val Ser Leu Gly Ala Ala Ile Lys Glu
            980             985             990

Leu Ser Glu Thr Ser Asp Pro Leu  Leu Arg Gln Glu Ile  Glu Ala Lys
            995             1000            1005

Ile Gly  Ile Met Ala Val Asn  Leu Thr Thr Ala Thr  Thr Ala Ile
1010            1015            1020

Ile Thr  Ser Ser Leu Gly Ile  Ala Ser Gly Phe Ser  Ile Leu Leu
1025            1030            1035

Val Pro  Leu Ala Gly Ile Ser  Ala Gly Ile Pro Ser  Leu Val Asn
1040            1045            1050

Asn Glu  Leu Val Leu Arg Asp  Lys Ala Thr Lys Val  Val Asp Tyr
1055            1060            1065

Phe Lys  His Val Ser Leu Val  Glu Thr Glu Gly Val  Phe Thr Leu
1070            1075            1080

Leu Asp  Asp Lys Ile Met Met  Pro Gln Asp Asp Leu  Val Ile Ser
1085            1090            1095

Glu Ile  Asp Phe Asn Asn Asn  Ser Ile Val Leu Gly  Lys Cys Glu
1100            1105            1110

Ile Trp  Arg Met Glu Gly Gly  Ser Gly His Thr Val  Thr Asp Asp
1115            1120            1125

Ile Asp  His Phe Phe Ser Ala  Pro Ser Ile Thr Tyr  Arg Glu Pro
1130            1135            1140

His Leu  Ser Ile Tyr Asp Val  Leu Glu Val Gln Lys  Glu Glu Leu
1145            1150            1155

Asp Leu  Ser Lys Asp Leu Met  Val Leu Pro Asn Ala  Pro Asn Arg
1160            1165            1170
```

-continued

Val Phe Ala Trp Glu Thr Gly Trp Thr Pro Gly Leu Arg Ser Leu
1175                1180                1185

Glu Asn Asp Gly Thr Lys Leu Leu Asp Arg Ile Arg Asp Asn Tyr
    1190                1195                1200

Glu Gly Glu Phe Tyr Trp Arg Tyr Phe Ala Phe Ile Ala Asp Ala
1205                1210                1215

Leu Ile Thr Thr Leu Lys Pro Arg Tyr Glu Asp Thr Asn Ile Arg
1220                1225                1230

Ile Asn Leu Asp Ser Asn Thr Arg Ser Phe Ile Val Pro Ile Ile
1235                1240                1245

Thr Thr Glu Tyr Ile Arg Glu Lys Leu Ser Tyr Ser Phe Tyr Gly
1250                1255                1260

Ser Gly Gly Thr Tyr Ala Leu Ser Leu Ser Gln Tyr Asn Met Gly
1265                1270                1275

Ile Asn Ile Glu Leu Ser Glu Ser Asp Val Trp Ile Ile Asp Val
1280                1285                1290

Asp Asn Val Val Arg Asp Val Thr Ile Glu Ser Asp Lys Ile Lys
1295                1300                1305

Lys Gly Asp Leu Ile Glu Gly Ile Leu Ser Thr Leu Ser Ile Glu
1310                1315                1320

Glu Asn Lys Ile Ile Leu Asn Ser His Glu Ile Asn Phe Ser Gly
1325                1330                1335

Glu Val Asn Gly Ser Asn Gly Phe Val Ser Leu Thr Phe Ser Ile
1340                1345                1350

Leu Glu Gly Ile Asn Ala Ile Ile Glu Val Asp Leu Leu Ser Lys
1355                1360                1365

Ser Tyr Lys Leu Leu Ile Ser Gly Glu Leu Lys Ile Leu Met Leu
1370                1375                1380

Asn Ser Asn His Ile Gln Gln Lys Ile Asp Tyr Ile Gly Phe Asn
1385                1390                1395

Ser Glu Leu Gln Lys Asn Ile Pro Tyr Ser Phe Val Asp Ser Glu
1400                1405                1410

Gly Lys Glu Asn Gly Phe Ile Asn Gly Ser Thr Lys Glu Gly Leu
1415                1420                1425

Phe Val Ser Glu Leu Pro Asp Val Val Leu Ile Ser Lys Val Tyr
1430                1435                1440

Met Asp Asp Ser Lys Pro Ser Phe Gly Tyr Tyr Ser Asn Asn Leu
1445                1450                1455

Lys Asp Val Lys Val Ile Thr Lys Asp Asn Val Asn Ile Leu Thr
1460                1465                1470

Gly Tyr Tyr Leu Lys Asp Asp Ile Lys Ile Ser Leu Ser Leu Thr
1475                1480                1485

Leu Gln Asp Glu Lys Thr Ile Lys Leu Asn Ser Val His Leu Asp
1490                1495                1500

Glu Ser Gly Val Ala Glu Ile Leu Lys Phe Met Asn Arg Lys Gly
1505                1510                1515

Asn Thr Asn Thr Ser Asp Ser Leu Met Ser Phe Leu Glu Ser Met
1520                1525                1530

Asn Ile Lys Ser Ile Phe Val Asn Phe Leu Gln Ser Asn Ile Lys
1535                1540                1545

Phe Ile Leu Asp Ala Asn Phe Ile Ile Ser Gly Thr Thr Ser Ile
1550                1555                1560

Gly Gln Phe Glu Phe Ile Cys Asp Glu Asn Asp Asn Ile Gln Pro
1565                1570                1575

Tyr Phe Ile Lys Phe Asn Thr Leu Glu Thr Asn Tyr Thr Leu Tyr
1580            1585            1590

Val Gly Asn Arg Gln Asn Met Ile Val Glu Pro Asn Tyr Asp Leu
1595            1600            1605

Asp Asp Ser Gly Asp Ile Ser Ser Thr Val Ile Asn Phe Ser Gln
1610            1615            1620

Lys Tyr Leu Tyr Gly Ile Asp Ser Cys Val Asn Lys Val Val Ile
1625            1630            1635

Ser Pro Asn Ile Tyr Thr Asp Glu Ile Asn Ile Thr Pro Val Tyr
1640            1645            1650

Glu Thr Asn Asn Thr Tyr Pro Glu Val Ile Val Leu Asp Ala Asn
1655            1660            1665

Tyr Ile Asn Glu Lys Ile Asn Val Asn Ile Asn Asp Leu Ser Ile
1670            1675            1680

Arg Tyr Val Trp Ser Asn Asp Gly Asn Asp Phe Ile Leu Met Ser
1685            1690            1695

Thr Ser Glu Glu Asn Lys Val Ser Gln Val Lys Ile Arg Phe Val
1700            1705            1710

Asn Val Phe Lys Asp Lys Thr Leu Ala Asn Lys Leu Ser Phe Asn
1715            1720            1725

Phe Ser Asp Lys Gln Asp Val Pro Val Ser Glu Ile Ile Leu Ser
1730            1735            1740

Phe Thr Pro Ser Tyr Tyr Glu Asp Gly Leu Ile Gly Tyr Asp Leu
1745            1750            1755

Gly Leu Val Ser Leu Tyr Asn Glu Lys Phe Tyr Ile Asn Asn Phe
1760            1765            1770

Gly Met Met Val Ser Gly Leu Ile Tyr Ile Asn Asp Ser Leu Tyr
1775            1780            1785

Tyr Phe Lys Pro Pro Val Asn Asn Leu Ile Thr Gly Phe Val Thr
1790            1795            1800

Val Gly Asp Asp Lys Tyr Tyr Phe Asn Pro Ile Asn Gly Gly Ala
1805            1810            1815

Ala Ser Ile Gly Glu Thr Ile Ile Asp Asp Lys Asn Tyr Tyr Phe
1820            1825            1830

Asn Gln Ser Gly Val Leu Gln Thr Gly Val Phe Ser Thr Glu Asp
1835            1840            1845

Gly Phe Lys Tyr Phe Ala Pro Ala Asn Thr Leu Asp Glu Asn Leu
1850            1855            1860

Glu Gly Glu Ala Ile Asp Phe Thr Gly Lys Leu Ile Ile Asp Glu
1865            1870            1875

Asn Ile Tyr Tyr Phe Asp Asp Asn Tyr Arg Gly Ala Val Glu Trp
1880            1885            1890

Lys Glu Leu Asp Gly Glu Met His Tyr Phe Ser Pro Glu Thr Gly
1895            1900            1905

Lys Ala Phe Lys Gly Leu Asn Gln Ile Gly Asp Tyr Lys Tyr Tyr
1910            1915            1920

Phe Asn Ser Asp Gly Val Met Gln Lys Gly Phe Val Ser Ile Asn
1925            1930            1935

Asp Asn Lys His Tyr Phe Asp Asp Ser Gly Val Met Lys Val Gly
1940            1945            1950

Tyr Thr Glu Ile Asp Gly Lys His Phe Tyr Phe Ala Glu Asn Gly
1955            1960            1965

Glu Met Gln Ile Gly Val Phe Asn Thr Glu Asp Gly Phe Lys Tyr

```
                    1970                1975                1980
Phe Ala His His Asn Glu Asp Leu Gly Asn Glu Glu Gly Glu Glu
    1985                1990                1995

Ile Ser Tyr Ser Gly Ile Leu Asn Phe Asn Asn Lys Ile Tyr Tyr
    2000                2005                2010

Phe Asp Asp Ser Phe Thr Ala Val Val Gly Trp Lys Asp Leu Glu
    2015                2020                2025

Asp Gly Ser Lys Tyr Tyr Phe Asp Glu Asp Thr Ala Glu Ala Tyr
    2030                2035                2040

Ile Gly Leu Ser Leu Ile Asn Asp Gly Gln Tyr Tyr Phe Asn Asp
    2045                2050                2055

Asp Gly Ile Met Gln Val Gly Phe Val Thr Ile Asn Asp Lys Val
    2060                2065                2070

Phe Tyr Phe Ser Asp Ser Gly Ile Ile Glu Ser Gly Val Gln Asn
    2075                2080                2085

Ile Asp Asp Asn Tyr Phe Tyr Ile Asp Asp Asn Gly Ile Val Gln
    2090                2095                2100

Ile Gly Val Phe Asp Thr Ser Asp Gly Tyr Lys Tyr Phe Ala Pro
    2105                2110                2115

Ala Asn Thr Val Asn Asp Asn Ile Tyr Gly Gln Ala Val Glu Tyr
    2120                2125                2130

Ser Gly Leu Val Arg Val Gly Glu Asp Val Tyr Tyr Phe Gly Glu
    2135                2140                2145

Thr Tyr Thr Ile Glu Thr Gly Trp Ile Tyr Asp Met Glu Asn Glu
    2150                2155                2160

Ser Asp Lys Tyr Tyr Phe Asn Pro Glu Thr Lys Lys Ala Cys Lys
    2165                2170                2175

Gly Ile Asn Leu Ile Asp Asp Ile Lys Tyr Tyr Phe Asp Glu Lys
    2180                2185                2190

Gly Ile Met Arg Thr Gly Leu Ile Ser Phe Glu Asn Asn Asn Tyr
    2195                2200                2205

Tyr Phe Asn Glu Asn Gly Glu Met Gln Phe Gly Tyr Ile Asn Ile
    2210                2215                2220

Glu Asp Lys Met Phe Tyr Phe Gly Glu Asp Gly Val Met Gln Ile
    2225                2230                2235

Gly Val Phe Asn Thr Pro Asp Gly Phe Lys Tyr Phe Ala His Gln
    2240                2245                2250

Asn Thr Leu Asp Glu Asn Phe Glu Gly Glu Ser Ile Asn Tyr Thr
    2255                2260                2265

Gly Trp Leu Asp Leu Asp Glu Lys Arg Tyr Tyr Phe Thr Asp Glu
    2270                2275                2280

Tyr Ile Ala Ala Thr Gly Ser Val Ile Ile Asp Gly Glu Glu Tyr
    2285                2290                2295

Tyr Phe Asp Pro Asp Thr Ala Gln Leu Val Ile Ser Glu His His
    2300                2305                2310

His His His His
    2315

<210> SEQ ID NO 3
<211> LENGTH: 3134
<212> TYPE: PRT
<213> ORGANISM: Artificial Sequence
<220> FEATURE:
<223> OTHER INFORMATION: Fusion Protein Human Oct4/C. difficile aTcdA

<400> SEQUENCE: 3
```

```
Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Ala Gly His Leu Ala Ser Asp
        50                  55                  60

Phe Ala Phe Ser Pro Pro Gly Gly Gly Asp Gly Pro Gly Gly
65              70              75                  80

Pro Glu Pro Gly Trp Val Asp Pro Arg Thr Trp Leu Ser Phe Gln Gly
                    85                  90                  95

Pro Pro Gly Gly Pro Gly Ile Gly Pro Gly Val Gly Pro Gly Ser Glu
                100                 105                 110

Val Trp Gly Ile Pro Pro Cys Pro Pro Tyr Glu Phe Cys Gly Gly
            115                 120                 125

Met Ala Tyr Cys Gly Pro Gln Val Gly Val Gly Leu Val Pro Gln Gly
            130                 135                 140

Gly Leu Glu Thr Ser Gln Pro Glu Gly Glu Ala Gly Val Gly Val Glu
145                 150                 155                 160

Ser Asn Ser Asp Gly Ala Ser Pro Glu Pro Cys Thr Val Thr Pro Gly
                165                 170                 175

Ala Val Lys Leu Glu Lys Glu Lys Leu Glu Gln Asn Pro Glu Glu Ser
                180                 185                 190

Gln Asp Ile Lys Ala Leu Gln Lys Glu Leu Glu Gln Phe Ala Lys Leu
            195                 200                 205

Leu Lys Gln Lys Arg Ile Thr Leu Gly Tyr Thr Gln Ala Asp Val Gly
            210                 215                 220

Leu Thr Leu Gly Val Leu Phe Gly Lys Val Phe Ser Gln Thr Thr Ile
225                 230                 235                 240

Cys Arg Phe Glu Ala Leu Gln Leu Ser Phe Lys Asn Met Cys Lys Leu
                245                 250                 255

Arg Pro Leu Leu Gln Lys Trp Val Glu Glu Ala Asp Asn Asn Glu Asn
                260                 265                 270

Leu Gln Glu Ile Cys Lys Ala Glu Thr Leu Val Gln Ala Arg Lys Arg
            275                 280                 285

Lys Arg Thr Ser Ile Glu Asn Arg Val Arg Gly Asn Leu Glu Asn Leu
            290                 295                 300

Phe Leu Gln Cys Pro Lys Pro Thr Leu Gln Gln Ile Ser His Ile Ala
305                 310                 315                 320

Gln Gln Leu Gly Leu Glu Lys Asp Val Val Arg Val Trp Phe Cys Asn
                325                 330                 335

Arg Arg Gln Lys Gly Lys Arg Ser Ser Ser Asp Tyr Ala Gln Arg Glu
                340                 345                 350

Asp Phe Glu Ala Ala Gly Ser Pro Phe Ser Gly Gly Pro Val Ser Phe
            355                 360                 365

Pro Leu Ala Pro Gly Pro His Phe Gly Thr Pro Gly Tyr Gly Ser Pro
            370                 375                 380

His Phe Thr Ala Leu Tyr Ser Ser Val Pro Phe Pro Glu Gly Glu Ala
385                 390                 395                 400

Phe Pro Pro Val Ser Val Thr Thr Leu Gly Ser Pro Met His Ser Asn
                405                 410                 415

Ala Ala Ala Ser Leu Ile Ser Lys Glu Glu Leu Ile Lys Leu Ala Tyr
```

```
                420                 425                 430
Ser Ile Arg Pro Arg Glu Asn Glu Tyr Lys Thr Ile Leu Thr Asn Leu
            435                 440                 445
Asp Glu Tyr Asn Lys Leu Thr Thr Asn Asn Glu Asn Lys Tyr Leu
        450                 455                 460
Gln Leu Lys Lys Leu Asn Glu Ser Ile Asp Val Phe Met Asn Lys Tyr
465                 470                 475                 480
Lys Thr Ser Ser Arg Asn Arg Ala Leu Ser Asn Leu Lys Lys Asp Ile
                485                 490                 495
Leu Lys Glu Val Ile Leu Ile Lys Asn Ser Asn Thr Ser Pro Val Glu
                500                 505                 510
Lys Asn Leu His Phe Val Trp Ile Gly Gly Glu Val Ser Asp Ile Ala
                515                 520                 525
Leu Glu Tyr Ile Lys Gln Trp Ala Asp Ile Asn Ala Glu Tyr Asn Ile
                530                 535                 540
Lys Leu Trp Tyr Asp Ser Glu Ala Phe Leu Val Asn Thr Leu Lys Lys
545                 550                 555                 560
Ala Ile Val Glu Ser Ser Thr Thr Glu Ala Leu Gln Leu Leu Glu Glu
                565                 570                 575
Glu Ile Gln Asn Pro Gln Phe Asp Asn Met Lys Phe Tyr Lys Lys Arg
                580                 585                 590
Met Glu Phe Ile Tyr Asp Arg Gln Lys Arg Phe Ile Asn Tyr Tyr Lys
                595                 600                 605
Ser Gln Ile Asn Lys Pro Thr Val Pro Thr Ile Asp Asp Ile Ile Lys
                610                 615                 620
Ser His Leu Val Ser Glu Tyr Asn Arg Asp Glu Thr Val Leu Glu Ser
625                 630                 635                 640
Tyr Arg Thr Asn Ser Leu Arg Lys Ile Asn Ser Asn His Gly Ile Asp
                645                 650                 655
Ile Arg Ala Asn Ser Leu Phe Thr Glu Gln Glu Leu Leu Asn Ile Tyr
                660                 665                 670
Ser Gln Glu Leu Leu Asn Arg Gly Asn Leu Ala Ala Ala Ser Asp Ile
                675                 680                 685
Val Arg Leu Leu Ala Leu Lys Asn Phe Gly Gly Val Tyr Leu Ala Val
                690                 695                 700
Ala Met Leu Pro Gly Ile His Ser Asp Leu Phe Lys Thr Ile Ser Arg
705                 710                 715                 720
Pro Ser Ser Ile Gly Leu Asp Arg Trp Glu Met Ile Lys Leu Glu Ala
                725                 730                 735
Ile Met Lys Tyr Lys Lys Tyr Ile Asn Asn Tyr Thr Ser Glu Asn Phe
                740                 745                 750
Asp Lys Leu Asp Gln Gln Leu Lys Asp Asn Phe Lys Leu Ile Ile Glu
                755                 760                 765
Ser Lys Ser Glu Lys Ser Glu Ile Phe Ser Lys Leu Glu Asn Leu Asn
                770                 775                 780
Val Ser Asp Leu Glu Ile Lys Ile Ala Phe Ala Leu Gly Ser Val Ile
785                 790                 795                 800
Asn Gln Ala Leu Ile Ser Lys Gln Gly Ser Tyr Leu Thr Asn Leu Val
                805                 810                 815
Ile Glu Gln Val Lys Asn Arg Tyr Gln Phe Leu Asn Gln His Leu Asn
                820                 825                 830
Pro Ala Ile Glu Ser Asp Asn Asn Phe Thr Asp Thr Thr Lys Ile Phe
                835                 840                 845
```

-continued

His Asp Ser Leu Phe Asn Ser Ala Thr Ala Glu Asn Ser Met Phe Leu
850                 855                 860

Thr Lys Ile Ala Pro Tyr Leu Gln Val Gly Phe Met Pro Glu Ala Arg
865                 870                 875                 880

Ser Thr Ile Ser Leu Ser Gly Pro Gly Ala Tyr Ala Ser Ala Tyr Tyr
            885                 890                 895

Asp Phe Ile Asn Leu Gln Glu Asn Thr Ile Glu Lys Thr Leu Lys Ala
            900                 905                 910

Ser Asp Leu Ile Glu Phe Lys Phe Pro Glu Asn Asn Leu Ser Gln Leu
            915                 920                 925

Thr Glu Gln Glu Ile Asn Ser Leu Trp Ser Phe Asp Gln Ala Ser Ala
930                 935                 940

Lys Tyr Gln Phe Glu Lys Tyr Val Arg Asp Tyr Thr Gly Gly Ser Leu
945                 950                 955                 960

Ser Glu Asp Asn Gly Val Asp Phe Asn Lys Asn Thr Ala Leu Asp Lys
            965                 970                 975

Asn Tyr Leu Leu Asn Asn Lys Ile Pro Ser Asn Asn Val Glu Glu Ala
            980                 985                 990

Gly Ser Lys Asn Tyr Val His Tyr Ile Ile Gln Leu Gln Gly Asp Asp
            995                 1000                1005

Ile Ser Tyr Glu Ala Thr Cys Asn Leu Phe Ser Lys Asn Pro Lys
    1010            1015            1020

Asn Ser Ile Ile Ile Gln Arg Asn Met Asn Glu Ser Ala Lys Ser
    1025            1030            1035

Tyr Phe Leu Ser Asp Asp Gly Glu Ser Ile Leu Glu Leu Asn Lys
    1040            1045            1050

Tyr Arg Ile Pro Glu Arg Leu Lys Asn Lys Glu Lys Val Lys Val
    1055            1060            1065

Thr Phe Ile Gly His Gly Lys Asp Glu Phe Asn Thr Ser Glu Phe
    1070            1075            1080

Ala Arg Leu Ser Val Asp Ser Leu Ser Asn Glu Ile Ser Ser Phe
    1085            1090            1095

Leu Asp Thr Ile Lys Leu Asp Ile Ser Pro Lys Asn Val Glu Val
    1100            1105            1110

Asn Leu Leu Gly Cys Asn Met Phe Ser Tyr Asp Phe Asn Val Glu
    1115            1120            1125

Glu Thr Tyr Pro Gly Lys Leu Leu Leu Ser Ile Met Asp Lys Ile
    1130            1135            1140

Thr Ser Thr Leu Pro Asp Val Asn Lys Asn Ser Ile Thr Ile Gly
    1145            1150            1155

Ala Asn Gln Tyr Glu Val Arg Ile Asn Ser Glu Gly Arg Lys Glu
    1160            1165            1170

Leu Leu Ala His Ser Gly Lys Trp Ile Asn Lys Glu Glu Ala Ile
    1175            1180            1185

Met Ser Asp Leu Ser Ser Lys Glu Tyr Ile Phe Phe Asp Ser Ile
    1190            1195            1200

Asp Asn Lys Leu Lys Ala Lys Ser Lys Asn Ile Pro Gly Leu Ala
    1205            1210            1215

Ser Ile Ser Glu Asp Ile Lys Thr Leu Leu Leu Asp Ala Ser Val
    1220            1225            1230

Ser Pro Asp Thr Lys Phe Ile Leu Asn Asn Leu Lys Leu Asn Ile
    1235            1240            1245

Glu Ser Ser Ile Gly Asp Tyr Ile Tyr Tyr Glu Lys Leu Glu Pro
    1250            1255            1260

```
Val Lys Asn Ile Ile His Asn Ser Ile Asp Asp Leu Ile Asp Glu
    1265            1270                1275
Phe Asn Leu Leu Glu Asn Val Ser Asp Glu Leu Tyr Glu Leu Lys
    1280            1285                1290
Lys Leu Asn Asn Leu Asp Glu Lys Tyr Leu Ile Ser Phe Glu Asp
    1295            1300                1305
Ile Ser Lys Asn Asn Ser Thr Tyr Ser Val Arg Phe Ile Asn Lys
    1310            1315                1320
Ser Asn Gly Glu Ser Val Tyr Val Glu Thr Glu Lys Glu Ile Phe
    1325            1330                1335
Ser Lys Tyr Ser Glu His Ile Thr Lys Glu Ile Ser Thr Ile Lys
    1340            1345                1350
Asn Ser Ile Ile Thr Asp Val Asn Gly Asn Leu Leu Asp Asn Ile
    1355            1360                1365
Gln Leu Asp His Thr Ser Gln Val Asn Thr Leu Asn Ala Ala Phe
    1370            1375                1380
Phe Ile Gln Ser Leu Ile Asp Tyr Ser Ser Asn Lys Asp Val Leu
    1385            1390                1395
Asn Asp Leu Ser Thr Ser Val Lys Val Gln Leu Tyr Ala Gln Leu
    1400            1405                1410
Phe Ser Thr Gly Leu Asn Thr Ile Tyr Asp Ser Ile Gln Leu Val
    1415            1420                1425
Asn Leu Ile Ser Asn Ala Val Asn Asp Thr Ile Asn Val Leu Pro
    1430            1435                1440
Thr Ile Thr Glu Gly Ile Pro Ile Val Ser Thr Ile Leu Asp Gly
    1445            1450                1455
Ile Asn Leu Gly Ala Ala Ile Lys Glu Leu Leu Asp Glu His Asp
    1460            1465                1470
Pro Leu Leu Lys Lys Glu Leu Glu Ala Lys Val Gly Val Leu Ala
    1475            1480                1485
Ile Asn Met Ser Leu Ser Ile Ala Ala Thr Val Ala Ser Ile Val
    1490            1495                1500
Gly Ile Gly Ala Glu Val Thr Ile Phe Leu Leu Pro Ile Ala Gly
    1505            1510                1515
Ile Ser Ala Gly Ile Pro Ser Leu Val Asn Asn Glu Leu Ile Leu
    1520            1525                1530
His Asp Lys Ala Thr Ser Val Val Asn Tyr Phe Asn His Leu Ser
    1535            1540                1545
Glu Ser Lys Lys Tyr Gly Pro Leu Lys Thr Glu Asp Asp Lys Ile
    1550            1555                1560
Leu Val Pro Ile Asp Asp Leu Val Ile Ser Glu Ile Asp Phe Asn
    1565            1570                1575
Asn Asn Ser Ile Lys Leu Gly Thr Cys Asn Ile Leu Ala Met Glu
    1580            1585                1590
Gly Gly Ser Gly His Thr Val Thr Gly Asn Ile Asp His Phe Phe
    1595            1600                1605
Ser Ser Pro Ser Ile Ser Ser His Ile Pro Ser Leu Ser Ile Tyr
    1610            1615                1620
Ser Ala Ile Gly Ile Glu Thr Glu Asn Leu Asp Phe Ser Lys Lys
    1625            1630                1635
Ile Met Met Leu Pro Asn Ala Pro Ser Arg Val Phe Trp Trp Glu
    1640            1645                1650
Thr Gly Ala Val Pro Gly Leu Arg Ser Leu Glu Asn Asp Gly Thr
```

```
            1655                1660                1665

Arg Leu Leu Asp Ser Ile Arg Asp Leu Tyr Pro Gly Lys Phe Tyr
    1670                1675                1680

Trp Arg Phe Tyr Ala Phe Phe Asp Tyr Ala Ile Thr Thr Leu Lys
    1685                1690                1695

Pro Val Tyr Glu Asp Thr Asn Ile Lys Ile Lys Leu Asp Lys Asp
    1700                1705                1710

Thr Arg Asn Phe Ile Met Pro Thr Ile Thr Thr Asn Glu Ile Arg
    1715                1720                1725

Asn Lys Leu Ser Tyr Ser Phe Asp Gly Ala Gly Gly Thr Tyr Ser
    1730                1735                1740

Leu Leu Leu Ser Ser Tyr Pro Ile Ser Thr Asn Ile Asn Leu Ser
    1745                1750                1755

Lys Asp Asp Leu Trp Ile Phe Asn Ile Asp Asn Glu Val Arg Glu
    1760                1765                1770

Ile Ser Ile Glu Asn Gly Thr Ile Lys Lys Gly Lys Leu Ile Lys
    1775                1780                1785

Asp Val Leu Ser Lys Ile Asp Ile Asn Lys Asn Lys Leu Ile Ile
    1790                1795                1800

Gly Asn Gln Thr Ile Asp Phe Ser Gly Asp Ile Asp Asn Lys Asp
    1805                1810                1815

Arg Tyr Ile Phe Leu Thr Cys Glu Leu Asp Asp Lys Ile Ser Leu
    1820                1825                1830

Ile Ile Glu Ile Asn Leu Val Ala Lys Ser Tyr Ser Leu Leu Leu
    1835                1840                1845

Ser Gly Asp Lys Asn Tyr Leu Ile Ser Asn Leu Ser Asn Thr Ile
    1850                1855                1860

Glu Lys Ile Asn Thr Leu Gly Leu Asp Ser Lys Asn Ile Ala Tyr
    1865                1870                1875

Asn Tyr Thr Asp Glu Ser Asn Asn Lys Tyr Phe Gly Ala Ile Ser
    1880                1885                1890

Lys Thr Ser Gln Lys Ser Ile Ile His Tyr Lys Lys Asp Ser Lys
    1895                1900                1905

Asn Ile Leu Glu Phe Tyr Asn Asp Ser Thr Leu Glu Phe Asn Ser
    1910                1915                1920

Lys Asp Phe Ile Ala Glu Asp Ile Asn Val Phe Met Lys Asp Asp
    1925                1930                1935

Ile Asn Thr Ile Thr Gly Lys Tyr Tyr Val Asp Asn Asn Thr Asp
    1940                1945                1950

Lys Ser Ile Asp Phe Ser Ile Ser Leu Val Ser Lys Asn Gln Val
    1955                1960                1965

Lys Val Asn Gly Leu Tyr Leu Asn Glu Ser Val Tyr Ser Ser Tyr
    1970                1975                1980

Leu Asp Phe Val Lys Asn Ser Asp Gly His His Asn Thr Ser Asn
    1985                1990                1995

Phe Met Asn Leu Phe Leu Asp Asn Ile Ser Phe Trp Lys Leu Phe
    2000                2005                2010

Gly Phe Glu Asn Ile Asn Phe Val Ile Asp Lys Tyr Phe Thr Leu
    2015                2020                2025

Val Gly Lys Thr Asn Leu Gly Tyr Val Glu Phe Ile Cys Asp Asn
    2030                2035                2040

Asn Lys Asn Ile Asp Ile Tyr Phe Gly Glu Trp Lys Thr Ser Ser
    2045                2050                2055
```

-continued

Ser Lys Ser Thr Ile Phe Ser Gly Asn Gly Arg Asn Val Val Val
2060            2065            2070

Glu Pro Ile Tyr Asn Pro Asp Thr Gly Glu Asp Ile Ser Thr Ser
2075            2080            2085

Leu Asp Phe Ser Tyr Glu Pro Leu Tyr Gly Ile Asp Arg Tyr Ile
2090            2095            2100

Asn Lys Val Leu Ile Ala Pro Asp Leu Tyr Thr Ser Leu Ile Asn
2105            2110            2115

Ile Asn Thr Asn Tyr Tyr Ser Asn Glu Tyr Tyr Pro Glu Ile Ile
2120            2125            2130

Val Leu Asn Pro Asn Thr Phe His Lys Lys Val Asn Ile Asn Leu
2135            2140            2145

Asp Ser Ser Ser Phe Glu Tyr Lys Trp Ser Thr Glu Gly Ser Asp
2150            2155            2160

Phe Ile Leu Val Arg Tyr Leu Glu Glu Ser Asn Lys Lys Ile Leu
2165            2170            2175

Gln Lys Ile Arg Ile Lys Gly Ile Leu Ser Asn Thr Gln Ser Phe
2180            2185            2190

Asn Lys Met Ser Ile Asp Phe Lys Asp Ile Lys Lys Leu Ser Leu
2195            2200            2205

Gly Tyr Ile Met Ser Asn Phe Lys Ser Phe Asn Ser Glu Asn Glu
2210            2215            2220

Leu Asp Arg Asp His Leu Gly Phe Lys Ile Ile Asp Asn Lys Thr
2225            2230            2235

Tyr Tyr Tyr Asp Glu Asp Ser Lys Leu Val Lys Gly Leu Ile Asn
2240            2245            2250

Ile Asn Asn Ser Leu Phe Tyr Phe Asp Pro Ile Glu Phe Asn Leu
2255            2260            2265

Val Thr Gly Trp Gln Thr Ile Asn Gly Lys Lys Tyr Tyr Phe Asp
2270            2275            2280

Ile Asn Thr Gly Ala Ala Leu Thr Ser Tyr Lys Ile Ile Asn Gly
2285            2290            2295

Lys His Phe Tyr Phe Asn Asn Asp Gly Val Met Gln Leu Gly Val
2300            2305            2310

Phe Lys Gly Pro Asp Gly Phe Glu Tyr Phe Ala Pro Ala Asn Thr
2315            2320            2325

Gln Asn Asn Asn Ile Glu Gly Gln Ala Ile Val Tyr Gln Ser Lys
2330            2335            2340

Phe Leu Thr Leu Asn Gly Lys Lys Tyr Tyr Phe Asp Asn Asn Ser
2345            2350            2355

Lys Ala Val Thr Gly Trp Arg Ile Ile Asn Asn Glu Lys Tyr Tyr
2360            2365            2370

Phe Asn Pro Asn Asn Ala Ile Ala Ala Val Gly Leu Gln Val Ile
2375            2380            2385

Asp Asn Asn Lys Tyr Tyr Phe Asn Pro Asp Thr Ala Ile Ile Ser
2390            2395            2400

Lys Gly Trp Gln Thr Val Asn Gly Ser Arg Tyr Tyr Phe Asp Thr
2405            2410            2415

Asp Thr Ala Ile Ala Phe Asn Gly Tyr Lys Thr Ile Asp Gly Lys
2420            2425            2430

His Phe Tyr Phe Asp Ser Asp Cys Val Val Lys Ile Gly Val Phe
2435            2440            2445

Ser Thr Ser Asn Gly Phe Glu Tyr Phe Ala Pro Ala Asn Thr Tyr
2450            2455            2460

```
Asn Asn Asn Ile Glu Gly Gln Ala Ile Tyr Gln Ser Lys Phe
    2465                2470                2475

Leu Thr Leu Asn Gly Lys Lys Tyr Tyr Phe Asp Asn Asn Ser Lys
    2480                2485                2490

Ala Val Thr Gly Leu Gln Thr Ile Asp Ser Lys Lys Tyr Tyr Phe
    2495                2500                2505

Asn Thr Asn Thr Ala Glu Ala Ala Thr Gly Trp Gln Thr Ile Asp
    2510                2515                2520

Gly Lys Lys Tyr Tyr Phe Asn Thr Asn Thr Ala Glu Ala Ala Thr
    2525                2530                2535

Gly Trp Gln Thr Ile Asp Gly Lys Lys Tyr Tyr Phe Asn Thr Asn
    2540                2545                2550

Thr Ala Ile Ala Ser Thr Gly Tyr Thr Ile Ile Asn Gly Lys His
    2555                2560                2565

Phe Tyr Phe Asn Thr Asp Gly Ile Met Gln Ile Gly Val Phe Lys
    2570                2575                2580

Gly Pro Asn Gly Phe Glu Tyr Phe Ala Pro Ala Asn Thr Asp Ala
    2585                2590                2595

Asn Asn Ile Glu Gly Gln Ala Ile Leu Tyr Gln Asn Glu Phe Leu
    2600                2605                2610

Thr Leu Asn Gly Lys Lys Tyr Tyr Phe Gly Ser Asp Ser Lys Ala
    2615                2620                2625

Val Thr Gly Trp Arg Ile Ile Asn Asn Lys Lys Tyr Tyr Phe Asn
    2630                2635                2640

Pro Asn Asn Ala Ile Ala Ala Ile His Leu Cys Thr Ile Asn Asn
    2645                2650                2655

Asp Lys Tyr Tyr Phe Ser Tyr Asp Gly Ile Leu Gln Asn Gly Tyr
    2660                2665                2670

Ile Thr Ile Glu Arg Asn Asn Phe Tyr Phe Asp Ala Asn Asn Glu
    2675                2680                2685

Ser Lys Met Val Thr Gly Val Phe Lys Gly Pro Asn Gly Phe Glu
    2690                2695                2700

Tyr Phe Ala Pro Ala Asn Thr His Asn Asn Asn Ile Glu Gly Gln
    2705                2710                2715

Ala Ile Val Tyr Gln Asn Lys Phe Leu Thr Leu Asn Gly Lys Lys
    2720                2725                2730

Tyr Tyr Phe Asp Asn Asp Ser Lys Ala Val Thr Gly Trp Gln Thr
    2735                2740                2745

Ile Asp Gly Lys Lys Tyr Tyr Phe Asn Leu Asn Thr Ala Glu Ala
    2750                2755                2760

Ala Thr Gly Trp Gln Thr Ile Asp Gly Lys Lys Tyr Tyr Phe Asn
    2765                2770                2775

Leu Asn Thr Ala Glu Ala Ala Thr Gly Trp Gln Thr Ile Asp Gly
    2780                2785                2790

Lys Lys Tyr Tyr Phe Asn Thr Asn Thr Phe Ile Ala Ser Thr Gly
    2795                2800                2805

Tyr Thr Ser Ile Asn Gly Lys His Phe Tyr Phe Asn Thr Asp Gly
    2810                2815                2820

Ile Met Gln Ile Gly Val Phe Lys Gly Pro Asn Gly Phe Glu Tyr
    2825                2830                2835

Phe Ala Pro Ala Asn Thr Asp Ala Asn Asn Ile Glu Gly Gln Ala
    2840                2845                2850

Ile Leu Tyr Gln Asn Lys Phe Leu Thr Leu Asn Gly Lys Lys Tyr
```

2855                2860                2865

Tyr Phe Gly Ser Asp Ser Lys Ala Val Thr Gly Leu Arg Thr Ile
            2870                2875                2880

Asp Gly Lys Lys Tyr Tyr Phe Asn Thr Asn Thr Ala Val Ala Val
        2885                2890                2895

Thr Gly Trp Gln Thr Ile Asn Gly Lys Lys Tyr Tyr Phe Asn Thr
    2900                2905                2910

Asn Thr Ser Ile Ala Ser Thr Gly Tyr Thr Ile Ile Ser Gly Lys
2915                2920                2925

His Phe Tyr Phe Asn Thr Asp Gly Ile Met Gln Ile Gly Val Phe
            2930                2935                2940

Lys Gly Pro Asp Gly Phe Glu Tyr Phe Ala Pro Ala Asn Thr Asp
        2945                2950                2955

Ala Asn Asn Ile Glu Gly Gln Ala Ile Arg Tyr Gln Asn Arg Phe
    2960                2965                2970

Leu Tyr Leu His Asp Asn Ile Tyr Tyr Phe Gly Asn Asn Ser Lys
2975                2980                2985

Ala Ala Thr Gly Trp Val Thr Ile Asp Gly Asn Arg Tyr Tyr Phe
            2990                2995                3000

Glu Pro Asn Thr Ala Met Gly Ala Asn Gly Tyr Lys Thr Ile Asp
        3005                3010                3015

Asn Lys Asn Phe Tyr Phe Arg Asn Gly Leu Pro Gln Ile Gly Val
    3020                3025                3030

Phe Lys Gly Ser Asn Gly Phe Glu Tyr Phe Ala Pro Ala Asn Thr
3035                3040                3045

Asp Ala Asn Asn Ile Glu Gly Gln Ala Ile Arg Tyr Gln Asn Arg
            3050                3055                3060

Phe Leu His Leu Leu Gly Lys Ile Tyr Tyr Phe Gly Asn Asn Ser
        3065                3070                3075

Lys Ala Val Thr Gly Trp Gln Thr Ile Asn Gly Lys Val Tyr Tyr
    3080                3085                3090

Phe Met Pro Asp Thr Ala Met Ala Ala Ala Gly Gly Leu Phe Glu
3095                3100                3105

Ile Asp Gly Val Ile Tyr Phe Phe Gly Val Asp Gly Val Lys Ala
            3110                3115                3120

Pro Gly Ile Tyr Gly His His His His His
        3125                3130

<210> SEQ ID NO 4
<211> LENGTH: 2661
<212> TYPE: PRT
<213> ORGANISM: Artificial Sequence
<220> FEATURE:
<223> OTHER INFORMATION: Fusion Protein Human Oct4/C. difficile TcdA

<400> SEQUENCE: 4

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
20 25 30

Leu Ala Gly Glu Leu Glu Gln Leu Arg Ala Arg Leu Glu His His Pro
35 40 45

Gln Gly Gln Arg Glu Pro Ser Gly Ala Ala Gly His Leu Ala Ser Asp
50 55 60

Phe Ala Phe Ser Pro Pro Pro Gly Gly Gly Gly Asp Gly Pro Gly Gly
65 70 75 80

```
Pro Glu Pro Gly Trp Val Asp Pro Arg Thr Trp Leu Ser Phe Gln Gly
                85                  90                  95

Pro Pro Gly Gly Pro Gly Ile Gly Pro Gly Val Gly Pro Gly Ser Glu
            100                 105                 110

Val Trp Gly Ile Pro Pro Cys Pro Pro Tyr Glu Phe Cys Gly Gly
            115                 120                 125

Met Ala Tyr Cys Gly Pro Gln Val Gly Val Gly Leu Val Pro Gln Gly
130                 135                 140

Gly Leu Glu Thr Ser Gln Pro Glu Gly Glu Ala Gly Val Gly Val Glu
145                 150                 155                 160

Ser Asn Ser Asp Gly Ala Ser Pro Glu Pro Cys Thr Val Thr Pro Gly
                165                 170                 175

Ala Val Lys Leu Glu Lys Glu Lys Leu Glu Gln Asn Pro Glu Glu Ser
            180                 185                 190

Gln Asp Ile Lys Ala Leu Gln Lys Glu Leu Glu Gln Phe Ala Lys Leu
            195                 200                 205

Leu Lys Gln Lys Arg Ile Thr Leu Gly Tyr Thr Gln Ala Asp Val Gly
210                 215                 220

Leu Thr Leu Gly Val Leu Phe Gly Lys Val Phe Ser Gln Thr Thr Ile
225                 230                 235                 240

Cys Arg Phe Glu Ala Leu Gln Leu Ser Phe Lys Asn Met Cys Lys Leu
            245                 250                 255

Arg Pro Leu Leu Gln Lys Trp Val Glu Glu Ala Asp Asn Asn Glu Asn
            260                 265                 270

Leu Gln Glu Ile Cys Lys Ala Glu Thr Leu Val Gln Ala Arg Lys Arg
            275                 280                 285

Lys Arg Thr Ser Ile Glu Asn Arg Val Arg Gly Asn Leu Glu Asn Leu
            290                 295                 300

Phe Leu Gln Cys Pro Lys Pro Thr Leu Gln Gln Ile Ser His Ile Ala
305                 310                 315                 320

Gln Gln Leu Gly Leu Glu Lys Asp Val Val Arg Val Trp Phe Cys Asn
                325                 330                 335

Arg Arg Gln Lys Gly Lys Arg Ser Ser Ser Asp Tyr Ala Gln Arg Glu
            340                 345                 350

Asp Phe Glu Ala Ala Gly Ser Pro Phe Ser Gly Gly Pro Val Ser Phe
            355                 360                 365

Pro Leu Ala Pro Gly Pro His Phe Gly Thr Pro Gly Tyr Gly Ser Pro
370                 375                 380

His Phe Thr Ala Leu Tyr Ser Ser Val Pro Phe Pro Glu Gly Glu Ala
385                 390                 395                 400

Phe Pro Pro Val Ser Val Thr Thr Leu Gly Ser Pro Met His Ser Asn
                405                 410                 415

Ala Ala Ala Ser Ala Tyr Tyr Asp Phe Ile Asn Leu Gln Glu Asn Thr
            420                 425                 430

Ile Glu Lys Thr Leu Lys Ala Ser Asp Leu Ile Glu Phe Lys Phe Pro
            435                 440                 445

Glu Asn Asn Leu Ser Gln Leu Thr Glu Gln Glu Ile Asn Ser Leu Trp
            450                 455                 460

Ser Phe Asp Gln Ala Ser Ala Lys Tyr Gln Phe Glu Lys Tyr Val Arg
465                 470                 475                 480

Asp Tyr Thr Gly Gly Ser Leu Ser Glu Asp Asn Gly Val Asp Phe Asn
                485                 490                 495

Lys Asn Thr Ala Leu Asp Lys Asn Tyr Leu Leu Asn Asn Lys Ile Pro
```

-continued

```
                500                 505                 510
Ser Asn Asn Val Glu Glu Ala Gly Ser Lys Asn Tyr Val His Tyr Ile
        515                 520                 525
Ile Gln Leu Gln Gly Asp Asp Ile Ser Tyr Glu Ala Thr Cys Asn Leu
        530                 535                 540
Phe Ser Lys Asn Pro Lys Asn Ser Ile Ile Ile Gln Arg Asn Met Asn
545                 550                 555                 560
Glu Ser Ala Lys Ser Tyr Phe Leu Ser Asp Asp Gly Glu Ser Ile Leu
                565                 570                 575
Glu Leu Asn Lys Tyr Arg Ile Pro Glu Arg Leu Lys Asn Lys Glu Lys
                580                 585                 590
Val Lys Val Thr Phe Ile Gly His Gly Lys Asp Glu Phe Asn Thr Ser
                595                 600                 605
Glu Phe Ala Arg Leu Ser Val Asp Ser Leu Ser Asn Glu Ile Ser Ser
        610                 615                 620
Phe Leu Asp Thr Ile Lys Leu Asp Ile Ser Pro Lys Asn Val Glu Val
625                 630                 635                 640
Asn Leu Leu Gly Cys Asn Met Phe Ser Tyr Asp Phe Asn Val Glu Glu
                645                 650                 655
Thr Tyr Pro Gly Lys Leu Leu Leu Ser Ile Met Asp Lys Ile Thr Ser
                660                 665                 670
Thr Leu Pro Asp Val Asn Lys Asn Ser Ile Thr Ile Gly Ala Asn Gln
                675                 680                 685
Tyr Glu Val Arg Ile Asn Ser Glu Gly Arg Lys Glu Leu Leu Ala His
        690                 695                 700
Ser Gly Lys Trp Ile Asn Lys Glu Glu Ala Ile Met Ser Asp Leu Ser
705                 710                 715                 720
Ser Lys Glu Tyr Ile Phe Phe Asp Ser Ile Asp Asn Lys Leu Lys Ala
                725                 730                 735
Lys Ser Lys Asn Ile Pro Gly Leu Ala Ser Ile Ser Glu Asp Ile Lys
                740                 745                 750
Thr Leu Leu Leu Asp Ala Ser Val Ser Pro Asp Thr Lys Phe Ile Leu
        755                 760                 765
Asn Asn Leu Lys Leu Asn Ile Glu Ser Ser Ile Gly Asp Tyr Ile Tyr
770                 775                 780
Tyr Glu Lys Leu Glu Pro Val Lys Asn Ile Ile His Asn Ser Ile Asp
785                 790                 795                 800
Asp Leu Ile Asp Glu Phe Asn Leu Leu Glu Asn Val Ser Asp Glu Leu
                805                 810                 815
Tyr Glu Leu Lys Lys Leu Asn Asn Leu Asp Glu Lys Tyr Leu Ile Ser
                820                 825                 830
Phe Glu Asp Ile Ser Lys Asn Asn Ser Thr Tyr Ser Val Arg Phe Ile
        835                 840                 845
Asn Lys Ser Asn Gly Glu Ser Val Tyr Val Glu Thr Glu Lys Glu Ile
        850                 855                 860
Phe Ser Lys Tyr Ser Glu His Ile Thr Lys Glu Ile Ser Thr Ile Lys
865                 870                 875                 880
Asn Ser Ile Ile Thr Asp Val Asn Gly Asn Leu Leu Asp Asn Ile Gln
                885                 890                 895
Leu Asp His Thr Ser Gln Val Asn Thr Leu Asn Ala Ala Phe Phe Ile
                900                 905                 910
Gln Ser Leu Ile Asp Tyr Ser Ser Asn Lys Asp Val Leu Asn Asp Leu
        915                 920                 925
```

-continued

Ser Thr Ser Val Lys Val Gln Leu Tyr Ala Gln Leu Phe Ser Thr Gly
    930               935               940

Leu Asn Thr Ile Tyr Asp Ser Ile Gln Leu Val Asn Leu Ile Ser Asn
945               950               955               960

Ala Val Asn Asp Thr Ile Asn Val Leu Pro Thr Ile Thr Glu Gly Ile
            965               970               975

Pro Ile Val Ser Thr Ile Leu Asp Gly Ile Asn Leu Gly Ala Ala Ile
            980               985               990

Lys Glu Leu Leu Asp Glu His Asp Pro Leu Leu Lys Lys Glu Leu Glu
        995               1000              1005

Ala Lys Val Gly Val Leu Ala Ile Asn Met Ser Leu Ser Ile Ala
    1010              1015              1020

Ala Thr Val Ala Ser Ile Val Gly Ile Gly Ala Glu Val Thr Ile
    1025              1030              1035

Phe Leu Leu Pro Ile Ala Gly Ile Ser Ala Gly Ile Pro Ser Leu
    1040              1045              1050

Val Asn Asn Glu Leu Ile Leu His Asp Lys Ala Thr Ser Val Val
    1055              1060              1065

Asn Tyr Phe Asn His Leu Ser Glu Ser Lys Tyr Gly Pro Leu
    1070              1075              1080

Lys Thr Glu Asp Asp Lys Ile Leu Val Pro Ile Asp Asp Leu Val
    1085              1090              1095

Ile Ser Glu Ile Asp Phe Asn Asn Asn Ser Ile Lys Leu Gly Thr
    1100              1105              1110

Cys Asn Ile Leu Ala Met Glu Gly Gly Ser Gly His Thr Val Thr
    1115              1120              1125

Gly Asn Ile Asp His Phe Phe Ser Ser Pro Ser Ile Ser Ser His
    1130              1135              1140

Ile Pro Ser Leu Ser Ile Tyr Ser Ala Ile Gly Ile Glu Thr Glu
    1145              1150              1155

Asn Leu Asp Phe Ser Lys Lys Ile Met Met Leu Pro Asn Ala Pro
    1160              1165              1170

Ser Arg Val Phe Trp Trp Glu Thr Gly Ala Val Pro Gly Leu Arg
    1175              1180              1185

Ser Leu Glu Asn Asp Gly Thr Arg Leu Leu Asp Ser Ile Arg Asp
    1190              1195              1200

Leu Tyr Pro Gly Lys Phe Tyr Trp Arg Phe Tyr Ala Phe Phe Asp
    1205              1210              1215

Tyr Ala Ile Thr Thr Leu Lys Pro Val Tyr Glu Asp Thr Asn Ile
    1220              1225              1230

Lys Ile Lys Leu Asp Lys Asp Thr Arg Asn Phe Ile Met Pro Thr
    1235              1240              1245

Ile Thr Thr Asn Glu Ile Arg Asn Lys Leu Ser Tyr Ser Phe Asp
    1250              1255              1260

Gly Ala Gly Gly Thr Tyr Ser Leu Leu Leu Ser Ser Tyr Pro Ile
    1265              1270              1275

Ser Thr Asn Ile Asn Leu Ser Lys Asp Asp Leu Trp Ile Phe Asn
    1280              1285              1290

Ile Asp Asn Glu Val Arg Glu Ile Ser Ile Glu Asn Gly Thr Ile
    1295              1300              1305

Lys Lys Gly Lys Leu Ile Lys Asp Val Leu Ser Lys Ile Asp Ile
    1310              1315              1320

Asn Lys Asn Lys Leu Ile Ile Gly Asn Gln Thr Ile Asp Phe Ser
    1325              1330              1335

-continued

```
Gly Asp Ile Asp Asn Lys Asp Arg Tyr Ile Phe Leu Thr Cys Glu
    1340                1345                1350

Leu Asp Asp Lys Ile Ser Leu Ile Ile Glu Ile Asn Leu Val Ala
    1355                1360                1365

Lys Ser Tyr Ser Leu Leu Leu Ser Gly Asp Lys Asn Tyr Leu Ile
    1370                1375                1380

Ser Asn Leu Ser Asn Thr Ile Glu Lys Ile Asn Thr Leu Gly Leu
    1385                1390                1395

Asp Ser Lys Asn Ile Ala Tyr Asn Tyr Thr Asp Glu Ser Asn Asn
    1400                1405                1410

Lys Tyr Phe Gly Ala Ile Ser Lys Thr Ser Gln Lys Ser Ile Ile
    1415                1420                1425

His Tyr Lys Lys Asp Ser Lys Asn Ile Leu Glu Phe Tyr Asn Asp
    1430                1435                1440

Ser Thr Leu Glu Phe Asn Ser Lys Asp Phe Ile Ala Glu Asp Ile
    1445                1450                1455

Asn Val Phe Met Lys Asp Asp Ile Asn Thr Ile Thr Gly Lys Tyr
    1460                1465                1470

Tyr Val Asp Asn Asn Thr Asp Lys Ser Ile Asp Phe Ser Ile Ser
    1475                1480                1485

Leu Val Ser Lys Asn Gln Val Lys Val Asn Gly Leu Tyr Leu Asn
    1490                1495                1500

Glu Ser Val Tyr Ser Ser Tyr Leu Asp Phe Val Lys Asn Ser Asp
    1505                1510                1515

Gly His His Asn Thr Ser Asn Phe Met Asn Leu Phe Leu Asp Asn
    1520                1525                1530

Ile Ser Phe Trp Lys Leu Phe Gly Phe Glu Asn Ile Asn Phe Val
    1535                1540                1545

Ile Asp Lys Tyr Phe Thr Leu Val Gly Lys Thr Asn Leu Gly Tyr
    1550                1555                1560

Val Glu Phe Ile Cys Asp Asn Asn Lys Asn Ile Asp Ile Tyr Phe
    1565                1570                1575

Gly Glu Trp Lys Thr Ser Ser Ser Lys Ser Thr Ile Phe Ser Gly
    1580                1585                1590

Asn Gly Arg Asn Val Val Glu Pro Ile Tyr Asn Pro Asp Thr
    1595                1600                1605

Gly Glu Asp Ile Ser Thr Ser Leu Asp Phe Ser Tyr Glu Pro Leu
    1610                1615                1620

Tyr Gly Ile Asp Arg Tyr Ile Asn Lys Val Leu Ile Ala Pro Asp
    1625                1630                1635

Leu Tyr Thr Ser Leu Ile Asn Ile Asn Thr Asn Tyr Tyr Ser Asn
    1640                1645                1650

Glu Tyr Tyr Pro Glu Ile Ile Val Leu Asn Pro Asn Thr Phe His
    1655                1660                1665

Lys Lys Val Asn Ile Asn Leu Asp Ser Ser Ser Phe Glu Tyr Lys
    1670                1675                1680

Trp Ser Thr Glu Gly Ser Asp Phe Ile Leu Val Arg Tyr Leu Glu
    1685                1690                1695

Glu Ser Asn Lys Lys Ile Leu Gln Lys Ile Arg Ile Lys Gly Ile
    1700                1705                1710

Leu Ser Asn Thr Gln Ser Phe Asn Lys Met Ser Ile Asp Phe Lys
    1715                1720                1725

Asp Ile Lys Lys Leu Ser Leu Gly Tyr Ile Met Ser Asn Phe Lys
```

-continued

```
                1730                 1735                 1740

Ser Phe Asn Ser Glu Asn Glu Leu Asp Arg Asp His Leu Gly Phe
    1745                 1750                 1755

Lys Ile Ile Asp Asn Lys Thr Tyr Tyr Tyr Asp Glu Asp Ser Lys
    1760                 1765                 1770

Leu Val Lys Gly Leu Ile Asn Ile Asn Asn Ser Leu Phe Tyr Phe
    1775                 1780                 1785

Asp Pro Ile Glu Phe Asn Leu Val Thr Gly Trp Gln Thr Ile Asn
    1790                 1795                 1800

Gly Lys Lys Tyr Tyr Phe Asp Ile Asn Thr Gly Ala Ala Leu Thr
    1805                 1810                 1815

Ser Tyr Lys Ile Ile Asn Gly Lys His Phe Tyr Phe Asn Asn Asp
    1820                 1825                 1830

Gly Val Met Gln Leu Gly Val Phe Lys Gly Pro Asp Gly Phe Glu
    1835                 1840                 1845

Tyr Phe Ala Pro Ala Asn Thr Gln Asn Asn Asn Ile Glu Gly Gln
    1850                 1855                 1860

Ala Ile Val Tyr Gln Ser Lys Phe Leu Thr Leu Asn Gly Lys Lys
    1865                 1870                 1875

Tyr Tyr Phe Asp Asn Asn Ser Lys Ala Val Thr Gly Trp Arg Ile
    1880                 1885                 1890

Ile Asn Asn Glu Lys Tyr Tyr Phe Asn Pro Asn Asn Ala Ile Ala
    1895                 1900                 1905

Ala Val Gly Leu Gln Val Ile Asp Asn Asn Lys Tyr Tyr Phe Asn
    1910                 1915                 1920

Pro Asp Thr Ala Ile Ile Ser Lys Gly Trp Gln Thr Val Asn Gly
    1925                 1930                 1935

Ser Arg Tyr Tyr Phe Asp Thr Asp Thr Ala Ile Ala Phe Asn Gly
    1940                 1945                 1950

Tyr Lys Thr Ile Asp Gly Lys His Phe Tyr Phe Asp Ser Asp Cys
    1955                 1960                 1965

Val Val Lys Ile Gly Val Phe Ser Thr Ser Asn Gly Phe Glu Tyr
    1970                 1975                 1980

Phe Ala Pro Ala Asn Thr Tyr Asn Asn Asn Ile Glu Gly Gln Ala
    1985                 1990                 1995

Ile Val Tyr Gln Ser Lys Phe Leu Thr Leu Asn Gly Lys Lys Tyr
    2000                 2005                 2010

Tyr Phe Asp Asn Asn Ser Lys Ala Val Thr Gly Leu Gln Thr Ile
    2015                 2020                 2025

Asp Ser Lys Lys Tyr Tyr Phe Asn Thr Asn Thr Ala Glu Ala Ala
    2030                 2035                 2040

Thr Gly Trp Gln Thr Ile Asp Gly Lys Lys Tyr Tyr Phe Asn Thr
    2045                 2050                 2055

Asn Thr Ala Glu Ala Ala Thr Gly Trp Gln Thr Ile Asp Gly Lys
    2060                 2065                 2070

Lys Tyr Tyr Phe Asn Thr Asn Thr Ala Ile Ala Ser Thr Gly Tyr
    2075                 2080                 2085

Thr Ile Ile Asn Gly Lys His Phe Tyr Phe Asn Thr Asp Gly Ile
    2090                 2095                 2100

Met Gln Ile Gly Val Phe Lys Gly Pro Asn Gly Phe Glu Tyr Phe
    2105                 2110                 2115

Ala Pro Ala Asn Thr Asp Ala Asn Asn Ile Glu Gly Gln Ala Ile
    2120                 2125                 2130
```

```
Leu Tyr Gln Asn Glu Phe Leu Thr Leu Asn Gly Lys Lys Tyr Tyr
2135                2140                2145

Phe Gly Ser Asp Ser Lys Ala Val Thr Gly Trp Arg Ile Ile Asn
2150                2155                2160

Asn Lys Lys Tyr Tyr Phe Asn Pro Asn Asn Ala Ile Ala Ala Ile
2165                2170                2175

His Leu Cys Thr Ile Asn Asn Asp Lys Tyr Tyr Phe Ser Tyr Asp
2180                2185                2190

Gly Ile Leu Gln Asn Gly Tyr Ile Thr Ile Glu Arg Asn Asn Phe
2195                2200                2205

Tyr Phe Asp Ala Asn Asn Glu Ser Lys Met Val Thr Gly Val Phe
2210                2215                2220

Lys Gly Pro Asn Gly Phe Glu Tyr Phe Ala Pro Ala Asn Thr His
2225                2230                2235

Asn Asn Asn Ile Glu Gly Gln Ala Ile Val Tyr Gln Asn Lys Phe
2240                2245                2250

Leu Thr Leu Asn Gly Lys Lys Tyr Tyr Phe Asp Asn Asp Ser Lys
2255                2260                2265

Ala Val Thr Gly Trp Gln Thr Ile Asp Gly Lys Lys Tyr Tyr Phe
2270                2275                2280

Asn Leu Asn Thr Ala Glu Ala Ala Thr Gly Trp Gln Thr Ile Asp
2285                2290                2295

Gly Lys Lys Tyr Tyr Phe Asn Leu Asn Thr Ala Glu Ala Ala Thr
2300                2305                2310

Gly Trp Gln Thr Ile Asp Gly Lys Lys Tyr Tyr Phe Asn Thr Asn
2315                2320                2325

Thr Phe Ile Ala Ser Thr Gly Tyr Thr Ser Ile Asn Gly Lys His
2330                2335                2340

Phe Tyr Phe Asn Thr Asp Gly Ile Met Gln Ile Gly Val Phe Lys
2345                2350                2355

Gly Pro Asn Gly Phe Glu Tyr Phe Ala Pro Ala Asn Thr Asp Ala
2360                2365                2370

Asn Asn Ile Glu Gly Gln Ala Ile Leu Tyr Gln Asn Lys Phe Leu
2375                2380                2385

Thr Leu Asn Gly Lys Lys Tyr Tyr Phe Gly Ser Asp Ser Lys Ala
2390                2395                2400

Val Thr Gly Leu Arg Thr Ile Asp Gly Lys Lys Tyr Tyr Phe Asn
2405                2410                2415

Thr Asn Thr Ala Val Ala Val Thr Gly Trp Gln Thr Ile Asn Gly
2420                2425                2430

Lys Lys Tyr Tyr Phe Asn Thr Asn Thr Ser Ile Ala Ser Thr Gly
2435                2440                2445

Tyr Thr Ile Ile Ser Gly Lys His Phe Tyr Phe Asn Thr Asp Gly
2450                2455                2460

Ile Met Gln Ile Gly Val Phe Lys Gly Pro Asp Gly Phe Glu Tyr
2465                2470                2475

Phe Ala Pro Ala Asn Thr Asp Ala Asn Asn Ile Glu Gly Gln Ala
2480                2485                2490

Ile Arg Tyr Gln Asn Arg Phe Leu Tyr Leu His Asp Asn Ile Tyr
2495                2500                2505

Tyr Phe Gly Asn Asn Ser Lys Ala Ala Thr Gly Trp Val Thr Ile
2510                2515                2520

Asp Gly Asn Arg Tyr Tyr Phe Glu Pro Asn Thr Ala Met Gly Ala
2525                2530                2535
```

-continued

Asn Gly Tyr Lys Thr Ile Asp Asn Lys Asn Phe Tyr Phe Arg Asn
    2540                2545                2550

Gly Leu Pro Gln Ile Gly Val Phe Lys Gly Ser Asn Gly Phe Glu
    2555                2560                2565

Tyr Phe Ala Pro Ala Asn Thr Asp Ala Asn Asn Ile Glu Gly Gln
    2570                2575                2580

Ala Ile Arg Tyr Gln Asn Arg Phe Leu His Leu Leu Gly Lys Ile
    2585                2590                2595

Tyr Tyr Phe Gly Asn Asn Ser Lys Ala Val Thr Gly Trp Gln Thr
    2600                2605                2610

Ile Asn Gly Lys Val Tyr Tyr Phe Met Pro Asp Thr Ala Met Ala
    2615                2620                2625

Ala Ala Gly Gly Leu Phe Glu Ile Asp Gly Val Ile Tyr Phe Phe
    2630                2635                2640

Gly Val Asp Gly Val Lys Ala Pro Gly Ile Tyr Gly His His His
    2645                2650                2655

His His His
    2660

<210> SEQ ID NO 5
<211> LENGTH: 2747
<212> TYPE: PRT
<213> ORGANISM: Artificial Sequence
<220> FEATURE:
<223> OTHER INFORMATION: Fusion Protein Human Sox2/C. difficile TcdB

<400> SEQUENCE: 5

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Gln Leu Arg Ala Arg Leu Glu His His Pro
            35                  40                  45

Gln Gly Gln Arg Glu Pro Ser Gly Ala Tyr Asn Met Met Glu Thr Glu
        50                  55                  60

Leu Lys Pro Pro Gly Pro Gln Gln Thr Ser Gly Gly Gly Gly Asn
65                  70                  75                  80

Ser Thr Ala Ala Ala Ala Gly Gly Asn Gln Lys Asn Ser Pro Asp Arg
                85                  90                  95

Val Lys Arg Pro Met Asn Ala Phe Met Val Trp Ser Arg Gly Gln Arg
            100                 105                 110

Arg Lys Met Ala Gln Glu Asn Pro Lys Met His Asn Ser Glu Ile Ser
        115                 120                 125

Lys Arg Leu Gly Ala Glu Trp Lys Leu Leu Ser Glu Thr Glu Lys Arg
    130                 135                 140

Pro Phe Ile Asp Glu Ala Lys Arg Leu Arg Ala Leu His Met Lys Glu
145                 150                 155                 160

His Pro Asp Tyr Lys Tyr Arg Pro Arg Arg Lys Thr Lys Thr Leu Met
                165                 170                 175

Lys Lys Asp Lys Tyr Thr Leu Pro Gly Gly Leu Leu Ala Pro Gly Gly
            180                 185                 190

Asn Ser Met Ala Ser Gly Val Gly Val Gly Ala Gly Leu Gly Ala Gly
        195                 200                 205

Val Asn Gln Arg Met Asp Ser Tyr Ala His Met Asn Gly Trp Ser Asn
    210                 215                 220

```
Gly Ser Tyr Ser Met Met Gln Asp Gln Leu Gly Tyr Pro Gln His Pro
225                 230                 235                 240

Gly Leu Asn Ala His Gly Ala Ala Gln Met Gln Pro Met His Arg Tyr
            245                 250                 255

Asp Val Ser Ala Leu Gln Tyr Asn Ser Met Thr Ser Ser Gln Thr Tyr
            260                 265                 270

Met Asn Gly Ser Pro Thr Tyr Ser Met Ser Tyr Ser Gln Gln Gly Thr
            275                 280                 285

Pro Gly Met Ala Leu Gly Ser Met Gly Ser Val Val Lys Ser Glu Ala
            290                 295                 300

Ser Ser Ser Pro Pro Val Val Thr Ser Ser Ser His Ser Arg Ala Pro
305                 310                 315                 320

Cys Gln Ala Gly Asp Leu Arg Asp Met Ile Ser Met Tyr Leu Pro Gly
            325                 330                 335

Ala Glu Val Pro Glu Pro Ala Ala Pro Ser Arg Leu His Met Ser Gln
            340                 345                 350

His Tyr Gln Ser Gly Pro Val Pro Gly Thr Ala Ile Asn Gly Thr Leu
            355                 360                 365

Pro Leu Ser His Met Ala Ala Ser Leu Val Asn Arg Lys Gln Leu
370                 375                 380

Glu Lys Met Ala Asn Val Arg Phe Arg Thr Gln Glu Asp Glu Tyr Val
385                 390                 395                 400

Ala Ile Leu Asp Ala Leu Glu Glu Tyr His Asn Met Ser Glu Asn Thr
            405                 410                 415

Val Val Glu Lys Tyr Leu Lys Leu Lys Asp Ile Asn Ser Leu Thr Asp
            420                 425                 430

Ile Tyr Ile Asp Thr Tyr Lys Lys Ser Gly Arg Asn Lys Ala Leu Lys
            435                 440                 445

Lys Phe Lys Glu Tyr Leu Val Thr Glu Val Leu Glu Leu Lys Asn Asn
            450                 455                 460

Asn Leu Thr Pro Val Glu Lys Asn Leu His Phe Val Trp Ile Gly Gly
465                 470                 475                 480

Gln Ile Asn Asp Thr Ala Ile Asn Tyr Ile Asn Gln Trp Lys Asp Val
            485                 490                 495

Asn Ser Asp Tyr Asn Val Asn Val Phe Tyr Asp Ser Asn Ala Phe Leu
            500                 505                 510

Ile Asn Thr Leu Lys Lys Thr Val Val Glu Ser Ala Ile Asn Asp Thr
            515                 520                 525

Leu Glu Ser Phe Arg Glu Asn Leu Asn Asp Pro Arg Phe Asp Tyr Asn
530                 535                 540

Lys Phe Phe Arg Lys Arg Met Glu Ile Ile Tyr Asp Lys Gln Lys Asn
545                 550                 555                 560

Phe Ile Asn Tyr Tyr Lys Ala Gln Arg Glu Glu Asn Pro Glu Leu Ile
            565                 570                 575

Ile Asp Asp Ile Val Lys Thr Tyr Leu Ser Asn Glu Tyr Ser Lys Glu
            580                 585                 590

Ile Asp Glu Leu Asn Thr Tyr Ile Glu Glu Ser Leu Asn Lys Ile Thr
            595                 600                 605

Gln Asn Ser Gly Asn Asp Val Arg Asn Phe Glu Glu Phe Lys Asn Gly
            610                 615                 620

Glu Ser Phe Asn Leu Tyr Glu Gln Glu Leu Val Glu Arg Trp Asn Leu
625                 630                 635                 640

Ala Ala Ala Ser Asp Ile Leu Arg Ile Ser Ala Leu Lys Glu Ile Gly
            645                 650                 655
```

```
Gly Met Tyr Leu Ala Val Ala Met Leu Pro Gly Ile Gln Pro Asp Leu
            660                 665                 670

Phe Glu Ser Ile Glu Lys Pro Ser Val Thr Val Asp Phe Trp Glu
            675                 680                 685

Met Thr Lys Leu Glu Ala Ile Met Lys Tyr Lys Glu Tyr Ile Pro Glu
690                 695                 700

Tyr Thr Ser Glu His Phe Asp Met Leu Asp Glu Val Gln Ser Ser
705                 710                 715                 720

Phe Glu Ser Val Leu Ala Ser Lys Ser Asp Lys Ser Glu Ile Phe Ser
            725                 730                 735

Ser Leu Gly Asp Met Glu Ala Ser Pro Leu Glu Val Lys Ile Ala Phe
            740                 745                 750

Asn Ser Lys Gly Ile Ile Asn Gln Gly Leu Ile Ser Val Lys Asp Ser
            755                 760                 765

Tyr Cys Ser Asn Leu Ile Val Lys Gln Ile Glu Asn Arg Tyr Lys Ile
            770                 775                 780

Leu Asn Asn Ser Leu Asn Pro Ala Ile Ser Glu Asp Asn Asp Phe Asn
785                 790                 795                 800

Thr Thr Thr Asn Thr Phe Ile Asp Ser Ile Met Ala Glu Ala Asn Ala
                    805                 810                 815

Asp Asn Gly Arg Phe Met Met Glu Leu Gly Lys Tyr Leu Arg Val Gly
                    820                 825                 830

Phe Phe Pro Asp Val Lys Thr Thr Ile Asn Leu Ser Gly Pro Glu Ala
            835                 840                 845

Tyr Ala Ala Tyr Gln Asp Leu Leu Met Phe Lys Glu Gly Ser Met
            850                 855                 860

Asn Ile His Leu Ile Glu Ala Asp Leu Arg Asn Phe Glu Ile Ser Lys
865                 870                 875                 880

Thr Asn Ile Ser Gln Ser Thr Glu Gln Glu Met Ala Ser Leu Trp Ser
                    885                 890                 895

Phe Asp Asp Ala Arg Ala Lys Ala Gln Phe Glu Glu Tyr Lys Arg Asn
            900                 905                 910

Tyr Phe Glu Gly Ser Leu Gly Glu Asp Asp Asn Leu Asp Phe Ser Gln
            915                 920                 925

Asn Ile Val Val Asp Lys Glu Tyr Leu Leu Glu Lys Ile Ser Ser Leu
930                 935                 940

Ala Arg Ser Ser Glu Arg Gly Tyr Ile His Tyr Ile Val Gln Leu Gln
945                 950                 955                 960

Gly Asp Lys Ile Ser Tyr Glu Ala Ala Cys Asn Leu Phe Ala Lys Thr
            965                 970                 975

Pro Tyr Asp Ser Val Leu Phe Gln Lys Asn Ile Glu Asp Ser Glu Ile
            980                 985                 990

Ala Tyr Tyr Tyr Asn Pro Gly Asp  Gly Glu Ile Gln Glu  Ile Asp Lys
            995                 1000                1005

Tyr Lys  Ile Pro Ser Ile Ile  Ser Asp Arg Pro Lys  Ile Lys Leu
    1010                1015                1020

Thr Phe  Ile Gly His Gly Lys  Asp Glu Phe Asn Thr  Asp Ile Phe
    1025                1030                1035

Ala Gly  Phe Asp Val Asp Ser  Leu Ser Thr Glu Ile  Glu Ala Ala
    1040                1045                1050

Ile Asp  Leu Ala Lys Glu Asp  Ile Ser Pro Lys Ser  Ile Glu Ile
    1055                1060                1065

Asn Leu  Leu Gly Cys Asn Met  Phe Ser Tyr Ser Ile  Asn Val Glu
```

```
              1070                1075                1080

Glu Thr Tyr Pro Gly Lys Leu Leu Leu Lys Val Lys Asp Lys Ile
1085                1090                1095

Ser Glu Leu Met Pro Ser Ile Ser Gln Asp Ser Ile Ile Val Ser
1100                1105                1110

Ala Asn Gln Tyr Glu Val Arg Ile Asn Ser Glu Gly Arg Arg Glu
1115                1120                1125

Leu Leu Asp His Ser Gly Glu Trp Ile Asn Lys Glu Glu Ser Ile
1130                1135                1140

Ile Lys Asp Ile Ser Ser Lys Glu Tyr Ile Ser Phe Asn Pro Lys
1145                1150                1155

Glu Asn Lys Ile Thr Val Lys Ser Lys Asn Leu Pro Glu Leu Ser
1160                1165                1170

Thr Leu Leu Gln Glu Ile Arg Asn Asn Ser Asn Ser Ser Asp Ile
1175                1180                1185

Glu Leu Glu Glu Lys Val Met Leu Thr Glu Cys Glu Ile Asn Val
1190                1195                1200

Ile Ser Asn Ile Asp Thr Gln Ile Val Glu Glu Arg Ile Glu Glu
1205                1210                1215

Ala Lys Asn Leu Thr Ser Asp Ser Ile Asn Tyr Ile Lys Asp Glu
1220                1225                1230

Phe Lys Leu Ile Glu Ser Ile Ser Asp Ala Leu Cys Asp Leu Lys
1235                1240                1245

Gln Gln Asn Glu Leu Glu Asp Ser His Phe Ile Ser Phe Glu Asp
1250                1255                1260

Ile Ser Glu Thr Asp Glu Gly Phe Ser Ile Arg Phe Ile Asn Lys
1265                1270                1275

Glu Thr Gly Glu Ser Ile Phe Val Glu Thr Glu Lys Thr Ile Phe
1280                1285                1290

Ser Glu Tyr Ala Asn His Ile Thr Glu Glu Ile Ser Lys Ile Lys
1295                1300                1305

Gly Thr Ile Phe Asp Thr Val Asn Gly Lys Leu Val Lys Lys Val
1310                1315                1320

Asn Leu Asp Thr Thr His Glu Val Asn Thr Leu Asn Ala Ala Phe
1325                1330                1335

Phe Ile Gln Ser Leu Ile Glu Tyr Asn Ser Ser Lys Glu Ser Leu
1340                1345                1350

Ser Asn Leu Ser Val Ala Met Lys Val Gln Val Tyr Ala Gln Leu
1355                1360                1365

Phe Ser Thr Gly Leu Asn Thr Ile Thr Asp Ala Ala Lys Val Val
1370                1375                1380

Glu Leu Val Ser Thr Ala Leu Asp Glu Thr Ile Asp Leu Leu Pro
1385                1390                1395

Thr Leu Ser Glu Gly Leu Pro Ile Ile Ala Thr Ile Ile Asp Gly
1400                1405                1410

Val Ser Leu Gly Ala Ala Ile Lys Glu Leu Ser Glu Thr Ser Asp
1415                1420                1425

Pro Leu Leu Arg Gln Glu Ile Glu Ala Lys Ile Gly Ile Met Ala
1430                1435                1440

Val Asn Leu Thr Thr Ala Thr Thr Ala Ile Ile Thr Ser Ser Leu
1445                1450                1455

Gly Ile Ala Ser Gly Phe Ser Ile Leu Leu Val Pro Leu Ala Gly
1460                1465                1470
```

```
Ile Ser Ala Gly Ile Pro Ser Leu Val Asn Asn Glu Leu Val Leu
1475                1480                1485

Arg Asp Lys Ala Thr Lys Val Val Asp Tyr Phe Lys His Val Ser
1490                1495                1500

Leu Val Glu Thr Glu Gly Val Phe Thr Leu Leu Asp Asp Lys Ile
1505                1510                1515

Met Met Pro Gln Asp Asp Leu Val Ile Ser Glu Ile Asp Phe Asn
1520                1525                1530

Asn Asn Ser Ile Val Leu Gly Lys Cys Glu Ile Trp Arg Met Glu
1535                1540                1545

Gly Gly Ser Gly His Thr Val Thr Asp Asp Ile Asp His Phe Phe
1550                1555                1560

Ser Ala Pro Ser Ile Thr Tyr Arg Glu Pro His Leu Ser Ile Tyr
1565                1570                1575

Asp Val Leu Glu Val Gln Lys Glu Glu Leu Asp Leu Ser Lys Asp
1580                1585                1590

Leu Met Val Leu Pro Asn Ala Pro Asn Arg Val Phe Ala Trp Glu
1595                1600                1605

Thr Gly Trp Thr Pro Gly Leu Arg Ser Leu Glu Asn Asp Gly Thr
1610                1615                1620

Lys Leu Leu Asp Arg Ile Arg Asp Asn Tyr Glu Gly Glu Phe Tyr
1625                1630                1635

Trp Arg Tyr Phe Ala Phe Ile Ala Asp Ala Leu Ile Thr Thr Leu
1640                1645                1650

Lys Pro Arg Tyr Glu Asp Thr Asn Ile Arg Ile Asn Leu Asp Ser
1655                1660                1665

Asn Thr Arg Ser Phe Ile Val Pro Ile Ile Thr Thr Glu Tyr Ile
1670                1675                1680

Arg Glu Lys Leu Ser Tyr Ser Phe Tyr Gly Ser Gly Gly Thr Tyr
1685                1690                1695

Ala Leu Ser Leu Ser Gln Tyr Asn Met Gly Ile Asn Ile Glu Leu
1700                1705                1710

Ser Glu Ser Asp Val Trp Ile Ile Asp Val Asp Asn Val Val Arg
1715                1720                1725

Asp Val Thr Ile Glu Ser Asp Lys Ile Lys Lys Gly Asp Leu Ile
1730                1735                1740

Glu Gly Ile Leu Ser Thr Leu Ser Ile Glu Glu Asn Lys Ile Ile
1745                1750                1755

Leu Asn Ser His Glu Ile Asn Phe Ser Gly Glu Val Asn Gly Ser
1760                1765                1770

Asn Gly Phe Val Ser Leu Thr Phe Ser Ile Leu Glu Gly Ile Asn
1775                1780                1785

Ala Ile Ile Glu Val Asp Leu Leu Ser Lys Ser Tyr Lys Leu Leu
1790                1795                1800

Ile Ser Gly Glu Leu Lys Ile Leu Met Leu Asn Ser Asn His Ile
1805                1810                1815

Gln Gln Lys Ile Asp Tyr Ile Gly Phe Asn Ser Glu Leu Gln Lys
1820                1825                1830

Asn Ile Pro Tyr Ser Phe Val Asp Ser Glu Gly Lys Glu Asn Gly
1835                1840                1845

Phe Ile Asn Gly Ser Thr Lys Glu Gly Leu Phe Val Ser Glu Leu
1850                1855                1860

Pro Asp Val Val Leu Ile Ser Lys Val Tyr Met Asp Asp Ser Lys
1865                1870                1875
```

```
Pro Ser Phe Gly Tyr Tyr Ser Asn Asn Leu Lys Asp Val Lys Val
    1880            1885                1890

Ile Thr Lys Asp Asn Val Asn Ile Leu Thr Gly Tyr Tyr Leu Lys
    1895            1900                1905

Asp Asp Ile Lys Ile Ser Leu Ser Leu Thr Leu Gln Asp Glu Lys
    1910            1915                1920

Thr Ile Lys Leu Asn Ser Val His Leu Asp Glu Ser Gly Val Ala
    1925            1930                1935

Glu Ile Leu Lys Phe Met Asn Arg Lys Gly Asn Thr Asn Thr Ser
    1940            1945                1950

Asp Ser Leu Met Ser Phe Leu Glu Ser Met Asn Ile Lys Ser Ile
    1955            1960                1965

Phe Val Asn Phe Leu Gln Ser Asn Ile Lys Phe Ile Leu Asp Ala
    1970            1975                1980

Asn Phe Ile Ile Ser Gly Thr Thr Ser Ile Gly Gln Phe Glu Phe
    1985            1990                1995

Ile Cys Asp Glu Asn Asp Asn Ile Gln Pro Tyr Phe Ile Lys Phe
    2000            2005                2010

Asn Thr Leu Glu Thr Asn Tyr Thr Leu Tyr Val Gly Asn Arg Gln
    2015            2020                2025

Asn Met Ile Val Glu Pro Asn Tyr Asp Leu Asp Asp Ser Gly Asp
    2030            2035                2040

Ile Ser Ser Thr Val Ile Asn Phe Ser Gln Lys Tyr Leu Tyr Gly
    2045            2050                2055

Ile Asp Ser Cys Val Asn Lys Val Val Ile Ser Pro Asn Ile Tyr
    2060            2065                2070

Thr Asp Glu Ile Asn Ile Thr Pro Val Tyr Glu Thr Asn Asn Thr
    2075            2080                2085

Tyr Pro Glu Val Ile Val Leu Asp Ala Asn Tyr Ile Asn Glu Lys
    2090            2095                2100

Ile Asn Val Asn Ile Asn Asp Leu Ser Ile Arg Tyr Val Trp Ser
    2105            2110                2115

Asn Asp Gly Asn Asp Phe Ile Leu Met Ser Thr Ser Glu Glu Asn
    2120            2125                2130

Lys Val Ser Gln Val Lys Ile Arg Phe Val Asn Val Phe Lys Asp
    2135            2140                2145

Lys Thr Leu Ala Asn Lys Leu Ser Phe Asn Phe Ser Asp Lys Gln
    2150            2155                2160

Asp Val Pro Val Ser Glu Ile Ile Leu Ser Phe Thr Pro Ser Tyr
    2165            2170                2175

Tyr Glu Asp Gly Leu Ile Gly Tyr Asp Leu Gly Leu Val Ser Leu
    2180            2185                2190

Tyr Asn Glu Lys Phe Tyr Ile Asn Asn Phe Gly Met Met Val Ser
    2195            2200                2205

Gly Leu Ile Tyr Ile Asn Asp Ser Leu Tyr Tyr Phe Lys Pro Pro
    2210            2215                2220

Val Asn Asn Leu Ile Thr Gly Phe Val Thr Val Gly Asp Asp Lys
    2225            2230                2235

Tyr Tyr Phe Asn Pro Ile Asn Gly Gly Ala Ala Ser Ile Gly Glu
    2240            2245                2250

Thr Ile Ile Asp Asp Lys Asn Tyr Tyr Phe Asn Gln Ser Gly Val
    2255            2260                2265

Leu Gln Thr Gly Val Phe Ser Thr Glu Asp Gly Phe Lys Tyr Phe
```

-continued

```
            2270                2275                 2280

Ala Pro  Ala Asn Thr Leu  Asp Glu Asn Leu  Glu Gly Glu Ala Ile
    2285                2290                2295

Asp Phe  Thr Gly Lys Leu  Ile Ile Asp Glu  Asn Ile Tyr Tyr Phe
    2300                2305                2310

Asp Asp  Asn Tyr Arg Gly  Ala Val Glu Trp  Lys Glu Leu Asp Gly
    2315                2320                2325

Glu Met  His Tyr Phe Ser  Pro Glu Thr Gly  Lys Ala Phe Lys Gly
    2330                2335                2340

Leu Asn  Gln Ile Gly Asp  Tyr Lys Tyr Tyr  Phe Asn Ser Asp Gly
    2345                2350                2355

Val Met  Gln Lys Gly Phe  Val Ser Ile Asn  Asp Asn Lys His Tyr
    2360                2365                2370

Phe Asp  Asp Ser Gly Val  Met Lys Val Gly  Tyr Thr Glu Ile Asp
    2375                2380                2385

Gly Lys  His Phe Tyr Phe  Ala Glu Asn Gly  Glu Met Gln Ile Gly
    2390                2395                2400

Val Phe  Asn Thr Glu Asp  Gly Phe Lys Tyr  Phe Ala His His Asn
    2405                2410                2415

Glu Asp  Leu Gly Asn Glu  Glu Gly Glu Ile  Ser Tyr Ser Gly
    2420                2425                2430

Ile Leu  Asn Phe Asn Asn  Lys Ile Tyr Tyr  Phe Asp Asp Ser Phe
    2435                2440                2445

Thr Ala  Val Val Gly Trp  Lys Asp Leu Glu  Asp Gly Ser Lys Tyr
    2450                2455                2460

Tyr Phe  Asp Glu Asp Thr  Ala Glu Ala Tyr  Ile Gly Leu Ser Leu
    2465                2470                2475

Ile Asn  Asp Gly Gln Tyr  Tyr Phe Asn Asp  Asp Gly Ile Met Gln
    2480                2485                2490

Val Gly  Phe Val Thr Ile  Asn Asp Lys Val  Phe Tyr Phe Ser Asp
    2495                2500                2505

Ser Gly  Ile Ile Glu Ser  Gly Val Gln Asn  Ile Asp Asp Asn Tyr
    2510                2515                2520

Phe Tyr  Ile Asp Asp Asn  Gly Ile Val Gln  Ile Gly Val Phe Asp
    2525                2530                2535

Thr Ser  Asp Gly Tyr Lys  Tyr Phe Ala Pro  Ala Asn Thr Val Asn
    2540                2545                2550

Asp Asn  Ile Tyr Gly Gln  Ala Val Glu Tyr  Ser Gly Leu Val Arg
    2555                2560                2565

Val Gly  Glu Asp Val Tyr  Tyr Phe Gly Glu  Thr Tyr Thr Ile Glu
    2570                2575                2580

Thr Gly  Trp Ile Tyr Asp  Met Glu Asn Glu  Ser Asp Lys Tyr Tyr
    2585                2590                2595

Phe Asn  Pro Glu Thr Lys  Lys Ala Cys Lys  Gly Ile Asn Leu Ile
    2600                2605                2610

Asp Asp  Ile Lys Tyr Tyr  Phe Asp Glu Lys  Gly Ile Met Arg Thr
    2615                2620                2625

Gly Leu  Ile Ser Phe Glu  Asn Asn Asn Tyr  Tyr Phe Asn Glu Asn
    2630                2635                2640

Gly Glu  Met Gln Phe Gly  Tyr Ile Asn Ile  Glu Asp Lys Met Phe
    2645                2650                2655

Tyr Phe  Gly Glu Asp Gly  Val Met Gln Ile  Gly Val Phe Asn Thr
    2660                2665                2670
```

-continued

Pro Asp Gly Phe Lys Tyr Phe Ala His Gln Asn Thr Leu Asp Glu
2675                2680                2685

Asn Phe Glu Gly Glu Ser Ile Asn Tyr Thr Gly Trp Leu Asp Leu
2690                2695                2700

Asp Glu Lys Arg Tyr Tyr Phe Thr Asp Glu Tyr Ile Ala Ala Thr
2705                2710                2715

Gly Ser Val Ile Ile Asp Gly Glu Glu Tyr Tyr Phe Asp Pro Asp
2720                2725                2730

Thr Ala Gln Leu Val Ile Ser Glu His His His His His His
2735                2740                2745

<210> SEQ ID NO 6
<211> LENGTH: 2274
<212> TYPE: PRT
<213> ORGANISM: Artificial Sequence
<220> FEATURE:
<223> OTHER INFORMATION: Fusion Protein Human Sox2/C. difficile TcdB

<400> SEQUENCE: 6

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Tyr Asn Met Met Glu Thr Glu
        50                  55                  60

Leu Lys Pro Pro Gly Pro Gln Thr Ser Gly Gly Gly Gly Asn
65                  70                  75                  80

Ser Thr Ala Ala Ala Gly Gly Asn Gln Lys Asn Ser Pro Asp Arg
                85                  90                  95

Val Lys Arg Pro Met Asn Ala Phe Met Val Trp Ser Arg Gly Gln Arg
            100                 105                 110

Arg Lys Met Ala Gln Glu Asn Pro Lys Met His Asn Ser Glu Ile Ser
        115                 120                 125

Lys Arg Leu Gly Ala Glu Trp Lys Leu Leu Ser Glu Thr Glu Lys Arg
    130                 135                 140

Pro Phe Ile Asp Glu Ala Lys Arg Leu Arg Ala Leu His Met Lys Glu
145                 150                 155                 160

His Pro Asp Tyr Lys Tyr Arg Pro Arg Arg Lys Thr Lys Thr Leu Met
                165                 170                 175

Lys Lys Asp Lys Tyr Thr Leu Pro Gly Gly Leu Leu Ala Pro Gly Gly
            180                 185                 190

Asn Ser Met Ala Ser Gly Val Gly Val Gly Ala Gly Leu Gly Ala Gly
        195                 200                 205

Val Asn Gln Arg Met Asp Ser Tyr Ala His Met Asn Gly Trp Ser Asn
    210                 215                 220

Gly Ser Tyr Ser Met Met Gln Asp Gln Leu Gly Tyr Pro Gln His Pro
225                 230                 235                 240

Gly Leu Asn Ala His Gly Ala Ala Gln Met Gln Pro Met His Arg Tyr
                245                 250                 255

Asp Val Ser Ala Leu Gln Tyr Asn Ser Met Thr Ser Ser Gln Thr Tyr
            260                 265                 270

Met Asn Gly Ser Pro Thr Tyr Ser Met Ser Tyr Ser Gln Gln Gly Thr
        275                 280                 285

Pro Gly Met Ala Leu Gly Ser Met Gly Ser Val Val Lys Ser Glu Ala

```
                290                 295                 300
Ser Ser Ser Pro Pro Val Val Thr Ser Ser His Ser Arg Ala Pro
305                 310                 315                 320

Cys Gln Ala Gly Asp Leu Arg Asp Met Ile Ser Met Tyr Leu Pro Gly
                325                 330                 335

Ala Glu Val Pro Glu Pro Ala Ala Pro Ser Arg Leu His Met Ser Gln
                340                 345                 350

His Tyr Gln Ser Gly Pro Val Pro Gly Thr Ala Ile Asn Gly Thr Leu
                355                 360                 365

Pro Leu Ser His Met Ala Ala Tyr Ala Ala Tyr Gln Asp Leu Leu
370                 375                 380

Met Phe Lys Glu Gly Ser Met Asn Ile His Leu Ile Glu Ala Asp Leu
385                 390                 395                 400

Arg Asn Phe Glu Ile Ser Lys Thr Asn Ile Ser Gln Ser Thr Glu Gln
                405                 410                 415

Glu Met Ala Ser Leu Trp Ser Phe Asp Asp Ala Arg Ala Lys Ala Gln
                420                 425                 430

Phe Glu Glu Tyr Lys Arg Asn Tyr Phe Glu Gly Ser Leu Gly Glu Asp
                435                 440                 445

Asp Asn Leu Asp Phe Ser Gln Asn Ile Val Val Asp Lys Glu Tyr Leu
                450                 455                 460

Leu Glu Lys Ile Ser Ser Leu Ala Arg Ser Glu Arg Gly Tyr Ile
465                 470                 475                 480

His Tyr Ile Val Gln Leu Gln Gly Asp Lys Ile Ser Tyr Glu Ala Ala
                485                 490                 495

Cys Asn Leu Phe Ala Lys Thr Pro Tyr Asp Ser Val Leu Phe Gln Lys
                500                 505                 510

Asn Ile Glu Asp Ser Glu Ile Ala Tyr Tyr Asn Pro Gly Asp Gly
                515                 520                 525

Glu Ile Gln Glu Ile Asp Lys Tyr Lys Ile Pro Ser Ile Ile Ser Asp
                530                 535                 540

Arg Pro Lys Ile Lys Leu Thr Phe Ile Gly His Gly Lys Asp Glu Phe
545                 550                 555                 560

Asn Thr Asp Ile Phe Ala Gly Phe Asp Val Asp Ser Leu Ser Thr Glu
                565                 570                 575

Ile Glu Ala Ala Ile Asp Leu Ala Lys Glu Asp Ile Ser Pro Lys Ser
                580                 585                 590

Ile Glu Ile Asn Leu Leu Gly Cys Asn Met Phe Ser Tyr Ser Ile Asn
                595                 600                 605

Val Glu Glu Thr Tyr Pro Gly Lys Leu Leu Lys Val Lys Asp Lys
                610                 615                 620

Ile Ser Glu Leu Met Pro Ser Ile Ser Gln Asp Ser Ile Ile Val Ser
625                 630                 635                 640

Ala Asn Gln Tyr Glu Val Arg Ile Asn Ser Glu Gly Arg Arg Glu Leu
                645                 650                 655

Leu Asp His Ser Gly Glu Trp Ile Asn Lys Glu Glu Ser Ile Ile Lys
                660                 665                 670

Asp Ile Ser Ser Lys Glu Tyr Ile Ser Phe Asn Pro Lys Glu Asn Lys
                675                 680                 685

Ile Thr Val Lys Ser Lys Asn Leu Pro Glu Leu Ser Thr Leu Leu Gln
                690                 695                 700

Glu Ile Arg Asn Asn Ser Asn Ser Ser Asp Ile Glu Leu Glu Glu Lys
705                 710                 715                 720
```

-continued

Val Met Leu Thr Glu Cys Glu Ile Asn Val Ile Ser Asn Ile Asp Thr
                725                 730                 735

Gln Ile Val Glu Glu Arg Ile Glu Glu Ala Lys Asn Leu Thr Ser Asp
            740                 745                 750

Ser Ile Asn Tyr Ile Lys Asp Glu Phe Lys Leu Ile Glu Ser Ile Ser
        755                 760                 765

Asp Ala Leu Cys Asp Leu Lys Gln Gln Asn Glu Leu Glu Asp Ser His
    770                 775                 780

Phe Ile Ser Phe Glu Asp Ile Ser Glu Thr Asp Glu Gly Phe Ser Ile
785                 790                 795                 800

Arg Phe Ile Asn Lys Glu Thr Gly Glu Ser Ile Phe Val Glu Thr Glu
                805                 810                 815

Lys Thr Ile Phe Ser Glu Tyr Ala Asn His Ile Thr Glu Glu Ile Ser
            820                 825                 830

Lys Ile Lys Gly Thr Ile Phe Asp Thr Val Asn Gly Lys Leu Val Lys
        835                 840                 845

Lys Val Asn Leu Asp Thr Thr His Glu Val Asn Thr Leu Asn Ala Ala
    850                 855                 860

Phe Phe Ile Gln Ser Leu Ile Glu Tyr Asn Ser Ser Lys Glu Ser Leu
865                 870                 875                 880

Ser Asn Leu Ser Val Ala Met Lys Val Gln Val Tyr Ala Gln Leu Phe
                885                 890                 895

Ser Thr Gly Leu Asn Thr Ile Thr Asp Ala Ala Lys Val Val Glu Leu
            900                 905                 910

Val Ser Thr Ala Leu Asp Glu Thr Ile Asp Leu Leu Pro Thr Leu Ser
        915                 920                 925

Glu Gly Leu Pro Ile Ile Ala Thr Ile Ile Asp Gly Val Ser Leu Gly
    930                 935                 940

Ala Ala Ile Lys Glu Leu Ser Glu Thr Ser Asp Pro Leu Leu Arg Gln
945                 950                 955                 960

Glu Ile Glu Ala Lys Ile Gly Ile Met Ala Val Asn Leu Thr Thr Ala
                965                 970                 975

Thr Thr Ala Ile Ile Thr Ser Ser Leu Gly Ile Ala Ser Gly Phe Ser
            980                 985                 990

Ile Leu Leu Val Pro Leu Ala Gly Ile Ser Ala Gly Ile Pro Ser Leu
        995                 1000                1005

Val Asn Asn Glu Leu Val Leu Arg Asp Lys Ala Thr Lys Val Val
    1010                1015                1020

Asp Tyr Phe Lys His Val Ser Leu Val Glu Thr Glu Gly Val Phe
    1025                1030                1035

Thr Leu Leu Asp Asp Lys Ile Met Met Pro Gln Asp Asp Leu Val
    1040                1045                1050

Ile Ser Glu Ile Asp Phe Asn Asn Ser Ile Val Leu Gly Lys
    1055                1060                1065

Cys Glu Ile Trp Arg Met Glu Gly Gly Ser Gly His Thr Val Thr
    1070                1075                1080

Asp Asp Ile Asp His Phe Phe Ser Ala Pro Ser Ile Thr Tyr Arg
    1085                1090                1095

Glu Pro His Leu Ser Ile Tyr Asp Val Leu Glu Val Gln Lys Glu
    1100                1105                1110

Glu Leu Asp Leu Ser Lys Asp Leu Met Val Leu Pro Asn Ala Pro
    1115                1120                1125

Asn Arg Val Phe Ala Trp Glu Thr Gly Trp Thr Pro Gly Leu Arg
    1130                1135                1140

```
Ser Leu Glu Asn Asp Gly Thr Lys Leu Leu Asp Arg Ile Arg Asp
1145                1150                1155

Asn Tyr Glu Gly Glu Phe Tyr Trp Arg Tyr Phe Ala Phe Ile Ala
1160                1165                1170

Asp Ala Leu Ile Thr Thr Leu Lys Pro Arg Tyr Glu Asp Thr Asn
1175                1180                1185

Ile Arg Ile Asn Leu Asp Ser Asn Thr Arg Ser Phe Ile Val Pro
1190                1195                1200

Ile Ile Thr Thr Glu Tyr Ile Arg Glu Lys Leu Ser Tyr Ser Phe
1205                1210                1215

Tyr Gly Ser Gly Gly Thr Tyr Ala Leu Ser Leu Ser Gln Tyr Asn
1220                1225                1230

Met Gly Ile Asn Ile Glu Leu Ser Glu Ser Asp Val Trp Ile Ile
1235                1240                1245

Asp Val Asp Asn Val Val Arg Asp Val Thr Ile Glu Ser Asp Lys
1250                1255                1260

Ile Lys Lys Gly Asp Leu Ile Glu Gly Ile Leu Ser Thr Leu Ser
1265                1270                1275

Ile Glu Glu Asn Lys Ile Ile Leu Asn Ser His Glu Ile Asn Phe
1280                1285                1290

Ser Gly Glu Val Asn Gly Ser Asn Gly Phe Val Ser Leu Thr Phe
1295                1300                1305

Ser Ile Leu Glu Gly Ile Asn Ala Ile Ile Glu Val Asp Leu Leu
1310                1315                1320

Ser Lys Ser Tyr Lys Leu Leu Ile Ser Gly Glu Leu Lys Ile Leu
1325                1330                1335

Met Leu Asn Ser Asn His Ile Gln Gln Lys Ile Asp Tyr Ile Gly
1340                1345                1350

Phe Asn Ser Glu Leu Gln Lys Asn Ile Pro Tyr Ser Phe Val Asp
1355                1360                1365

Ser Glu Gly Lys Glu Asn Gly Phe Ile Asn Gly Ser Thr Lys Glu
1370                1375                1380

Gly Leu Phe Val Ser Glu Leu Pro Asp Val Val Leu Ile Ser Lys
1385                1390                1395

Val Tyr Met Asp Asp Ser Lys Pro Ser Phe Gly Tyr Tyr Ser Asn
1400                1405                1410

Asn Leu Lys Asp Val Lys Val Ile Thr Lys Asp Asn Val Asn Ile
1415                1420                1425

Leu Thr Gly Tyr Tyr Leu Lys Asp Asp Ile Lys Ile Ser Leu Ser
1430                1435                1440

Leu Thr Leu Gln Asp Glu Lys Thr Ile Lys Leu Asn Ser Val His
1445                1450                1455

Leu Asp Glu Ser Gly Val Ala Glu Ile Leu Lys Phe Met Asn Arg
1460                1465                1470

Lys Gly Asn Thr Asn Thr Ser Asp Ser Leu Met Ser Phe Leu Glu
1475                1480                1485

Ser Met Asn Ile Lys Ser Ile Phe Val Asn Phe Leu Gln Ser Asn
1490                1495                1500

Ile Lys Phe Ile Leu Asp Ala Asn Phe Ile Ile Ser Gly Thr Thr
1505                1510                1515

Ser Ile Gly Gln Phe Glu Phe Ile Cys Asp Glu Asn Asp Asn Ile
1520                1525                1530

Gln Pro Tyr Phe Ile Lys Phe Asn Thr Leu Glu Thr Asn Tyr Thr
```

-continued

```
           1535                1540                1545

Leu Tyr Val Gly Asn Arg Gln Asn Met Ile Val Glu Pro Asn Tyr
    1550                1555                1560

Asp Leu Asp Asp Ser Gly Asp Ile Ser Ser Thr Val Ile Asn Phe
    1565                1570                1575

Ser Gln Lys Tyr Leu Tyr Gly Ile Asp Ser Cys Val Asn Lys Val
    1580                1585                1590

Val Ile Ser Pro Asn Ile Tyr Thr Asp Glu Ile Asn Ile Thr Pro
    1595                1600                1605

Val Tyr Glu Thr Asn Asn Thr Tyr Pro Glu Val Ile Val Leu Asp
    1610                1615                1620

Ala Asn Tyr Ile Asn Glu Lys Ile Asn Val Asn Ile Asn Asp Leu
    1625                1630                1635

Ser Ile Arg Tyr Val Trp Ser Asn Asp Gly Asn Asp Phe Ile Leu
    1640                1645                1650

Met Ser Thr Ser Glu Glu Asn Lys Val Ser Gln Val Lys Ile Arg
    1655                1660                1665

Phe Val Asn Val Phe Lys Asp Lys Thr Leu Ala Asn Lys Leu Ser
    1670                1675                1680

Phe Asn Phe Ser Asp Lys Gln Asp Val Pro Val Ser Glu Ile Ile
    1685                1690                1695

Leu Ser Phe Thr Pro Ser Tyr Tyr Glu Asp Gly Leu Ile Gly Tyr
    1700                1705                1710

Asp Leu Gly Leu Val Ser Leu Tyr Asn Glu Lys Phe Tyr Ile Asn
    1715                1720                1725

Asn Phe Gly Met Met Val Ser Gly Leu Ile Tyr Ile Asn Asp Ser
    1730                1735                1740

Leu Tyr Tyr Phe Lys Pro Pro Val Asn Asn Leu Ile Thr Gly Phe
    1745                1750                1755

Val Thr Val Gly Asp Asp Lys Tyr Tyr Phe Asn Pro Ile Asn Gly
    1760                1765                1770

Gly Ala Ala Ser Ile Gly Glu Thr Ile Ile Asp Asp Lys Asn Tyr
    1775                1780                1785

Tyr Phe Asn Gln Ser Gly Val Leu Gln Thr Gly Val Phe Ser Thr
    1790                1795                1800

Glu Asp Gly Phe Lys Tyr Phe Ala Pro Ala Asn Thr Leu Asp Glu
    1805                1810                1815

Asn Leu Glu Gly Glu Ala Ile Asp Phe Thr Gly Lys Leu Ile Ile
    1820                1825                1830

Asp Glu Asn Ile Tyr Tyr Phe Asp Asp Asn Tyr Arg Gly Ala Val
    1835                1840                1845

Glu Trp Lys Glu Leu Asp Gly Glu Met His Tyr Phe Ser Pro Glu
    1850                1855                1860

Thr Gly Lys Ala Phe Lys Gly Leu Asn Gln Ile Gly Asp Tyr Lys
    1865                1870                1875

Tyr Tyr Phe Asn Ser Asp Gly Val Met Gln Lys Gly Phe Val Ser
    1880                1885                1890

Ile Asn Asp Asn Lys His Tyr Phe Asp Asp Ser Gly Val Met Lys
    1895                1900                1905

Val Gly Tyr Thr Glu Ile Asp Gly Lys His Phe Tyr Phe Ala Glu
    1910                1915                1920

Asn Gly Glu Met Gln Ile Gly Val Phe Asn Thr Glu Asp Gly Phe
    1925                1930                1935
```

| | | | | | | | | | | |
|---|---|---|---|---|---|---|---|---|---|---|
| Lys | Tyr | Phe | Ala | His | His | Asn | Glu | Asp | Leu | Gly | Asn | Glu | Glu | Gly |
| | 1940 | | | | 1945 | | | | 1950 | |
| Glu | Glu | Ile | Ser | Tyr | Ser | Gly | Ile | Leu | Asn | Phe | Asn | Asn | Lys | Ile |
| | 1955 | | | | 1960 | | | | 1965 | |
| Tyr | Tyr | Phe | Asp | Asp | Ser | Phe | Thr | Ala | Val | Val | Gly | Trp | Lys | Asp |
| | 1970 | | | | 1975 | | | | 1980 | |
| Leu | Glu | Asp | Gly | Ser | Lys | Tyr | Tyr | Phe | Asp | Asp | Thr | Ala | Glu |
| | 1985 | | | | 1990 | | | | 1995 | |
| Ala | Tyr | Ile | Gly | Leu | Ser | Leu | Ile | Asn | Asp | Gly | Gln | Tyr | Tyr | Phe |
| | 2000 | | | | 2005 | | | | 2010 | |
| Asn | Asp | Asp | Gly | Ile | Met | Gln | Val | Gly | Phe | Val | Thr | Ile | Asn | Asp |
| | 2015 | | | | 2020 | | | | 2025 | |
| Lys | Val | Phe | Tyr | Phe | Ser | Asp | Ser | Gly | Ile | Ile | Glu | Ser | Gly | Val |
| | 2030 | | | | 2035 | | | | 2040 | |
| Gln | Asn | Ile | Asp | Asp | Asn | Tyr | Phe | Tyr | Ile | Asp | Asp | Asn | Gly | Ile |
| | 2045 | | | | 2050 | | | | 2055 | |
| Val | Gln | Ile | Gly | Val | Phe | Asp | Thr | Ser | Asp | Gly | Tyr | Lys | Tyr | Phe |
| | 2060 | | | | 2065 | | | | 2070 | |
| Ala | Pro | Ala | Asn | Thr | Val | Asn | Asp | Asn | Ile | Tyr | Gly | Gln | Ala | Val |
| | 2075 | | | | 2080 | | | | 2085 | |
| Glu | Tyr | Ser | Gly | Leu | Val | Arg | Val | Gly | Glu | Asp | Val | Tyr | Tyr | Phe |
| | 2090 | | | | 2095 | | | | 2100 | |
| Gly | Glu | Thr | Tyr | Thr | Ile | Glu | Thr | Gly | Trp | Ile | Tyr | Asp | Met | Glu |
| | 2105 | | | | 2110 | | | | 2115 | |
| Asn | Glu | Ser | Asp | Lys | Tyr | Tyr | Phe | Asn | Pro | Glu | Thr | Lys | Lys | Ala |
| | 2120 | | | | 2125 | | | | 2130 | |
| Cys | Lys | Gly | Ile | Asn | Leu | Ile | Asp | Asp | Ile | Lys | Tyr | Tyr | Phe | Asp |
| | 2135 | | | | 2140 | | | | 2145 | |
| Glu | Lys | Gly | Ile | Met | Arg | Thr | Gly | Leu | Ile | Ser | Phe | Glu | Asn | Asn |
| | 2150 | | | | 2155 | | | | 2160 | |
| Asn | Tyr | Tyr | Phe | Asn | Glu | Asn | Gly | Glu | Met | Gln | Phe | Gly | Tyr | Ile |
| | 2165 | | | | 2170 | | | | 2175 | |
| Asn | Ile | Glu | Asp | Lys | Met | Phe | Tyr | Phe | Gly | Glu | Asp | Gly | Val | Met |
| | 2180 | | | | 2185 | | | | 2190 | |
| Gln | Ile | Gly | Val | Phe | Asn | Thr | Pro | Asp | Gly | Phe | Lys | Tyr | Phe | Ala |
| | 2195 | | | | 2200 | | | | 2205 | |
| His | Gln | Asn | Thr | Leu | Asp | Glu | Asn | Phe | Glu | Gly | Glu | Ser | Ile | Asn |
| | 2210 | | | | 2215 | | | | 2220 | |
| Tyr | Thr | Gly | Trp | Leu | Asp | Leu | Asp | Glu | Lys | Arg | Tyr | Tyr | Phe | Thr |
| | 2225 | | | | 2230 | | | | 2235 | |
| Asp | Glu | Tyr | Ile | Ala | Ala | Thr | Gly | Ser | Val | Ile | Ile | Asp | Gly | Glu |
| | 2240 | | | | 2245 | | | | 2250 | |
| Glu | Tyr | Tyr | Phe | Asp | Pro | Asp | Thr | Ala | Gln | Leu | Val | Ile | Ser | Glu |
| | 2255 | | | | 2260 | | | | 2265 | |
| His | His | His | His | His | His |
| | 2270 |

```
<210> SEQ ID NO 7
<211> LENGTH: 3091
<212> TYPE: PRT
<213> ORGANISM: Artificial Sequence
<220> FEATURE:
<223> OTHER INFORMATION: Fusion Protein Human Sox 2/C. difficile aTcdA

<400> SEQUENCE: 7
```

Met Asp Glu Gln Gln Ser Gln Ala Val Ala Pro Val Tyr Val Gly Gly

-continued

```
1               5                   10                  15
Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Tyr Asn Met Met Glu Thr Glu
        50                  55                  60

Leu Lys Pro Pro Gly Pro Gln Gln Thr Ser Gly Gly Gly Gly Gly Asn
65                  70                  75                  80

Ser Thr Ala Ala Ala Gly Gly Asn Gln Lys Asn Ser Pro Asp Arg
            85                  90                  95

Val Lys Arg Pro Met Asn Ala Phe Met Val Trp Ser Arg Gly Gln Arg
            100                 105                 110

Arg Lys Met Ala Gln Glu Asn Pro Lys Met His Asn Ser Glu Ile Ser
            115                 120                 125

Lys Arg Leu Gly Ala Glu Trp Lys Leu Leu Ser Glu Thr Glu Lys Arg
            130                 135                 140

Pro Phe Ile Asp Glu Ala Lys Arg Leu Arg Ala Leu His Met Lys Glu
145                 150                 155                 160

His Pro Asp Tyr Lys Tyr Arg Pro Arg Arg Lys Thr Lys Thr Leu Met
                165                 170                 175

Lys Lys Asp Lys Tyr Thr Leu Pro Gly Gly Leu Leu Ala Pro Gly Gly
            180                 185                 190

Asn Ser Met Ala Ser Gly Val Gly Val Gly Ala Gly Leu Gly Ala Gly
            195                 200                 205

Val Asn Gln Arg Met Asp Ser Tyr Ala His Met Asn Gly Trp Ser Asn
            210                 215                 220

Gly Ser Tyr Ser Met Met Gln Asp Gln Leu Gly Tyr Pro Gln His Pro
225                 230                 235                 240

Gly Leu Asn Ala His Gly Ala Ala Gln Met Gln Pro Met His Arg Tyr
            245                 250                 255

Asp Val Ser Ala Leu Gln Tyr Asn Ser Met Thr Ser Ser Gln Thr Tyr
            260                 265                 270

Met Asn Gly Ser Pro Thr Tyr Ser Met Ser Tyr Ser Gln Gln Gly Thr
            275                 280                 285

Pro Gly Met Ala Leu Gly Ser Met Gly Ser Val Val Lys Ser Glu Ala
            290                 295                 300

Ser Ser Ser Pro Pro Val Val Thr Ser Ser Ser His Ser Arg Ala Pro
305                 310                 315                 320

Cys Gln Ala Gly Asp Leu Arg Asp Met Ile Ser Met Tyr Leu Pro Gly
            325                 330                 335

Ala Glu Val Pro Glu Pro Ala Ala Pro Ser Arg Leu His Met Ser Gln
            340                 345                 350

His Tyr Gln Ser Gly Pro Val Pro Gly Thr Ala Ile Asn Gly Thr Leu
            355                 360                 365

Pro Leu Ser His Met Ala Ala Ala Ser Leu Ile Ser Lys Glu Glu Leu
            370                 375                 380

Ile Lys Leu Ala Tyr Ser Ile Arg Pro Arg Glu Asn Glu Tyr Lys Thr
385                 390                 395                 400

Ile Leu Thr Asn Leu Asp Glu Tyr Asn Lys Leu Thr Thr Asn Asn Asn
            405                 410                 415

Glu Asn Lys Tyr Leu Gln Leu Lys Lys Leu Asn Glu Ser Ile Asp Val
            420                 425                 430
```

```
Phe Met Asn Lys Tyr Lys Thr Ser Ser Arg Asn Arg Ala Leu Ser Asn
        435                 440                 445
Leu Lys Lys Asp Ile Leu Lys Glu Val Ile Leu Ile Lys Asn Ser Asn
        450                 455                 460
Thr Ser Pro Val Glu Lys Asn Leu His Phe Val Trp Ile Gly Gly Glu
465                 470                 475                 480
Val Ser Asp Ile Ala Leu Glu Tyr Ile Lys Gln Trp Ala Asp Ile Asn
                485                 490                 495
Ala Glu Tyr Asn Ile Lys Leu Trp Tyr Asp Ser Glu Ala Phe Leu Val
                500                 505                 510
Asn Thr Leu Lys Lys Ala Ile Val Glu Ser Ser Thr Thr Glu Ala Leu
            515                 520                 525
Gln Leu Leu Glu Glu Glu Ile Gln Asn Pro Gln Phe Asp Asn Met Lys
530                 535                 540
Phe Tyr Lys Lys Arg Met Glu Phe Ile Tyr Asp Arg Gln Lys Arg Phe
545                 550                 555                 560
Ile Asn Tyr Tyr Lys Ser Gln Ile Asn Lys Pro Thr Val Pro Thr Ile
                565                 570                 575
Asp Asp Ile Ile Lys Ser His Leu Val Ser Glu Tyr Asn Arg Asp Glu
                580                 585                 590
Thr Val Leu Glu Ser Tyr Arg Thr Asn Ser Leu Arg Lys Ile Asn Ser
            595                 600                 605
Asn His Gly Ile Asp Ile Arg Ala Asn Ser Leu Phe Thr Glu Gln Glu
        610                 615                 620
Leu Leu Asn Ile Tyr Ser Gln Glu Leu Leu Asn Arg Gly Asn Leu Ala
625                 630                 635                 640
Ala Ala Ser Asp Ile Val Arg Leu Leu Ala Leu Lys Asn Phe Gly Gly
                645                 650                 655
Val Tyr Leu Ala Val Ala Met Leu Pro Gly Ile His Ser Asp Leu Phe
                660                 665                 670
Lys Thr Ile Ser Arg Pro Ser Ser Ile Gly Leu Asp Arg Trp Glu Met
            675                 680                 685
Ile Lys Leu Glu Ala Ile Met Lys Tyr Lys Lys Tyr Ile Asn Asn Tyr
        690                 695                 700
Thr Ser Glu Asn Phe Asp Lys Leu Asp Gln Gln Leu Lys Asp Asn Phe
705                 710                 715                 720
Lys Leu Ile Ile Glu Ser Lys Ser Glu Lys Ser Glu Ile Phe Ser Lys
                725                 730                 735
Leu Glu Asn Leu Asn Val Ser Asp Leu Glu Ile Lys Ile Ala Phe Ala
            740                 745                 750
Leu Gly Ser Val Ile Asn Gln Ala Leu Ile Ser Lys Gln Gly Ser Tyr
            755                 760                 765
Leu Thr Asn Leu Val Ile Glu Gln Val Lys Asn Arg Tyr Gln Phe Leu
        770                 775                 780
Asn Gln His Leu Asn Pro Ala Ile Glu Ser Asp Asn Asn Phe Thr Asp
785                 790                 795                 800
Thr Thr Lys Ile Phe His Asp Ser Leu Phe Asn Ser Ala Thr Ala Glu
                805                 810                 815
Asn Ser Met Phe Leu Thr Lys Ile Ala Pro Tyr Leu Gln Val Gly Phe
            820                 825                 830
Met Pro Glu Ala Arg Ser Thr Ile Ser Leu Ser Gly Pro Gly Ala Tyr
        835                 840                 845
Ala Ser Ala Tyr Tyr Asp Phe Ile Asn Leu Gln Glu Asn Thr Ile Glu
850                 855                 860
```

```
Lys Thr Leu Lys Ala Ser Asp Leu Ile Glu Phe Lys Phe Pro Glu Asn
865                 870                 875                 880

Asn Leu Ser Gln Leu Thr Glu Gln Glu Ile Asn Ser Leu Trp Ser Phe
                885                 890                 895

Asp Gln Ala Ser Ala Lys Tyr Gln Phe Glu Lys Tyr Val Arg Asp Tyr
            900                 905                 910

Thr Gly Gly Ser Leu Ser Glu Asp Asn Gly Val Asp Phe Asn Lys Asn
        915                 920                 925

Thr Ala Leu Asp Lys Asn Tyr Leu Leu Asn Asn Lys Ile Pro Ser Asn
    930                 935                 940

Asn Val Glu Glu Ala Gly Ser Lys Asn Tyr Val His Tyr Ile Ile Gln
945                 950                 955                 960

Leu Gln Gly Asp Asp Ile Ser Tyr Glu Ala Thr Cys Asn Leu Phe Ser
                965                 970                 975

Lys Asn Pro Lys Asn Ser Ile Ile Ile Gln Arg Asn Met Asn Glu Ser
            980                 985                 990

Ala Lys Ser Tyr Phe Leu Ser Asp Asp Gly Glu Ser Ile Leu Glu Leu
        995                 1000                1005

Asn Lys Tyr Arg Ile Pro Glu Arg Leu Lys Asn Lys Glu Lys Val
1010            1015                1020

Lys Val Thr Phe Ile Gly His Gly Lys Asp Glu Phe Asn Thr Ser
1025            1030                1035

Glu Phe Ala Arg Leu Ser Val Asp Ser Leu Ser Asn Glu Ile Ser
1040            1045                1050

Ser Phe Leu Asp Thr Ile Lys Leu Asp Ile Ser Pro Lys Asn Val
1055            1060                1065

Glu Val Asn Leu Leu Gly Cys Asn Met Phe Ser Tyr Asp Phe Asn
1070            1075                1080

Val Glu Glu Thr Tyr Pro Gly Lys Leu Leu Ser Ile Met Asp
1085            1090                1095

Lys Ile Thr Ser Thr Leu Pro Asp Val Asn Lys Asn Ser Ile Thr
1100            1105                1110

Ile Gly Ala Asn Gln Tyr Glu Val Arg Ile Asn Ser Glu Gly Arg
1115            1120                1125

Lys Glu Leu Leu Ala His Ser Gly Lys Trp Ile Asn Lys Glu Glu
1130            1135                1140

Ala Ile Met Ser Asp Leu Ser Ser Lys Glu Tyr Ile Phe Phe Asp
1145            1150                1155

Ser Ile Asp Asn Lys Leu Lys Ala Lys Ser Lys Asn Ile Pro Gly
1160            1165                1170

Leu Ala Ser Ile Ser Glu Asp Ile Lys Thr Leu Leu Leu Asp Ala
1175            1180                1185

Ser Val Ser Pro Asp Thr Lys Phe Ile Leu Asn Asn Leu Lys Leu
1190            1195                1200

Asn Ile Glu Ser Ser Ile Gly Asp Tyr Ile Tyr Tyr Glu Lys Leu
1205            1210                1215

Glu Pro Val Lys Asn Ile Ile His Asn Ser Ile Asp Asp Leu Ile
1220            1225                1230

Asp Glu Phe Asn Leu Leu Glu Asn Val Ser Asp Glu Leu Tyr Glu
1235            1240                1245

Leu Lys Lys Leu Asn Asn Leu Asp Glu Lys Tyr Leu Ile Ser Phe
1250            1255                1260

Glu Asp Ile Ser Lys Asn Asn Ser Thr Tyr Ser Val Arg Phe Ile
```

-continued

```
            1265                1270                1275
Asn Lys Ser Asn Gly Glu Ser Val Tyr Val Glu Thr Glu Lys Glu
        1280                1285                1290

Ile Phe Ser Lys Tyr Ser Glu His Ile Thr Lys Glu Ile Ser Thr
        1295                1300                1305

Ile Lys Asn Ser Ile Ile Thr Asp Val Asn Gly Asn Leu Leu Asp
        1310                1315                1320

Asn Ile Gln Leu Asp His Thr Ser Gln Val Asn Thr Leu Asn Ala
        1325                1330                1335

Ala Phe Phe Ile Gln Ser Leu Ile Asp Tyr Ser Ser Asn Lys Asp
        1340                1345                1350

Val Leu Asn Asp Leu Ser Thr Ser Val Lys Val Gln Leu Tyr Ala
        1355                1360                1365

Gln Leu Phe Ser Thr Gly Leu Asn Thr Ile Tyr Asp Ser Ile Gln
        1370                1375                1380

Leu Val Asn Leu Ile Ser Asn Ala Val Asn Asp Thr Ile Asn Val
        1385                1390                1395

Leu Pro Thr Ile Thr Glu Gly Ile Pro Ile Val Ser Thr Ile Leu
        1400                1405                1410

Asp Gly Ile Asn Leu Gly Ala Ala Ile Lys Glu Leu Leu Asp Glu
        1415                1420                1425

His Asp Pro Leu Leu Lys Lys Glu Leu Glu Ala Lys Val Gly Val
        1430                1435                1440

Leu Ala Ile Asn Met Ser Leu Ser Ile Ala Ala Thr Val Ala Ser
        1445                1450                1455

Ile Val Gly Ile Gly Ala Glu Val Thr Ile Phe Leu Leu Pro Ile
        1460                1465                1470

Ala Gly Ile Ser Ala Gly Ile Pro Ser Leu Val Asn Asn Glu Leu
        1475                1480                1485

Ile Leu His Asp Lys Ala Thr Ser Val Val Asn Tyr Phe Asn His
        1490                1495                1500

Leu Ser Glu Ser Lys Lys Tyr Gly Pro Leu Lys Thr Glu Asp Asp
        1505                1510                1515

Lys Ile Leu Val Pro Ile Asp Asp Leu Val Ile Ser Glu Ile Asp
        1520                1525                1530

Phe Asn Asn Asn Ser Ile Lys Leu Gly Thr Cys Asn Ile Leu Ala
        1535                1540                1545

Met Glu Gly Gly Ser Gly His Thr Val Thr Gly Asn Ile Asp His
        1550                1555                1560

Phe Phe Ser Ser Pro Ser Ile Ser Ser His Ile Pro Ser Leu Ser
        1565                1570                1575

Ile Tyr Ser Ala Ile Gly Ile Glu Thr Glu Asn Leu Asp Phe Ser
        1580                1585                1590

Lys Lys Ile Met Met Leu Pro Asn Ala Pro Ser Arg Val Phe Trp
        1595                1600                1605

Trp Glu Thr Gly Ala Val Pro Gly Leu Arg Ser Leu Glu Asn Asp
        1610                1615                1620

Gly Thr Arg Leu Leu Asp Ser Ile Arg Asp Leu Tyr Pro Gly Lys
        1625                1630                1635

Phe Tyr Trp Arg Phe Tyr Ala Phe Phe Asp Tyr Ala Ile Thr Thr
        1640                1645                1650

Leu Lys Pro Val Tyr Glu Asp Thr Asn Ile Lys Ile Lys Leu Asp
        1655                1660                1665
```

-continued

Lys Asp Thr Arg Asn Phe Ile Met Pro Thr Ile Thr Thr Asn Glu
1670                1675                1680

Ile Arg Asn Lys Leu Ser Tyr Ser Phe Asp Gly Ala Gly Gly Thr
1685                1690                1695

Tyr Ser Leu Leu Leu Ser Ser Tyr Pro Ile Ser Thr Asn Ile Asn
1700                1705                1710

Leu Ser Lys Asp Asp Leu Trp Ile Phe Asn Ile Asp Asn Glu Val
1715                1720                1725

Arg Glu Ile Ser Ile Glu Asn Gly Thr Ile Lys Lys Gly Lys Leu
1730                1735                1740

Ile Lys Asp Val Leu Ser Lys Ile Asp Ile Asn Lys Asn Lys Leu
1745                1750                1755

Ile Ile Gly Asn Gln Thr Ile Asp Phe Ser Gly Asp Ile Asp Asn
1760                1765                1770

Lys Asp Arg Tyr Ile Phe Leu Thr Cys Glu Leu Asp Asp Lys Ile
1775                1780                1785

Ser Leu Ile Ile Glu Ile Asn Leu Val Ala Lys Ser Tyr Ser Leu
1790                1795                1800

Leu Leu Ser Gly Asp Lys Asn Tyr Leu Ile Ser Asn Leu Ser Asn
1805                1810                1815

Thr Ile Glu Lys Ile Asn Thr Leu Gly Leu Asp Ser Lys Asn Ile
1820                1825                1830

Ala Tyr Asn Tyr Thr Asp Glu Ser Asn Asn Lys Tyr Phe Gly Ala
1835                1840                1845

Ile Ser Lys Thr Ser Gln Lys Ser Ile Ile His Tyr Lys Lys Asp
1850                1855                1860

Ser Lys Asn Ile Leu Glu Phe Tyr Asn Asp Ser Thr Leu Glu Phe
1865                1870                1875

Asn Ser Lys Asp Phe Ile Ala Glu Asp Ile Asn Val Phe Met Lys
1880                1885                1890

Asp Asp Ile Asn Thr Ile Thr Gly Lys Tyr Tyr Val Asp Asn Asn
1895                1900                1905

Thr Asp Lys Ser Ile Asp Phe Ser Ile Ser Leu Val Ser Lys Asn
1910                1915                1920

Gln Val Lys Val Asn Gly Leu Tyr Leu Asn Glu Ser Val Tyr Ser
1925                1930                1935

Ser Tyr Leu Asp Phe Val Lys Asn Ser Asp Gly His His Asn Thr
1940                1945                1950

Ser Asn Phe Met Asn Leu Phe Leu Asp Asn Ile Ser Phe Trp Lys
1955                1960                1965

Leu Phe Gly Phe Glu Asn Ile Asn Phe Val Ile Asp Lys Tyr Phe
1970                1975                1980

Thr Leu Val Gly Lys Thr Asn Leu Gly Tyr Val Glu Phe Ile Cys
1985                1990                1995

Asp Asn Asn Lys Asn Ile Asp Ile Tyr Phe Gly Glu Trp Lys Thr
2000                2005                2010

Ser Ser Ser Lys Ser Thr Ile Phe Ser Gly Asn Gly Arg Asn Val
2015                2020                2025

Val Val Glu Pro Ile Tyr Asn Pro Asp Thr Gly Glu Asp Ile Ser
2030                2035                2040

Thr Ser Leu Asp Phe Ser Tyr Glu Pro Leu Tyr Gly Ile Asp Arg
2045                2050                2055

Tyr Ile Asn Lys Val Leu Ile Ala Pro Asp Leu Tyr Thr Ser Leu
2060                2065                2070

```
Ile Asn Ile Asn Thr Asn Tyr Tyr Ser Asn Glu Tyr Tyr Pro Glu
2075                2080                2085

Ile Ile Val Leu Asn Pro Asn Thr Phe His Lys Lys Val Asn Ile
2090                2095                2100

Asn Leu Asp Ser Ser Ser Phe Glu Tyr Lys Trp Ser Thr Glu Gly
2105                2110                2115

Ser Asp Phe Ile Leu Val Arg Tyr Leu Glu Glu Ser Asn Lys Lys
2120                2125                2130

Ile Leu Gln Lys Ile Arg Ile Lys Gly Ile Leu Ser Asn Thr Gln
2135                2140                2145

Ser Phe Asn Lys Met Ser Ile Asp Phe Lys Asp Ile Lys Lys Leu
2150                2155                2160

Ser Leu Gly Tyr Ile Met Ser Asn Phe Lys Ser Phe Asn Ser Glu
2165                2170                2175

Asn Glu Leu Asp Arg Asp His Leu Gly Phe Lys Ile Ile Asp Asn
2180                2185                2190

Lys Thr Tyr Tyr Asp Glu Asp Ser Lys Leu Val Lys Gly Leu
2195                2200                2205

Ile Asn Ile Asn Asn Ser Leu Phe Tyr Phe Asp Pro Ile Glu Phe
2210                2215                2220

Asn Leu Val Thr Gly Trp Gln Thr Ile Asn Gly Lys Lys Tyr Tyr
2225                2230                2235

Phe Asp Ile Asn Thr Gly Ala Ala Leu Thr Ser Tyr Lys Ile Ile
2240                2245                2250

Asn Gly Lys His Phe Tyr Phe Asn Asn Asp Gly Val Met Gln Leu
2255                2260                2265

Gly Val Phe Lys Gly Pro Asp Gly Phe Glu Tyr Phe Ala Pro Ala
2270                2275                2280

Asn Thr Gln Asn Asn Asn Ile Glu Gly Gln Ala Ile Val Tyr Gln
2285                2290                2295

Ser Lys Phe Leu Thr Leu Asn Gly Lys Lys Tyr Tyr Phe Asp Asn
2300                2305                2310

Asn Ser Lys Ala Val Thr Gly Trp Arg Ile Ile Asn Asn Glu Lys
2315                2320                2325

Tyr Tyr Phe Asn Pro Asn Asn Ala Ile Ala Ala Val Gly Leu Gln
2330                2335                2340

Val Ile Asp Asn Asn Lys Tyr Tyr Phe Asn Pro Asp Thr Ala Ile
2345                2350                2355

Ile Ser Lys Gly Trp Gln Thr Val Asn Gly Ser Arg Tyr Tyr Phe
2360                2365                2370

Asp Thr Asp Thr Ala Ile Ala Phe Asn Gly Tyr Lys Thr Ile Asp
2375                2380                2385

Gly Lys His Phe Tyr Phe Asp Ser Asp Cys Val Val Lys Ile Gly
2390                2395                2400

Val Phe Ser Thr Ser Asn Gly Phe Glu Tyr Phe Ala Pro Ala Asn
2405                2410                2415

Thr Tyr Asn Asn Asn Ile Glu Gly Gln Ala Ile Val Tyr Gln Ser
2420                2425                2430

Lys Phe Leu Thr Leu Asn Gly Lys Lys Tyr Tyr Phe Asp Asn Asn
2435                2440                2445

Ser Lys Ala Val Thr Gly Leu Gln Thr Ile Asp Ser Lys Lys Tyr
2450                2455                2460

Tyr Phe Asn Thr Asn Thr Ala Glu Ala Ala Thr Gly Trp Gln Thr
```

```
                    2465                2470                2475

Ile Asp Gly Lys Lys Tyr Tyr Phe Asn Thr Asn Thr Ala Glu Ala
                    2480                2485                2490

Ala Thr Gly Trp Gln Thr Ile Asp Gly Lys Lys Tyr Tyr Phe Asn
                    2495                2500                2505

Thr Asn Thr Ala Ile Ala Ser Thr Gly Tyr Thr Ile Ile Asn Gly
                    2510                2515                2520

Lys His Phe Tyr Phe Asn Thr Asp Gly Ile Met Gln Ile Gly Val
                    2525                2530                2535

Phe Lys Gly Pro Asn Gly Phe Glu Tyr Phe Ala Pro Ala Asn Thr
                    2540                2545                2550

Asp Ala Asn Asn Ile Glu Gly Gln Ala Ile Leu Tyr Gln Asn Glu
                    2555                2560                2565

Phe Leu Thr Leu Asn Gly Lys Lys Tyr Tyr Phe Gly Ser Asp Ser
                    2570                2575                2580

Lys Ala Val Thr Gly Trp Arg Ile Ile Asn Asn Lys Lys Tyr Tyr
                    2585                2590                2595

Phe Asn Pro Asn Asn Ala Ile Ala Ala Ile His Leu Cys Thr Ile
                    2600                2605                2610

Asn Asn Asp Lys Tyr Tyr Phe Ser Tyr Asp Gly Ile Leu Gln Asn
                    2615                2620                2625

Gly Tyr Ile Thr Ile Glu Arg Asn Asn Phe Tyr Phe Asp Ala Asn
                    2630                2635                2640

Asn Glu Ser Lys Met Val Thr Gly Val Phe Lys Gly Pro Asn Gly
                    2645                2650                2655

Phe Glu Tyr Phe Ala Pro Ala Asn Thr His Asn Asn Asn Ile Glu
                    2660                2665                2670

Gly Gln Ala Ile Val Tyr Gln Asn Lys Phe Leu Thr Leu Asn Gly
                    2675                2680                2685

Lys Lys Tyr Tyr Phe Asp Asn Asp Ser Lys Ala Val Thr Gly Trp
                    2690                2695                2700

Gln Thr Ile Asp Gly Lys Lys Tyr Tyr Phe Asn Leu Asn Thr Ala
                    2705                2710                2715

Glu Ala Ala Thr Gly Trp Gln Thr Ile Asp Gly Lys Lys Tyr Tyr
                    2720                2725                2730

Phe Asn Leu Asn Thr Ala Glu Ala Ala Thr Gly Trp Gln Thr Ile
                    2735                2740                2745

Asp Gly Lys Lys Tyr Tyr Phe Asn Thr Asn Thr Phe Ile Ala Ser
                    2750                2755                2760

Thr Gly Tyr Thr Ser Ile Asn Gly Lys His Phe Tyr Phe Asn Thr
                    2765                2770                2775

Asp Gly Ile Met Gln Ile Gly Val Phe Lys Gly Pro Asn Gly Phe
                    2780                2785                2790

Glu Tyr Phe Ala Pro Ala Asn Thr Asp Ala Asn Asn Ile Glu Gly
                    2795                2800                2805

Gln Ala Ile Leu Tyr Gln Asn Lys Phe Leu Thr Leu Asn Gly Lys
                    2810                2815                2820

Lys Tyr Tyr Phe Gly Ser Asp Ser Lys Ala Val Thr Gly Leu Arg
                    2825                2830                2835

Thr Ile Asp Gly Lys Lys Tyr Tyr Phe Asn Thr Asn Thr Ala Val
                    2840                2845                2850

Ala Val Thr Gly Trp Gln Thr Ile Asn Gly Lys Lys Tyr Tyr Phe
                    2855                2860                2865
```

```
Asn Thr Asn Thr Ser Ile Ala Ser Thr Gly Tyr Thr Ile Ile Ser
        2870                2875                2880

Gly Lys His Phe Tyr Phe Asn Thr Asp Gly Ile Met Gln Ile Gly
    2885                2890                2895

Val Phe Lys Gly Pro Asp Gly Phe Glu Tyr Phe Ala Pro Ala Asn
    2900                2905                2910

Thr Asp Ala Asn Asn Ile Glu Gly Gln Ala Ile Arg Tyr Gln Asn
    2915                2920                2925

Arg Phe Leu Tyr Leu His Asp Asn Ile Tyr Tyr Phe Gly Asn Asn
    2930                2935                2940

Ser Lys Ala Ala Thr Gly Trp Val Thr Ile Asp Gly Asn Arg Tyr
    2945                2950                2955

Tyr Phe Glu Pro Asn Thr Ala Met Gly Ala Asn Gly Tyr Lys Thr
    2960                2965                2970

Ile Asp Asn Lys Asn Phe Tyr Phe Arg Asn Gly Leu Pro Gln Ile
    2975                2980                2985

Gly Val Phe Lys Gly Ser Asn Gly Phe Glu Tyr Phe Ala Pro Ala
    2990                2995                3000

Asn Thr Asp Ala Asn Asn Ile Glu Gly Gln Ala Ile Arg Tyr Gln
    3005                3010                3015

Asn Arg Phe Leu His Leu Leu Gly Lys Ile Tyr Tyr Phe Gly Asn
    3020                3025                3030

Asn Ser Lys Ala Val Thr Gly Trp Gln Thr Ile Asn Gly Lys Val
    3035                3040                3045

Tyr Tyr Phe Met Pro Asp Thr Ala Met Ala Ala Ala Gly Gly Leu
    3050                3055                3060

Phe Glu Ile Asp Gly Val Ile Tyr Phe Phe Gly Val Asp Gly Val
    3065                3070                3075

Lys Ala Pro Gly Ile Tyr Gly His His His His His His
    3080                3085                3090

<210> SEQ ID NO 8
<211> LENGTH: 2618
<212> TYPE: PRT
<213> ORGANISM: Artificial Sequence
<220> FEATURE:
<223> OTHER INFORMATION: Fusion Protein Human Sox 2/C. difficile TcdA

<400> SEQUENCE: 8

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Tyr Asn Met Met Glu Thr Glu
        50                  55                  60

Leu Lys Pro Pro Gly Pro Gln Gln Thr Ser Gly Gly Gly Gly Asn
65                  70                  75                  80

Ser Thr Ala Ala Ala Ala Gly Gly Asn Gln Lys Asn Ser Pro Asp Arg
                85                  90                  95

Val Lys Arg Pro Met Asn Ala Phe Met Val Trp Ser Arg Gly Gln Arg
                100                 105                 110

Arg Lys Met Ala Gln Glu Asn Pro Lys Met His Asn Ser Glu Ile Ser
            115                 120                 125

Lys Arg Leu Gly Ala Glu Trp Lys Leu Leu Ser Glu Thr Glu Lys Arg
```

```
              130                 135                 140
Pro Phe Ile Asp Glu Ala Lys Arg Leu Arg Ala Leu His Met Lys Glu
145                 150                 155                 160

His Pro Asp Tyr Lys Tyr Arg Pro Arg Arg Lys Thr Lys Thr Leu Met
                165                 170                 175

Lys Lys Asp Lys Tyr Thr Leu Pro Gly Gly Leu Leu Ala Pro Gly Gly
                180                 185                 190

Asn Ser Met Ala Ser Gly Val Gly Val Gly Ala Gly Leu Gly Ala Gly
                195                 200                 205

Val Asn Gln Arg Met Asp Ser Tyr Ala His Met Asn Gly Trp Ser Asn
210                 215                 220

Gly Ser Tyr Ser Met Met Gln Asp Gln Leu Gly Tyr Pro Gln His Pro
225                 230                 235                 240

Gly Leu Asn Ala His Gly Ala Ala Gln Met Gln Pro Met His Arg Tyr
                245                 250                 255

Asp Val Ser Ala Leu Gln Tyr Asn Ser Met Thr Ser Ser Gln Thr Tyr
                260                 265                 270

Met Asn Gly Ser Pro Thr Tyr Ser Met Ser Tyr Ser Gln Gln Gly Thr
                275                 280                 285

Pro Gly Met Ala Leu Gly Ser Met Gly Ser Val Val Lys Ser Glu Ala
290                 295                 300

Ser Ser Ser Pro Pro Val Val Thr Ser Ser Ser His Ser Arg Ala Pro
305                 310                 315                 320

Cys Gln Ala Gly Asp Leu Arg Asp Met Ile Ser Met Tyr Leu Pro Gly
                325                 330                 335

Ala Glu Val Pro Glu Pro Ala Ala Pro Ser Arg Leu His Met Ser Gln
                340                 345                 350

His Tyr Gln Ser Gly Pro Val Pro Gly Thr Ala Ile Asn Gly Thr Leu
                355                 360                 365

Pro Leu Ser His Met Ala Ala Ser Ala Tyr Tyr Asp Phe Ile Asn
370                 375                 380

Leu Gln Glu Asn Thr Ile Glu Lys Thr Leu Lys Ala Ser Asp Leu Ile
385                 390                 395                 400

Glu Phe Lys Phe Pro Glu Asn Asn Leu Ser Gln Leu Thr Glu Gln Glu
                405                 410                 415

Ile Asn Ser Leu Trp Ser Phe Asp Gln Ala Ser Ala Lys Tyr Gln Phe
                420                 425                 430

Glu Lys Tyr Val Arg Asp Tyr Thr Gly Gly Ser Leu Ser Glu Asp Asn
                435                 440                 445

Gly Val Asp Phe Asn Lys Asn Thr Ala Leu Asp Lys Asn Tyr Leu Leu
450                 455                 460

Asn Asn Lys Ile Pro Ser Asn Asn Val Glu Glu Ala Gly Ser Lys Asn
465                 470                 475                 480

Tyr Val His Tyr Ile Ile Gln Leu Gln Gly Asp Asp Ile Ser Tyr Glu
                485                 490                 495

Ala Thr Cys Asn Leu Phe Ser Lys Asn Pro Lys Asn Ser Ile Ile Ile
                500                 505                 510

Gln Arg Asn Met Asn Glu Ser Ala Lys Ser Tyr Phe Leu Ser Asp Asp
                515                 520                 525

Gly Glu Ser Ile Leu Glu Leu Asn Lys Tyr Arg Ile Pro Glu Arg Leu
                530                 535                 540

Lys Asn Lys Glu Lys Val Lys Val Thr Phe Ile Gly His Gly Lys Asp
545                 550                 555                 560
```

-continued

```
Glu Phe Asn Thr Ser Glu Phe Ala Arg Leu Ser Val Asp Ser Leu Ser
                565                 570                 575
Asn Glu Ile Ser Ser Phe Leu Asp Thr Ile Lys Leu Asp Ile Ser Pro
            580                 585                 590
Lys Asn Val Glu Val Asn Leu Leu Gly Cys Asn Met Phe Ser Tyr Asp
        595                 600                 605
Phe Asn Val Glu Glu Thr Tyr Pro Gly Lys Leu Leu Leu Ser Ile Met
    610                 615                 620
Asp Lys Ile Thr Ser Thr Leu Pro Asp Val Asn Lys Asn Ser Ile Thr
625                 630                 635                 640
Ile Gly Ala Asn Gln Tyr Glu Val Arg Ile Asn Ser Glu Gly Arg Lys
                645                 650                 655
Glu Leu Leu Ala His Ser Gly Lys Trp Ile Asn Lys Glu Glu Ala Ile
            660                 665                 670
Met Ser Asp Leu Ser Ser Lys Glu Tyr Ile Phe Phe Asp Ser Ile Asp
        675                 680                 685
Asn Lys Leu Lys Ala Lys Ser Lys Asn Ile Pro Gly Leu Ala Ser Ile
    690                 695                 700
Ser Glu Asp Ile Lys Thr Leu Leu Leu Asp Ala Ser Val Ser Pro Asp
705                 710                 715                 720
Thr Lys Phe Ile Leu Asn Asn Leu Lys Leu Asn Ile Glu Ser Ser Ile
                725                 730                 735
Gly Asp Tyr Ile Tyr Tyr Glu Lys Leu Glu Pro Val Lys Asn Ile Ile
            740                 745                 750
His Asn Ser Ile Asp Asp Leu Ile Asp Glu Phe Asn Leu Leu Glu Asn
        755                 760                 765
Val Ser Asp Glu Leu Tyr Glu Leu Lys Lys Leu Asn Asn Leu Asp Glu
    770                 775                 780
Lys Tyr Leu Ile Ser Phe Glu Asp Ile Ser Lys Asn Asn Ser Thr Tyr
785                 790                 795                 800
Ser Val Arg Phe Ile Asn Lys Ser Asn Gly Glu Ser Val Tyr Val Glu
                805                 810                 815
Thr Glu Lys Glu Ile Phe Ser Lys Tyr Ser Glu His Ile Thr Lys Glu
            820                 825                 830
Ile Ser Thr Ile Lys Asn Ser Ile Ile Thr Asp Val Asn Gly Asn Leu
        835                 840                 845
Leu Asp Asn Ile Gln Leu Asp His Thr Ser Gln Val Asn Thr Leu Asn
    850                 855                 860
Ala Ala Phe Phe Ile Gln Ser Leu Ile Asp Tyr Ser Ser Asn Lys Asp
865                 870                 875                 880
Val Leu Asn Asp Leu Ser Thr Ser Val Lys Val Gln Leu Tyr Ala Gln
                885                 890                 895
Leu Phe Ser Thr Gly Leu Asn Thr Ile Tyr Asp Ser Ile Gln Leu Val
            900                 905                 910
Asn Leu Ile Ser Asn Ala Val Asn Asp Thr Ile Asn Val Leu Pro Thr
        915                 920                 925
Ile Thr Glu Gly Ile Pro Ile Val Ser Thr Ile Leu Asp Gly Ile Asn
    930                 935                 940
Leu Gly Ala Ala Ile Lys Glu Leu Leu Asp Glu His Asp Pro Leu Leu
945                 950                 955                 960
Lys Lys Glu Leu Glu Ala Lys Val Gly Val Leu Ala Ile Asn Met Ser
                965                 970                 975
Leu Ser Ile Ala Ala Thr Val Ala Ser Ile Val Gly Ile Gly Ala Glu
            980                 985                 990
```

-continued

```
Val Thr Ile Phe Leu Leu Pro Ile Ala Gly Ile Ser Ala Gly Ile Pro
        995                 1000                1005

Ser Leu Val Asn Asn Glu Leu Ile Leu His Asp Lys Ala Thr Ser
    1010                1015                1020

Val Val Asn Tyr Phe Asn His Leu Ser Glu Ser Lys Lys Tyr Gly
    1025                1030                1035

Pro Leu Lys Thr Glu Asp Asp Lys Ile Leu Val Pro Ile Asp Asp
    1040                1045                1050

Leu Val Ile Ser Glu Ile Asp Phe Asn Asn Asn Ser Ile Lys Leu
    1055                1060                1065

Gly Thr Cys Asn Ile Leu Ala Met Glu Gly Gly Ser Gly His Thr
    1070                1075                1080

Val Thr Gly Asn Ile Asp His Phe Phe Ser Ser Pro Ser Ile Ser
    1085                1090                1095

Ser His Ile Pro Ser Leu Ser Ile Tyr Ser Ala Ile Gly Ile Glu
    1100                1105                1110

Thr Glu Asn Leu Asp Phe Ser Lys Lys Ile Met Met Leu Pro Asn
    1115                1120                1125

Ala Pro Ser Arg Val Phe Trp Trp Glu Thr Gly Ala Val Pro Gly
    1130                1135                1140

Leu Arg Ser Leu Glu Asn Asp Gly Thr Arg Leu Leu Asp Ser Ile
    1145                1150                1155

Arg Asp Leu Tyr Pro Gly Lys Phe Tyr Trp Arg Phe Tyr Ala Phe
    1160                1165                1170

Phe Asp Tyr Ala Ile Thr Thr Leu Lys Pro Val Tyr Glu Asp Thr
    1175                1180                1185

Asn Ile Lys Ile Lys Leu Asp Lys Asp Thr Arg Asn Phe Ile Met
    1190                1195                1200

Pro Thr Ile Thr Thr Asn Glu Ile Arg Asn Lys Leu Ser Tyr Ser
    1205                1210                1215

Phe Asp Gly Ala Gly Gly Thr Tyr Ser Leu Leu Leu Ser Ser Tyr
    1220                1225                1230

Pro Ile Ser Thr Asn Ile Asn Leu Ser Lys Asp Asp Leu Trp Ile
    1235                1240                1245

Phe Asn Ile Asp Asn Glu Val Arg Glu Ile Ser Ile Glu Asn Gly
    1250                1255                1260

Thr Ile Lys Lys Gly Lys Leu Ile Lys Asp Val Leu Ser Lys Ile
    1265                1270                1275

Asp Ile Asn Lys Asn Lys Leu Ile Ile Gly Asn Gln Thr Ile Asp
    1280                1285                1290

Phe Ser Gly Asp Ile Asp Asn Lys Asp Arg Tyr Ile Phe Leu Thr
    1295                1300                1305

Cys Glu Leu Asp Asp Lys Ile Ser Leu Ile Ile Glu Ile Asn Leu
    1310                1315                1320

Val Ala Lys Ser Tyr Ser Leu Leu Leu Ser Gly Asp Lys Asn Tyr
    1325                1330                1335

Leu Ile Ser Asn Leu Ser Asn Thr Ile Glu Lys Ile Asn Thr Leu
    1340                1345                1350

Gly Leu Asp Ser Lys Asn Ile Ala Tyr Asn Tyr Thr Asp Glu Ser
    1355                1360                1365

Asn Asn Lys Tyr Phe Gly Ala Ile Ser Lys Thr Ser Gln Lys Ser
    1370                1375                1380

Ile Ile His Tyr Lys Lys Asp Ser Lys Asn Ile Leu Glu Phe Tyr
```

```
              1385                1390                1395

Asn Asp Ser Thr Leu Glu Phe Asn Ser Lys Asp Phe Ile Ala Glu
        1400                1405                1410

Asp Ile Asn Val Phe Met Lys Asp Asp Ile Asn Thr Ile Thr Gly
        1415                1420                1425

Lys Tyr Tyr Val Asp Asn Asn Thr Asp Lys Ser Ile Asp Phe Ser
        1430                1435                1440

Ile Ser Leu Val Ser Lys Asn Gln Val Lys Val Asn Gly Leu Tyr
        1445                1450                1455

Leu Asn Glu Ser Val Tyr Ser Ser Tyr Leu Asp Phe Val Lys Asn
        1460                1465                1470

Ser Asp Gly His His Asn Thr Ser Asn Phe Met Asn Leu Phe Leu
        1475                1480                1485

Asp Asn Ile Ser Phe Trp Lys Leu Phe Gly Phe Glu Asn Ile Asn
        1490                1495                1500

Phe Val Ile Asp Lys Tyr Phe Thr Leu Val Gly Lys Thr Asn Leu
        1505                1510                1515

Gly Tyr Val Glu Phe Ile Cys Asp Asn Asn Lys Asn Ile Asp Ile
        1520                1525                1530

Tyr Phe Gly Glu Trp Lys Thr Ser Ser Lys Ser Thr Ile Phe
        1535                1540                1545

Ser Gly Asn Gly Arg Asn Val Val Val Glu Pro Ile Tyr Asn Pro
        1550                1555                1560

Asp Thr Gly Glu Asp Ile Ser Thr Ser Leu Asp Phe Ser Tyr Glu
        1565                1570                1575

Pro Leu Tyr Gly Ile Asp Arg Tyr Ile Asn Lys Val Leu Ile Ala
        1580                1585                1590

Pro Asp Leu Tyr Thr Ser Leu Ile Asn Ile Asn Thr Asn Tyr Tyr
        1595                1600                1605

Ser Asn Glu Tyr Tyr Pro Glu Ile Ile Val Leu Asn Pro Asn Thr
        1610                1615                1620

Phe His Lys Lys Val Asn Ile Asn Leu Asp Ser Ser Phe Glu
        1625                1630                1635

Tyr Lys Trp Ser Thr Glu Gly Ser Asp Phe Ile Leu Val Arg Tyr
        1640                1645                1650

Leu Glu Glu Ser Asn Lys Lys Ile Leu Gln Lys Ile Arg Ile Lys
        1655                1660                1665

Gly Ile Leu Ser Asn Thr Gln Ser Phe Asn Lys Met Ser Ile Asp
        1670                1675                1680

Phe Lys Asp Ile Lys Lys Leu Ser Leu Gly Tyr Ile Met Ser Asn
        1685                1690                1695

Phe Lys Ser Phe Asn Ser Glu Asn Glu Leu Asp Arg Asp His Leu
        1700                1705                1710

Gly Phe Lys Ile Ile Asp Asn Lys Thr Tyr Tyr Tyr Asp Glu Asp
        1715                1720                1725

Ser Lys Leu Val Lys Gly Leu Ile Asn Ile Asn Asn Ser Leu Phe
        1730                1735                1740

Tyr Phe Asp Pro Ile Glu Phe Asn Leu Val Thr Gly Trp Gln Thr
        1745                1750                1755

Ile Asn Gly Lys Lys Tyr Tyr Phe Asp Ile Asn Thr Gly Ala Ala
        1760                1765                1770

Leu Thr Ser Tyr Lys Ile Ile Asn Gly Lys His Phe Tyr Phe Asn
        1775                1780                1785
```

-continued

Asn Asp Gly Val Met Gln Leu Gly Val Phe Lys Gly Pro Asp Gly
1790                1795                1800

Phe Glu Tyr Phe Ala Pro Ala Asn Thr Gln Asn Asn Asn Ile Glu
1805                1810                1815

Gly Gln Ala Ile Val Tyr Gln Ser Lys Phe Leu Thr Leu Asn Gly
1820                1825                1830

Lys Lys Tyr Tyr Phe Asp Asn Asn Ser Lys Ala Val Thr Gly Trp
1835                1840                1845

Arg Ile Ile Asn Asn Glu Lys Tyr Tyr Phe Asn Pro Asn Asn Ala
1850                1855                1860

Ile Ala Ala Val Gly Leu Gln Val Ile Asp Asn Asn Lys Tyr Tyr
1865                1870                1875

Phe Asn Pro Asp Thr Ala Ile Ile Ser Lys Gly Trp Gln Thr Val
1880                1885                1890

Asn Gly Ser Arg Tyr Tyr Phe Asp Thr Asp Thr Ala Ile Ala Phe
1895                1900                1905

Asn Gly Tyr Lys Thr Ile Asp Gly Lys His Phe Tyr Phe Asp Ser
1910                1915                1920

Asp Cys Val Val Lys Ile Gly Val Phe Ser Thr Ser Asn Gly Phe
1925                1930                1935

Glu Tyr Phe Ala Pro Ala Asn Thr Tyr Asn Asn Asn Ile Glu Gly
1940                1945                1950

Gln Ala Ile Val Tyr Gln Ser Lys Phe Leu Thr Leu Asn Gly Lys
1955                1960                1965

Lys Tyr Tyr Phe Asp Asn Asn Ser Lys Ala Val Thr Gly Leu Gln
1970                1975                1980

Thr Ile Asp Ser Lys Lys Tyr Tyr Phe Asn Thr Asn Thr Ala Glu
1985                1990                1995

Ala Ala Thr Gly Trp Gln Thr Ile Asp Gly Lys Lys Tyr Tyr Phe
2000                2005                2010

Asn Thr Asn Thr Ala Glu Ala Thr Gly Trp Gln Thr Ile Asp
2015                2020                2025

Gly Lys Lys Tyr Tyr Phe Asn Thr Asn Thr Ala Ile Ala Ser Thr
2030                2035                2040

Gly Tyr Thr Ile Ile Asn Gly Lys His Phe Tyr Phe Asn Thr Asp
2045                2050                2055

Gly Ile Met Gln Ile Gly Val Phe Lys Gly Pro Asn Gly Phe Glu
2060                2065                2070

Tyr Phe Ala Pro Ala Asn Thr Asp Ala Asn Asn Ile Glu Gly Gln
2075                2080                2085

Ala Ile Leu Tyr Gln Asn Glu Phe Leu Thr Leu Asn Gly Lys Lys
2090                2095                2100

Tyr Tyr Phe Gly Ser Asp Ser Lys Ala Val Thr Gly Trp Arg Ile
2105                2110                2115

Ile Asn Asn Lys Lys Tyr Tyr Phe Asn Pro Asn Asn Ala Ile Ala
2120                2125                2130

Ala Ile His Leu Cys Thr Ile Asn Asn Asp Lys Tyr Tyr Phe Ser
2135                2140                2145

Tyr Asp Gly Ile Leu Gln Asn Gly Tyr Ile Thr Ile Glu Arg Asn
2150                2155                2160

Asn Phe Tyr Phe Asp Ala Asn Asn Glu Ser Lys Met Val Thr Gly
2165                2170                2175

Val Phe Lys Gly Pro Asn Gly Phe Glu Tyr Phe Ala Pro Ala Asn
2180                2185                2190

-continued

Thr His Asn Asn Asn Ile Glu Gly Gln Ala Ile Val Tyr Gln Asn
    2195                2200                2205

Lys Phe Leu Thr Leu Asn Gly Lys Lys Tyr Tyr Phe Asp Asn Asp
    2210                2215                2220

Ser Lys Ala Val Thr Gly Trp Gln Thr Ile Asp Gly Lys Lys Tyr
    2225                2230                2235

Tyr Phe Asn Leu Asn Thr Ala Glu Ala Ala Thr Gly Trp Gln Thr
    2240                2245                2250

Ile Asp Gly Lys Lys Tyr Tyr Phe Asn Leu Asn Thr Ala Glu Ala
    2255                2260                2265

Ala Thr Gly Trp Gln Thr Ile Asp Gly Lys Lys Tyr Tyr Phe Asn
    2270                2275                2280

Thr Asn Thr Phe Ile Ala Ser Thr Gly Tyr Thr Ser Ile Asn Gly
    2285                2290                2295

Lys His Phe Tyr Phe Asn Thr Asp Gly Ile Met Gln Ile Gly Val
    2300                2305                2310

Phe Lys Gly Pro Asn Gly Phe Glu Tyr Phe Ala Pro Ala Asn Thr
    2315                2320                2325

Asp Ala Asn Asn Ile Glu Gly Gln Ala Ile Leu Tyr Gln Asn Lys
    2330                2335                2340

Phe Leu Thr Leu Asn Gly Lys Lys Tyr Tyr Phe Gly Ser Asp Ser
    2345                2350                2355

Lys Ala Val Thr Gly Leu Arg Thr Ile Asp Gly Lys Lys Tyr Tyr
    2360                2365                2370

Phe Asn Thr Asn Thr Ala Val Ala Val Thr Gly Trp Gln Thr Ile
    2375                2380                2385

Asn Gly Lys Lys Tyr Tyr Phe Asn Thr Asn Thr Ser Ile Ala Ser
    2390                2395                2400

Thr Gly Tyr Thr Ile Ile Ser Gly Lys His Phe Tyr Phe Asn Thr
    2405                2410                2415

Asp Gly Ile Met Gln Ile Gly Val Phe Lys Gly Pro Asp Gly Phe
    2420                2425                2430

Glu Tyr Phe Ala Pro Ala Asn Thr Asp Ala Asn Asn Ile Glu Gly
    2435                2440                2445

Gln Ala Ile Arg Tyr Gln Asn Arg Phe Leu Tyr Leu His Asp Asn
    2450                2455                2460

Ile Tyr Tyr Phe Gly Asn Asn Ser Lys Ala Ala Thr Gly Trp Val
    2465                2470                2475

Thr Ile Asp Gly Asn Arg Tyr Tyr Phe Glu Pro Asn Thr Ala Met
    2480                2485                2490

Gly Ala Asn Gly Tyr Lys Thr Ile Asp Asn Lys Asn Phe Tyr Phe
    2495                2500                2505

Arg Asn Gly Leu Pro Gln Ile Gly Val Phe Lys Gly Ser Asn Gly
    2510                2515                2520

Phe Glu Tyr Phe Ala Pro Ala Asn Thr Asp Ala Asn Asn Ile Glu
    2525                2530                2535

Gly Gln Ala Ile Arg Tyr Gln Asn Arg Phe Leu His Leu Leu Gly
    2540                2545                2550

Lys Ile Tyr Tyr Phe Gly Asn Asn Ser Lys Ala Val Thr Gly Trp
    2555                2560                2565

Gln Thr Ile Asn Gly Lys Val Tyr Tyr Phe Met Pro Asp Thr Ala
    2570                2575                2580

Met Ala Ala Ala Gly Gly Leu Phe Glu Ile Asp Gly Val Ile Tyr

```
                  2585                2590                2595
        Phe Phe Gly Val Asp Gly Val Lys Ala Pro Gly Ile Tyr Gly His
                2600                2605                2610

His His His His His
                2615

<210> SEQ ID NO 9
<211> LENGTH: 782
<212> TYPE: PRT
<213> ORGANISM: Clostridium botulinum

<400> SEQUENCE: 9

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Glu Gly
            20                  25                  30

Leu Ala Gly Glu Leu Glu Gln Leu Arg Ala Arg Leu Glu His His Pro
        35                  40                  45

Gln Gly Gln Arg Glu Pro Ser Met Leu Val Ser Lys Phe Glu Asn Ser
    50                  55                  60

Val Lys Asn Ser Asn Lys Asn Tyr Phe Thr Ile Asn Gly Leu Met Gly
65                  70                  75                  80

Tyr Tyr Phe Glu Asn Asp Phe Phe Asn Leu Asn Ile Ile Ser Pro Thr
                85                  90                  95

Leu Asp Gly Asn Leu Thr Phe Ser Lys Glu Asp Ile Asn Ser Ile Leu
            100                 105                 110

Gly Asn Lys Ile Ile Lys Ser Ala Arg Trp Ile Gly Leu Ile Lys Pro
        115                 120                 125

Ser Ile Thr Gly Glu Tyr Ile Leu Ser Thr Asn Ser Pro Asn Cys Arg
    130                 135                 140

Val Glu Leu Asn Gly Glu Ile Phe Asn Leu Ser Leu Asn Thr Ser Asn
145                 150                 155                 160

Thr Val Asn Leu Ile Gln Gly Asn Val Tyr Asp Ile Arg Ile Glu Gln
                165                 170                 175

Leu Met Ser Glu Asn Gln Leu Leu Lys Asn Tyr Glu Gly Ile Lys Leu
            180                 185                 190

Tyr Trp Glu Thr Ser Asp Ile Ile Lys Glu Ile Pro Ser Glu Val
        195                 200                 205

Leu Leu Lys Pro Asn Tyr Ser Asn Thr Asn Glu Lys Ser Lys Phe Ile
    210                 215                 220

Pro Asn Asn Thr Leu Phe Ser Asn Ala Lys Leu Lys Ala Asn Ala Asn
225                 230                 235                 240

Arg Asp Thr Asp Arg Asp Gly Ile Pro Asp Glu Trp Glu Ile Asn Gly
                245                 250                 255

Tyr Thr Val Met Asn Gln Lys Ala Val Ala Trp Asp Lys Phe Ala
            260                 265                 270

Ala Asn Gly Tyr Lys Lys Tyr Val Ser Asn Pro Phe Lys Pro Cys Thr
        275                 280                 285

Ala Asn Asp Pro Tyr Thr Asp Phe Glu Lys Val Ser Gly Gln Ile Asp
    290                 295                 300

Pro Ser Val Ser Met Val Ala Arg Asp Pro Met Ile Ser Ala Tyr Pro
305                 310                 315                 320

Ile Val Gly Val Gln Met Glu Arg Leu Val Val Ser Lys Ser Glu Thr
                325                 330                 335

Ile Thr Gly Asp Ser Thr Lys Ser Met Ser Lys Ser Thr Ser His Ser
```

-continued

```
                340                 345                 350
Ser Thr Asn Ile Asn Thr Val Gly Ala Glu Val Ser Gly Ser Leu Gln
            355                 360                 365

Leu Ala Gly Gly Ile Phe Pro Val Phe Ser Met Ser Ala Ser Ala Asn
370                 375                 380

Tyr Ser His Thr Trp Gln Asn Thr Ser Thr Val Asp Asp Thr Thr Gly
385                 390                 395                 400

Glu Ser Phe Ser Gln Gly Leu Ser Ile Asn Thr Ala Glu Ser Ala Tyr
                405                 410                 415

Ile Asn Pro Asn Ile Arg Tyr Tyr Asn Thr Gly Thr Ala Pro Val Tyr
            420                 425                 430

Asn Val Thr Pro Thr Thr Thr Ile Val Ile Asp Lys Gln Ser Val Ala
                435                 440                 445

Thr Ile Lys Gly Gln Glu Ser Leu Ile Gly Asp Tyr Leu Asn Pro Gly
            450                 455                 460

Gly Thr Tyr Pro Ile Ile Gly Glu Pro Met Ala Leu Asn Thr Met
465                 470                 475                 480

Asp Gln Phe Ser Ser Arg Leu Ile Pro Ile Asn Tyr Asn Gln Leu Lys
                485                 490                 495

Ser Ile Asp Asn Gly Gly Thr Val Met Leu Ser Thr Ser Gln Phe Thr
            500                 505                 510

Gly Asn Phe Ala Lys Tyr Asn Ser Asn Gly Asn Leu Val Thr Asp Gly
                515                 520                 525

Asn Asn Trp Gly Pro Tyr Leu Gly Thr Ile Lys Ser Thr Thr Ala Ser
            530                 535                 540

Leu Thr Leu Ser Leu Pro Asp Gln Thr Thr Gln Val Ala Val Val Ala
545                 550                 555                 560

Pro Asn Phe Ser Asp Pro Glu Asp Lys Thr Pro Arg Leu Thr Leu Glu
                565                 570                 575

Gln Ala Leu Val Lys Ala Phe Arg Leu Glu Lys Lys Asn Gly Lys Phe
            580                 585                 590

Tyr Phe His Gly Met Glu Ile Ser Ala Asn Gln Lys Ile Gln Val Phe
                595                 600                 605

Leu Asp Arg Asn Thr Asn Val Asp Phe Glu Asn Gln Leu Lys Asn Thr
            610                 615                 620

Ala Asn Lys Asp Ile Met Asn Cys Ile Ile Lys Arg Asn Met Asn Ile
625                 630                 635                 640

Leu Val Lys Val Ile Thr Phe Lys Glu Asn Ile Ser Ser Ile Asn Ile
                645                 650                 655

Ile Asn Asp Thr Asn Phe Gly Val Glu Ser Met Thr Gly Leu Ser Lys
            660                 665                 670

Arg Ile Lys Gly Asn Asp Gly Ile Tyr Arg Ala Ser Thr Lys Ser Phe
            675                 680                 685

Ser Phe Lys Ser Lys Glu Ile Lys Tyr Pro Gly Phe Tyr Arg Met
            690                 695                 700

Arg Phe Val Ile Gln Ser Tyr Glu Pro Phe Thr Cys Asn Phe Lys Leu
705                 710                 715                 720

Phe Asn Asn Leu Ile Tyr Ser Asn Ser Phe Asp Ile Gly Tyr Tyr Asp
                725                 730                 735

Glu Phe Phe Tyr Phe Tyr Cys Asn Gly Ser Lys Ser Phe Phe Asp Ile
            740                 745                 750

Ser Cys Asp Ile Ile Asn Ser Ile Asn Arg Leu Ser Gly Val Phe Leu
            755                 760                 765
```

Ile Glu Leu Asp Lys Leu Ile Ile His His His His His His
770                 775                 780

<210> SEQ ID NO 10
<211> LENGTH: 855
<212> TYPE: PRT
<213> ORGANISM: Artificial Sequence
<220> FEATURE:
<223> OTHER INFORMATION: Fusion Protein with Human Oct4/C. Botulinum
      C2I

<400> SEQUENCE: 10

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Ala Gly His Leu Ala Ser Asp
        50                  55                  60

Phe Ala Phe Ser Pro Pro Gly Gly Gly Asp Gly Pro Gly Gly
65                  70                  75                  80

Pro Glu Pro Gly Trp Val Asp Pro Arg Thr Trp Leu Ser Phe Gln Gly
                85                  90                  95

Pro Pro Gly Gly Pro Gly Ile Gly Pro Val Gly Pro Gly Ser Glu
            100                 105                 110

Val Trp Gly Ile Pro Pro Cys Pro Pro Tyr Glu Phe Cys Gly Gly
        115                 120                 125

Met Ala Tyr Cys Gly Pro Gln Val Gly Val Gly Leu Val Pro Gln Gly
130                 135                 140

Gly Leu Glu Thr Ser Gln Pro Glu Gly Glu Ala Gly Val Gly Val Glu
145                 150                 155                 160

Ser Asn Ser Asp Gly Ala Ser Pro Glu Pro Cys Thr Val Thr Pro Gly
                165                 170                 175

Ala Val Lys Leu Glu Lys Glu Lys Leu Glu Gln Asn Pro Glu Glu Ser
            180                 185                 190

Gln Asp Ile Lys Ala Leu Gln Lys Glu Leu Glu Gln Phe Ala Lys Leu
        195                 200                 205

Leu Lys Gln Lys Arg Ile Thr Leu Gly Tyr Thr Gln Ala Asp Val Gly
    210                 215                 220

Leu Thr Leu Gly Val Leu Phe Gly Lys Val Phe Ser Gln Thr Thr Ile
225                 230                 235                 240

Cys Arg Phe Glu Ala Leu Gln Leu Ser Phe Lys Asn Met Cys Lys Leu
                245                 250                 255

Arg Pro Leu Leu Gln Lys Trp Val Glu Glu Ala Asp Asn Asn Glu Asn
            260                 265                 270

Leu Gln Glu Ile Cys Lys Ala Glu Thr Leu Val Gln Ala Arg Lys Arg
        275                 280                 285

Lys Arg Thr Ser Ile Glu Asn Arg Val Arg Gly Asn Leu Glu Asn Leu
    290                 295                 300

Phe Leu Gln Cys Pro Lys Pro Thr Leu Gln Gln Ile Ser His Ile Ala
305                 310                 315                 320

Gln Gln Leu Gly Leu Glu Lys Asp Val Val Arg Val Trp Phe Cys Asn
                325                 330                 335

Arg Arg Gln Lys Gly Lys Arg Ser Ser Asp Tyr Ala Gln Arg Glu
            340                 345                 350

-continued

```
Asp Phe Glu Ala Ala Gly Ser Pro Phe Ser Gly Gly Pro Val Ser Phe
            355                 360                 365

Pro Leu Ala Pro Gly Pro His Phe Gly Thr Pro Gly Tyr Gly Ser Pro
    370                 375                 380

His Phe Thr Ala Leu Tyr Ser Ser Val Pro Phe Pro Glu Gly Glu Ala
385                 390                 395                 400

Phe Pro Pro Val Ser Val Thr Thr Leu Gly Ser Pro Met His Ser Asn
                405                 410                 415

Ala Ala Met Pro Ile Ile Lys Glu Pro Ile Asp Phe Ile Asn Lys Pro
            420                 425                 430

Glu Ser Glu Ala Lys Lys Trp Gly Lys Glu Glu Lys Arg Trp Phe
    435                 440                 445

Thr Lys Leu Asn Asn Leu Glu Glu Val Ala Val Asn Gln Leu Lys Asn
    450                 455                 460

Lys Glu Tyr Lys Thr Lys Ile Asp Asn Phe Ser Thr Asp Ile Leu Phe
465                 470                 475                 480

Ser Ser Leu Thr Ala Ile Glu Ile Met Lys Glu Asp Glu Asn Arg Asn
                485                 490                 495

Leu Phe Asp Val Glu Arg Ile Arg Glu Ala Leu Leu Lys Asn Thr Leu
                500                 505                 510

Asp Arg Asp Ala Ile Gly Tyr Val Asn Phe Thr Pro Lys Glu Leu Gly
    515                 520                 525

Ile Asn Phe Ser Ile Arg Asp Val Glu Leu Asp Arg Asp Ile Ser Asp
    530                 535                 540

Glu Thr Leu Asp Lys Val Arg Gln Gln Ile Ile Asn Gln Glu Tyr Thr
545                 550                 555                 560

Lys Phe Ser Phe Ile Ser Leu Gly Leu Asn Asp Asn Ser Ile Asn Glu
                565                 570                 575

Ser Val Pro Val Ile Val Lys Thr Arg Val Pro Thr Thr Phe Asp Tyr
                580                 585                 590

Gly Val Leu Asn Asp Lys Glu Ala Val Ala Leu Leu Leu Asn Gln Gly
    595                 600                 605

Phe Ser Ile Ile Pro Glu Ser Ala Ile Ile Thr Thr Ile Lys Gly Lys
    610                 615                 620

Asp Tyr Ile Leu Ile Glu Gly Ser Leu Ser Gln Glu Leu Asp Phe Tyr
625                 630                 635                 640

Asn Lys Gly Ser Glu Ala Trp Gly Ala Glu Asn Tyr Gly Asp Tyr Ile
                645                 650                 655

Ser Lys Leu Ser His Glu Gln Leu Gly Ala Leu Glu Gly Tyr Leu His
                660                 665                 670

Ser Asp Tyr Lys Ala Ile Asn Ser Tyr Leu Arg Asn Asn Arg Val Pro
    675                 680                 685

Asn Asn Asp Glu Leu Asn Lys Lys Ile Glu Leu Ile Ser Ser Ala Leu
    690                 695                 700

Ser Val Lys Pro Ile Pro Gln Thr Leu Ile Ala Tyr Arg Arg Val Asp
705                 710                 715                 720

Gly Ile Pro Phe Asp Leu Pro Ser Asp Phe Ser Phe Asp Lys Lys Glu
                725                 730                 735

Asn Gly Glu Ile Ile Ala Asp Lys Gln Lys Leu Asn Glu Phe Ile Asp
                740                 745                 750

Lys Trp Thr Gly Lys Glu Ile Glu Asn Leu Ser Phe Ser Ser Thr Ser
    755                 760                 765

Leu Lys Ser Thr Pro Ser Ser Phe Ser Lys Ser Arg Phe Ile Phe Arg
    770                 775                 780
```

```
Leu Arg Leu Ser Glu Gly Ala Ile Gly Ala Phe Ile Tyr Gly Phe Ser
785                 790                 795                 800

Gly Phe Gln Ala Ala Gln Ala Ile Leu Leu Asn Lys Asn Ser Thr Phe
            805                 810                 815

Lys Ile Phe Arg Ile Thr Pro Ile Thr Ser Ile Ile Asn Arg Val Thr
            820                 825                 830

Lys Met Thr Gln Val Val Ile Asp Ala Glu Gly Ile Gln Asn Lys Glu
            835                 840                 845

Ile His His His His His His
    850                 855

<210> SEQ ID NO 11
<211> LENGTH: 647
<212> TYPE: PRT
<213> ORGANISM: Artificial Sequence
<220> FEATURE:
<223> OTHER INFORMATION: Fusion Protein of Human Oct4/C. botulinum C2I

<400> SEQUENCE: 11

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
            20                  25                  30

Leu Ala Gly Glu Leu Glu Gln Leu Arg Ala Arg Leu Glu His His Pro
        35                  40                  45

Gln Gly Gln Arg Glu Pro Ser Gly Ala Met Pro Ile Ile Lys Glu Pro
    50                  55                  60

Ile Asp Phe Ile Asn Lys Pro Glu Ser Glu Ala Lys Lys Trp Gly Lys
65              70                  75                  80

Glu Glu Glu Lys Arg Trp Phe Thr Lys Leu Asn Asn Leu Glu Glu Val
                85                  90                  95

Ala Val Asn Gln Leu Lys Asn Lys Glu Tyr Lys Thr Lys Ile Asp Asn
            100                 105                 110

Phe Ser Thr Asp Ile Leu Phe Ser Ser Leu Thr Ala Ile Glu Ile Met
        115                 120                 125

Lys Glu Asp Glu Asn Arg Asn Leu Phe Asp Val Glu Arg Ile Arg Glu
    130                 135                 140

Ala Leu Leu Lys Asn Thr Leu Asp Arg Asp Ala Ile Gly Tyr Val Asn
145                 150                 155                 160

Phe Thr Pro Lys Glu Leu Gly Ile Asn Phe Ser Ile Arg Asp Val Glu
                165                 170                 175

Leu Asp Arg Asp Ile Ser Asp Glu Thr Leu Asp Lys Val Arg Gln Gln
            180                 185                 190

Ile Ile Asn Gln Glu Tyr Thr Lys Phe Ser Phe Ile Ser Leu Gly Leu
        195                 200                 205

Asn Asp Asn Ser Ile Asn Glu Ser Val Pro Val Ile Val Lys Thr Arg
    210                 215                 220

Val Pro Thr Thr Phe Asp Tyr Gly Val Leu Asn Asp Lys Gly Ala Ala
225                 230                 235                 240

Gly His Leu Ala Ser Asp Phe Ala Phe Ser Pro Pro Gly Gly Gly Gly
                245                 250                 255

Gly Asp Gly Pro Gly Gly Pro Glu Pro Gly Trp Val Asp Pro Arg Thr
            260                 265                 270

Trp Leu Ser Phe Gln Gly Pro Pro Gly Gly Pro Gly Ile Gly Pro Gly
        275                 280                 285
```

Val Gly Pro Gly Ser Glu Val Trp Gly Ile Pro Pro Cys Pro Pro
            290             295             300

Tyr Glu Phe Cys Gly Gly Met Ala Tyr Cys Gly Pro Gln Val Gly Val
305             310             315             320

Gly Leu Val Pro Gln Gly Gly Leu Glu Thr Ser Gln Pro Glu Gly Glu
            325             330             335

Ala Gly Val Gly Val Glu Ser Asn Ser Asp Gly Ala Ser Pro Glu Pro
            340             345             350

Cys Thr Val Thr Pro Gly Ala Val Lys Leu Glu Lys Glu Lys Leu Glu
            355             360             365

Gln Asn Pro Glu Glu Ser Gln Asp Ile Lys Ala Leu Gln Lys Glu Leu
            370             375             380

Glu Gln Phe Ala Lys Leu Leu Lys Gln Lys Arg Ile Thr Leu Gly Tyr
385             390             395             400

Thr Gln Ala Asp Val Gly Leu Thr Leu Gly Val Leu Phe Gly Lys Val
            405             410             415

Phe Ser Gln Thr Thr Ile Cys Arg Phe Glu Ala Leu Gln Leu Ser Phe
            420             425             430

Lys Asn Met Cys Lys Leu Arg Pro Leu Leu Gln Lys Trp Val Glu Glu
            435             440             445

Ala Asp Asn Asn Glu Asn Leu Gln Glu Ile Cys Lys Ala Glu Thr Leu
450             455             460

Val Gln Ala Arg Lys Arg Lys Arg Thr Ser Ile Glu Asn Arg Val Arg
465             470             475             480

Gly Asn Leu Glu Asn Leu Phe Leu Gln Cys Pro Lys Pro Thr Leu Gln
            485             490             495

Gln Ile Ser His Ile Ala Gln Gln Leu Gly Leu Glu Lys Asp Val Val
            500             505             510

Arg Val Trp Phe Cys Asn Arg Arg Gln Lys Gly Lys Arg Ser Ser Ser
            515             520             525

Asp Tyr Ala Gln Arg Glu Asp Phe Glu Ala Ala Gly Ser Pro Phe Ser
            530             535             540

Gly Gly Pro Val Ser Phe Pro Leu Ala Pro Gly Pro His Phe Gly Thr
545             550             555             560

Pro Gly Tyr Gly Ser Pro His Phe Thr Ala Leu Tyr Ser Ser Val Pro
            565             570             575

Phe Pro Glu Gly Glu Ala Phe Pro Pro Val Ser Val Thr Thr Leu Gly
            580             585             590

Ser Pro Met His Ser Asn Ala Ala Leu Leu Asn Lys Asn Ser Thr Phe
            595             600             605

Lys Ile Phe Arg Ile Thr Pro Ile Thr Ser Ile Asn Arg Val Thr
            610             615             620

Lys Met Thr Gln Val Val Ile Asp Ala Glu Gly Ile Gln Asn Lys Glu
625             630             635             640

Ile His His His His His His
            645

<210> SEQ ID NO 12
<211> LENGTH: 812
<212> TYPE: PRT
<213> ORGANISM: Artificial Sequence
<220> FEATURE:
<223> OTHER INFORMATION: Protein Fusion Human Sox2/C. botulinum C2I

<400> SEQUENCE: 12

Met Asp Glu Gln Gln Ser Gln Ala Val Ala Pro Val Tyr Val Gly Gly

-continued

```
1               5               10              15
Met Asp Glu Lys Thr Thr Gly Trp Arg Gly Gly His Val Val Glu Gly
                20              25              30

Leu Ala Gly Glu Leu Glu Gln Leu Arg Ala Arg Leu Glu His His Pro
                35              40              45

Gln Gly Gln Arg Glu Pro Ser Gly Ala Tyr Asn Met Met Glu Thr Glu
50              55              60

Leu Lys Pro Gly Pro Gln Gln Thr Ser Gly Gly Gly Gly Gly Gly Asn
65              70              75              80

Ser Thr Ala Ala Ala Gly Gly Asn Gln Lys Asn Ser Pro Asp Arg
                85              90              95

Val Lys Arg Pro Met Asn Ala Phe Met Val Trp Ser Arg Gly Gln Arg
                100             105             110

Arg Lys Met Ala Gln Glu Asn Pro Lys Met His Asn Ser Glu Ile Ser
                115             120             125

Lys Arg Leu Gly Ala Glu Trp Lys Leu Leu Ser Glu Thr Glu Lys Arg
                130             135             140

Pro Phe Ile Asp Glu Ala Lys Arg Leu Arg Ala Leu His Met Lys Glu
145             150             155             160

His Pro Asp Tyr Lys Tyr Arg Pro Arg Arg Lys Thr Lys Thr Leu Met
                165             170             175

Lys Lys Asp Lys Tyr Thr Leu Pro Gly Gly Leu Leu Ala Pro Gly Gly
                180             185             190

Asn Ser Met Ala Ser Gly Val Gly Val Gly Ala Gly Leu Gly Ala Gly
                195             200             205

Val Asn Gln Arg Met Asp Ser Tyr Ala His Met Asn Gly Trp Ser Asn
                210             215             220

Gly Ser Tyr Ser Met Met Gln Asp Gln Leu Gly Tyr Pro Gln His Pro
225             230             235             240

Gly Leu Asn Ala His Gly Ala Ala Gln Met Gln Pro Met His Arg Tyr
                245             250             255

Asp Val Ser Ala Leu Gln Tyr Asn Ser Met Thr Ser Ser Gln Thr Tyr
                260             265             270

Met Asn Gly Ser Pro Thr Tyr Ser Met Ser Tyr Ser Gln Gln Gly Thr
                275             280             285

Pro Gly Met Ala Leu Gly Ser Met Gly Ser Val Val Lys Ser Glu Ala
                290             295             300

Ser Ser Ser Pro Pro Val Val Thr Ser Ser Ser His Ser Arg Ala Pro
305             310             315             320

Cys Gln Ala Gly Asp Leu Arg Asp Met Ile Ser Met Tyr Leu Pro Gly
                325             330             335

Ala Glu Val Pro Glu Pro Ala Ala Pro Ser Arg Leu His Met Ser Gln
                340             345             350

His Tyr Gln Ser Gly Pro Val Pro Gly Thr Ala Ile Asn Gly Thr Leu
                355             360             365

Pro Leu Ser His Met Ala Ala Met Pro Ile Ile Lys Glu Pro Ile Asp
370             375             380

Phe Ile Asn Lys Pro Glu Ser Glu Ala Lys Lys Trp Gly Lys Glu Glu
385             390             395             400

Glu Lys Arg Trp Phe Thr Lys Leu Asn Asn Leu Glu Glu Val Ala Val
                405             410             415

Asn Gln Leu Lys Asn Lys Glu Tyr Lys Thr Lys Ile Asp Asn Phe Ser
                420             425             430
```

```
Thr Asp Ile Leu Phe Ser Ser Leu Thr Ala Ile Glu Ile Met Lys Glu
        435                 440                 445

Asp Glu Asn Arg Asn Leu Phe Asp Val Glu Arg Ile Arg Glu Ala Leu
    450                 455                 460

Leu Lys Asn Thr Leu Asp Arg Asp Ala Ile Gly Tyr Val Asn Phe Thr
465                 470                 475                 480

Pro Lys Glu Leu Gly Ile Asn Phe Ser Ile Arg Asp Val Glu Leu Asp
                485                 490                 495

Arg Asp Ile Ser Asp Glu Thr Leu Asp Lys Val Arg Gln Gln Ile Ile
            500                 505                 510

Asn Gln Glu Tyr Thr Lys Phe Ser Phe Ile Ser Leu Gly Leu Asn Asp
        515                 520                 525

Asn Ser Ile Asn Glu Ser Val Pro Val Ile Val Lys Thr Arg Val Pro
    530                 535                 540

Thr Thr Phe Asp Tyr Gly Val Leu Asn Asp Lys Glu Ala Val Ala Leu
545                 550                 555                 560

Leu Leu Asn Gln Gly Phe Ser Ile Ile Pro Glu Ser Ala Ile Ile Thr
                565                 570                 575

Thr Ile Lys Gly Lys Asp Tyr Ile Leu Ile Glu Gly Ser Leu Ser Gln
            580                 585                 590

Glu Leu Asp Phe Tyr Asn Lys Gly Ser Glu Ala Trp Gly Ala Glu Asn
        595                 600                 605

Tyr Gly Asp Tyr Ile Ser Lys Leu Ser His Glu Gln Leu Gly Ala Leu
    610                 615                 620

Glu Gly Tyr Leu His Ser Asp Tyr Lys Ala Ile Asn Ser Tyr Leu Arg
625                 630                 635                 640

Asn Asn Arg Val Pro Asn Asn Asp Glu Leu Asn Lys Lys Ile Glu Leu
                645                 650                 655

Ile Ser Ser Ala Leu Ser Val Lys Pro Ile Pro Gln Thr Leu Ile Ala
            660                 665                 670

Tyr Arg Arg Val Asp Gly Ile Pro Phe Asp Leu Pro Ser Asp Phe Ser
        675                 680                 685

Phe Asp Lys Lys Glu Asn Gly Glu Ile Ile Ala Asp Lys Gln Lys Leu
    690                 695                 700

Asn Glu Phe Ile Asp Lys Trp Thr Gly Lys Glu Ile Glu Asn Leu Ser
705                 710                 715                 720

Phe Ser Ser Thr Ser Leu Lys Ser Thr Pro Ser Ser Phe Ser Lys Ser
                725                 730                 735

Arg Phe Ile Phe Arg Leu Arg Leu Ser Glu Gly Ala Ile Gly Ala Phe
            740                 745                 750

Ile Tyr Gly Phe Ser Gly Phe Gln Ala Ala Gln Ala Ile Leu Leu Asn
        755                 760                 765

Lys Asn Ser Thr Phe Lys Ile Phe Arg Ile Thr Pro Ile Thr Ser Ile
    770                 775                 780

Ile Asn Arg Val Thr Lys Met Thr Gln Val Val Ile Asp Ala Glu Gly
785                 790                 795                 800

Ile Gln Asn Lys Glu Ile His His His His His
                805                 810
```

<210> SEQ ID NO 13
<211> LENGTH: 604
<212> TYPE: PRT
<213> ORGANISM: Artificial Sequence
<220> FEATURE:
<223> OTHER INFORMATION: Fusion Protein Human Sox2/C. botulinum C2I

<400> SEQUENCE: 13

```
Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
            20                  25                  30

Leu Ala Gly Glu Leu Glu Gln Leu Arg Ala Arg Leu Glu His His Pro
        35                  40                  45

Gln Gly Gln Arg Glu Pro Ser Gly Ala Met Pro Ile Ile Lys Glu Pro
    50                  55                  60

Ile Asp Phe Ile Asn Lys Pro Glu Ser Glu Ala Lys Lys Trp Gly Lys
65                  70                  75                  80

Glu Glu Glu Lys Arg Trp Phe Thr Lys Leu Asn Asn Leu Glu Glu Val
                85                  90                  95

Ala Val Asn Gln Leu Lys Asn Lys Glu Tyr Lys Thr Lys Ile Asp Asn
            100                 105                 110

Phe Ser Thr Asp Ile Leu Phe Ser Ser Leu Thr Ala Ile Glu Ile Met
        115                 120                 125

Lys Glu Asp Glu Asn Arg Asn Leu Phe Asp Val Glu Arg Ile Arg Glu
    130                 135                 140

Ala Leu Leu Lys Asn Thr Leu Asp Arg Asp Ala Ile Gly Tyr Val Asn
145                 150                 155                 160

Phe Thr Pro Lys Glu Leu Gly Ile Asn Phe Ser Ile Arg Asp Val Glu
                165                 170                 175

Leu Asp Arg Asp Ile Ser Asp Glu Thr Leu Asp Lys Val Arg Gln Gln
            180                 185                 190

Ile Ile Asn Gln Glu Tyr Thr Lys Phe Ser Phe Ile Ser Leu Gly Leu
        195                 200                 205

Asn Asp Asn Ser Ile Asn Glu Ser Val Pro Val Ile Val Lys Thr Arg
    210                 215                 220

Val Pro Thr Thr Phe Asp Tyr Gly Val Leu Asn Asp Lys Gly Ala Tyr
225                 230                 235                 240

Asn Met Met Glu Thr Glu Leu Lys Pro Pro Gly Pro Gln Gln Thr Ser
                245                 250                 255

Gly Gly Gly Gly Gly Asn Ser Thr Ala Ala Ala Gly Gly Asn Gln
            260                 265                 270

Lys Asn Ser Pro Asp Arg Val Lys Arg Pro Met Asn Ala Phe Met Val
        275                 280                 285

Trp Ser Arg Gly Gln Arg Arg Lys Met Ala Gln Glu Asn Pro Lys Met
    290                 295                 300

His Asn Ser Glu Ile Ser Lys Arg Leu Gly Ala Glu Trp Lys Leu Leu
305                 310                 315                 320

Ser Glu Thr Glu Lys Arg Pro Phe Ile Asp Glu Ala Lys Arg Leu Arg
                325                 330                 335

Ala Leu His Met Lys Glu His Pro Asp Tyr Lys Tyr Arg Pro Arg Arg
            340                 345                 350

Lys Thr Lys Thr Leu Met Lys Lys Asp Lys Tyr Thr Leu Pro Gly Gly
        355                 360                 365

Leu Leu Ala Pro Gly Gly Asn Ser Met Ala Ser Gly Val Gly Val Gly
    370                 375                 380

Ala Gly Leu Gly Ala Gly Val Asn Gln Arg Met Asp Ser Tyr Ala His
385                 390                 395                 400

Met Asn Gly Trp Ser Asn Gly Ser Tyr Ser Met Met Gln Asp Gln Leu
                405                 410                 415
```

```
Gly Tyr Pro Gln His Pro Gly Leu Asn Ala His Gly Ala Ala Gln Met
            420                 425                 430
Gln Pro Met His Arg Tyr Asp Val Ser Ala Leu Gln Tyr Asn Ser Met
                435                 440                 445
Thr Ser Ser Gln Thr Tyr Met Asn Gly Ser Pro Thr Tyr Ser Met Ser
        450                 455                 460
Tyr Ser Gln Gln Gly Thr Pro Gly Met Ala Leu Gly Ser Met Gly Ser
465                 470                 475                 480
Val Val Lys Ser Glu Ala Ser Ser Pro Val Val Thr Ser Ser
                485                 490                 495
Ser His Ser Arg Ala Pro Cys Gln Ala Gly Asp Leu Arg Asp Met Ile
            500                 505                 510
Ser Met Tyr Leu Pro Gly Ala Glu Val Pro Glu Pro Ala Ala Pro Ser
                515                 520                 525
Arg Leu His Met Ser Gln His Tyr Gln Ser Gly Pro Val Pro Gly Thr
            530                 535                 540
Ala Ile Asn Gly Thr Leu Pro Leu Ser His Met Ala Ala Leu Leu Asn
545                 550                 555                 560
Lys Asn Ser Thr Phe Lys Ile Phe Arg Ile Thr Pro Ile Thr Ser Ile
                565                 570                 575
Ile Asn Arg Val Thr Lys Met Thr Gln Val Val Ile Asp Ala Glu Gly
            580                 585                 590
Ile Gln Asn Lys Glu Ile His His His His His His
            595                 600
```

<210> SEQ ID NO 14
<211> LENGTH: 1868
<212> TYPE: PRT
<213> ORGANISM: Artificial Sequence
<220> FEATURE:
<223> OTHER INFORMATION: Fusion Protein Human Oct4/C. Botulinum
      BoNT/C1/C. difficile TcdB

<400> SEQUENCE: 14

```
Met Asp Glu Gln Gln Ser Gln Ala Val Ala Pro Val Tyr Val Gly Gly
1               5                   10                  15
Met Asp Glu Lys Thr Thr Gly Trp Arg Gly Gly His Val Val Glu Gly
                20                  25                  30
Leu Ala Gly Glu Leu Glu Gln Leu Arg Ala Arg Leu Glu His His Pro
        35                  40                  45
Gln Gly Gln Arg Glu Pro Ser Gly Ala Ala Gly His Leu Ala Ser Asp
    50                  55                  60
Phe Ala Phe Ser Pro Pro Gly Gly Gly Gly Asp Gly Pro Gly Gly
65                  70                  75                  80
Pro Glu Pro Gly Trp Val Asp Pro Arg Thr Trp Leu Ser Phe Gln Gly
                85                  90                  95
Pro Pro Gly Gly Pro Gly Ile Gly Pro Gly Val Gly Pro Gly Ser Glu
            100                 105                 110
Val Trp Gly Ile Pro Pro Cys Pro Pro Tyr Glu Phe Cys Gly Gly
            115                 120                 125
Met Ala Tyr Cys Gly Pro Gln Val Gly Val Gly Leu Val Pro Gln Gly
        130                 135                 140
Gly Leu Glu Thr Ser Gln Pro Glu Gly Glu Ala Gly Val Gly Val Glu
145                 150                 155                 160
Ser Asn Ser Asp Gly Ala Ser Pro Glu Pro Cys Thr Val Thr Pro Gly
                165                 170                 175
```

-continued

```
Ala Val Lys Leu Glu Lys Glu Lys Leu Glu Gln Asn Pro Glu Ser
            180                 185                 190

Gln Asp Ile Lys Ala Leu Gln Lys Glu Leu Glu Gln Phe Ala Lys Leu
        195                 200                 205

Leu Lys Gln Lys Arg Ile Thr Leu Gly Tyr Thr Gln Ala Asp Val Gly
210                 215                 220

Leu Thr Leu Gly Val Leu Phe Gly Lys Val Phe Ser Gln Thr Thr Ile
225                 230                 235                 240

Cys Arg Phe Glu Ala Leu Gln Leu Ser Phe Lys Asn Met Cys Lys Leu
                245                 250                 255

Arg Pro Leu Leu Gln Lys Trp Val Glu Ala Asp Asn Asn Glu Asn
            260                 265                 270

Leu Gln Glu Ile Cys Lys Ala Glu Thr Leu Val Gln Ala Arg Lys Arg
        275                 280                 285

Lys Arg Thr Ser Ile Glu Asn Arg Val Arg Gly Asn Leu Glu Asn Leu
    290                 295                 300

Phe Leu Gln Cys Pro Lys Pro Thr Leu Gln Gln Ile Ser His Ile Ala
305                 310                 315                 320

Gln Gln Leu Gly Leu Glu Lys Asp Val Val Arg Val Trp Phe Cys Asn
                325                 330                 335

Arg Arg Gln Lys Gly Lys Arg Ser Ser Ser Asp Tyr Ala Gln Arg Glu
            340                 345                 350

Asp Phe Glu Ala Ala Gly Ser Pro Phe Ser Gly Gly Pro Val Ser Phe
        355                 360                 365

Pro Leu Ala Pro Gly Pro His Phe Gly Thr Pro Gly Tyr Gly Ser Pro
370                 375                 380

His Phe Thr Ala Leu Tyr Ser Ser Val Pro Phe Pro Glu Gly Glu Ala
385                 390                 395                 400

Phe Pro Pro Val Ser Val Thr Thr Leu Gly Ser Pro Met His Ser Asn
                405                 410                 415

Ala Ala Ala Ser Leu Val Asn Arg Lys Gln Leu Glu Lys Met Ala Asn
            420                 425                 430

Val Arg Phe Arg Thr Gln Glu Asp Glu Tyr Val Ala Ile Leu Asp Ala
        435                 440                 445

Leu Glu Glu Tyr His Asn Met Ser Glu Asn Thr Val Val Glu Lys Tyr
    450                 455                 460

Leu Lys Leu Lys Met Pro Ile Thr Ile Asn Asn Phe Asn Tyr Ser Asp
465                 470                 475                 480

Pro Val Asp Asn Lys Asn Ile Leu Tyr Leu Asp Thr His Leu Asn Thr
                485                 490                 495

Leu Ala Asn Glu Pro Glu Lys Ala Phe Arg Ile Thr Gly Asn Ile Trp
            500                 505                 510

Val Ile Pro Asp Arg Phe Ser Arg Asn Ser Asn Pro Asn Leu Asn Lys
        515                 520                 525

Pro Pro Arg Val Thr Ser Pro Lys Ser Gly Tyr Tyr Asp Pro Asn Tyr
    530                 535                 540

Leu Ser Thr Asp Ser Asp Lys Asp Pro Phe Leu Lys Glu Ile Ile Lys
545                 550                 555                 560

Leu Phe Lys Arg Ile Asn Ser Arg Glu Ile Gly Glu Glu Leu Ile Tyr
                565                 570                 575

Arg Leu Ser Thr Asp Ile Pro Phe Pro Gly Asn Asn Asn Thr Pro Ile
            580                 585                 590

Asn Thr Phe Asp Phe Asp Val Asp Phe Asn Ser Val Asp Val Lys Thr
        595                 600                 605
```

```
Arg Gln Gly Asn Asn Trp Val Lys Thr Gly Ser Ile Asn Pro Ser Val
    610                 615                 620

Ile Ile Thr Gly Pro Arg Glu Asn Ile Ile Asp Pro Glu Thr Ser Thr
625                 630                 635                 640

Phe Lys Leu Thr Asn Asn Thr Phe Ala Ala Gln Glu Gly Phe Gly Ala
                645                 650                 655

Leu Ser Ile Ile Ser Ile Ser Pro Arg Phe Met Leu Thr Tyr Ser Asn
                660                 665                 670

Ala Thr Asn Asp Val Gly Glu Gly Arg Phe Ser Lys Ser Glu Phe Cys
            675                 680                 685

Met Asp Pro Ile Leu Ile Leu Met Ala Ala Leu Asn Ala Ala Met His
    690                 695                 700

Asn Leu Tyr Gly Ile Ala Ile Pro Asn Asp Gln Thr Ile Ser Ser Val
705                 710                 715                 720

Thr Ser Asn Ile Phe Tyr Ser Gln Tyr Asn Val Lys Leu Glu Tyr Ala
                725                 730                 735

Glu Ile Tyr Ala Phe Gly Gly Pro Thr Ile Asp Leu Ile Pro Lys Ser
            740                 745                 750

Ala Arg Lys Tyr Phe Glu Glu Lys Ala Leu Asp Tyr Tyr Arg Ser Ile
    755                 760                 765

Ala Lys Arg Leu Asn Ser Ile Thr Thr Ala Asn Pro Ser Ser Phe Asn
770                 775                 780

Lys Tyr Ile Gly Glu Tyr Lys Gln Lys Leu Ile Arg Lys Tyr Arg Phe
785                 790                 795                 800

Val Val Glu Ser Ser Gly Glu Val Thr Val Asn Arg Asn Lys Phe Val
                805                 810                 815

Glu Leu Tyr Asn Glu Leu Thr Gln Ile Phe Thr Glu Phe Asn Tyr Ala
            820                 825                 830

Lys Ile Tyr Asn Val Gln Asn Arg Lys Ile Tyr Leu Ser Asn Val Tyr
    835                 840                 845

Thr Pro Val Thr Ala Asn Ile Leu Asp Asp Asn Val Tyr Asp Ile Gln
850                 855                 860

Asn Gly Phe Asn Ile Pro Lys Ser Asn Leu Asn Val Leu Phe Met Gly
865                 870                 875                 880

Gln Asn Leu Ser Arg Asn Pro Ala Leu Arg Lys Val Asn Pro Glu Asn
                885                 890                 895

Met Leu Tyr Leu Phe Thr Lys Phe Cys His Lys Ala Ile Asp Gly Arg
            900                 905                 910

Ser Leu Tyr Asn Lys Thr Leu Asp Cys Arg Glu Leu Leu Val Lys Asn
    915                 920                 925

Thr Asp Leu Pro Phe Ile Gly Asp Ile Ser Asp Val Lys Thr Asp Ile
    930                 935                 940

Phe Leu Arg Lys Asp Ile Asn Glu Glu Thr Glu Val Ile Tyr Tyr Pro
945                 950                 955                 960

Asp Asn Val Ser Val Asp Gln Val Ile Leu Ser Lys Asn Thr Ser Glu
                965                 970                 975

His Gly Gln Leu Asp Leu Leu Tyr Pro Ser Ile Asp Ser Glu Ser Glu
            980                 985                 990

Ile Leu Pro Gly Glu Asn Gln Val Phe Tyr Asp Asn Arg Thr Gln Asn
    995                 1000                1005

Val Asp Tyr Leu Asn Ser Tyr Tyr Tyr Leu Glu Ser Gln Lys Leu
    1010                1015                1020

Ser Asp Asn Val Glu Asp Phe Thr Phe Thr Arg Ser Ile Glu Glu
```

-continued

```
              1025                1030                1035

Ala Leu Asp Asn Ser Ala Lys Val Tyr Thr Tyr Phe Pro Thr Leu
    1040                1045                1050

Ala Asn Lys Val Asn Ala Gly Val Gln Gly Gly Leu Phe Leu Met
    1055                1060                1065

Trp Ala Asn Asp Val Val Glu Asp Phe Thr Thr Asn Ile Leu Arg
    1070                1075                1080

Lys Asp Thr Leu Asp Lys Ile Ser Asp Val Ser Ala Ile Ile Pro
    1085                1090                1095

Tyr Ile Gly Pro Ala Leu Asn Ile Ser Asn Ser Val Arg Arg Gly
    1100                1105                1110

Asn Phe Thr Glu Ala Phe Ala Val Thr Gly Val Thr Ile Leu Leu
    1115                1120                1125

Glu Ala Phe Pro Glu Phe Thr Ile Pro Ala Leu Gly Ala Phe Val
    1130                1135                1140

Ile Tyr Ser Lys Val Gln Glu Arg Asn Glu Ile Ile Lys Thr Ile
    1145                1150                1155

Asp Asn Cys Leu Glu Gln Arg Ile Lys Arg Trp Lys Asp Ser Tyr
    1160                1165                1170

Glu Trp Met Met Gly Thr Trp Leu Ser Arg Ile Ile Thr Gln Phe
    1175                1180                1185

Asn Asn Ile Ser Tyr Gln Met Tyr Asp Ser Leu Asn Tyr Gln Ala
    1190                1195                1200

Gly Ala Ile Lys Ala Lys Ile Asp Leu Glu Tyr Lys Lys Tyr Ser
    1205                1210                1215

Gly Ser Asp Lys Glu Asn Ile Lys Ser Gln Val Glu Asn Leu Lys
    1220                1225                1230

Asn Ser Leu Asp Val Lys Ile Ser Glu Ala Met Asn Asn Ile Asn
    1235                1240                1245

Lys Phe Ile Arg Glu Cys Ser Val Thr Tyr Leu Phe Lys Asn Met
    1250                1255                1260

Leu Pro Lys Val Ile Asp Glu Leu Asn Glu Phe Asp Arg Asn Thr
    1265                1270                1275

Lys Ala Lys Leu Ile Asn Leu Ile Asp Ser His Asn Ile Ile Leu
    1280                1285                1290

Val Gly Glu Val Asp Lys Leu Lys Ala Lys Val Asn Asn Ser Phe
    1295                1300                1305

Gln Asn Thr Ile Pro Phe Asn Ile Phe Ser Tyr Thr Asn Asn Ser
    1310                1315                1320

Leu Leu Lys Asp Ile Ile Asn Glu Tyr Phe Asn Asn Ile Asn Asp
    1325                1330                1335

Ser Lys Ile Leu Ser Leu Gln Asn Arg Lys Asn Leu Ile Thr Gly
    1340                1345                1350

Phe Val Thr Val Gly Asp Asp Lys Tyr Tyr Phe Asn Pro Ile Asn
    1355                1360                1365

Gly Gly Ala Ala Ser Ile Gly Glu Thr Ile Ile Asp Asp Lys Asn
    1370                1375                1380

Tyr Tyr Phe Asn Gln Ser Gly Val Leu Gln Thr Gly Val Phe Ser
    1385                1390                1395

Thr Glu Asp Gly Phe Lys Tyr Phe Ala Pro Ala Asn Thr Leu Asp
    1400                1405                1410

Glu Asn Leu Glu Gly Glu Ala Ile Asp Phe Thr Gly Lys Leu Ile
    1415                1420                1425
```

-continued

| | | | | | | | | | | | |
|---|---|---|---|---|---|---|---|---|---|---|---|
| Ile | Asp | Glu | Asn | Ile | Tyr | Tyr | Phe | Asp | Asn | Tyr | Arg | Gly | Ala |
| 1430 | | | | | 1435 | | | | | 1440 | | | |
| Val | Glu | Trp | Lys | Glu | Leu | Asp | Gly | Glu | Met | His | Tyr | Phe | Ser | Pro |
| 1445 | | | | | 1450 | | | | | 1455 | | | | |
| Glu | Thr | Gly | Lys | Ala | Phe | Lys | Gly | Leu | Asn | Gln | Ile | Gly | Asp | Tyr |
| 1460 | | | | | 1465 | | | | | 1470 | | | | |
| Lys | Tyr | Tyr | Phe | Asn | Ser | Asp | Gly | Val | Met | Gln | Lys | Gly | Phe | Val |
| 1475 | | | | | 1480 | | | | | 1485 | | | | |
| Ser | Ile | Asn | Asp | Asn | Lys | His | Tyr | Phe | Asp | Asp | Ser | Gly | Val | Met |
| 1490 | | | | | 1495 | | | | | 1500 | | | | |
| Lys | Val | Gly | Tyr | Thr | Glu | Ile | Asp | Gly | Lys | His | Phe | Tyr | Phe | Ala |
| 1505 | | | | | 1510 | | | | | 1515 | | | | |
| Glu | Asn | Gly | Glu | Met | Gln | Ile | Gly | Val | Phe | Asn | Thr | Glu | Asp | Gly |
| 1520 | | | | | 1525 | | | | | 1530 | | | | |
| Phe | Lys | Tyr | Phe | Ala | His | His | Asn | Glu | Asp | Leu | Gly | Asn | Glu | Glu |
| 1535 | | | | | 1540 | | | | | 1545 | | | | |
| Gly | Glu | Glu | Ile | Ser | Tyr | Ser | Gly | Ile | Leu | Asn | Phe | Asn | Asn | Lys |
| 1550 | | | | | 1555 | | | | | 1560 | | | | |
| Ile | Tyr | Tyr | Phe | Asp | Asp | Ser | Phe | Thr | Ala | Val | Val | Gly | Trp | Lys |
| 1565 | | | | | 1570 | | | | | 1575 | | | | |
| Asp | Leu | Glu | Asp | Gly | Ser | Lys | Tyr | Tyr | Phe | Asp | Glu | Asp | Thr | Ala |
| 1580 | | | | | 1585 | | | | | 1590 | | | | |
| Glu | Ala | Tyr | Ile | Gly | Leu | Ser | Leu | Ile | Asn | Asp | Gly | Gln | Tyr | Tyr |
| 1595 | | | | | 1600 | | | | | 1605 | | | | |
| Phe | Asn | Asp | Asp | Gly | Ile | Met | Gln | Val | Gly | Phe | Val | Thr | Ile | Asn |
| 1610 | | | | | 1615 | | | | | 1620 | | | | |
| Asp | Lys | Val | Phe | Tyr | Phe | Ser | Asp | Ser | Gly | Ile | Ile | Glu | Ser | Gly |
| 1625 | | | | | 1630 | | | | | 1635 | | | | |
| Val | Gln | Asn | Ile | Asp | Asp | Asn | Tyr | Phe | Tyr | Ile | Asp | Asp | Asn | Gly |
| 1640 | | | | | 1645 | | | | | 1650 | | | | |
| Ile | Val | Gln | Ile | Gly | Val | Phe | Asp | Thr | Ser | Asp | Gly | Tyr | Lys | Tyr |
| 1655 | | | | | 1660 | | | | | 1665 | | | | |
| Phe | Ala | Pro | Ala | Asn | Thr | Val | Asn | Asp | Asn | Ile | Tyr | Gly | Gln | Ala |
| 1670 | | | | | 1675 | | | | | 1680 | | | | |
| Val | Glu | Tyr | Ser | Gly | Leu | Val | Arg | Val | Gly | Glu | Asp | Val | Tyr | Tyr |
| 1685 | | | | | 1690 | | | | | 1695 | | | | |
| Phe | Gly | Glu | Thr | Tyr | Thr | Ile | Glu | Thr | Gly | Trp | Ile | Tyr | Asp | Met |
| 1700 | | | | | 1705 | | | | | 1710 | | | | |
| Glu | Asn | Glu | Ser | Asp | Lys | Tyr | Tyr | Phe | Asn | Pro | Glu | Thr | Lys | Lys |
| 1715 | | | | | 1720 | | | | | 1725 | | | | |
| Ala | Cys | Lys | Gly | Ile | Asn | Leu | Ile | Asp | Asp | Ile | Lys | Tyr | Tyr | Phe |
| 1730 | | | | | 1735 | | | | | 1740 | | | | |
| Asp | Glu | Lys | Gly | Ile | Met | Arg | Thr | Gly | Leu | Ile | Ser | Phe | Glu | Asn |
| 1745 | | | | | 1750 | | | | | 1755 | | | | |
| Asn | Asn | Tyr | Tyr | Phe | Asn | Glu | Asn | Gly | Glu | Met | Gln | Phe | Gly | Tyr |
| 1760 | | | | | 1765 | | | | | 1770 | | | | |
| Ile | Asn | Ile | Glu | Asp | Lys | Met | Phe | Tyr | Phe | Gly | Glu | Asp | Gly | Val |
| 1775 | | | | | 1780 | | | | | 1785 | | | | |
| Met | Gln | Ile | Gly | Val | Phe | Asn | Thr | Pro | Asp | Gly | Phe | Lys | Tyr | Phe |
| 1790 | | | | | 1795 | | | | | 1800 | | | | |
| Ala | His | Gln | Asn | Thr | Leu | Asp | Glu | Asn | Phe | Glu | Gly | Glu | Ser | Ile |
| 1805 | | | | | 1810 | | | | | 1815 | | | | |
| Asn | Tyr | Thr | Gly | Trp | Leu | Asp | Leu | Asp | Glu | Lys | Arg | Tyr | Tyr | Phe |
| 1820 | | | | | 1825 | | | | | 1830 | | | | |

-continued

```
Thr Asp Glu Tyr Ile Ala Ala Thr Gly Ser Val Ile Ile Asp Gly
    1835                1840                1845

Glu Glu Tyr Tyr Phe Asp Pro Asp Thr Ala Gln Leu Val Ile Ser
    1850                1855                1860

Glu His His His His
    1865

<210> SEQ ID NO 15
<211> LENGTH: 1778
<212> TYPE: PRT
<213> ORGANISM: Artificial Sequence
<220> FEATURE:
<223> OTHER INFORMATION: Fusion Protein Human Sox2/C. botulinum
      BoNT/C1/C. difficile TcdB

<400> SEQUENCE: 15

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Tyr Asn Met Met Glu Thr Glu
        50                  55                  60

Leu Lys Pro Pro Gly Pro Gln Thr Ser Gly Gly Gly Gly Asn
65                  70                  75                  80

Ser Thr Ala Ala Ala Gly Gly Asn Gln Lys Asn Ser Pro Asp Arg
                85                  90                  95

Val Lys Arg Pro Met Asn Ala Phe Met Val Trp Ser Arg Gly Gln Arg
            100                 105                 110

Arg Lys Met Ala Gln Glu Asn Pro Lys Met His Asn Ser Glu Ile Ser
        115                 120                 125

Lys Arg Leu Gly Ala Glu Trp Lys Leu Leu Ser Glu Thr Glu Lys Arg
    130                 135                 140

Pro Phe Ile Asp Glu Ala Lys Arg Leu Arg Ala Leu His Met Lys Glu
145                 150                 155                 160

His Pro Asp Tyr Lys Tyr Arg Pro Arg Arg Lys Thr Lys Thr Leu Met
                165                 170                 175

Lys Lys Asp Lys Tyr Thr Leu Pro Gly Gly Leu Leu Ala Pro Gly Gly
            180                 185                 190

Asn Ser Met Ala Ser Gly Val Gly Val Gly Ala Gly Leu Gly Ala Gly
        195                 200                 205

Val Asn Gln Arg Met Asp Ser Tyr Ala His Met Asn Gly Trp Ser Asn
    210                 215                 220

Gly Ser Tyr Ser Met Met Gln Asp Gln Leu Gly Tyr Pro Gln His Pro
225                 230                 235                 240

Gly Leu Asn Ala His Gly Ala Ala Gln Met Gln Pro Met His Arg Tyr
                245                 250                 255

Asp Val Ser Ala Leu Gln Tyr Asn Ser Met Thr Ser Ser Gln Thr Tyr
            260                 265                 270

Met Asn Gly Ser Pro Thr Tyr Ser Met Ser Tyr Ser Gln Gln Gly Thr
        275                 280                 285

Pro Gly Met Ala Leu Gly Ser Met Gly Ser Val Val Lys Ser Glu Ala
    290                 295                 300

Ser Ser Ser Pro Pro Val Val Thr Ser Ser Ser His Ser Arg Ala Pro
305                 310                 315                 320
```

-continued

Cys Gln Ala Gly Asp Leu Arg Asp Met Ile Ser Met Tyr Leu Pro Gly
                325                 330                 335

Ala Glu Val Pro Glu Pro Ala Ala Pro Ser Arg Leu His Met Ser Gln
            340                 345                 350

His Tyr Gln Ser Gly Pro Val Pro Gly Thr Ala Ile Asn Gly Thr Leu
        355                 360                 365

Pro Leu Ser His Met Ala Ala Ala Met Pro Ile Thr Ile Asn Asn Phe
    370                 375                 380

Asn Tyr Ser Asp Pro Val Asp Asn Lys Asn Ile Leu Tyr Leu Asp Thr
385                 390                 395                 400

His Leu Asn Thr Leu Ala Asn Glu Pro Glu Lys Ala Phe Arg Ile Thr
                405                 410                 415

Gly Asn Ile Trp Val Ile Pro Asp Arg Phe Ser Arg Asn Ser Asn Pro
            420                 425                 430

Asn Leu Asn Lys Pro Pro Arg Val Thr Ser Pro Lys Ser Gly Tyr Tyr
        435                 440                 445

Asp Pro Asn Tyr Leu Ser Thr Asp Ser Asp Lys Asp Pro Phe Leu Lys
    450                 455                 460

Glu Ile Ile Lys Leu Phe Lys Arg Ile Asn Ser Arg Glu Ile Gly Glu
465                 470                 475                 480

Glu Leu Ile Tyr Arg Leu Ser Thr Asp Ile Pro Phe Pro Gly Asn Asn
                485                 490                 495

Asn Thr Pro Ile Asn Thr Phe Asp Phe Asp Val Asp Phe Asn Ser Val
            500                 505                 510

Asp Val Lys Thr Arg Gln Gly Asn Asn Trp Val Lys Thr Gly Ser Ile
        515                 520                 525

Asn Pro Ser Val Ile Ile Thr Gly Pro Arg Glu Asn Ile Ile Asp Pro
    530                 535                 540

Glu Thr Ser Thr Phe Lys Leu Thr Asn Asn Thr Phe Ala Ala Gln Glu
545                 550                 555                 560

Gly Phe Gly Ala Leu Ser Ile Ile Ser Ile Ser Pro Arg Phe Met Leu
                565                 570                 575

Thr Tyr Ser Asn Ala Thr Asn Asp Val Gly Glu Gly Arg Phe Ser Lys
            580                 585                 590

Ser Glu Phe Cys Met Asp Pro Ile Leu Ile Leu Met Ala Ala Leu Asn
        595                 600                 605

Ala Ala Met His Asn Leu Tyr Gly Ile Ala Ile Pro Asn Asp Gln Thr
    610                 615                 620

Ile Ser Ser Val Thr Ser Asn Ile Phe Tyr Ser Gln Tyr Asn Val Lys
625                 630                 635                 640

Leu Glu Tyr Ala Glu Ile Tyr Ala Phe Gly Gly Pro Thr Ile Asp Leu
                645                 650                 655

Ile Pro Lys Ser Ala Arg Lys Tyr Phe Glu Glu Lys Ala Leu Asp Tyr
            660                 665                 670

Tyr Arg Ser Ile Ala Lys Arg Leu Asn Ser Ile Thr Thr Ala Asn Pro
        675                 680                 685

Ser Ser Phe Asn Lys Tyr Ile Gly Glu Tyr Lys Gln Lys Leu Ile Arg
    690                 695                 700

Lys Tyr Arg Phe Val Val Glu Ser Ser Gly Glu Val Thr Val Asn Arg
705                 710                 715                 720

Asn Lys Phe Val Glu Leu Tyr Asn Glu Leu Thr Gln Ile Phe Thr Glu
                725                 730                 735

Phe Asn Tyr Ala Lys Ile Tyr Asn Val Gln Asn Arg Lys Ile Tyr Leu

```
                740               745               750
Ser Asn Val Tyr Thr Pro Val Thr Ala Asn Ile Leu Asp Asp Asn Val
                    755               760               765
Tyr Asp Ile Gln Asn Gly Phe Asn Ile Pro Lys Ser Asn Leu Asn Val
                    770               775               780
Leu Phe Met Gly Gln Asn Leu Ser Arg Asn Pro Ala Leu Arg Lys Val
785               790               795               800
Asn Pro Glu Asn Met Leu Tyr Leu Phe Thr Lys Phe Cys His Lys Ala
                    805               810               815
Ile Asp Gly Arg Ser Leu Tyr Asn Lys Thr Leu Asp Cys Arg Glu Leu
                    820               825               830
Leu Val Lys Asn Thr Asp Leu Pro Phe Ile Gly Asp Ile Ser Asp Val
                    835               840               845
Lys Thr Asp Ile Phe Leu Arg Lys Asp Ile Asn Glu Glu Thr Glu Val
                    850               855               860
Ile Tyr Tyr Pro Asp Asn Val Ser Val Asp Gln Val Ile Leu Ser Lys
865               870               875               880
Asn Thr Ser Glu His Gly Gln Leu Asp Leu Leu Tyr Pro Ser Ile Asp
                    885               890               895
Ser Glu Ser Glu Ile Leu Pro Gly Glu Asn Gln Val Phe Tyr Asp Asn
                    900               905               910
Arg Thr Gln Asn Val Asp Tyr Leu Asn Ser Tyr Tyr Leu Glu Ser
                    915               920               925
Gln Lys Leu Ser Asp Asn Val Glu Asp Phe Thr Phe Thr Arg Ser Ile
                    930               935               940
Glu Glu Ala Leu Asp Asn Ser Ala Lys Val Tyr Thr Tyr Phe Pro Thr
945               950               955               960
Leu Ala Asn Lys Val Asn Ala Gly Val Gln Gly Gly Leu Phe Leu Met
                    965               970               975
Trp Ala Asn Asp Val Val Glu Asp Phe Thr Thr Asn Ile Leu Arg Lys
                    980               985               990
Asp Thr Leu Asp Lys Ile Ser Asp Val Ser Ala Ile Ile Pro Tyr Ile
                    995               1000              1005
Gly Pro Ala Leu Asn Ile Ser Asn Ser Val Arg Arg Gly Asn Phe
                1010              1015              1020
Thr Glu Ala Phe Ala Val Thr Gly Val Thr Ile Leu Leu Glu Ala
                1025              1030              1035
Phe Pro Glu Phe Thr Ile Pro Ala Leu Gly Ala Phe Val Ile Tyr
                1040              1045              1050
Ser Lys Val Gln Glu Arg Asn Glu Ile Ile Lys Thr Ile Asp Asn
                1055              1060              1065
Cys Leu Glu Gln Arg Ile Lys Arg Trp Lys Asp Ser Tyr Glu Trp
                1070              1075              1080
Met Met Gly Thr Trp Leu Ser Arg Ile Ile Thr Gln Phe Asn Asn
                1085              1090              1095
Ile Ser Tyr Gln Met Tyr Asp Ser Leu Asn Tyr Gln Ala Gly Ala
                1100              1105              1110
Ile Lys Ala Lys Ile Asp Leu Glu Tyr Lys Lys Tyr Ser Gly Ser
                1115              1120              1125
Asp Lys Glu Asn Ile Lys Ser Gln Val Glu Asn Leu Lys Asn Ser
                1130              1135              1140
Leu Asp Val Lys Ile Ser Glu Ala Met Asn Asn Ile Asn Lys Phe
                1145              1150              1155
```

-continued

Ile Arg Glu Cys Ser Val Thr Tyr Leu Phe Lys Asn Met Leu Pro
1160                     1165                1170

Lys Val Ile Asp Glu Leu Asn Glu Phe Asp Arg Asn Thr Lys Ala
1175                     1180                1185

Lys Leu Ile Asn Leu Ile Asp Ser His Asn Ile Ile Leu Val Gly
1190                     1195                1200

Glu Val Asp Lys Leu Lys Ala Lys Val Asn Asn Ser Phe Gln Asn
1205                     1210                1215

Thr Ile Pro Phe Asn Ile Phe Ser Tyr Thr Asn Asn Ser Leu Leu
1220                     1225                1230

Lys Asp Ile Ile Asn Glu Tyr Phe Asn Asn Ile Asn Asp Ser Lys
1235                     1240                1245

Ile Leu Ser Leu Gln Asn Arg Lys Asn Leu Ile Thr Gly Phe Val
1250                     1255                1260

Thr Val Gly Asp Asp Lys Tyr Tyr Phe Asn Pro Ile Asn Gly Gly
1265                     1270                1275

Ala Ala Ser Ile Gly Glu Thr Ile Ile Asp Asp Lys Asn Tyr Tyr
1280                     1285                1290

Phe Asn Gln Ser Gly Val Leu Gln Thr Gly Val Phe Ser Thr Glu
1295                     1300                1305

Asp Gly Phe Lys Tyr Phe Ala Pro Ala Asn Thr Leu Asp Glu Asn
1310                     1315                1320

Leu Glu Gly Glu Ala Ile Asp Phe Thr Gly Lys Leu Ile Ile Asp
1325                     1330                1335

Glu Asn Ile Tyr Tyr Phe Asp Asp Asn Tyr Arg Gly Ala Val Glu
1340                     1345                1350

Trp Lys Glu Leu Asp Gly Glu Met His Tyr Phe Ser Pro Glu Thr
1355                     1360                1365

Gly Lys Ala Phe Lys Gly Leu Asn Gln Ile Gly Asp Tyr Lys Tyr
1370                     1375                1380

Tyr Phe Asn Ser Asp Gly Val Met Gln Lys Gly Phe Val Ser Ile
1385                     1390                1395

Asn Asp Asn Lys His Tyr Phe Asp Asp Ser Gly Val Met Lys Val
1400                     1405                1410

Gly Tyr Thr Glu Ile Asp Gly Lys His Phe Tyr Phe Ala Glu Asn
1415                     1420                1425

Gly Glu Met Gln Ile Gly Val Phe Asn Thr Glu Asp Gly Phe Lys
1430                     1435                1440

Tyr Phe Ala His His Asn Glu Asp Leu Gly Asn Glu Glu Gly Glu
1445                     1450                1455

Glu Ile Ser Tyr Ser Gly Ile Leu Asn Phe Asn Asn Lys Ile Tyr
1460                     1465                1470

Tyr Phe Asp Asp Ser Phe Thr Ala Val Val Gly Trp Lys Asp Leu
1475                     1480                1485

Glu Asp Gly Ser Lys Tyr Tyr Phe Asp Glu Asp Thr Ala Glu Ala
1490                     1495                1500

Tyr Ile Gly Leu Ser Leu Ile Asn Asp Gly Gln Tyr Tyr Phe Asn
1505                     1510                1515

Asp Asp Gly Ile Met Gln Val Gly Phe Val Thr Ile Asn Asp Lys
1520                     1525                1530

Val Phe Tyr Phe Ser Asp Ser Gly Ile Ile Glu Ser Gly Val Gln
1535                     1540                1545

Asn Ile Asp Asp Asn Tyr Phe Tyr Ile Asp Asp Asn Gly Ile Val
1550                     1555                1560

```
Gln Ile Gly Val Phe Asp Thr Ser Asp Gly Tyr Lys Tyr Phe Ala
    1565                1570                1575
Pro Ala Asn Thr Val Asn Asp Asn Ile Tyr Gly Gln Ala Val Glu
    1580                1585                1590
Tyr Ser Gly Leu Val Arg Val Gly Glu Asp Val Tyr Tyr Phe Gly
    1595                1600                1605
Glu Thr Tyr Thr Ile Glu Thr Gly Trp Ile Tyr Asp Met Glu Asn
    1610                1615                1620
Glu Ser Asp Lys Tyr Tyr Phe Asn Pro Glu Thr Lys Lys Ala Cys
    1625                1630                1635
Lys Gly Ile Asn Leu Ile Asp Asp Ile Lys Tyr Tyr Phe Asp Glu
    1640                1645                1650
Lys Gly Ile Met Arg Thr Gly Leu Ile Ser Phe Glu Asn Asn Asn
    1655                1660                1665
Tyr Tyr Phe Asn Glu Asn Gly Glu Met Gln Phe Gly Tyr Ile Asn
    1670                1675                1680
Ile Glu Asp Lys Met Phe Tyr Phe Gly Glu Asp Gly Val Met Gln
    1685                1690                1695
Ile Gly Val Phe Asn Thr Pro Asp Gly Phe Lys Tyr Phe Ala His
    1700                1705                1710
Gln Asn Thr Leu Asp Glu Asn Phe Glu Gly Glu Ser Ile Asn Tyr
    1715                1720                1725
Thr Gly Trp Leu Asp Leu Asp Glu Lys Arg Tyr Tyr Phe Thr Asp
    1730                1735                1740
Glu Tyr Ile Ala Ala Thr Gly Ser Val Ile Ile Asp Gly Glu Glu
    1745                1750                1755
Tyr Tyr Phe Asp Pro Asp Thr Ala Gln Leu Val Ile Ser Glu His
    1760                1765                1770
His His His His His
    1775

<210> SEQ ID NO 16
<211> LENGTH: 2052
<212> TYPE: PRT
<213> ORGANISM: Artificial Sequence
<220> FEATURE:
<223> OTHER INFORMATION: Fusion Protein Human Oct4/C. Botulinum
      BoNTC1/Human Transferrin

<400> SEQUENCE: 16

Met Asp Glu Gln Gln Ser Gln Ala Val Ala Pro Val Tyr Val Gly Gly
1               5                   10                  15
Met Asp Glu Lys Thr Thr Gly Trp Arg Gly Gly His Val Val Glu Gly
                20                  25                  30
Leu Ala Gly Glu Leu Glu Gln Leu Arg Ala Arg Leu Glu His His Pro
        35                  40                  45
Gln Gly Gln Arg Glu Pro Ser Gly Ala Ala Gly His Leu Ala Ser Asp
    50                  55                  60
Phe Ala Phe Ser Pro Pro Gly Gly Gly Gly Asp Gly Pro Gly Gly
65                  70                  75                  80
Pro Glu Pro Gly Trp Val Asp Pro Arg Thr Trp Leu Ser Phe Gln Gly
                85                  90                  95
Pro Pro Gly Gly Pro Gly Ile Gly Pro Gly Val Gly Pro Gly Ser Glu
            100                 105                 110
Val Trp Gly Ile Pro Pro Cys Pro Pro Tyr Glu Phe Cys Gly Gly
        115                 120                 125
```

```
Met Ala Tyr Cys Gly Pro Gln Val Gly Val Gly Leu Val Pro Gln Gly
    130                 135                 140
Gly Leu Glu Thr Ser Gln Pro Glu Gly Glu Ala Gly Val Gly Val Glu
145                 150                 155                 160
Ser Asn Ser Asp Gly Ala Ser Pro Glu Pro Cys Thr Val Thr Pro Gly
                165                 170                 175
Ala Val Lys Leu Glu Lys Glu Lys Leu Glu Gln Asn Pro Glu Glu Ser
            180                 185                 190
Gln Asp Ile Lys Ala Leu Gln Lys Glu Leu Glu Gln Phe Ala Lys Leu
        195                 200                 205
Leu Lys Gln Lys Arg Ile Thr Leu Gly Tyr Thr Gln Ala Asp Val Gly
    210                 215                 220
Leu Thr Leu Gly Val Leu Phe Gly Lys Val Phe Ser Gln Thr Thr Ile
225                 230                 235                 240
Cys Arg Phe Glu Ala Leu Gln Leu Ser Phe Lys Asn Met Cys Lys Leu
                245                 250                 255
Arg Pro Leu Leu Gln Lys Trp Val Glu Glu Ala Asp Asn Asn Glu Asn
            260                 265                 270
Leu Gln Glu Ile Cys Lys Ala Glu Thr Leu Val Gln Ala Arg Lys Arg
        275                 280                 285
Lys Arg Thr Ser Ile Glu Asn Arg Val Arg Gly Asn Leu Glu Asn Leu
    290                 295                 300
Phe Leu Gln Cys Pro Lys Pro Thr Leu Gln Gln Ile Ser His Ile Ala
305                 310                 315                 320
Gln Gln Leu Gly Leu Glu Lys Asp Val Val Arg Val Trp Phe Cys Asn
                325                 330                 335
Arg Arg Gln Lys Gly Lys Arg Ser Ser Ser Asp Tyr Ala Gln Arg Glu
            340                 345                 350
Asp Phe Glu Ala Ala Gly Ser Pro Phe Ser Gly Gly Pro Val Ser Phe
        355                 360                 365
Pro Leu Ala Pro Gly Pro His Phe Gly Thr Pro Gly Tyr Gly Ser Pro
    370                 375                 380
His Phe Thr Ala Leu Tyr Ser Ser Val Pro Phe Pro Glu Gly Glu Ala
385                 390                 395                 400
Phe Pro Pro Val Ser Val Thr Thr Leu Gly Ser Pro Met His Ser Asn
                405                 410                 415
Ala Ala Ala Ser Leu Val Asn Arg Lys Gln Leu Glu Lys Met Ala Asn
            420                 425                 430
Val Arg Phe Arg Thr Gln Glu Asp Glu Tyr Val Ala Ile Leu Asp Ala
        435                 440                 445
Leu Glu Glu Tyr His Asn Met Ser Glu Asn Thr Val Val Glu Lys Tyr
    450                 455                 460
Leu Lys Leu Lys Met Pro Ile Thr Ile Asn Asn Phe Asn Tyr Ser Asp
465                 470                 475                 480
Pro Val Asp Asn Lys Asn Ile Leu Tyr Leu Asp Thr His Leu Asn Thr
                485                 490                 495
Leu Ala Asn Glu Pro Glu Lys Ala Phe Arg Ile Thr Gly Asn Ile Trp
            500                 505                 510
Val Ile Pro Asp Arg Phe Ser Arg Asn Ser Asn Pro Asn Leu Asn Lys
        515                 520                 525
Pro Pro Arg Val Thr Ser Pro Lys Ser Gly Tyr Tyr Asp Pro Asn Tyr
    530                 535                 540
Leu Ser Thr Asp Ser Asp Lys Asp Pro Phe Leu Lys Glu Ile Ile Lys
```

```
            545                 550                 555                 560
Leu Phe Lys Arg Ile Asn Ser Arg Glu Ile Gly Glu Leu Ile Tyr
                565                 570                 575
Arg Leu Ser Thr Asp Ile Pro Phe Pro Gly Asn Asn Asn Thr Pro Ile
                580                 585                 590
Asn Thr Phe Asp Phe Asp Val Asp Phe Asn Ser Val Asp Val Lys Thr
                595                 600                 605
Arg Gln Gly Asn Asn Trp Val Lys Thr Gly Ser Ile Asn Pro Ser Val
            610                 615                 620
Ile Ile Thr Gly Pro Arg Glu Asn Ile Ile Asp Pro Glu Thr Ser Thr
625                 630                 635                 640
Phe Lys Leu Thr Asn Asn Thr Phe Ala Ala Gln Glu Gly Phe Gly Ala
                645                 650                 655
Leu Ser Ile Ile Ser Ile Ser Pro Arg Phe Met Leu Thr Tyr Ser Asn
                660                 665                 670
Ala Thr Asn Asp Val Gly Glu Gly Arg Phe Ser Lys Ser Glu Phe Cys
                675                 680                 685
Met Asp Pro Ile Leu Ile Leu Met Ala Ala Leu Asn Ala Ala Met His
            690                 695                 700
Asn Leu Tyr Gly Ile Ala Ile Pro Asn Asp Gln Thr Ile Ser Ser Val
705                 710                 715                 720
Thr Ser Asn Ile Phe Tyr Ser Gln Tyr Asn Val Lys Leu Glu Tyr Ala
                725                 730                 735
Glu Ile Tyr Ala Phe Gly Gly Pro Thr Ile Asp Leu Ile Pro Lys Ser
                740                 745                 750
Ala Arg Lys Tyr Phe Glu Glu Lys Ala Leu Asp Tyr Tyr Arg Ser Ile
                755                 760                 765
Ala Lys Arg Leu Asn Ser Ile Thr Thr Ala Asn Pro Ser Ser Phe Asn
            770                 775                 780
Lys Tyr Ile Gly Glu Tyr Lys Gln Lys Leu Ile Arg Lys Tyr Arg Phe
785                 790                 795                 800
Val Val Glu Ser Ser Gly Glu Val Thr Val Asn Arg Asn Lys Phe Val
                805                 810                 815
Glu Leu Tyr Asn Glu Leu Thr Gln Ile Phe Thr Glu Phe Asn Tyr Ala
                820                 825                 830
Lys Ile Tyr Asn Val Gln Asn Arg Lys Ile Tyr Leu Ser Asn Val Tyr
                835                 840                 845
Thr Pro Val Thr Ala Asn Ile Leu Asp Asp Asn Val Tyr Asp Ile Gln
            850                 855                 860
Asn Gly Phe Asn Ile Pro Lys Ser Asn Leu Asn Val Leu Phe Met Gly
865                 870                 875                 880
Gln Asn Leu Ser Arg Asn Pro Ala Leu Arg Lys Val Asn Pro Glu Asn
                885                 890                 895
Met Leu Tyr Leu Phe Thr Lys Phe Cys His Lys Ala Ile Asp Gly Arg
                900                 905                 910
Ser Leu Tyr Asn Lys Thr Leu Asp Cys Arg Glu Leu Leu Val Lys Asn
                915                 920                 925
Thr Asp Leu Pro Phe Ile Gly Asp Ile Ser Asp Val Lys Thr Asp Ile
            930                 935                 940
Phe Leu Arg Lys Asp Ile Asn Glu Glu Thr Glu Val Ile Tyr Tyr Pro
945                 950                 955                 960
Asp Asn Val Ser Val Asp Gln Val Ile Leu Ser Lys Asn Thr Ser Glu
                965                 970                 975
```

-continued

His Gly Gln Leu Asp Leu Leu Tyr Pro Ser Ile Asp Ser Glu Ser Glu
                980                 985                 990

Ile Leu Pro Gly Glu Asn Gln Val Phe Tyr Asp Asn Arg Thr Gln Asn
            995                 1000                1005

Val Asp Tyr Leu Asn Ser Tyr Tyr Leu Glu Ser Gln Lys Leu
    1010                1015            1020

Ser Asp Asn Val Glu Asp Phe Thr Phe Thr Arg Ser Ile Glu Glu
    1025            1030                1035

Ala Leu Asp Asn Ser Ala Lys Val Tyr Thr Tyr Phe Pro Thr Leu
    1040            1045                1050

Ala Asn Lys Val Asn Ala Gly Val Gln Gly Gly Leu Phe Leu Met
    1055            1060                1065

Trp Ala Asn Asp Val Val Glu Asp Phe Thr Thr Asn Ile Leu Arg
    1070            1075                1080

Lys Asp Thr Leu Asp Lys Ile Ser Asp Val Ser Ala Ile Ile Pro
    1085            1090                1095

Tyr Ile Gly Pro Ala Leu Asn Ile Ser Asn Ser Val Arg Arg Gly
    1100            1105                1110

Asn Phe Thr Glu Ala Phe Ala Val Thr Gly Val Thr Ile Leu Leu
    1115            1120                1125

Glu Ala Phe Pro Glu Phe Thr Ile Pro Ala Leu Gly Ala Phe Val
    1130            1135                1140

Ile Tyr Ser Lys Val Gln Glu Arg Asn Glu Ile Ile Lys Thr Ile
    1145            1150                1155

Asp Asn Cys Leu Glu Gln Arg Ile Lys Arg Trp Lys Asp Ser Tyr
    1160            1165                1170

Glu Trp Met Met Gly Thr Trp Leu Ser Arg Ile Ile Thr Gln Phe
    1175            1180                1185

Asn Asn Ile Ser Tyr Gln Met Tyr Asp Ser Leu Asn Tyr Gln Ala
    1190            1195                1200

Gly Ala Ile Lys Ala Lys Ile Asp Leu Glu Tyr Lys Lys Tyr Ser
    1205            1210                1215

Gly Ser Asp Lys Glu Asn Ile Lys Ser Gln Val Glu Asn Leu Lys
    1220            1225                1230

Asn Ser Leu Asp Val Lys Ile Ser Glu Ala Met Asn Asn Ile Asn
    1235            1240                1245

Lys Phe Ile Arg Glu Cys Ser Val Thr Tyr Leu Phe Lys Asn Met
    1250            1255                1260

Leu Pro Lys Val Ile Asp Glu Leu Asn Glu Phe Asp Arg Asn Thr
    1265            1270                1275

Lys Ala Lys Leu Ile Asn Leu Ile Asp Ser His Asn Ile Ile Leu
    1280            1285                1290

Val Gly Glu Val Asp Lys Leu Lys Ala Lys Val Asn Asn Ser Phe
    1295            1300                1305

Gln Asn Thr Ile Pro Phe Asn Ile Phe Ser Tyr Thr Asn Asn Ser
    1310            1315                1320

Leu Leu Lys Asp Ile Ile Asn Glu Tyr Phe Asn Asn Ile Asn Asp
    1325            1330                1335

Ser Lys Ile Leu Ser Leu Gln Asn Arg Lys Met Arg Leu Ala Val
    1340            1345                1350

Gly Ala Leu Leu Val Cys Ala Val Leu Gly Leu Cys Leu Ala Val
    1355            1360                1365

Pro Asp Lys Thr Val Arg Trp Cys Ala Val Ser Glu His Glu Ala
    1370            1375                1380

```
Thr Lys Cys Gln Ser Phe Arg Asp His Met Lys Ser Val Ile Pro
1385                1390                1395
Ser Asp Gly Pro Ser Val Ala Cys Val Lys Lys Ala Ser Tyr Leu
1400                1405                1410
Asp Cys Ile Arg Ala Ile Ala Ala Asn Glu Ala Asp Ala Val Thr
1415                1420                1425
Leu Asp Ala Gly Leu Val Tyr Asp Ala Tyr Leu Ala Pro Asn Asn
1430                1435                1440
Leu Lys Pro Val Val Ala Glu Phe Tyr Gly Ser Lys Glu Asp Pro
1445                1450                1455
Gln Thr Phe Tyr Tyr Ala Val Ala Val Val Lys Lys Asp Ser Gly
1460                1465                1470
Phe Gln Met Asn Gln Leu Arg Gly Lys Lys Ser Cys His Thr Gly
1475                1480                1485
Leu Gly Arg Ser Ala Gly Trp Asn Ile Pro Ile Gly Leu Leu Tyr
1490                1495                1500
Cys Asp Leu Pro Glu Pro Arg Lys Pro Leu Glu Lys Ala Val Ala
1505                1510                1515
Asn Phe Phe Ser Gly Ser Cys Ala Pro Cys Ala Asp Gly Thr Asp
1520                1525                1530
Phe Pro Gln Leu Cys Gln Leu Cys Pro Gly Cys Gly Cys Ser Thr
1535                1540                1545
Leu Asn Gln Tyr Phe Gly Tyr Ser Gly Ala Phe Lys Cys Leu Lys
1550                1555                1560
Asp Gly Ala Gly Asp Val Ala Phe Val Lys His Ser Thr Ile Phe
1565                1570                1575
Glu Asn Leu Ala Asn Lys Ala Asp Arg Asp Gln Tyr Glu Leu Leu
1580                1585                1590
Cys Leu Asp Asn Thr Arg Lys Pro Val Asp Glu Tyr Lys Asp Cys
1595                1600                1605
His Leu Ala Gln Val Pro Ser His Thr Val Val Ala Arg Ser Met
1610                1615                1620
Gly Gly Lys Glu Asp Leu Ile Trp Glu Leu Leu Asn Gln Ala Gln
1625                1630                1635
Glu His Phe Gly Lys Asp Lys Ser Lys Glu Phe Gln Leu Phe Ser
1640                1645                1650
Ser Pro His Gly Lys Asp Leu Leu Phe Lys Asp Ser Ala His Gly
1655                1660                1665
Phe Leu Lys Val Pro Pro Arg Met Asp Ala Lys Met Tyr Leu Gly
1670                1675                1680
Tyr Glu Tyr Val Thr Ala Ile Arg Asn Leu Arg Glu Gly Thr Cys
1685                1690                1695
Pro Glu Ala Pro Thr Asp Glu Cys Lys Pro Val Lys Trp Cys Ala
1700                1705                1710
Leu Ser His His Glu Arg Leu Lys Cys Asp Glu Trp Ser Val Asn
1715                1720                1725
Ser Val Gly Lys Ile Glu Cys Val Ser Ala Glu Thr Thr Glu Asp
1730                1735                1740
Cys Ile Ala Lys Ile Met Asn Gly Glu Ala Asp Ala Met Ser Leu
1745                1750                1755
Asp Gly Gly Phe Val Tyr Ile Ala Gly Lys Cys Gly Leu Val Pro
1760                1765                1770
Val Leu Ala Glu Asn Tyr Asn Lys Ser Asp Asn Cys Glu Asp Thr
```

-continued

```
            1775                1780                1785

Pro Glu Ala Gly Tyr Phe Ala Val Ala Val Val Lys Lys Ser Ala
    1790                1795                1800

Ser Asp Leu Thr Trp Asp Asn Leu Lys Gly Lys Lys Ser Cys His
    1805                1810                1815

Thr Ala Val Gly Arg Thr Ala Gly Trp Asn Ile Pro Met Gly Leu
    1820                1825                1830

Leu Tyr Asn Lys Ile Asn His Cys Arg Phe Asp Glu Phe Phe Ser
    1835                1840                1845

Glu Gly Cys Ala Pro Gly Ser Lys Lys Asp Ser Ser Leu Cys Lys
    1850                1855                1860

Leu Cys Met Gly Ser Gly Leu Asn Leu Cys Glu Pro Asn Asn Lys
    1865                1870                1875

Glu Gly Tyr Tyr Gly Tyr Thr Gly Ala Phe Arg Cys Leu Val Glu
    1880                1885                1890

Lys Gly Asp Val Ala Phe Val Lys His Gln Thr Val Pro Gln Asn
    1895                1900                1905

Thr Gly Gly Lys Asn Pro Asp Pro Trp Ala Lys Asn Leu Asn Glu
    1910                1915                1920

Lys Asp Tyr Glu Leu Leu Cys Leu Asp Gly Thr Arg Lys Pro Val
    1925                1930                1935

Glu Glu Tyr Ala Asn Cys His Leu Ala Arg Ala Pro Asn His Ala
    1940                1945                1950

Val Val Thr Arg Lys Asp Lys Glu Ala Cys Val His Lys Ile Leu
    1955                1960                1965

Arg Gln Gln Gln His Leu Phe Gly Ser Asn Val Thr Asp Cys Ser
    1970                1975                1980

Gly Asn Phe Cys Leu Phe Arg Ser Glu Thr Lys Asp Leu Leu Phe
    1985                1990                1995

Arg Asp Asp Thr Val Cys Leu Ala Lys Leu His Asp Arg Asn Thr
    2000                2005                2010

Tyr Glu Lys Tyr Leu Gly Glu Glu Tyr Val Lys Ala Val Gly Asn
    2015                2020                2025

Leu Arg Lys Cys Ser Thr Ser Ser Leu Leu Glu Ala Cys Thr Phe
    2030                2035                2040

Arg Arg Pro His His His His His His
    2045                2050

<210> SEQ ID NO 17
<211> LENGTH: 1960
<212> TYPE: PRT
<213> ORGANISM: Artificial Sequence
<220> FEATURE:
<223> OTHER INFORMATION: Fusion Protein Human Sox2/C. botulinum BoNT/C1/
      Human Transferrin

<400> SEQUENCE: 17

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Tyr Asn Met Met Glu Thr Glu
        50                  55                  60

Leu Lys Pro Pro Gly Pro Gln Gln Thr Ser Gly Gly Gly Gly Gly Asn
```

```
                65                  70                  75                  80
Ser Thr Ala Ala Ala Gly Gly Asn Gln Lys Asn Ser Pro Asp Arg
                    85                  90                  95

Val Lys Arg Pro Met Asn Ala Phe Met Val Trp Ser Arg Gly Gln Arg
                100                 105                 110

Arg Lys Met Ala Gln Glu Asn Pro Lys Met His Asn Ser Glu Ile Ser
                115                 120                 125

Lys Arg Leu Gly Ala Glu Trp Lys Leu Leu Ser Glu Thr Glu Lys Arg
                130                 135                 140

Pro Phe Ile Asp Glu Ala Lys Arg Leu Arg Ala Leu His Met Lys Glu
145                 150                 155                 160

His Pro Asp Tyr Lys Tyr Arg Pro Arg Arg Lys Thr Lys Thr Leu Met
                    165                 170                 175

Lys Lys Asp Lys Tyr Thr Leu Pro Gly Gly Leu Leu Ala Pro Gly Gly
                180                 185                 190

Asn Ser Met Ala Ser Gly Val Gly Val Gly Ala Gly Leu Gly Ala Gly
                195                 200                 205

Val Asn Gln Arg Met Asp Ser Tyr Ala His Met Asn Gly Trp Ser Asn
210                 215                 220

Gly Ser Tyr Ser Met Met Gln Asp Gln Leu Gly Tyr Pro Gln His Pro
225                 230                 235                 240

Gly Leu Asn Ala His Gly Ala Ala Gln Met Gln Pro Met His Arg Tyr
                245                 250                 255

Asp Val Ser Ala Leu Gln Tyr Asn Ser Met Thr Ser Ser Gln Thr Tyr
                260                 265                 270

Met Asn Gly Ser Pro Thr Tyr Ser Met Ser Tyr Ser Gln Gln Gly Thr
                275                 280                 285

Pro Gly Met Ala Leu Gly Ser Met Gly Ser Val Val Lys Ser Glu Ala
                290                 295                 300

Ser Ser Ser Pro Pro Val Val Thr Ser Ser Ser His Ser Arg Ala Pro
305                 310                 315                 320

Cys Gln Ala Gly Asp Leu Arg Asp Met Ile Ser Met Tyr Leu Pro Gly
                    325                 330                 335

Ala Glu Val Pro Glu Pro Ala Ala Pro Ser Arg Leu His Met Ser Gln
                340                 345                 350

His Tyr Gln Ser Gly Pro Val Pro Gly Thr Ala Ile Asn Gly Thr Leu
                355                 360                 365

Pro Leu Ser His Met Ala Ala Ala Met Pro Ile Thr Ile Asn Asn Phe
370                 375                 380

Asn Tyr Ser Asp Pro Val Asp Asn Lys Asn Ile Leu Tyr Leu Asp Thr
385                 390                 395                 400

His Leu Asn Thr Leu Ala Asn Glu Pro Glu Lys Ala Phe Arg Ile Thr
                    405                 410                 415

Gly Asn Ile Trp Val Ile Pro Arg Phe Ser Arg Asn Ser Asn Pro
                420                 425                 430

Asn Leu Asn Lys Pro Pro Arg Val Thr Ser Pro Lys Ser Gly Tyr Tyr
                435                 440                 445

Asp Pro Asn Tyr Leu Ser Thr Asp Ser Asp Lys Asp Pro Phe Leu Lys
                450                 455                 460

Glu Ile Ile Lys Leu Phe Lys Arg Ile Asn Ser Arg Glu Ile Gly Glu
465                 470                 475                 480

Glu Leu Ile Tyr Arg Leu Ser Thr Asp Ile Pro Phe Pro Gly Asn Asn
                    485                 490                 495
```

-continued

```
Asn Thr Pro Ile Asn Thr Phe Asp Phe Asp Val Asp Phe Asn Ser Val
            500                 505                 510
Asp Val Lys Thr Arg Gln Gly Asn Asn Trp Val Lys Thr Gly Ser Ile
        515                 520                 525
Asn Pro Ser Val Ile Ile Thr Gly Pro Arg Glu Asn Ile Ile Asp Pro
    530                 535                 540
Glu Thr Ser Thr Phe Lys Leu Thr Asn Asn Thr Phe Ala Ala Gln Glu
545                 550                 555                 560
Gly Phe Gly Ala Leu Ser Ile Ile Ser Ile Ser Pro Arg Phe Met Leu
                565                 570                 575
Thr Tyr Ser Asn Ala Thr Asn Asp Val Gly Glu Gly Arg Phe Ser Lys
            580                 585                 590
Ser Glu Phe Cys Met Asp Pro Ile Leu Ile Leu Met Ala Ala Leu Asn
        595                 600                 605
Ala Ala Met His Asn Leu Tyr Gly Ile Ala Ile Pro Asn Asp Gln Thr
    610                 615                 620
Ile Ser Ser Val Thr Ser Asn Ile Phe Tyr Ser Gln Tyr Asn Val Lys
625                 630                 635                 640
Leu Glu Tyr Ala Glu Ile Tyr Ala Phe Gly Gly Pro Thr Ile Asp Leu
                645                 650                 655
Ile Pro Lys Ser Ala Arg Lys Tyr Phe Glu Glu Lys Ala Leu Asp Tyr
            660                 665                 670
Tyr Arg Ser Ile Ala Lys Arg Leu Asn Ser Ile Thr Thr Ala Asn Pro
        675                 680                 685
Ser Ser Phe Asn Lys Tyr Ile Gly Glu Tyr Lys Gln Lys Leu Ile Arg
    690                 695                 700
Lys Tyr Arg Phe Val Val Glu Ser Ser Gly Glu Val Thr Val Asn Arg
705                 710                 715                 720
Asn Lys Phe Val Glu Leu Tyr Asn Glu Leu Thr Gln Ile Phe Thr Glu
                725                 730                 735
Phe Asn Tyr Ala Lys Ile Tyr Asn Val Gln Asn Arg Lys Ile Tyr Leu
            740                 745                 750
Ser Asn Val Tyr Thr Pro Val Thr Ala Asn Ile Leu Asp Asp Asn Val
        755                 760                 765
Tyr Asp Ile Gln Asn Gly Phe Asn Ile Pro Lys Ser Asn Leu Asn Val
    770                 775                 780
Leu Phe Met Gly Gln Asn Leu Ser Arg Asn Pro Ala Leu Arg Lys Val
785                 790                 795                 800
Asn Pro Glu Asn Met Leu Tyr Leu Phe Thr Lys Phe Cys His Lys Ala
                805                 810                 815
Ile Asp Gly Arg Ser Leu Tyr Asn Lys Thr Leu Asp Cys Arg Glu Leu
            820                 825                 830
Leu Val Lys Asn Thr Asp Leu Pro Phe Ile Gly Asp Ile Ser Asp Val
        835                 840                 845
Lys Thr Asp Ile Phe Leu Arg Lys Asp Ile Asn Glu Glu Thr Glu Val
    850                 855                 860
Ile Tyr Tyr Pro Asp Asn Val Ser Val Asp Gln Val Ile Leu Ser Lys
865                 870                 875                 880
Asn Thr Ser Glu His Gly Gln Leu Asp Leu Leu Tyr Pro Ser Ile Asp
                885                 890                 895
Ser Glu Ser Glu Ile Leu Pro Gly Glu Asn Gln Val Phe Tyr Asp Asn
            900                 905                 910
Arg Thr Gln Asn Val Asp Tyr Leu Asn Ser Tyr Tyr Leu Glu Ser
        915                 920                 925
```

```
Gln Lys Leu Ser Asp Asn Val Glu Asp Phe Thr Phe Thr Arg Ser Ile
    930                 935                 940

Glu Glu Ala Leu Asp Asn Ser Ala Lys Val Tyr Thr Tyr Phe Pro Thr
945                 950                 955                 960

Leu Ala Asn Lys Val Asn Ala Gly Val Gln Gly Gly Leu Phe Leu Met
                965                 970                 975

Trp Ala Asn Asp Val Val Glu Asp Phe Thr Thr Asn Ile Leu Arg Lys
            980                 985                 990

Asp Thr Leu Asp Lys Ile Ser Asp Val Ser Ala Ile Ile Pro Tyr Ile
        995                 1000                1005

Gly Pro Ala Leu Asn Ile Ser Asn Ser Val Arg Arg Gly Asn Phe
    1010                1015                1020

Thr Glu Ala Phe Ala Val Thr Gly Val Thr Ile Leu Leu Glu Ala
    1025                1030                1035

Phe Pro Glu Phe Thr Ile Pro Ala Leu Gly Ala Phe Val Ile Tyr
    1040                1045                1050

Ser Lys Val Gln Glu Arg Asn Glu Ile Ile Lys Thr Ile Asp Asn
    1055                1060                1065

Cys Leu Glu Gln Arg Ile Lys Arg Trp Lys Asp Ser Tyr Glu Trp
    1070                1075                1080

Met Met Gly Thr Trp Leu Ser Arg Ile Ile Thr Gln Phe Asn Asn
    1085                1090                1095

Ile Ser Tyr Gln Met Tyr Asp Ser Leu Asn Tyr Gln Ala Gly Ala
    1100                1105                1110

Ile Lys Ala Lys Ile Asp Leu Glu Tyr Lys Lys Tyr Ser Gly Ser
    1115                1120                1125

Asp Lys Glu Asn Ile Lys Ser Gln Val Glu Asn Leu Lys Asn Ser
    1130                1135                1140

Leu Asp Val Lys Ile Ser Glu Ala Met Asn Asn Ile Asn Lys Phe
    1145                1150                1155

Ile Arg Glu Cys Ser Val Thr Tyr Leu Phe Lys Asn Met Leu Pro
    1160                1165                1170

Lys Val Ile Asp Glu Leu Asn Glu Phe Asp Arg Asn Thr Lys Ala
    1175                1180                1185

Lys Leu Ile Asn Leu Ile Asp Ser His Asn Ile Ile Leu Val Gly
    1190                1195                1200

Glu Val Asp Lys Leu Lys Ala Lys Val Asn Asn Ser Phe Gln Asn
    1205                1210                1215

Thr Ile Pro Phe Asn Ile Phe Ser Tyr Thr Asn Asn Ser Leu Leu
    1220                1225                1230

Lys Asp Ile Ile Asn Glu Tyr Phe Asn Asn Ile Asn Asp Ser Lys
    1235                1240                1245

Ile Leu Ser Leu Gln Asn Arg Lys Met Arg Leu Ala Val Gly Ala
    1250                1255                1260

Leu Leu Val Cys Ala Val Leu Gly Leu Cys Leu Ala Val Pro Asp
    1265                1270                1275

Lys Thr Val Arg Trp Cys Ala Val Ser Glu His Glu Ala Thr Lys
    1280                1285                1290

Cys Gln Ser Phe Arg Asp His Met Lys Ser Val Ile Pro Ser Asp
    1295                1300                1305

Gly Pro Ser Val Ala Cys Val Lys Lys Ala Ser Tyr Leu Asp Cys
    1310                1315                1320

Ile Arg Ala Ile Ala Ala Asn Glu Ala Asp Ala Val Thr Leu Asp
```

```
                1325                1330                1335

Ala Gly Leu Val Tyr Asp Ala Tyr Leu Ala Pro Asn Asn Leu Lys
    1340                1345                1350

Pro Val Val Ala Glu Phe Tyr Gly Ser Lys Glu Asp Pro Gln Thr
    1355                1360                1365

Phe Tyr Tyr Ala Val Ala Val Val Lys Lys Asp Ser Gly Phe Gln
    1370                1375                1380

Met Asn Gln Leu Arg Gly Lys Lys Ser Cys His Thr Gly Leu Gly
    1385                1390                1395

Arg Ser Ala Gly Trp Asn Ile Pro Ile Gly Leu Leu Tyr Cys Asp
    1400                1405                1410

Leu Pro Glu Pro Arg Lys Pro Leu Glu Lys Ala Val Ala Asn Phe
    1415                1420                1425

Phe Ser Gly Ser Cys Ala Pro Cys Ala Asp Gly Thr Asp Phe Pro
    1430                1435                1440

Gln Leu Cys Gln Leu Cys Pro Gly Cys Gly Cys Ser Thr Leu Asn
    1445                1450                1455

Gln Tyr Phe Gly Tyr Ser Gly Ala Phe Lys Cys Leu Lys Asp Gly
    1460                1465                1470

Ala Gly Asp Val Ala Phe Val Lys His Ser Thr Ile Phe Glu Asn
    1475                1480                1485

Leu Ala Asn Lys Ala Asp Arg Asp Gln Tyr Glu Leu Leu Cys Leu
    1490                1495                1500

Asp Asn Thr Arg Lys Pro Val Asp Glu Tyr Lys Asp Cys His Leu
    1505                1510                1515

Ala Gln Val Pro Ser His Thr Val Val Ala Arg Ser Met Gly Gly
    1520                1525                1530

Lys Glu Asp Leu Ile Trp Glu Leu Leu Asn Gln Ala Gln Glu His
    1535                1540                1545

Phe Gly Lys Asp Lys Ser Lys Glu Phe Gln Leu Phe Ser Ser Pro
    1550                1555                1560

His Gly Lys Asp Leu Leu Phe Lys Asp Ser Ala His Gly Phe Leu
    1565                1570                1575

Lys Val Pro Pro Arg Met Asp Ala Lys Met Tyr Leu Gly Tyr Glu
    1580                1585                1590

Tyr Val Thr Ala Ile Arg Asn Leu Arg Glu Gly Thr Cys Pro Glu
    1595                1600                1605

Ala Pro Thr Asp Glu Cys Lys Pro Val Lys Trp Cys Ala Leu Ser
    1610                1615                1620

His His Glu Arg Leu Lys Cys Asp Glu Trp Ser Val Asn Ser Val
    1625                1630                1635

Gly Lys Ile Glu Cys Val Ser Ala Glu Thr Thr Glu Asp Cys Ile
    1640                1645                1650

Ala Lys Ile Met Asn Gly Glu Ala Asp Ala Met Ser Leu Asp Gly
    1655                1660                1665

Gly Phe Val Tyr Ile Ala Gly Lys Cys Gly Leu Val Pro Val Leu
    1670                1675                1680

Ala Glu Asn Tyr Asn Lys Ser Asp Asn Cys Glu Asp Thr Pro Glu
    1685                1690                1695

Ala Gly Tyr Phe Ala Val Ala Val Val Lys Lys Ser Ala Ser Asp
    1700                1705                1710

Leu Thr Trp Asp Asn Leu Lys Gly Lys Lys Ser Cys His Thr Ala
    1715                1720                1725
```

-continued

```
Val Gly Arg Thr Ala Gly Trp Asn Ile Pro Met Gly Leu Leu Tyr
    1730                1735                1740

Asn Lys Ile Asn His Cys Arg Phe Asp Glu Phe Phe Ser Glu Gly
    1745                1750                1755

Cys Ala Pro Gly Ser Lys Lys Asp Ser Ser Leu Cys Lys Leu Cys
    1760                1765                1770

Met Gly Ser Gly Leu Asn Leu Cys Glu Pro Asn Lys Glu Gly
    1775                1780                1785

Tyr Tyr Gly Tyr Thr Gly Ala Phe Arg Cys Leu Val Glu Lys Gly
    1790                1795                1800

Asp Val Ala Phe Val Lys His Gln Thr Val Pro Gln Asn Thr Gly
    1805                1810                1815

Gly Lys Asn Pro Asp Pro Trp Ala Lys Asn Leu Asn Glu Lys Asp
    1820                1825                1830

Tyr Glu Leu Leu Cys Leu Asp Gly Thr Arg Lys Pro Val Glu Glu
    1835                1840                1845

Tyr Ala Asn Cys His Leu Ala Arg Ala Pro Asn His Ala Val Val
    1850                1855                1860

Thr Arg Lys Asp Lys Glu Ala Cys Val His Lys Ile Leu Arg Gln
    1865                1870                1875

Gln Gln His Leu Phe Gly Ser Asn Val Thr Asp Cys Ser Gly Asn
    1880                1885                1890

Phe Cys Leu Phe Arg Ser Glu Thr Lys Asp Leu Leu Phe Arg Asp
    1895                1900                1905

Asp Thr Val Cys Leu Ala Lys Leu His Asp Arg Asn Thr Tyr Glu
    1910                1915                1920

Lys Tyr Leu Gly Glu Glu Tyr Val Lys Ala Val Gly Asn Leu Arg
    1925                1930                1935

Lys Cys Ser Thr Ser Ser Leu Leu Glu Ala Cys Thr Phe Arg Arg
    1940                1945                1950

Pro His His His His His His
    1955                1960

<210> SEQ ID NO 18
<211> LENGTH: 1437
<212> TYPE: PRT
<213> ORGANISM: Artificial Sequence
<220> FEATURE:
<223> OTHER INFORMATION: Fusion Protein of Human Oct4/C. butulinum and
      Human ILGF

<400> SEQUENCE: 18

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Ala Gly His Leu Ala Ser Asp
        50                  55                  60

Phe Ala Phe Ser Pro Pro Gly Gly Gly Gly Asp Gly Pro Gly Gly
65                  70                  75                  80

Pro Glu Pro Gly Trp Val Asp Pro Arg Thr Trp Leu Ser Phe Gln Gly
                85                  90                  95

Pro Pro Gly Gly Pro Gly Ile Gly Pro Gly Val Gly Pro Gly Ser Glu
            100                 105                 110
```

```
Val Trp Gly Ile Pro Pro Cys Pro Pro Tyr Glu Phe Cys Gly
        115                 120                 125
Met Ala Tyr Cys Gly Pro Gln Val Gly Val Gly Leu Val Pro Gln Gly
        130                 135                 140
Gly Leu Glu Thr Ser Gln Pro Glu Gly Glu Ala Gly Val Gly Val Glu
145                 150                 155                 160
Ser Asn Ser Asp Gly Ala Ser Pro Glu Pro Cys Thr Val Thr Pro Gly
                165                 170                 175
Ala Val Lys Leu Glu Lys Glu Lys Leu Glu Gln Asn Pro Glu Glu Ser
                180                 185                 190
Gln Asp Ile Lys Ala Leu Gln Lys Glu Leu Glu Gln Phe Ala Lys Leu
        195                 200                 205
Leu Lys Gln Lys Arg Ile Thr Leu Gly Tyr Thr Gln Ala Asp Val Gly
210                 215                 220
Leu Thr Leu Gly Val Leu Phe Gly Lys Val Phe Ser Gln Thr Thr Ile
225                 230                 235                 240
Cys Arg Phe Glu Ala Leu Gln Leu Ser Phe Lys Asn Met Cys Lys Leu
                245                 250                 255
Arg Pro Leu Leu Gln Lys Trp Val Glu Ala Asp Asn Asn Glu Asn
        260                 265                 270
Leu Gln Glu Ile Cys Lys Ala Glu Thr Leu Val Gln Ala Arg Lys Arg
        275                 280                 285
Lys Arg Thr Ser Ile Glu Asn Arg Val Arg Gly Asn Leu Glu Asn Leu
290                 295                 300
Phe Leu Gln Cys Pro Lys Pro Thr Leu Gln Gln Ile Ser His Ile Ala
305                 310                 315                 320
Gln Gln Leu Gly Leu Glu Lys Asp Val Val Arg Val Trp Phe Cys Asn
                325                 330                 335
Arg Arg Gln Lys Gly Lys Arg Ser Ser Ser Asp Tyr Ala Gln Arg Glu
        340                 345                 350
Asp Phe Glu Ala Ala Gly Ser Pro Phe Ser Gly Gly Pro Val Ser Phe
        355                 360                 365
Pro Leu Ala Pro Gly Pro His Phe Gly Thr Pro Gly Tyr Gly Ser Pro
        370                 375                 380
His Phe Thr Ala Leu Tyr Ser Ser Val Pro Phe Pro Glu Gly Glu Ala
385                 390                 395                 400
Phe Pro Pro Val Ser Val Thr Thr Leu Gly Ser Pro Met His Ser Asn
                405                 410                 415
Ala Ala Ala Ser Leu Val Asn Arg Lys Gln Leu Glu Lys Met Ala Asn
        420                 425                 430
Val Arg Phe Arg Thr Gln Glu Asp Glu Tyr Val Ala Ile Leu Asp Ala
        435                 440                 445
Leu Glu Glu Tyr His Asn Met Ser Glu Asn Thr Val Val Glu Lys Tyr
        450                 455                 460
Leu Lys Leu Lys Met Pro Ile Thr Ile Asn Asn Phe Asn Tyr Ser Asp
465                 470                 475                 480
Pro Val Asp Asn Lys Asn Ile Leu Tyr Leu Asp Thr His Leu Asn Thr
                485                 490                 495
Leu Ala Asn Glu Pro Glu Lys Ala Phe Arg Ile Thr Gly Asn Ile Trp
        500                 505                 510
Val Ile Pro Asp Arg Phe Ser Arg Asn Ser Asn Pro Asn Leu Asn Lys
        515                 520                 525
Pro Pro Arg Val Thr Ser Pro Lys Ser Gly Tyr Tyr Asp Pro Asn Tyr
        530                 535                 540
```

```
Leu Ser Thr Asp Ser Asp Lys Asp Pro Phe Leu Lys Glu Ile Ile Lys
545                 550                 555                 560

Leu Phe Lys Arg Ile Asn Ser Arg Glu Ile Gly Glu Leu Ile Tyr
                565                 570                 575

Arg Leu Ser Thr Asp Ile Pro Phe Pro Gly Asn Asn Thr Pro Ile
            580                 585                 590

Asn Thr Phe Asp Phe Asp Val Asp Phe Asn Ser Val Asp Val Lys Thr
        595                 600                 605

Arg Gln Gly Asn Asn Trp Val Lys Thr Gly Ser Ile Asn Pro Ser Val
    610                 615                 620

Ile Ile Thr Gly Pro Arg Glu Asn Ile Ile Asp Pro Glu Thr Ser Thr
625                 630                 635                 640

Phe Lys Leu Thr Asn Asn Thr Phe Ala Ala Gln Glu Gly Phe Gly Ala
                645                 650                 655

Leu Ser Ile Ile Ser Ile Ser Pro Arg Phe Met Leu Thr Tyr Ser Asn
                660                 665                 670

Ala Thr Asn Asp Val Gly Glu Gly Arg Phe Ser Lys Ser Glu Phe Cys
            675                 680                 685

Met Asp Pro Ile Leu Ile Leu Met Ala Ala Leu Asn Ala Ala Met His
690                 695                 700

Asn Leu Tyr Gly Ile Ala Ile Pro Asn Asp Gln Thr Ile Ser Ser Val
705                 710                 715                 720

Thr Ser Asn Ile Phe Tyr Ser Gln Tyr Asn Val Lys Leu Glu Tyr Ala
                725                 730                 735

Glu Ile Tyr Ala Phe Gly Gly Pro Thr Ile Asp Leu Ile Pro Lys Ser
                740                 745                 750

Ala Arg Lys Tyr Phe Glu Glu Lys Ala Leu Asp Tyr Tyr Arg Ser Ile
            755                 760                 765

Ala Lys Arg Leu Asn Ser Ile Thr Thr Ala Asn Pro Ser Ser Phe Asn
770                 775                 780

Lys Tyr Ile Gly Glu Tyr Lys Gln Lys Leu Ile Arg Lys Tyr Arg Phe
785                 790                 795                 800

Val Val Glu Ser Ser Gly Glu Val Thr Val Asn Arg Asn Lys Phe Val
                805                 810                 815

Glu Leu Tyr Asn Glu Leu Thr Gln Ile Phe Thr Glu Phe Asn Tyr Ala
                820                 825                 830

Lys Ile Tyr Asn Val Gln Asn Arg Lys Ile Tyr Leu Ser Asn Val Tyr
            835                 840                 845

Thr Pro Val Thr Ala Asn Ile Leu Asp Asp Asn Val Tyr Asp Ile Gln
850                 855                 860

Asn Gly Phe Asn Ile Pro Lys Ser Asn Leu Asn Val Leu Phe Met Gly
865                 870                 875                 880

Gln Asn Leu Ser Arg Asn Pro Ala Leu Arg Lys Val Asn Pro Glu Asn
                885                 890                 895

Met Leu Tyr Leu Phe Thr Lys Phe Cys His Lys Ala Ile Asp Gly Arg
                900                 905                 910

Ser Leu Tyr Asn Lys Thr Leu Asp Cys Arg Glu Leu Leu Val Lys Asn
            915                 920                 925

Thr Asp Leu Pro Phe Ile Gly Asp Ile Ser Asp Val Lys Thr Asp Ile
            930                 935                 940

Phe Leu Arg Lys Asp Ile Asn Glu Glu Thr Glu Val Ile Tyr Tyr Pro
945                 950                 955                 960

Asp Asn Val Ser Val Asp Gln Val Ile Leu Ser Lys Asn Thr Ser Glu
```

-continued

```
                965                 970                 975
His Gly Gln Leu Asp Leu Leu Tyr Pro Ser Ile Asp Ser Glu Ser Glu
                980                 985                 990
Ile Leu Pro Gly Glu Asn Gln Val Phe Tyr Asp Asn Arg Thr Gln Asn
            995                1000                1005
Val Asp Tyr Leu Asn Ser Tyr Tyr Tyr Leu Glu Ser Gln Lys Leu
        1010                1015                1020
Ser Asp Asn Val Glu Asp Phe Thr Phe Thr Arg Ser Ile Glu Glu
        1025                1030                1035
Ala Leu Asp Asn Ser Ala Lys Val Tyr Thr Tyr Phe Pro Thr Leu
        1040                1045                1050
Ala Asn Lys Val Asn Ala Gly Val Gln Gly Gly Leu Phe Leu Met
        1055                1060                1065
Trp Ala Asn Asp Val Val Glu Asp Phe Thr Thr Asn Ile Leu Arg
        1070                1075                1080
Lys Asp Thr Leu Asp Lys Ile Ser Asp Val Ser Ala Ile Ile Pro
        1085                1090                1095
Tyr Ile Gly Pro Ala Leu Asn Ile Ser Asn Ser Val Arg Arg Gly
        1100                1105                1110
Asn Phe Thr Glu Ala Phe Ala Val Thr Gly Val Thr Ile Leu Leu
        1115                1120                1125
Glu Ala Phe Pro Glu Phe Thr Ile Pro Ala Leu Gly Ala Phe Val
        1130                1135                1140
Ile Tyr Ser Lys Val Gln Glu Arg Asn Glu Ile Ile Lys Thr Ile
        1145                1150                1155
Asp Asn Cys Leu Glu Gln Arg Ile Lys Arg Trp Lys Asp Ser Tyr
        1160                1165                1170
Glu Trp Met Met Gly Thr Trp Leu Ser Arg Ile Ile Thr Gln Phe
        1175                1180                1185
Asn Asn Ile Ser Tyr Gln Met Tyr Asp Ser Leu Asn Tyr Gln Ala
        1190                1195                1200
Gly Ala Ile Lys Ala Lys Ile Asp Leu Glu Tyr Lys Lys Tyr Ser
        1205                1210                1215
Gly Ser Asp Lys Glu Asn Ile Lys Ser Gln Val Glu Asn Leu Lys
        1220                1225                1230
Asn Ser Leu Asp Val Lys Ile Ser Glu Ala Met Asn Asn Ile Asn
        1235                1240                1245
Lys Phe Ile Arg Glu Cys Ser Val Thr Tyr Leu Phe Lys Asn Met
        1250                1255                1260
Leu Pro Lys Val Ile Asp Glu Leu Asn Glu Phe Asp Arg Asn Thr
        1265                1270                1275
Lys Ala Lys Leu Ile Asn Leu Ile Asp Ser His Asn Ile Ile Leu
        1280                1285                1290
Val Gly Glu Val Asp Lys Leu Lys Ala Lys Val Asn Asn Ser Phe
        1295                1300                1305
Gln Asn Thr Ile Pro Phe Asn Ile Phe Ser Tyr Thr Asn Asn Ser
        1310                1315                1320
Leu Leu Lys Asp Ile Ile Asn Glu Tyr Phe Asn Asn Ile Asn Asp
        1325                1330                1335
Ser Lys Ile Leu Ser Leu Gln Asn Arg Lys Ser Thr Phe Thr Glu
        1340                1345                1350
Tyr Ile Lys Ser Arg Pro Gly Pro Glu Thr Leu Cys Gly Ala Glu
        1355                1360                1365
```

-continued

```
Leu Val Asp Ala Leu Gln Phe Val Cys Gly Asp Arg Gly Phe Tyr
    1370            1375            1380

Phe Asn Lys Pro Thr Gly Tyr Gly Ser Ser Ser Arg Arg Ala Pro
    1385            1390            1395

Gln Thr Gly Ile Val Asp Glu Cys Cys Phe Arg Ser Cys Asp Leu
    1400            1405            1410

Arg Arg Leu Glu Met Tyr Cys Ala Pro Leu Lys Pro Ala Lys Ser
    1415            1420            1425

Ala Glu Ala His His His His His His
    1430            1435

<210> SEQ ID NO 19
<211> LENGTH: 1345
<212> TYPE: PRT
<213> ORGANISM: Artificial Sequence
<220> FEATURE:
<223> OTHER INFORMATION: Fusion Protein of Human Sox2/C. botulinum
      BoNT/C1 and Human ILGF

<400> SEQUENCE: 19

Met Asp Glu Gln Gln Ser Gln Ala Val Ala Pro Val Tyr Val Gly Gly
1               5                   10                  15

Met Asp Glu Lys Thr Thr Gly Trp Arg Gly Gly His Val Val Glu Gly
                20                  25                  30

Leu Ala Gly Glu Leu Glu Gln Leu Arg Ala Arg Leu Glu His His Pro
            35                  40                  45

Gln Gly Gln Arg Glu Pro Ser Gly Ala Tyr Asn Met Met Glu Thr Glu
        50                  55                  60

Leu Lys Pro Pro Gly Pro Gln Gln Thr Ser Gly Gly Gly Gly Asn
65                  70                  75                  80

Ser Thr Ala Ala Ala Ala Gly Gly Asn Gln Lys Asn Ser Pro Asp Arg
                85                  90                  95

Val Lys Arg Pro Met Asn Ala Phe Met Val Trp Ser Arg Gly Gln Arg
            100                 105                 110

Arg Lys Met Ala Gln Glu Asn Pro Lys Met His Asn Ser Glu Ile Ser
        115                 120                 125

Lys Arg Leu Gly Ala Glu Trp Lys Leu Leu Ser Glu Thr Glu Lys Arg
    130                 135                 140

Pro Phe Ile Asp Glu Ala Lys Arg Leu Arg Ala Leu His Met Lys Glu
145                 150                 155                 160

His Pro Asp Tyr Lys Tyr Arg Pro Arg Arg Lys Thr Lys Thr Leu Met
                165                 170                 175

Lys Lys Asp Lys Tyr Thr Leu Pro Gly Gly Leu Leu Ala Pro Gly Gly
            180                 185                 190

Asn Ser Met Ala Ser Gly Val Gly Val Gly Ala Gly Leu Gly Ala Gly
        195                 200                 205

Val Asn Gln Arg Met Asp Ser Tyr Ala His Met Asn Gly Trp Ser Asn
    210                 215                 220

Gly Ser Tyr Ser Met Met Gln Asp Gln Leu Gly Tyr Pro Gln His Pro
225                 230                 235                 240

Gly Leu Asn Ala His Gly Ala Ala Gln Met Gln Pro Met His Arg Tyr
                245                 250                 255

Asp Val Ser Ala Leu Gln Tyr Asn Ser Met Thr Ser Ser Gln Thr Tyr
            260                 265                 270

Met Asn Gly Ser Pro Thr Tyr Ser Met Ser Tyr Ser Gln Gln Gly Thr
        275                 280                 285
```

-continued

Pro Gly Met Ala Leu Gly Ser Met Gly Ser Val Val Lys Ser Glu Ala
            290                 295                 300

Ser Ser Ser Pro Pro Val Val Thr Ser Ser His Ser Arg Ala Pro
305                 310                 315                 320

Cys Gln Ala Gly Asp Leu Arg Asp Met Ile Ser Met Tyr Leu Pro Gly
                325                 330                 335

Ala Glu Val Pro Glu Pro Ala Ala Pro Ser Arg Leu His Met Ser Gln
            340                 345                 350

His Tyr Gln Ser Gly Pro Val Pro Gly Thr Ala Ile Asn Gly Thr Leu
        355                 360                 365

Pro Leu Ser His Met Ala Ala Ala Met Pro Ile Thr Ile Asn Asn Phe
    370                 375                 380

Asn Tyr Ser Asp Pro Val Asp Asn Lys Asn Ile Leu Tyr Leu Asp Thr
385                 390                 395                 400

His Leu Asn Thr Leu Ala Asn Glu Pro Glu Lys Ala Phe Arg Ile Thr
                405                 410                 415

Gly Asn Ile Trp Val Ile Pro Asp Arg Phe Ser Arg Asn Ser Asn Pro
            420                 425                 430

Asn Leu Asn Lys Pro Pro Arg Val Thr Ser Pro Lys Ser Gly Tyr Tyr
        435                 440                 445

Asp Pro Asn Tyr Leu Ser Thr Asp Ser Asp Lys Asp Pro Phe Leu Lys
    450                 455                 460

Glu Ile Ile Lys Leu Phe Lys Arg Ile Asn Ser Arg Glu Ile Gly Glu
465                 470                 475                 480

Glu Leu Ile Tyr Arg Leu Ser Thr Asp Ile Pro Phe Pro Gly Asn Asn
                485                 490                 495

Asn Thr Pro Ile Asn Thr Phe Asp Phe Asp Val Asp Phe Asn Ser Val
            500                 505                 510

Asp Val Lys Thr Arg Gln Gly Asn Asn Trp Val Lys Thr Gly Ser Ile
        515                 520                 525

Asn Pro Ser Val Ile Ile Thr Gly Pro Arg Glu Asn Ile Ile Asp Pro
    530                 535                 540

Glu Thr Ser Thr Phe Lys Leu Thr Asn Asn Thr Phe Ala Ala Gln Glu
545                 550                 555                 560

Gly Phe Gly Ala Leu Ser Ile Ile Ser Ile Ser Pro Arg Phe Met Leu
                565                 570                 575

Thr Tyr Ser Asn Ala Thr Asn Asp Val Gly Glu Gly Arg Phe Ser Lys
            580                 585                 590

Ser Glu Phe Cys Met Asp Pro Ile Leu Ile Leu Met Ala Ala Leu Asn
        595                 600                 605

Ala Ala Met His Asn Leu Tyr Gly Ile Ala Ile Pro Asn Asp Gln Thr
    610                 615                 620

Ile Ser Ser Val Thr Ser Asn Ile Phe Tyr Ser Gln Tyr Asn Val Lys
625                 630                 635                 640

Leu Glu Tyr Ala Glu Ile Tyr Ala Phe Gly Gly Pro Thr Ile Asp Leu
                645                 650                 655

Ile Pro Lys Ser Ala Arg Lys Tyr Phe Glu Glu Lys Ala Leu Asp Tyr
            660                 665                 670

Tyr Arg Ser Ile Ala Lys Arg Leu Asn Ser Ile Thr Thr Ala Asn Pro
        675                 680                 685

Ser Ser Phe Asn Lys Tyr Ile Gly Glu Tyr Lys Gln Lys Leu Ile Arg
    690                 695                 700

Lys Tyr Arg Phe Val Val Glu Ser Gly Glu Val Thr Val Asn Arg
705                 710                 715                 720

```
Asn Lys Phe Val Glu Leu Tyr Asn Glu Leu Thr Gln Ile Phe Thr Glu
            725                 730                 735

Phe Asn Tyr Ala Lys Ile Tyr Asn Val Gln Asn Arg Lys Ile Tyr Leu
            740                 745                 750

Ser Asn Val Tyr Thr Pro Val Thr Ala Asn Ile Leu Asp Asp Asn Val
            755                 760                 765

Tyr Asp Ile Gln Asn Gly Phe Asn Ile Pro Lys Ser Asn Leu Asn Val
            770                 775                 780

Leu Phe Met Gly Gln Asn Leu Ser Arg Asn Pro Ala Leu Arg Lys Val
785                 790                 795                 800

Asn Pro Glu Asn Met Leu Tyr Leu Phe Thr Lys Phe Cys His Lys Ala
            805                 810                 815

Ile Asp Gly Arg Ser Leu Tyr Asn Lys Thr Leu Asp Cys Arg Glu Leu
            820                 825                 830

Leu Val Lys Asn Thr Asp Leu Pro Phe Ile Gly Asp Ile Ser Asp Val
            835                 840                 845

Lys Thr Asp Ile Phe Leu Arg Lys Asp Ile Asn Glu Glu Thr Glu Val
            850                 855                 860

Ile Tyr Tyr Pro Asp Asn Val Ser Val Asp Gln Val Ile Leu Ser Lys
865                 870                 875                 880

Asn Thr Ser Glu His Gly Gln Leu Asp Leu Leu Tyr Pro Ser Ile Asp
            885                 890                 895

Ser Glu Ser Glu Ile Leu Pro Gly Glu Asn Gln Val Phe Tyr Asp Asn
            900                 905                 910

Arg Thr Gln Asn Val Asp Tyr Leu Asn Ser Tyr Tyr Leu Glu Ser
            915                 920                 925

Gln Lys Leu Ser Asp Asn Val Glu Asp Phe Thr Phe Thr Arg Ser Ile
            930                 935                 940

Glu Glu Ala Leu Asp Asn Ser Ala Lys Val Tyr Thr Tyr Phe Pro Thr
945                 950                 955                 960

Leu Ala Asn Lys Val Asn Ala Gly Val Gln Gly Gly Leu Phe Leu Met
            965                 970                 975

Trp Ala Asn Asp Val Val Glu Asp Phe Thr Thr Asn Ile Leu Arg Lys
            980                 985                 990

Asp Thr Leu Asp Lys Ile Ser Asp  Val Ser Ala Ile Ile  Pro Tyr Ile
            995                 1000                1005

Gly Pro Ala Leu Asn Ile Ser  Asn Ser Val Arg Arg  Gly Asn Phe
    1010                1015                1020

Thr Glu Ala Phe Ala Val Thr  Gly Val Thr Ile Leu  Leu Glu Ala
    1025                1030                1035

Phe Pro Glu Phe Thr Ile Pro  Ala Leu Gly Ala Phe  Val Ile Tyr
    1040                1045                1050

Ser Lys Val Gln Glu Arg Asn  Glu Ile Ile Lys Thr  Ile Asp Asn
    1055                1060                1065

Cys Leu Glu Gln Arg Ile Lys  Arg Trp Lys Asp Ser  Tyr Glu Trp
    1070                1075                1080

Met Met Gly Thr Trp Leu Ser  Arg Ile Ile Thr Gln  Phe Asn Asn
    1085                1090                1095

Ile Ser Tyr Gln Met Tyr Asp  Ser Leu Asn Tyr Gln  Ala Gly Ala
    1100                1105                1110

Ile Lys Ala Lys Ile Asp Leu  Glu Tyr Lys Lys Tyr  Ser Gly Ser
    1115                1120                1125

Asp Lys Glu Asn Ile Lys Ser  Gln Val Glu Asn Leu  Lys Asn Ser
```

```
              1130                1135                1140

Leu Asp Val Lys Ile Ser Glu Ala Met Asn Asn Ile Asn Lys Phe
        1145                1150                1155

Ile Arg Glu Cys Ser Val Thr Tyr Leu Phe Lys Asn Met Leu Pro
        1160                1165                1170

Lys Val Ile Asp Glu Leu Asn Glu Phe Asp Arg Asn Thr Lys Ala
        1175                1180                1185

Lys Leu Ile Asn Leu Ile Asp Ser His Asn Ile Ile Leu Val Gly
        1190                1195                1200

Glu Val Asp Lys Leu Lys Ala Lys Val Asn Asn Ser Phe Gln Asn
        1205                1210                1215

Thr Ile Pro Phe Asn Ile Phe Ser Tyr Thr Asn Asn Ser Leu Leu
        1220                1225                1230

Lys Asp Ile Ile Asn Glu Tyr Phe Asn Asn Ile Asn Asp Ser Lys
        1235                1240                1245

Ile Leu Ser Leu Gln Asn Arg Lys Ser Thr Phe Thr Glu Tyr Ile
        1250                1255                1260

Lys Ser Arg Pro Gly Pro Glu Thr Leu Cys Gly Ala Glu Leu Val
        1265                1270                1275

Asp Ala Leu Gln Phe Val Cys Gly Asp Arg Gly Phe Tyr Phe Asn
        1280                1285                1290

Lys Pro Thr Gly Tyr Gly Ser Ser Ser Arg Arg Ala Pro Gln Thr
        1295                1300                1305

Gly Ile Val Asp Glu Cys Cys Phe Arg Ser Cys Asp Leu Arg Arg
        1310                1315                1320

Leu Glu Met Tyr Cys Ala Pro Leu Lys Pro Ala Lys Ser Ala Glu
        1325                1330                1335

Ala His His His His His His
        1340                1345
```